(12) United States Patent
Ko et al.

(10) Patent No.: US 7,291,744 B2
(45) Date of Patent: Nov. 6, 2007

(54) N-UREIDOALKYL-AMINO COMPOUNDS AS MODULATORS OF CHEMOKINE RECEPTOR ACTIVITY

(75) Inventors: Soo S. Ko, Hockessin, DE (US); Douglas G. Batt, Wilmington, DE (US); George V. Delucca, Pennington, NJ (US); John V. Duncia, Newtown, PA (US); Daniel S. Gardner, Furlong, PA (US); Joseph B. Santella, Springfield, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 334 days.

(21) Appl. No.: 10/987,808

(22) Filed: Nov. 12, 2004

(65) Prior Publication Data

US 2005/0153970 A1    Jul. 14, 2005

Related U.S. Application Data

(60) Provisional application No. 60/519,506, filed on Nov. 13, 2003.

(51) Int. Cl.
C07D 239/02 (2006.01)
C07D 285/08 (2006.01)
C07D 277/22 (2006.01)
C07D 277/24 (2006.01)
C07D 257/04 (2006.01)
C07D 231/56 (2006.01)
C07D 317/44 (2006.01)

(52) U.S. Cl. .......................... 548/253; 564/48; 564/52; 549/438; 549/439; 548/128; 548/194; 548/361.1; 544/335; 514/256; 514/361; 514/363; 514/371

(58) Field of Classification Search ...................... None
See application file for complete search history.

(56) References Cited

U.S. PATENT DOCUMENTS

| | | | |
|---|---|---|---|
| 5,106,873 A | 4/1992 | O'Brien et al. |
| 5,317,020 A | 5/1994 | Emonds-Alt et al. |
| 5,547,966 A | 8/1996 | Atwal et al. |
| 5,668,151 A | 9/1997 | Poindexter et al. |
| 5,872,135 A | 2/1999 | deSolms |
| 6,022,861 A | 2/2000 | Scarborough et al. |
| 6,211,154 B1 | 4/2001 | Scarborough et al. |
| 6,297,233 B1 | 10/2001 | Stein et al. |
| 6,329,395 B1 | 12/2001 | Dugar et al. |
| 6,331,541 B1 | 12/2001 | Ko et al. |
| 6,362,177 B1 | 3/2002 | Shiota et al. |
| 6,410,566 B1 | 6/2002 | Shiota et al. |
| 6,444,686 B1 | 9/2002 | Ko et al. |
| 6,486,180 B1 | 11/2002 | Ko et al. |
| 6,492,400 B1 | 12/2002 | Ko et al. |
| 6,521,592 B2 | 2/2003 | Ko et al. |
| 6,525,069 B1 | 2/2003 | Ko et al. |
| 6,586,446 B1 | 7/2003 | Santella, III et al. |
| 6,605,623 B1 | 8/2003 | Ko et al. |
| 6,608,227 B1 | 8/2003 | Wacker et al. |
| 6,780,857 B2 | 8/2004 | Ko et al. |
| 6,784,200 B2 | 8/2004 | Duncia et al. |
| 2002/0055418 A1 | 5/2002 | Beaulieu et al. |
| 2003/0114489 A1 | 6/2003 | Ko et al. |
| 2004/0002515 A1 | 1/2004 | Ko et al. |
| 2004/0034063 A1 | 2/2004 | Ko et al. |
| 2004/0058960 A1 | 3/2004 | Ko et al. |
| 2004/0067935 A1 | 4/2004 | Batt |
| 2004/0209876 A1 | 10/2004 | Duncia et al. |

FOREIGN PATENT DOCUMENTS

| | | |
|---|---|---|
| JP | 05148233 | 6/1993 |
| JP | 11139969 | 5/1999 |
| WO | WO 9315047 | 8/1993 |
| WO | WO 9422835 | 10/1994 |
| WO | WO 9743251 | 11/1997 |
| WO | WO 9818786 | 5/1998 |
| WO | WO 9925686 | 5/1999 |
| WO | WO 9931064 | 6/1999 |
| WO | WO 9964394 | 12/1999 |
| WO | WO 0017197 | 3/2000 |
| WO | WO 0035449 | 6/2000 |
| WO | WO 0035451 | 6/2000 |
| WO | WO 0035452 | 6/2000 |

(Continued)

OTHER PUBLICATIONS

U.S. Appl. No. 11/021,042, filed Dec. 23, 2004, Ko et al.

(Continued)

*Primary Examiner*—Brian Davis
(74) *Attorney, Agent, or Firm*—Mary K. VanAtten

(57) ABSTRACT

The present application describes modulators of chemokine receptors of formula (I):

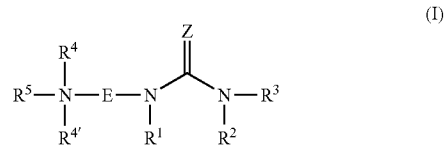

or pharmaceutically acceptable salt forms thereof, useful for the prevention of asthma and other allergic diseases.

22 Claims, No Drawings

FOREIGN PATENT DOCUMENTS

| | | |
|---|---|---|
| WO | WO 0035453 | 6/2000 |
| WO | WO 0035454 | 6/2000 |
| WO | WO 0078794 | 12/2000 |
| WO | WO 0109088 | 2/2001 |
| WO | WO 0129000 | 4/2001 |
| WO | WO 0218335 | 3/2002 |
| WO | WO 0222592 | 3/2002 |
| WO | WO 0230890 | 4/2002 |
| WO | WO 0249648 | 6/2002 |
| WO | WO 02059081 | 8/2002 |

OTHER PUBLICATIONS

U.S. Appl. No. 10/983,367, filed Nov. 8, 2004, Ko et al.
U.S. Appl. No. 10/613,841, filed Jul. 3, 2003, Wacker et al.

N-UREIDOALKYL-AMINO COMPOUNDS AS MODULATORS OF CHEMOKINE RECEPTOR ACTIVITY

CROSS-REFERENCE TO RELATED APPLICATIONS

The present application claims the priority benefit of U.S. Provisional Application No. 60/519,506, filed Nov. 13, 2003, which is expressly incorporated fully herein by reference.

FIELD OF THE INVENTION

This invention relates generally to modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J. Med., 338, 436-445 (1998) and Rollins, Blood, 90, 909-928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1,-2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-trans-membrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-1α, RANTES, MCP-1] (Power et al., J. Biol. Chem., 270, 19495-19500 (1995), Luster, New Eng. J. Med., 338, 436-445 (1998)); CCR-5 (or "CKR-5" OR "CC-CKR-5") [MIP-1α, RANTES, MIP-1β] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [1-309, TARC, MIP-1β] (Napolitano et al., J. Immunol., 157, 2759-2763 (1996), Bernardini et al., Eur. J. Immunol., 28, 582-588 (1998)); and CCR-10 (or "CKR-10" or "CC-CKR-10") [MCP-1, MCP-3] (Bonini et al, DNA and Cell Biol., 16, 1249-1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741-748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

SUMMARY OF THE INVENTION

Accordingly, one aspect of the present invention is to provide novel agonists or antagonists of CCR-3, or pharmaceutically acceptable salts or prodrugs thereof.

It is another aspect of the present invention to provide pharmaceutical compositions comprising a pharmaceutically acceptable carrier and a therapeutically effective amount of at least one of the compounds of the present invention or a pharmaceutically acceptable salt or prodrug form thereof.

In another aspect, the present invention provides a method for treating inflammatory diseases and allergic disorders comprising administering to a host in need of such treatment a therapeutically effective amount of at least one of the compounds of the present invention or a pharmaceutically acceptable salt or prodrug form thereof.

In another aspect, the present invention provides novel compounds for use in therapy.

In another aspect, the present invention provides the use of novel compounds for the manufacture of a medicament for the treatment of allergic disorders.

These and other features, which will become apparent during the following detailed description, have been achieved by the inventors' discovery that compounds of formula (I):

$$R^5-\underset{R^{4'}}{\underset{|}{N}}-E-\underset{R^1}{\underset{|}{N}}-\overset{Z}{\overset{\|}{C}}-\underset{R^2}{\underset{|}{N}}-R^3 \quad (I)$$

or stereoisomers or pharmaceutically acceptable salts thereof, wherein E, Z, $R^1$, $R^2$, $R^3$, $R^4$, $R^{4'}$, and $R^5$ are defined below, are effective modulators of chemokine activity.

DETAILED DESCRIPTION OF EMBODIMENTS OF THE INVENTION

Thus, in a first embodiment, the present invention provides novel compounds of formula (I):

$$R^5-\underset{R^{4'}}{\underset{|}{N}}-E-\underset{R^1}{\underset{|}{N}}-\overset{Z}{\overset{\|}{C}}-\underset{R^2}{\underset{|}{N}}-R^3 \quad (I)$$

or stereoisomers or pharmaceutically acceptable salts thereof, wherein:

Z is selected from O, S, $NR^{1a}$, CHCN, $CHNO_2$, and $C(CN)_2$;

$R^{1a}$ is selected from H, $C_{1-6}$ alkyl, $C_{3-6}$ cycloalkyl, $CONR^{1b}R^{1b}$, $OR^{1b}$, CN, $NO_2$, and $(CH_2)_w$phenyl;

$R^{1b}$ is independently selected from H, $C_{1-3}$ alkyl, $C_{3-6}$ cycloalkyl, and phenyl;

E is $-(CH_2)_v-(CHR^9)-(CHR^{11})-$;

$R^1$ and $R^2$ are independently selected from H, $C_{1-8}$ alkyl, $C_{3-8}$ alkenyl, $C_{3-8}$ alkynyl, $(CH_2)_rC_{3-6}$ cycloalkyl, and a $(CH_2)_r-C_{3-10}$ carbocyclic residue substituted with 0-5 $R^a$;

$R^a$, at each occurrence, is selected from $C_{1-4}$ alkyl, $C_{3-8}$ alkenyl, $C_{3-8}$ alkynyl, $(CH_2)_rC_{3-6}$ cycloalkyl, Cl, Br, I, F, $(CF_2)_rCF_3$, $NO_2$, CN, $(CH_2)_rNR^bR^b$, $(CH_2)_rOH$, $(CH_2)_rOR^c$, $(CH_2)_rSH$, $(CH_2)_rSR^c$, $(CH_2)_rC(O)R^b$, $(CH_2)_rC(O)NR^bR^b$, $(CH_2)_rNR^bC(O)R^b$, $(CH_2)_rC(O)OR^b$, $(CH_2)_rOC(O)R^c$, $(CH_2)_rCH(=NR^b)NR^bR^b$, $(CH_2)_rNHC(=NR^b)NR^bR^b$, $(CH_2)_rS(O)_pR^c$, $(CH_2)_rS(O)_2NR^bR^b$, $(CH_2)_rNR^bS(O)_2R^c$, and $(CH_2)_r$phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

alternatively, $R^2$ and $R^3$ join to form a 5, 6, or 7-membered ring substituted with 0-3 $R^a$;

$R^3$ is selected from a $(CR^{3'}R^{3'})_r-C_{3-10}$ carbocyclic residue substituted with 0-5 $R^{15}$ and a $(CR^{3'}R^{3'})_r$-5-10 membered heterocyclic system containing 1-4 heteroatoms selected from N, O, and S, substituted with 0-3 $R^{15}$;

$R^{3'}$, at each occurrence, is selected from H, $C_{1-6}$ alkyl, $(CH_2)_rC_{3-6}$ cycloalkyl, and phenyl;

$R^4$ is selected from H, $C_{1-6}$ alkyl, $(CH_2)_r-C_{1-3}$ perfluoroalkyl, $C(O)-C_{1-4}$ alkyl, $-SO_2-C_{1-4}$ alkyl, and a $(CH_2)_r-C_{3-10}$ carbocyclic residue substituted with 0-3 $R^{4c}$;

$R^{4'}$ is absent, taken with the nitrogen to which it is attached to form an N-oxide, or selected from $C_{1-8}$ alkyl, $C_{3-8}$ alkenyl, $C_{3-8}$ alkynyl, $(CH_2)_rC_{3-6}$ cycloalkyl, $(CH_2)_qC(O)R^{4b}$, $(CH_2)_qC(O)NR^{4a}R^{4a}$, $(CH_2)_qC(O)OR^{4b}$, and a $(CH_2)_r-C_{3-10}$ carbocyclic residue substituted with 0-3 $R^{4c}$;

$R^{4a}$, at each occurrence, is selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{3-8}$ alkenyl, $(CH_2)_rC_{3-6}$ cycloalkyl, $C_{3-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_r$ $SC_{1-5}$ alkyl, $(CH_2)_rNR^{4a}R^{4a}$, and $(CH_2)_r$phenyl;

$R^5$ is selected from $$R^{5a}\overset{R^{24a}\ R^{24b}}{\overset{|\ \ \ \ |}{\underset{|}{\mathrm{C}}}}\ \ \text{and ring B;}$$

ring B is a 5-7 membered cycloalkyl ring optionally containing a C=O, and being substituted with 0-2 $R^{16}$, wherein the cycloalkyl is fused with a benzo group substituted with 0-3 $R^{16}$ or is fused with a 5-6 membered aromatic heterocyclic ring having 0-3 N, 0-1 O, or 0-1 S, the heterocyclic ring being substituted with 0-3 $R^{16}$;

alternatively, ring B is selected from a $C_{3-10}$ carbocyclic residue substituted with 1-5 $R^{5a}$, and a 5-10 membered heterocyclic system containing 1-4 heteroatoms selected from N, O, and S, substituted with 1-3 $R^{5a}$;

$R^{5a}$ is selected from a $(CR^{5'}R^{5'})_r-C_{3-10}$ carbocyclic residue substituted with 0-5 $R^{16}$, and a $(CR^{5'}R^{5'})_r$-5-10 membered heterocyclic residue containing 1-4 heteroatoms selected from N, O, and S, substituted with 0-3 $R^{16}$;

$R^{5'}$, at each occurrence, is selected from H, $C_{1-6}$ alkyl, $(CH_2)_rC_{3-6}$ cycloalkyl, and phenyl;

$R^9$, is selected from $C_{1-6}$ alkyl, $C_{2-8}$ alkenyl, $C_{2-8}$ alkynyl, F, Cl, Br, I, $NO_2$, CN, $(CH_2)_rOH$, $(CH_2)_rSH$, $(CH_2)_r$ $OR^{9d}$, $(CH_2)_rSR^{9d}$, $(CH_2)_rNR^{9a}R^{9a}$, $(CH_2)_rC(O)OH$, $(CH_2)_rC(O)R^{9b}$, $(CH_2)_rC(O)NR^{9a}R^{9a}$, $(CH_2)_rNR^{9a}C(O)R^{9a}$, $(CH_2)_rNR^{9a}C(O)H$, $(CH_2)_rNR^{9a}C(O)NHR^{9a}$, $(CH_2)_rC(O)OR^{9b}$, $(CH_2)_rOC(O)R^{9b}$, $(CH_2)_rOC(O)NHR^{9a}$, $(CH_2)_rS(O)_pR^{9b}$, $(CH_2)_rS(O)_2NR^{9a}R^{9a}$, $(CH_2)_r\ NR^{9a}S(O)_2R^{9b}$, $C_{1-6}$ haloalkyl, a $(CH_2)_r-C_{3-10}$ carbocyclic residue substituted with 0-5 $R^{9c}$, and a $(CH_2)_r$-5-10 membered heterocyclic system containing 1-4 heteroatoms selected from N, O, and S, substituted with 0-3 $R^{9c}$;

$R^{9a}$, at each occurrence, is selected from H, $C_{1-6}$ alkyl, $C_{3-8}$ alkenyl, $C_{3-8}$ alkynyl, a $(CH_2)_r-C_{3-10}$ carbocyclic residue substituted with 0-5 $R^{9e}$, and a $(CH_2)_r$-5-10 membered heterocyclic system containing 1-4 heteroatoms selected from N, O, and S, substituted with 0-3 $R^{9e}$;

$R^{9b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0-2 $R^{9e}$, and a $(CH_2)_r$-5-6 membered heterocyclic system containing 1-4 heteroatoms selected from N, O, and S, substituted with 0-3 $R^{9e}$;

$R^{9c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{9f}R^{9f}$, $(CH_2)_r OH$, $(CH_2)_r OC_{1-4}$ alkyl, $(CH_2)_r SC_{1-4}$ alkyl, $(CH_2)_r C(O)OH$, $(CH_2)_r C(O)R^{9b}$, $(CH_2)_r C(O)NR^{9f}R^{9f}$, $(CH_2)_r NR^{9f}C(O)R^{9a}$, $(CH_2)_r C(O)OC_{1-4}$ alkyl, $(CH_2)_r OC(O)R^{9b}$, $(CH_2)_r C(=NR^{9f})NR^{9f}R^{9f}$, $(CH_2)_r S(O)_p R^{9b}$, $(CH_2)_r NHC(=NR^{9f})NR^{9f}R^{9f}$, $(CH_2)_r S(O)_2 NR^{9f}R^{9f}$, $(CH_2)_r NR^{9f}S(O)_2 R^{9b}$, and $(CH_2)_r$phenyl substituted with 0-3 $R^{9e}$;

$R^{9d}$, at each occurrence, is selected from $C_{1-6}$ alkyl, $C_{3-6}$ alkenyl, $C_{3-6}$ alkynyl, a $C_{3-10}$ carbocyclic residue substituted with 0-3 $R^{9c}$, and a 5-6 membered heterocyclic system containing 1-4 heteroatoms selected from the group consisting of N, O, and S substituted with 0-3 $R^{9c}$;

$R^{9e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_1$-5 alkyl, $(CH_2)_r NR^{9f}R^{9f}$, and $(CH_2)_r$phenyl;

$R^{9f}$, at each occurrence, is selected from H, $C_{1-6}$ alkyl, and $C_{3-6}$ cycloalkyl;

$R^{11}$, is selected from $C_{1-6}$ alkyl, $C_{2-8}$ alkenyl, $C_{2-8}$ alkynyl, $(CR'R')_q OH$, $(CH_2)_q SH$, $(CR'R')_q OR^{11d}$, $(CH_2)_q SR^{11d}$, $(CR'R')_q NR^{11a}R^{11a}$, $(CH_2)_q C(O)OH$, $(CH_2)_q C(O)R^{11b}$, $(CH_2)_q C(O)NR^{11a}R^{11a}$, $(CH_2)_q NR^{11a}C(O)R^{11a}$, $(CH_2)_q OC(O)NR^{11a}R^{11a}$, $(CH_2)_q NR^{11a}C(O)OR^{11b}$, $(CH_2)_q NR^{11a}C(O)NHR^{11a}$, $(CH_2)_q C(O)OR^{11b}$, $(CH_2)_q OC(O)R^{11b}$, $(CH_2)_q S(O)_p R^{11b}$, $(CH_2)_q S(O)_2 NR^{11a}R^{11a}$, $(CH_2)_q NR^{11a}S(O)_2 R^{11b}$, $C_{1-6}$ haloalkyl, a $(CR'R')$—$C_{3-10}$ carbocyclic residue substituted with 0-5 $R^{11c}$, and a $(R'R^{17})_r$-5-10 membered heterocyclic system containing 1-4 heteroatoms selected from N, O, and S, substituted with 0-3 $R^{11c}$;

$R^{11a}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{11e}$, and a $(CH_2)_r$-5-10 membered heterocyclic system containing 1-4 heteroatoms selected from N, O, and S, substituted with 0-3 $R^{11e}$;

alternatively, $R^{11a}$ and $R^{11a}$ along with the N to which they are attached, join to form a 5-6 membered heterocyclic system containing 1-2 heteroatoms selected from $NR^{11g}$, O, and S and optionally fused with a benzene ring or a 6-membered aromatic heterocycle;

$R^{11b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0-2 $R^{11e}$, and a $(CH_2)_r$-5-6 membered heterocyclic system containing 1-4 heteroatoms selected from N, O, and S, substituted with 0-3 $R^{11e}$;

$R^{11c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{11f}R^{11f}$, $(CH_2)_r OH$, $(CH_2)_r OC_{1-4}$ alkyl, $(CH_2)_r SC_{1-4}$ alkyl, $(CH_2)_r C(O)OH$, $(CH_2)_r C(O)R^{11b}$, $(CH_2)_r C(O)NR^{11f}R^{11f}$, $(CH_2)_r NR^{11f}C(O)R^{11a}$, $(CH_2)_r C(O)OC_{1-4}$ alkyl, $(CH_2)_r OC(O)R^{11b}$, $(CH_2)_r C(=NR^{11}f)NR^{11f}R^{11f}$, $(CH_2)_r NHC (=NR^{11f})NR^{11f}R^{11f}$, $(CH_2)_r S(O)_p R^{11b}$, $(CH_2)_r S(O)_2 NR^{11f}R^{11f}$, $(CH_2)_r NR^{11f}S(O)_2 R^{11b}$, and $(CH_2)_r$phenyl substituted with 0-3 $R^{11e}$;

$R^{11d}$, at each occurrence, is selected from $C_{1-6}$ alkyl, $C_{3-6}$ alkenyl, $C_{3-6}$ alkynyl, and a $C_{3-10}$ carbocyclic residue substituted with 0-3 $R^{11c}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{11f}R^{11f}$, and $(CH_2)_r$phenyl, wherein the phenyl on the $(CH_2)_r$phenyl is substituted with 0-5 substituents selected from F, Cl, Br, I, $NO_2$, $C_{1-6}$alkyl, OH, and $NR^{11f}R^{11f}$;

$R^{11f}$, at each occurrence, is selected from H, $C_{1-6}$ alkyl, and $C_{3-6}$ cycloalkyl;

$R^{11g}$ is selected from H, $C_{1-6}$ alkyl, $C_{3-6}$ cycloalkyl, $(CH_2)_r$phenyl, $C(O)R^{11f}$, $C(O)OR^{11h}$, and $SO_2 R^{11h}$;

$R^{11h}$, at each occurrence, is selected from $C_{1-6}$ alkyl, and $C_{3-6}$ cycloalkyl;

$R^{15}$, at each occurrence, is selected from $C_{1-8}$ alkyl, $(CR'R')_r C_{3-6}$ cycloalkyl, Cl, Br, I, F, $NO_2$, CN, $(CR'R')_r NR^{15a}R^{15a}$, $(CR'R')_r OH$, $(CR'R')_r O(CHR')_r R^{15d}$, $(CR'R')_r SH$, $(CR'R')_r C(O)H$, $(CR'R')_r S(CHR')_r R^{15d}$, $(CR'R')_r C(O)OH$, $(CR'R')_r C(O)(CHR')_r R^{15b}$, $(CR'R')_r C(O)NR^{15a}R^{15a}$, $(CR'R')_r NR^{15f}C(O)(CHR')_r R^{15b}$, $(CR'R')_r OC(O)NR^{15a}R^{15a}$, $(CR'R')_r NR^{15f}C(O)O(CHR')_r R^{15b}$, $(CR'R')_r NR^{15f}C(O)NR^{15f}R^{15f}$, $(CR'R')_r C(O)O(CHR')_r R^{15d}$, $(CR'R')_r OC(O)(CHR')_r R^{15b}$, $(CR'R')_r C(=NR^{15f})NR^{15a}R^{15a}$, $(CR'R')_r NHC (=NR^{15f})NR^{15f}R^{15f}$, $(CR'R')_r S(O)_p(CHR')_r R^{15b}$, $(CR'R')_r S(O)_2 NR^{15a}R^{15a}$, $(CR'R')_r NR^{15f}S(O)_2(CHR')_r R^{15b}$, $C_{1-6}$ haloalkyl, $C_{2-8}$ alkenyl substituted with 0-3 R', $C_{2-8}$ alkynyl substituted with 0-3 R', $(CR'R')_r$phenyl substituted with 0-3 $R^{15e}$, and a $(CH_2)_r$-5-10 membered heterocyclic system containing 1-4 heteroatoms selected from N, O, and S, substituted with 0-3 $R^{15e}$;

R', at each occurrence, is independently selected from H, $C_{1-6}$ alkyl, $C_{2-8}$ alkenyl, $C_{2-8}$ alkynyl, $(CH_2)_r C_{3-6}$ cycloalkyl, and $(CH_2)_r$phenyl substituted with $R^{15e}$;

$R^{15a}$, at each occurrence, is selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{15e}$, and a $(CH_2)_r$-5-10 membered heterocyclic system containing 1-4 heteroatoms selected from N, O, and S, substituted with 0-2 $R^{15e}$;

alternatively, two $R^{15a}$, along with the N to which they are attached, join to form a 5-6 membered non-aromatic heterocyclic system containing 1-2 heteroatoms selected from $NR^{15g}$, O, and S and optionally fused with a benzene ring or a 6-membered aromatic heterocycle;

$R^{15b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0-3 $R^{15e}$, and a $(CH_2)_r$-5-6 membered heterocyclic system containing 1-4 heteroatoms selected from N, O, and S, substituted with 0-2 $R^{15e}$;

$R^{15d}$, at each occurrence, is selected from $C_{3-8}$ alkenyl, $C_{3-8}$ alkynyl, methyl, $CF_3$, $C_{2-6}$ alkyl substituted with 0-3 $R^{15e}$, a $(CH_2)_r$—$C_{3-10}$ carbocyclic residue substituted with 0-3 $R^{15e}$, and a $(CH_2)_r$5-6 membered heterocyclic system containing 1-4 heteroatoms selected from N, O, and S, substituted with 0-3 $R^{15e}$;

$R^{15e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{15f}R^{15f}$, and $(CH_2)_r$phenyl;

$R^{15f}$, at each occurrence, is selected from H, $C_{1-6}$ alkyl, $C_{3-6}$ cycloalkyl, and phenyl;

$R^{15g}$ is selected from H, $C_{1-6}$ alkyl, $C_{3-6}$ cycloalkyl, $(CH_2)_r$phenyl, $C(O)R^{15f}$, $C(O)OR^{15h}$, and $SO_2R^{15h}$;

$R^{15h}$, at each occurrence, is selected from $C_{1-5}$ alkyl, and $C_{3-6}$ cycloalkyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a}$, $(CHR')_rOH$, $(CHR')_rO(CHR')_rR^{16d}$, $(CHR')_rSH$, $(CHR')_rC(O)H$, $(CHR')_rS(CHR')_rR^{16d}$, $(CHR')_rC(O)OH$, $(CHR')_rC(O)(CHR')_rR^{16b}$, $(CHR')_rC(O)NR^{16a}R^{16a}$, $(CHR')_rNR^{16f}C(O)(CHR')_rR^{16b}$, $(CHR')_rC(O)O(CHR')_rR^{16d}$, $(CHR')_rOC(O)(CHR')_rR^{16b}$, $(CHR')_rC(=NR^{16f})NR^{16a}R^{16a}$, $(CHR')_rNHC(=NR^{16f})NR^{16f}R^{16f}$, $(CHR')_rS(O)_p(CHR')_rR^{16b}$, $(CHR')_rS(O)_2NR^{16a}R^{16a}$, $(CHR')_rNR^{16f}S(O)_2(CHR')_rR^{16b}$, $C_{1-6}$ haloalkyl, $C_{2-8}$ alkenyl substituted with 0-3 R', $C_{2-8}$ alkynyl substituted with 0-3 R', and $(CHR')_r$phenyl substituted with 0-3 $R^{16e}$;

$R^{16a}$, at each occurrence, is selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{16e}$, and a $(CH_2)_r$-5-10 membered heterocyclic system containing 1-4 heteroatoms selected from N, O, and S, substituted with 0-2 $R^{16e}$;

$R^{16b}$, at each occurrence, is selected from $C_{1-6}$ alkyl, $C_{3-8}$ alkenyl, $C_{3-8}$ alkynyl, a $(CH_2)_rC_{3-6}$ carbocyclic residue substituted with 0-3 $R^{16e}$, and a $(CH_2)_r$-5-6 membered heterocyclic system containing 1-4 heteroatoms selected from N, O, and S, substituted with 0-2 $R^{16e}$;

$R^{16d}$, at each occurrence, is selected from $C_{3-8}$ alkenyl, $C_{3-8}$ alkynyl, methyl, $CF_3$, $C_{2-6}$ alkyl substituted with 0-3 $R^{16e}$, a $(CH_2)_r$—$C_{3-10}$ carbocyclic residue substituted with 0-3 $R^{16e}$, and a $(CH_2)_r$-5-6 membered heterocyclic system containing 1-4 heteroatoms selected from N, O, and S, substituted with 0-3 $R^{16e}$; $R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is selected from H, $C_{1-5}$ alkyl, and $C_{3-6}$ cycloalkyl, and phenyl;

$R^{18}$ at each occurrence is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rS(O)C_{1-5}$ alkyl, $(CH_2)_rS(O)_2C_{1-5}$ alkyl, $(CH_2)_rS(O)_2N(R^{18a})R^{18b}$, $(CH_2)_rN(R^{18c})C(O)C_{1-5}$ alkyl $(CH_2)_rN(R^{18c})S(O)_2C_{1-5}$ alkyl, $(CH_2)_rC(O)N(R^{18a})R^{18b}$, $(CH_2)_rC(O)OC_{1-5}$ alkyl, $(CH_2)_rC(O)C_{1-5}$ alkyl, and $(CH_2)_rN(R^{18a})R^{18b}$;

$R^{18a}$, $R^{18b}$, and $R^{18c}$ at each occurrence are independently selected from H, $C_{1-6}$ alkyl, and $C_{3-6}$ cycloalkyl;

$R^{19}$ at each occurrence is independently selected from $C_{1-6}$ alkyl, $C_{3-6}$ cycloalkyl, and phenyl substituted with 0-3 $R^{18}$;

alternatively, $R^{18a}$ and $R^{18b}$ along with the nitrogen to which both are attached form a pyrrolidine, piperidine, piperazine or morpholine ring;

$R^{24a}$ and $R^{24b}$, at each occurrence, are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_tOH$, $(CH_2)_tOR^{19}$, $(CH_2)_tSH$, $(CH_2)_tSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_tOC(O)R^{19}$, $(CH_2)_rS(O)R^{19}$, $(CH_2)_rS(O)_2R^{19}$, $(CH_2)_r$ $S(O)_2N(R^{18a})R^{18b}$, $(CH_2)_rN(R^{18c})S(O)_2R^{19}$, and $(CH_2)_r$phenyl substituted with 0-3 $R^{18}$;

t is selected from 0, 1, 2, 3, 4, and 5, with the proviso that when s is 1, then t can not be 0;

s is selected from 1, 2, 3, 4, and 5;

v is selected from 1 and 2;

w is selected from 0 and 1;

r is selected from 0, 1, 2, 3, 4, and 5;

q is selected from 1, 2, 3, 4, and 5; and p is selected from 0, 1, and 2.

In another embodiment, the present invention provides novel compounds of formula (I):

$R^{4'}$ is absent, taken with the nitrogen to which it is attached to form an N-oxide, or selected from $C_{1-8}$ alkyl, $(CH_2)_rC_{3-6}$ cycloalkyl, and $(CH_2)_r$-phenyl substituted with 0-3 $R^{4c}$;

$R^1$ and $R^2$ are independently selected from H and $C_{1-4}$ alkyl;

$R^{24a}$ and $R^{24b}$, at each occurrence, are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_tOH$, $(CH_2)_tOR^{19}$, $(CH_2)_tSH$, $(CH_2)_tSR^{19}$, $(CH_2)_rC(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_rOC(O)R^{19}$, and $(CH_2)_r$phenyl substituted with 0-3 $R^{18}$;

v is selected from 1 and 2;

q is selected from 1, 2, and 3; and r is selected from 0, 1, 2, and 3.

In another embodiment, the present invention provides novel compounds of formula (I):

$R^3$ is selected from a $(CR^{3'}H)_r$-carbocyclic residue substituted with 0-5 $R^{15}$, wherein the carbocyclic residue is selected from phenyl, $C_{3-6}$ cycloalkyl, naphthyl, and adamantyl; and a $(CR^{3'}H)_r$-heterocyclic system substituted with 0-3 $R^{15}$, wherein the heterocyclic system is selected from pyridinyl, thiophenyl, furanyl, indazolyl, benzothiazolyl, benzo[1,3]dioxolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{5a}$ is selected from $(CR^{5'}H)_r$-phenyl substituted with 0-5 $R^{16}$; and a $(CR^{5'}H)_r$-heterocyclic system substituted with 0-3 $R^{16}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, the present invention provides novel compounds of formula (I):

$R^{18}$ at each occurrence is independently selected from $C_{1-6}$ alkyl, $C_{3-6}$ cycloalkyl, Cl, F, Br, I, CN, $NO_2$, $(CF_2)_rCF_3$, $OC_{1-5}$ alkyl, $(CH_2)_rOH$, $SC_{1-5}$ alkyl, $N(R^{18c})C(O)C_{1-5}$ alkyl, $C(O)N(R^{18a})R^{18b}$, $C(O)OC_{1-5}$ alkyl, $C(O)C_{1-5}$ alkyl, and $N(R^{18a})R^{18b}$;

$R^{18a}$, $R^{18b}$, and $R^{18c}$ at each occurrence are independently selected from H, methyl, ethyl, propyl, i-propyl, butyl, i-butyl, t-butyl, cyclopropyl, cyclopentyl, and cyclohexyl;

$R^{19}$ at each occurrence is independently selected from methyl, ethyl, propyl, i-propyl, butyl, i-butyl, t-butyl, cyclopropyl, cyclopentyl, and cyclohexyl, and phenyl substituted with 0-3 $R^{18}$;

alternatively, $R^{18a}$ and $R^{18b}$ along with the nitrogen to which both are attached form a pyrrolidine, piperidine, piperazine or morpholine ring.

In another embodiment, the present invention provides novel compounds of formula (I):

$R^5$ is selected from

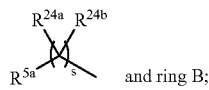

and ring B;

ring B is 1,2,3,4-tetrahydronaphthylenyl substituted with 0-3 $R^{16}$;

alternatively, ring B is selected from a $C_{3-10}$ carbocyclic residue substituted with 1-5 $R^{5a}$, wherein the carbocyclic residue is selected from phenyl and cyclohexyl, and a 5-10 membered heterocyclic system containing 1-4 heteroatoms selected from N, O, and S, substituted with 1-3 $R^{5a}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

r is selected from 0, 1, and 2.

In another embodiment, the present invention provides novel compounds of formula (I):

$R^3$ is a $C_{3-10}$ carbocyclic residue substituted with 0-3 $R^{15}$, wherein the carbocyclic residue is selected from cyclopropyl, cyclopentyl, cyclohexyl, phenyl, naphthyl and adamantyl, and a $(CR^{3'}H)_r$-heterocyclic system substituted with 0-3 $R^{15}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{11}$, is selected from $C_{1-6}$ alkyl, $(CH_2)_qOH$, $(CH_2)_qSH$, $(CH_2)_qOR^{11d}$, $(CH_2)_qSR^{11d}$, $(CH_2)_qNR^{11a}R^{11a}$, $(CH_2)_rC(O)R^{11b}$, $(CH_2)_rC(O)NR^{11a}R^{11a}$, $(CH_2)_qNR^{11a}C(O)R^{11a}$, $(CH_2)_qOC(O)NR^{11a}R^{11a}$, $(CH_2)_qNR^{11a}C(O)OR^{11b}$, $(CH_2)_qNR^{11a}C(O)NHR^{11a}$, $(CH_2)_rC(O)OR^{11b}$, $(CH_2)_qOC(O)R^{11b}$, $C_{1-6}$ haloalkyl, a $(CH_2)_r$—$C_{3-10}$ carbocyclic residue substituted with 0-5 $R^{11c}$ and a $(CH_2)_r$-5-10 membered heterocyclic system containing 1-4 heteroatoms selected from N, O, and S, substituted with 0-3 $R^{11c}$;

$R^{11a}$, at each occurrence, is selected from H, methyl, ethyl, propyl, i-propyl, butyl, pentyl, hexyl, a $(CH_2)_r$—$C_{3-10}$ carbocyclic residue substituted with 0-5 $R^{11e}$, wherein the carbocyclic residue is selected from cyclopropyl, cyclopentyl, cyclohexyl, and phenyl;

$R^{11b}$, at each occurrence, is selected from methyl, ethyl, propyl, i-propyl, butyl, pentyl, hexyl, a $(CH_2)_r$—$C_{3-6}$ carbocyclic residue substituted with 0-2 $R^{11e}$, wherein the carbocyclic residue is selected from cyclopropyl, cyclopentyl, cyclohexyl, and phenyl;

$R^{11d}$, at each occurrence, is selected from methyl, ethyl, propyl, i-propyl, butyl, pentyl, hexyl, and a $C_{3-10}$ carbocyclic residue substituted with 0-3 $R^{11c}$ wherein the carbocyclic residue is selected from cyclopropyl, cyclopentyl, cyclohexyl, and phenyl;

$R^{11e}$, at each occurrence, is selected from methyl, ethyl, propyl, i-propyl, butyl, pentyl, hexyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{11f}R^{11f}$, and $(CH_2)_r$phenyl, wherein the phenyl on the $(CH_2)_r$phenyl is substituted with 0-5 substituents selected from F, Cl, Br, I, $NO_2$, $C_{1-6}$alkyl, OH, and $NR^{11f}R^{11f}$;

$R^{15}$, at each occurrence, is selected from $C_{1-8}$ alkyl, $(CH_2)_rC_{3-6}$ cycloalkyl, $CF_3$, Cl, Br, I, F, $(CH_2)_rNR^{15a}R^{15a}$, $NO_2$, CN, OH, $(CH_2)_rOR^{15d}$, $(CH_2)_rC(O)R^{15b}$, $(CH_2)_rC(O)NR^{15a}R^{15a}$, $(CH_2)_rNR^{15f}C(O)R^{15b}$, $(CH_2)_rOC(O)NR^{15a}R^{15a}$, $(CH_2)_rNR^{15f}C(O)OR^{15b}$, $(CH_2)_rS(O)_pR^{15b}$, $(CH_2)_rS(O)_2NR^{15a}R^{15a}$, $(CH_2)_rNR^{15f}S(O)_2R^{15b}$, $C_{1-6}$ haloalkyl, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$;

$R^{15a}$, at each occurrence, are selected from H, $C_{1-6}$ alkyl, $C_{3-6}$ cycloalkyl, and $(CH_2)_r$phenyl substituted with 0-3 $R^{15e}$;

alternatively, $R^{15a}$, along with the N to which they are attached, join to form a 5-6 membered heterocyclic system containing 1-2 heteroatoms selected from $NR^{15g}$, O, and S and optionally fused with a benzene ring or a 6-membered aromatic heterocycle;

$R^{15b}$, at each occurrence, is selected from H, $C_{1-6}$ alkyl, $C_{3-6}$ cycloalkyl, and $(CH_2)_r$phenyl substituted with 0-3 $R^{15e}$;

$R^{15d}$, at each occurrence, is selected from $C_{1-6}$ alkyl, $CF_3$, and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl.

In another embodiment, the present invention provides novel compounds of formula (I):

Z is selected from O and S;

$R^1$ is H;

$R^2$ is H;

$R^3$ is a $C_{3-10}$ carbocyclic residue substituted with 0-3 $R^{15}$, wherein the carbocyclic residue is phenyl, and a $(CR^{3'}H)_r$-heterocyclic system substituted with 0-3 $R^{15}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{5a}$ is selected from a $(CH_2)_r$—$C_{3-10}$ carbocyclic residue substituted with 1-5 $R^{16}$ and a heterocyclic system substituted with 0-3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, the present invention provides novel compounds of formula (I), wherein the compound of formula (I) is selected from the compounds of the tables or the examples.

In another embodiment, the present invention provides novel compounds of formula (I):

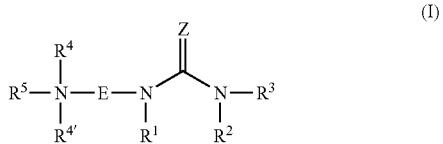

(I)

or stereoisomers or pharmaceutically acceptable salts thereof, wherein:

Z is selected from O, S, $NR^{1a}$, CHCN, $CHNO_2$, and C(CN);

$R^{1a}$ is selected from H, $C_{1-6}$ alkyl, $C_{3-6}$ cycloalkyl, $CONR^{1b}R^{1b}$, $OR^{1b}$, CN, $NO_2$, and $(CH_2)_w$phenyl;

$R^{1b}$ is independently selected from H, $C_{1-3}$ alkyl, $C_{3-6}$ cycloalkyl, and phenyl;

E is selected from

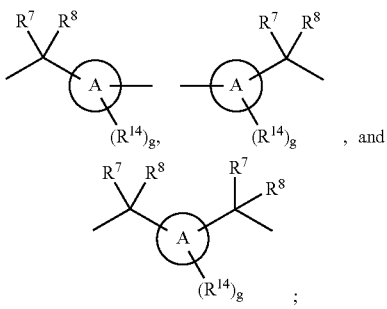

, and

;

ring A is a cyclohexyl ring;

$R^1$ and $R^2$ are independently selected from H, $C_{1-8}$ alkyl, $C_{3-8}$ alkenyl, $C_{3-8}$ alkynyl, $(CH_2)_r C_{3-6}$ cycloalkyl, and a $(CH_2)_r$—$C_{3-10}$ carbocyclic residue substituted with 0-5 $R^a$;

$R^a$, at each occurrence, is selected from $C_{1-4}$ alkyl, $C_{3-8}$ alkenyl, $C_{3-8}$ alkynyl, $(CH_2)_r C_{3-6}$ cycloalkyl, Cl, Br, I, F, $(CF_2)_r CF_3$, $NO_2$, CN, $(CH_2)_r NR^b R^b$, $(CH_2)_r OH$, $(CH_2)_r OR^c$, $(CH_2)_r SH$, $(CH_2)_r SR^c$, $(CH_2)_r C(O)R^b$, $(CH_2)_r C(O)NR^b R^b$, $(CH_2)_r NR^b C(O)R^b$, $(CH_2)_r C(O)OR^b$, $(CH_2)_r OC(O)R^c$, $(CH_2)_r CH(=NR^b)NR^b R^b$, $(CH_2)_r NHC(=NR^b)NR^b R^b$, $(CH_2)_r S(O)_p R^c$, $(CH_2)_r S(O)_2 NR^b R^b$, $(CH_2)_r NR^b S(O)_2 R^c$, and $(CH_2)_r$phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

alternatively, $R^2$ and $R^3$ join to form a 5, 6, or 7-membered ring substituted with 0-3 $R^a$;

$R^3$ is selected from a $(CR^{3'}R^{3'})_r$—$C_{3-10}$ carbocyclic residue substituted with 0-5 $R^{15}$ and a $(CR^{3'}R^{3'})_r$-5-10 membered heterocyclic system containing 1-4 heteroatoms selected from N, O, and S, substituted with 0-3 $R^{15}$;

$R^{3'}$, at each occurrence, is selected from H, $C_{1-6}$ alkyl, $(CH_2)_r C_{3-6}$ cycloalkyl, and phenyl;

$R^4$ is selected from H, $C_{1-6}$ alkyl, $(CH_2)_r$—$C_{1-3}$ perfluoroalkyl, —C(O)—$C_{1-4}$ alkyl, —$SO_2$—$C_{1-4}$ alkyl, and a $(CH_2)_r$—$C_{3-10}$ carbocyclic residue substituted with 0-3 $R^{4c}$;

$R^{4'}$ is absent, taken with the nitrogen to which it is attached to form an N-oxide, or selected from $C_{1-8}$ alkyl, $C_{3-8}$ alkenyl, $C_{3-8}$ alkynyl, $(CH_2)_r C_{3-6}$ cycloalkyl, $(CH_2)_q C(O)R^{4b}$, $(CH_2)_q C(O)NR^{4a}R^{4a}$, $(CH_2)_q C(O)OR^{4b}$, and a $(CH_2)_r$—$C_{3-10}$ carbocyclic residue substituted with 0-3 $R^{4c}$;

$R^{4a}$, at each occurrence, is selected from H, $C_{1-6}$ alkyl, $(CH_2)_r C_{3-6}$ cycloalkyl, and phenyl;

$R^{4b}$, at each occurrence, is selected from $C_{1-6}$ alkyl, $C_{3-8}$ alkenyl, $(CH_2)_r C_{3-6}$ cycloalkyl, $C_{3-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, $(CH_2)_r OH$, $(CH_2)_r SC_{1-5}$ alkyl, $(CH_2)_r NR^{4a}R^{4a}$, and $(CH_2)_r$phenyl;

$R^5$ is selected from

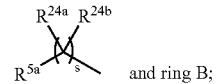

and ring B;

ring B is a 5-7 membered cycloalkyl ring optionally containing a C=O, and being substituted with 0-2 $R^{16}$, wherein the cycloalkyl is fused with a benzo group substituted with 0-3 $R^{16}$ or is fused with a 5-6 membered aromatic heterocyclic ring having 0-3 N, 0-1 O, or 0-1 S, the heterocyclic ring being substituted with 0-3 $R^{16}$;

alternatively, ring B is selected from a $C_{3-10}$ carbocyclic residue substituted with 1-5 $R^{5a}$, and a 5-10 membered heterocyclic system containing 1-4 heteroatoms selected from N, O, and S, substituted with 1-3 $R^{5a}$;

$R^{5a}$ is selected from a $(CH_2)_r$—$C_{3-10}$ carbocyclic residue substituted with 0-5 $R^{16}$, and a $(CH_2)_r$-5-10 membered heterocyclic residue containing 1-4 heteroatoms selected from N, O, and S, substituted with 0-3 $R^{16}$;

$R^7$, is selected from H, $C_{1-6}$ alkyl, $C_{2-8}$ alkenyl, $C_{2-8}$ alkynyl, $(CH_2)_q OH$, $(CH_2)_q SH$, $(CH_2)_q OR^{7d}$, $(CH_2)_q SR^{7d}$, $(CH_2)_q NR^{7a}R^{7a}$, $(CH_2)_r C(O)OH$, $(CH_2)_r C(O)R^{7b}$, $(CH_2)_r C(O)NR^{7a}R^{7a}$, $(CH_2)_q NR^{7a}C(O)R^{7a}$, $(CH_2)_q NR^{7a}C(O)H$, $(CH_2)_r C(O)OR^{7b}$, $(CH_2)_q OC(O)R^{7b}$, $(CH_2)_q S(O)_p R^{7b}$, $(CH_2)_q S(O)_2 NR^{7a}R^{7a}$, $(CH_2)_q NR^{7a}S(O)_2 R^{7b}$, $C_{1-6}$ haloalkyl, a $(CH_2)_r$—$C_{3-10}$ carbocyclic residue substituted with 0-3 $R^{7c}$, and a $(CH_2)_r$-5-10 membered heterocyclic system containing 1-4 heteroatoms selected from N, O, and S, substituted with 0-2 $R^{7c}$;

$R^{7a}$, at each occurrence, is selected from H, $C_{1-6}$ alkyl, $C_{3-8}$ alkenyl, $C_{3-8}$ alkynyl, $(CH_2)_r C_{3-6}$ cycloalkyl, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-3 $R^{7e}$;

$R^{7b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0-2 $R^{7e}$, and a $(CH_2)_r$-5-6 membered heterocyclic system containing 1-4 heteroatoms selected from N, O, and S, substituted with 0-3 $R^{7e}$;

$R^{7c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{7b}$, $(CH_2)_rC(O)NR^{7f}R^{7f}$, $(CH_2)_rNR^{7f}C(O)R^{7a}$, $(CH_2)_rC(O)OC_{1-14}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_rNHC(=NR^{7f})NR^{7f}R^{7f}$, $(CH_2)_rS(O)_2NR^{7f}R^{7f}$, $(CH_2)_rNR^{7f}S(O)_2R^{7b}$, and $(CH_2)_r$phenyl substituted with 0-3 $R^{7e}$;

$R^{7d}$, at each occurrence, is selected from $C_{1-6}$ alkyl substituted with 0-3 $R^{7e}$, $C_{3-8}$ alkenyl, $C_{3-8}$ alkynyl, and a $C_{3-10}$ carbocyclic residue substituted with 0-3 $R^{7c}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-6}$ alkyl, and $C_{3-6}$ cycloalkyl;

$R^8$ is selected from H, $C_{1-6}$ alkyl, $C_{3-6}$ cycloalkyl, and $(CH_2)_r$phenyl substituted with 0-3 $R^{8a}$;

$R^{8a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{14}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{14a}R^{14a}$, $(CHR')_rOH$, $(CHR')_rO(CHR')_rR^{14d}$, $(CHR')_rSH$, $(CHR')_rC(O)H$, $(CHR')_rS(CHR')_rR^{14d}$, $(CHR')_rC(O)OH$, $(CHR')_rC(O)(CHR')_rR^{14b}$, $(CHR')_rC(O)NR^{14a}R^{14a}$, $(CHR')_rNR^{14f}C(O)(CHR')_rR^{14b}$, $(CHR')_rC(O)O(CHR')_rR^{14d}$, $(CHR')_rOC(O)(CHR')_rR^{14b}$, $(CHR')_rC(=NR^{14f})NR^{14a}R^{14a}$, $(CHR')_rNHC(=NR^{14f})NR^{14f}R^{14f}$, $(CHR')_rS(O)_p(CHR')_rR^{14b}$, $(CHR')_rS(O)_2NR^{14a}R^{14a}$, $(CHR')_rNR^{14f}S(O)_2(CHR')_rR^{14b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{14e}$, and a $(CH_2)_r$-5-10 membered heterocyclic system containing 1-4 heteroatoms selected from N, O, and S, substituted with 0-2 $R^{14e}$, or two $R^{14}$ substituents on adjacent atoms on ring A form to join a 5-6 membered heterocyclic system containing 1-3 heteroatoms selected from N, O, and S substituted with 0-2 $R^{14e}$;

$R^{14a}$, at each occurrence, is selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{14e}$, and a $(CH_2)_r$-5-10 membered heterocyclic system containing 1-4 heteroatoms selected from N, O, and S, substituted with 0-2 $R^{14e}$;

$R^{14b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0-3 $R^{14e}$, and $(CH_2)_r$-5-6 membered heterocyclic system containing 1-4 heteroatoms selected from N, O, and S, substituted with 0-2 $R^{14e}$;

$R^{14d}$, at each occurrence, is selected from $C_{3-8}$ alkenyl, $C_{3-8}$ alkynyl, $C_{1-6}$ alkyl substituted with 0-3 $R^{14e}$, a $(CH_2)_r$—$C_{3-10}$ carbocyclic residue substituted with 0-3 $R^{14e}$, and a $(CH_2)_r$-5-6 membered heterocyclic system containing 1-4 heteroatoms selected from N, O, and S, substituted with 0-3 $R^{14e}$;

$R^{14e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{14f}R^{14f}$, and $(CH_2)_r$phenyl;

$R^{14f}$, at each occurrence, is selected from H, $C_{1-6}$ alkyl, $C_{3-6}$ cycloalkyl, and phenyl;

$R^{15}$, at each occurrence, is selected from $C_{1-8}$ alkyl, $(CR'R)_rC_{3-6}$ cycloalkyl, Cl, Br, I, F, $NO_2$, CN, $(CR'R)_rNR^{15a}R^{15a}$, $(CR'R)_rOH$, $(CR'R)_rO(CHR')_rR^{15d}$, $(CR'R)_r$ SH, $(CHR')_rC(O)H$, $(CR'R)_rS(CHR')_rR^{15d}$, $(CR'R)_rC(O)OH$, $(CR'R)_rC(O)$ $(CHR')_rR^{15b}$, $(CR'R)_rC(O)NR^{15a}R^{15a}$, $(CR'R)_rNR^{15f}C(O)$ $(CHR')_rR^{15b}$, $(CR'R)_rOC(O)NR^{15a}R^{15a}$, $(CR'R)_rNR^{15f}C(O)O(CHR')_r$ $R^{15b}$, $(CR'R)_rNR^{15f}C(O)NR^{15f}R^{15f}$, $(CR'R)_rC(O)O(CHR')_rR^{15d}$, $(CR'R)_rOC(O)$ $(CHR')_rR^{15b}$, $(CR'R)_rC(=NR^{15f})NR^{15a}R^{15a}$, $(CR'R)_rNHC(=NR^{15f})NR^{15f}R^{15f}$, $(CR'R)_rS(O)_p(CHR')_rR^{15b}$, $(CR'R)_rS(O)_2NR^{15a}R^{15a}$, $(CR'R)_rNR^{15f}S(O)2(CHR')_rR^{15b}$, $C_{1-6}$ haloalkyl, $C_{2-8}$ alkenyl substituted with 0-3 R', $C_{2-8}$ alkynyl substituted with 0-3 R', $(CR'R)_r$phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

R', at each occurrence, is independently selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{15e}$;

$R^{15a}$, at each occurrence, is selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{15e}$, and a $(CH_2)_r$-5-10 membered heterocyclic system containing 1-4 heteroatoms selected from N, O, and S, substituted with 0-2 $R^{15e}$;

alternatively, two $R^{15a}$, along with the N to which they are attached, join to form a 5-6 membered non-aromatic heterocyclic system containing 1-2 heteroatoms selected from $NR^{15g}$, O, and S and optionally fused with a benzene ring or a 6-membered aromatic heterocycle;

$R^{15b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0-3 $R^{15e}$, and $(CH_2)_r$-5-6 membered heterocyclic system containing 1-4 heteroatoms selected from N, O, and S, substituted with 0-2 $R^{15e}$;

$R^{15d}$, at each occurrence, is selected from $C_{3-8}$ alkenyl, $C_{3-8}$ alkynyl, methyl, $CF_3$, $C_{2-6}$ alkyl substituted with 0-3 $R^{15e}$, a $(CH_2)_r$—$C_{3-10}$ carbocyclic residue substituted with 0-3 $R^{15e}$, and a $(CH_2)_r$5-6 membered heterocyclic system containing 1-4 heteroatoms selected from N, O, and S, substituted with 0-3 $R^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, and $(CH_2)_r$phenyl;

$R^{15f}$, at each occurrence, is selected from H, $C_{1-6}$ alkyl, $C_{3-6}$ cycloalkyl, and phenyl;

$R^{15g}$ is selected from H, $C_{1-6}$ alkyl, $C_{3-6}$ cycloalkyl, $(CH_2)_r$phenyl, $C(O)R^{15f}$, $C(O)OR^{15}h$, and $SO_2R^{15h}$;

$R^{15h}$, at each occurrence, is selected from $C_{1-5}$ alkyl, and $C_{3-6}$ cycloalkyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a}$, $(CHR')_rOH$, $(CHR')_rO(CHR')_rR^{16d}$, $(CHR')_rSH$, $(CHR')_rC(O)H$, $(CHR')_rS(CHR')_rR^{16d}$, $(CHR')_rC(O)OH$, $(CHR')_rC(O)(CHR')_rR^{16b}$, $(CHR')_rC(O)NR^{16a}R^{16a}$, $(CHR')_rNR^{16f}C(O)(CHR')_rR^{16b}$, $(CHR')_rC(O)O(CHR')_rR^{16d}$, $(CHR')_rOC(O)(CHR')_rR^{16b}$, $(CHR')_rC(=NR^{16f})NR^{16a}R^{16a}$, $(CHR')_rNHC(=NR^{16f})NR^{16f}R^{16f}$, $(CHR')_rS(O)_p(CHR')_rR^{16b}$, $(CHR')_rS(O)_2NR^{16a}R^{16a}$, $(CHR')_rNR^{16f}S(O)_2(CHR')_rR^{16b}$, $C_{1-6}$ haloalkyl, $C_{2-8}$ alkenyl substituted with 0-3 R', $C_{2-8}$ alkynyl substituted with 0-3 R', and $(CHR')_r$phenyl substituted with 0-3 $R^{16e}$;

$R^{16a}$, at each occurrence, is selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{16e}$, and a $(CH_2)_r$-5-10 membered heterocyclic system containing 1-4 heteroatoms selected from N, O, and S, substituted with 0-2 $R^{16e}$;

$R^{16b}$, at each occurrence, is selected from $C_{1-6}$ alkyl, $C_{3-8}$ alkenyl, $C_{3-8}$ alkynyl, a $(CH_2)_r C_{3-6}$ carbocyclic residue substituted with 0-3 $R^{16e}$, and a $(CH_2)_r$-5-6 membered heterocyclic system containing 1-4 heteroatoms selected from N, O, and S, substituted with 0-2 $R^{16e}$;

$R^{16d}$, at each occurrence, is selected from $C_{3-8}$ alkenyl, $C_{3-8}$ alkynyl, methyl, $CF_3$, $C_{2-6}$ alkyl substituted with 0-3 $R^{16e}$, a $(CH_2)_r$—$C_{3-10}$ carbocyclic residue substituted with 0-3 $R^{16e}$, and a $(CH_2)_r$-5-6 membered heterocyclic system containing 1-4 heteroatoms selected from N, O, and S, substituted with 0-3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is selected from H, $C_{1-5}$ alkyl, and $C_{3-6}$ cycloalkyl, and phenyl;

$R^{18}$ at each occurrence is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rS(O)C_{1-5}$ alkyl, $(CH_2)_rS(O)_2C_{1-5}$ alkyl, $(CH_2)_rS(O)_2N(R^{18a})R^{18b}$, $(CH_2)_rN(R^{18c})C(O)C_{1-5}$ alkyl $(CH_2)_rN(R^{18C})S(O)_2C_{1-5}$ alkyl, $(CH_2)_rC(O)N(R^{18a})R^{18b}$, $(CH_2)_rC(O)OC_{1-5}$ alkyl, $(CH_2)_rC(O)C_{1-5}$ alkyl, and $(CH_2)_rN(R^{18a})R18b$;

$R^{18a}$, $R^{18b}$, and $R^{18c}$ at each occurrence are independently selected from H, $C_{1-6}$ alkyl, and $C_{3-6}$ cycloalkyl;

$R^{19}$ at each occurrence is independently selected from $C_{1-6}$ alkyl, $C_{3-6}$ cycloalkyl, and phenyl substituted with 0-3 $R^{18}$;

alternatively, $R^{18a}$ and $R^{18b}$ along with the nitrogen to which both are attached form a pyrrolidine, piperidine, piperazine or morpholine ring;

$R^{24a}$ and $R^{24b}$, at each occurrence, are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_tN(R^{18a})R^{18b}$, $(CH_2)_tOH$, $(CH_2)_tOR^{19}$, $(CH_2)_tSH$, $(CH_2)_tSR^{19}$, $(CH_2)_r$ C(O)OH, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_t$ $OC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, and $(CH_2)_r$phenyl substituted with 0-3 $R^{18}$;

g is selected from 0, 1, 2, 3, 4, and 5;
s is selected from 1, 2, 3, 4, and 5;
t is selected from 0, 1, 2, 3, 4, and 5, with the proviso that when s is 1, then t can not be 0;
w is selected from 0 and 1;
r is selected from 0, 1, 2, 3, 4, and 5;
q is selected from 1, 2, 3, 4, and 5; and
p is selected from 0, 1, and 2.

In another embodiment, the present invention provides novel compounds of formula (I):

$R^{4'}$ is absent, taken with the nitrogen to which it is attached to form an N-oxide, or selected from $C_{1-8}$ alkyl, $(CH_2)_rC_{3-6}$ cycloalkyl, and $(CH_2)_r$-phenyl substituted with 0-3 $R^{4c}$;

$R^1$ and $R^2$ are independently selected from H and $C_{1-4}$ alkyl;

$R^{24a}$ and $R^{24b}$, at each occurrence, are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_tN(R^{18a})R^{18b}$, $(CH_2)_tOH$, $(CH_2)_tOR^{19}$, $(CH_2)_tSH$, $(CH_2)_tSR^{19}$, $(CH_2)_r$ C(O)OH, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_t$ $OC(O)R^{19}$, and $(CH_2)_r$phenyl substituted with 0-3 $R^{18}$;

q is selected from 1, 2, and 3; and
r is selected from 0, 1, 2, and 3.

In another embodiment, the present invention provides novel compounds of formula (I):

$R^3$ is selected from a $(CR^{3'}H)_r$-carbocyclic residue substituted with 0-5 $R^{15}$, wherein the carbocyclic residue is selected from phenyl, $C_{3-6}$ cycloalkyl, naphthyl, and adamantyl; and a $(CR^{3'}H)_r$-heterocyclic system substituted with 0-3 $R^{15}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{5a}$ is selected from $(CR^{5'}H)_r$-phenyl substituted with 0-5 $R^{16}$; and a $(CR^{5'}H)_r$-heterocyclic system substituted with 0-3 $R^{16}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, the present invention provides novel compounds of formula (I):

$R^{18}$ at each occurrence is independently selected from $C_{1-6}$ alkyl, $C_{3-6}$ cycloalkyl, Cl, F, Br, I, CN, $NO_2$, $(CF_2)_rCF_3$, $OC_{1-5}$ alkyl, $(CH_2)_rOH$, $SC_{1-5}$ alkyl, $N(R^{18c})C(O)C_{1-5}$ alkyl, $C(O)N(R^{18a})R^{18b}$, $C(O)OC_{1-5}$ alkyl, $C(O)C_{1-5}$ alkyl, and $N(R^{18a})R^{18b}$;

$R^{18a}$, $R^{18b}$, and $R^{18c}$ at each occurrence are independently selected from H, methyl, ethyl, propyl, i-propyl, butyl, i-butyl, t-butyl, cyclopropyl, cyclopentyl, and cyclohexyl;

$R^{19}$ at each occurrence is independently selected from methyl, ethyl, propyl, i-propyl, butyl, i-butyl, t-butyl, cyclopropyl, cyclopentyl, and cyclohexyl, and phenyl substituted with 0-3 $R^{18}$;

alternatively, $R^{18a}$ and $R^{18b}$ along with the nitrogen to which both are attached form a pyrrolidine, piperidine, piperazine or morpholine ring;

In another embodiment, the present invention provides novel compounds of formula (I):

$R^5$ is selected from

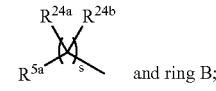 and ring B;

ring B is 1,2,3,4-tetrahydronaphthylenyl substituted with 0-3 $R^{16}$;

alternatively, ring B is selected from a $C_{3-10}$ carbocyclic residue substituted with 1-5 $R^{5a}$, wherein the carbocyclic residue is selected from phenyl and cyclohexyl, and a 5-10 membered heterocyclic system containing 1-4 heteroatoms selected from N, O, and S, substituted with 1-3 $R^{5a}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

r is selected from 0, 1, and 2.

In another embodiment, the present invention provides novel compounds of formula (I):

$R^3$ is a $C_{3-10}$ carbocyclic residue substituted with 0-3 $R^{15}$, wherein the carbocyclic residue is selected from cyclopropyl, cyclopentyl, cyclohexyl, phenyl, naphthyl and adamantyl, and a $(CR^{3'}H)_r$-heterocyclic system substituted with 0-3 $R^{15}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is selected from $C_{1-8}$ alkyl, $(CH_2)_rC_{3-6}$ cycloalkyl, $CF_3$, Cl, Br, I, F, $(CH_2)_r$ $NR^{15a}R^{15a}$, $NO_2$, CN, OH, $(CH_2)_rOR^{15d}$, $(CH_2)_rC(O)$ $R^{15b}$, $(CH_2)_rC(O)NR^{15a}R^{15a}$, $(CH_2)_rNR^{15f}C(O)R^{15b}$, $(CH_2)_rOC(O)NR^{15a}R^{15a}$, $(CH_2)_rNR^{15f}C(O)OR^{15b}$, $(CH_2)_rS(O)_pR^{15b}$, $(CH_2)_rS(O)_2NR^{15a}R^{15a}$, $(CH_2)_r$ $NR^{15f}S(O)_2R^{15b}$, $C_{1-6}$ haloalkyl, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$;

$R^{15a}$, at each occurrence, are selected from H, $C_{1-6}$ alkyl, $C_{3-6}$ cycloalkyl, and $(CH_2)_r$phenyl substituted with 0-3 $R^{15e}$;

alternatively, $R^{15a}$, along with the N to which they are attached, join to form a 5-6 membered heterocyclic system containing 1-2 heteroatoms selected from $NR^{15g}$, O, and S and optionally fused with a benzene ring or a 6-membered aromatic heterocycle;

$R^{15b}$, at each occurrence, is selected from H, $C_{1-6}$ alkyl, $C_{3-6}$ cycloalkyl, and $(CH_2)_r$phenyl substituted with 0-3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl.

In another embodiment, the present invention provides novel compounds of formula (I):

Z is selected from O and S;

$R^1$ is H;

$R^2$ is H;

$R^3$ is a $C_{3-10}$ carbocyclic residue substituted with 0-3 $R^{15}$, wherein the carbocyclic residue is phenyl, and a $(CR^{3'}H)_r$-heterocyclic system substituted with 0-3 $R^{15}$, wherein the heterocyclic system is selected from pyridinyl, thiophenyl, furanyl, indazolyl, benzo[1,3] dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{5a}$ is selected from a $(CH_2)_r$—$C_{3-10}$ carbocyclic residue substituted with 1-5 $R^{16}$ and a heterocyclic system substituted with 0-3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, the present invention provides novel compounds of formula (I), wherein the compound is selected from the compounds of the Tables and the Examples.

In another embodiment, the present invention provides a pharmaceutical composition, comprising a pharmaceutically acceptable carrier and a therapeutically effective amount of a compound of the present invention.

In another embodiment, the present invention provides a method for modulation of chemokine receptor activity comprising administering to a patient in need thereof a therapeutically effective amount of a compound of the present invention.

In another embodiment, the present invention provides a method for treating inflammatory disorders comprising administering to a patient in need thereof a therapeutically effective amount of a compound of the present invention.

In another embodiment, the present invention provides a method for treating disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

In another embodiment, the present invention provides a method of treating disorders selected from rheumatoid arthritis, transplantation, and multiple sclerosis.

In another embodiment, the present invention provides a method for treating asthma.

In another embodiment, the present invention provides a method for treating allergic rhinitis.

In another embodiment, the present invention provides a method for treating atopic dermatitis.

In another embodiment, the present invention provides a method for treating inflammatory bowel diseases.

In another embodiment, $R^1$ and $R^2$ are independently selected from H and $C_{1-4}$ alkyl.

In another embodiment, $R^1$ and $R^2$ are H.

In another embodiment, Z is selected from O and S.

In another embodiment, Z is 0.

In another embodiment, E is —$(CH_2)_v$—$(CHR^9)$— $(CHR^{11})$—; and v is 1.

In another embodiment, E is selected from

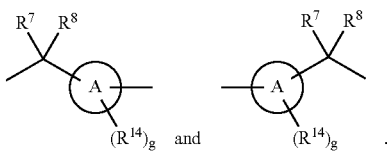

In another embodiment, E is selected from

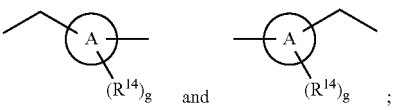

and wherein A is cyclohexyl.

In another embodiment, E is selected from

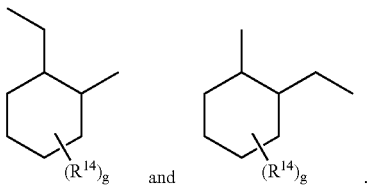

In another embodiment, $R^3$ is selected from a $(CR^{3'}H)_r$-carbocyclic residue substituted with 0-5 $R^{15}$, wherein the carbocyclic residue is selected from phenyl, $C_{3-6}$ cycloalkyl, naphthyl, and adamantyl; and a $(CR^{3'}H)_r$-heterocyclic system substituted with 0-3 $R^{15}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^3$ is selected from a methyl substituted with 0-2 $R^{10}$, $C_{2-8}$ alkyl substituted with 0-2 $R^7$, a $C_{3-10}$ carbocyclic residue substituted with 0-3 $R^{15}$, wherein the carbocyclic residue is selected from cyclopropyl, cyclobutyl, cyclopentyl, cyclohexyl, phenyl, naphthyl and adamantyl, and a $(CR^{3'}H)_r$-heterocyclic system substituted with 0-3 $R^{15}$, wherein the heterocyclic system is selected from pyridinyl, thiophenyl, furanyl, indazolyl, benzothiazolyl, benzimidazolyl, benzo[1,3]dioxolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^3$ is selected from a phenyl substituted with 0-2 $R^{15}$; and a $(CH_2)_r$-5-10 membered heterocyclic system containing 1-4 heteroatoms selected from N, O, and S, substituted with 0-2 $R^{15}$, wherein the heterocyclic system is selected from pyridinyl, morpholinyl, pyrazolyl, benzothiazolyl, benzo[1,3]dioxolyl, indazolyl, thiazolyl and r is 0, 1, or 2.

In another embodiment, $R^3$ is selected from a phenyl substituted with 0-2 $R^{15}$; and a $(CH_2)_r$-5-10 membered heterocyclic system containing 1-4 heteroatoms selected from N, O, and S, substituted with 0-2 $R^{15}$, wherein the heterocyclic system is selected from benzothiazolyl, benzo[1,3]dioxolyl, indazolyl, thiazolyl and r is 0, 1, or 2.

In another embodiment, $R^{4'}$ is absent.

In another embodiment, $R^5$ is selected from

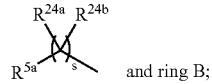

and ring B;

ring B is 1,2,3,4-tetrahydronaphthylenyl substituted with 0-3 $R^{16}$;
alternatively, ring B is selected from a $C_{3-10}$ carbocyclic residue substituted with 1-5 $R^{5a}$, wherein the carbocyclic residue is selected from phenyl and cyclohexyl.

In another embodiment, $R^{5a}$ is selected from $(CR^{5'}H)_r$-phenyl substituted with 0-5 $R^{16}$; and a $(CR^{5'}H)_r$-heterocyclic system substituted with 0-3 $R^{16}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^{5a}$ is selected from phenyl substituted with 0-3 $R^{16}$, and pyridinyl substituted with 0-3 $R^{16}$.

In another embodiment, $R^{5a}$ is selected from phenyl substituted with 0-1 $R^{16}$, and pyridinyl substituted with 0-1 $R^{16}$.

In another embodiment, $R^9$, is selected from methyl, ethyl, propyl, i-propyl, butyl, i-butyl, t-butyl, F, Cl, Br, I, $NO_2$, CN, $(CH_2)_rOH$, $(CH_2)_rSH$, $(CH_2)_rOR^{9d}$, $(CH_2)_rSR^{9d}$, $(CH_2)_r$—$C_{3-6}$ carbocyclic residue substituted with 0-1 $R^{9c}$, wherein the carbocyclic residue is selected from cyclopropyl, cyclopentyl, cyclohexyl, and phenyl; and $R^{9d}$ is selected from methyl, ethyl, propyl, i-propyl, butyl, i-butyl, t-butyl, pentyl, hexyl, cyclopropyl, and phenyl.

In another embodiment, $R^9$ is OH.

In another embodiment, $R^{11}$ is selected from $C_{1-6}$ alkyl, $(CH_2)_qOH$, $(CH_2)_qSH$, $(CH_2)_qOR^{11d}$, $(CH_2)_qR^{11d}$, $(CH_2)_qNR^{11a}R^{11a}$, $(CH_2)_rC(O)R^{11b}$, $(CH_2)_qC(O)NR^{11a}R^{11a}(CH_2)_qNR^{11a}C(O)R^{11a}$, $(CH_2)_qOC(O)NR^{11a}R^{11a}$, $(CH_2)_qNR^{11a}C(O)OR^{11b}$, $(CH_2)_qNR^{11a}C(O)NHR^{11a}$, $(CH_2)_rC(O)OR^{11b}$, $(CH_2)_qOC(O)R^{11b}$, $C_{1-6}$ haloalkyl, a $(CH_2)_r$—$C_{3-10}$ carbocyclic residue substituted with 0-5 $R^{11c}$, and a $(R'R')_r$-5-10 membered heterocyclic system containing 1-4 heteroatoms selected from N, O, and S, substituted with 0-3 $R^{11c}$;

$R^{11a}$, at each occurrence, are selected from H, methyl, ethyl, propyl, i-propyl, butyl, pentyl, hexyl, a $(CH_2)_r$—$C_{3-10}$ carbocyclic residue substituted with 0-5 $R^{11e}$, wherein the carbocyclic residue is selected from cyclopropyl, cyclopentyl, cyclohexyl;

$R^{11b}$, at each occurrence, is selected from methyl, ethyl, propyl, i-propyl, butyl, pentyl, hexyl, a $(CH_2)_r$—$C_{3-6}$ carbocyclic residue substituted with 0-2 $R^{11e}$, wherein the carbocyclic residue is selected from cyclopropyl, cyclopentyl, cyclohexyl;

$R^{11c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11f}R^{11f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{11b}$, $(CH_2)_rC(O)NR^{11f}R^{11f}$, $(CH_2)_rNR^{11f}C(O)R^{11a}$, $(CH_2)_rC(O)OC_{1-4}$alkyl, $(CH_2)_rOC(O)R^{11b}$, $(CH_2)_rC(=NR^{11f})NR^{11f}R^{11f}$, $(CH_2)_rNHC(=NR^{11f})NR^{11f}R^{11f}$, $(CH_2)_rS(O)_pR^{11b}$, $(CH_2)_rS(O)_2NR^{11f}R^{11f}$, $(CH_2)_rNR^{11f}S(O)_2R^{11b}$, and $(CH_2)_r$phenyl substituted with 0-3 $R^{11e}$;

$R^{11d}$, at each occurrence, is selected from methyl, ethyl, propyl, i-propyl, butyl, pentyl, hexyl, and a $C_{3-10}$ carbocyclic residue substituted with 0-3 $R^{11c}$ wherein the carbocyclic residue is selected from cyclopropyl, cyclopentyl, cyclohexyl;

$R^{11e}$, at each occurrence, is selected from methyl, ethyl, propyl, i-propyl, butyl, pentyl, hexyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{11f}R^{11f}$, and $(CH_2)_r$phenyl, wherein the phenyl on the $(CH_2)_r$phenyl is substituted with 0-5 substituents selected from F, Cl, Br, I, $NO_2$, $C_{1-6}$alkyl, OH, and $NR^{11f}R^{11f}$;

$R^{11f}$, at each occurrence, is selected from H, $C_{1-6}$ alkyl, and $C_{3-6}$ cycloalkyl;

$R^{11g}$ is selected from H, $C_{1-6}$ alkyl, $C_{3-6}$ cycloalkyl, $(CH_2)_r$phenyl, $C(O)R^{11f}$, $C(O)OR^{11h}$, and $SO_2R^{11h}$;

$R^{11h}$, at each occurrence, is selected from $C_{1-6}$ alkyl, and $C_{3-6}$ cycloalkyl.

In another embodiment, $R^{11}$ is selected from methyl, ethyl, propyl, i-propyl, butyl, pentyl, hexyl, $(CH_2)_qOH$, $(CH_2)_qOR^{11d}$, and a $(CH_2)_q$—$C_{3-10}$ carbocyclic residue substituted with 0-5 $R^{11c}$, wherein the carbocyclic residue is phenyl.

In another embodiment, $R^{11}$ is selected from methyl, ethyl, propyl, i-propyl, butyl, pentyl, and hexyl.

In another embodiment, $R^{11}$ is methyl.

In another embodiment, $R^{15}$, at each occurrence, is selected from $C_{1-8}$ alkyl, $(CH_2)_rC_{3-6}$ cycloalkyl, $CF_3$, Cl, Br, I, F, $(CH_2)_rNR^{15a}R^{15a}$, $NO_2$, CN, OH, $(CH_2)_rOR^{15d}$, $(CH_2)_rC(O)R^{15b}$, $(CH_2)_rC(O)NR^{15a}R^{15a}$, $(CH_2)_rNR^{15f}C(O)R^{15b}$, $(CH_2)_rOC(O)NR^{15a}R^{15a}$, $(CH_2)_rNR^{15f}C(O)OR^{15b}$, $(CH_2)_rS(O)_pR^{15b}$, $(CH_2)_rS(O)_2NR^{15a}R^{15a}$, $(CH_2)_rNR^{15f}S(O)_2R^{15b}$, $C_{1-6}$ haloalkyl, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$;

$R^{15a}$, at each occurrence, are selected from H, $C_{1-6}$ alkyl, $C_{3-6}$ cycloalkyl, and $(CH_2)_r$phenyl substituted with 0-3 $R^{15e}$;

alternatively, $R^{15a}$, along with the N to which they are attached, join to form a 5-6 membered heterocyclic system containing 1-2 heteroatoms selected from $NR^{15g}$, O, and S and optionally fused with a benzene ring or a 6-membered aromatic heterocycle;

$R^{15b}$, at each occurrence, is selected from H, $C_{1-6}$ alkyl, $C_{3-6}$ cycloalkyl, and $(CH_2)_r$phenyl substituted with 0-3 $R^{15e}$;

$R^{15d}$, at each occurrence, is selected from $C_{1-6}$ alkyl, $CF_3$, and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl.

In another embodiment, $R^{15}$, at each occurrence, is selected from methyl, ethyl, propyl, i-propyl, butyl, i-butyl, t-butyl, pentyl, hexyl, $(CH_2)_rC_{3-6}$ cycloalkyl, wherein cycloalkyl is selected from cyclohexyl and cyclopropyl, $CF_3$, Cl, Br, I, F, $(CH_2)_rNR^{15a}R^{15a}$, $NO_2$, CN, OH, $(CH_2)_rOR^{15d}$, $(CH_2)_rC(O)R^{15b}$, $(CH_2)_rC(O)NR^{15a}R^{15a}$, $(CH_2)_rNR^{15f}C(O)R^{15b}$, $(CH_2)_rOC(O)NR^{15a}R^{15a}$, $(CH_2)_rNR^{15f}C(O)OR^{15b}$, $(CH_2)_rS(O)_pR^{15b}$, $(CH_2)_rS(O)_2NR^{15a}R^{15a}$, $C_{1-6}$ haloalkyl, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$, wherein the heterocyclic system is selected from tetrazolyl, piperidinyl, pyrrolidinyl, imidazolyl, thiazolyl, pyrazolyl, pyridyl, thienyl, furanyl, pyrrolyl, oxazolyl, isoxazolyl, triazolyl, pyridazinyl, pyrimidinyl, pyrazinyl, morpholinyl, oxadiazolyl, and thiadiazolyl;

$R^{15a}$, at each occurrence, are selected from H, methyl, ethyl, propyl, i-propyl, butyl, i-butyl, t-butyl, pentyl, hexyl, cyclopropyl cyclohexyl, and $(CH_2)_r$phenyl substituted with 0-3 $R^{15e}$;

$R^{15b}$, at each occurrence, is selected from H, methyl, ethyl, propyl, i-propyl, butyl, i-butyl, t-butyl, pentyl, hexyl, cyclopropyl cyclohexyl, and $(CH_2)_r$phenyl substituted with 0-3 $R^{15e}$;

$R^{15d}$, at each occurrence, is selected from methyl, ethyl, propyl, i-propyl, butyl, i-butyl, t-butyl, pentyl, hexyl, $CF_3$, and phenyl;

$R^{15e}$, at each occurrence, is selected from methyl, ethyl, propyl, i-propyl, butyl, i-butyl, t-butyl, pentyl, hexyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and methyl, ethyl, propyl, i-propyl, butyl.

In another embodiment, $R^{15}$, at each occurrence, is selected from methyl, ethyl, propyl, i-propyl, butyl, i-butyl, t-butyl, pentyl, hexyl, $CF_3$, Cl, Br, I, F, OH, $OR^{15d}$, $C(O)R^{15b}$, phenyl substituted with 0-2 $R^{5e}$, and a $(CH_2)_r$-5-6 membered heterocyclic system containing 1-4 heteroatoms selected from N, O, and S, substituted with 0-2 $R^{15e}$, wherein the heterocyclic system is selected from tetrazolyl and pyrimidinyl;

$R^{15d}$, at each occurrence, is selected from methyl, ethyl, propyl, i-propyl, butyl, i-butyl, t-butyl, pentyl, hexyl, $CF_3$, and phenyl.

In another embodiment, $R^{16}$, at each occurrence, is selected from $C_{1-8}$ alkyl, $(CH_2)_rC_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0-3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0-3 $R^{16e}$;

$R^{16b}$, at each occurrence, is selected from H, $C_{1-6}$ alkyl, $C_{3-6}$ cycloalkyl, and $(CH_2)_r$phenyl substituted with 0-3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

In another embodiment, $R^{16}$ is selected from F, Cl, and Br.

In another embodiment, $R^{16}$ is F.

In another embodiment, $R^{24a}$ and $R^{24b}$, at each occurrence, are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rC(O)OH$, $(CH_2)_rC(O)R^{19}$, $(CH_2)_rC(O)$ N($R^{18a}$)$R^{18b}$, $(CH_2)_rN(R^{18c})C(O)R^{19}$, $(CH_2)_rC(O)OR^{19}$, $(CH_2)_rOC(O)R^{19}$, and $(CH_2)_r$phenyl substituted with 0-3 $R^{18}$.

In another embodiment, $R^{24a}$ and $R^{24b}$, at each occurrence, are independently selected from H, methyl, ethyl, propyl, i-propyl, butyl, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_rOC(O)R^{19}$, and $(CH_2)_r$phenyl substituted with 0-3 $R^{18}$.

In another embodiment, $R^{24a}$ and $R^{24b}$, at each occurrence, are independently selected from H, OH, methyl, ethyl, propyl, i-propyl, butyl.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional even more preferred embodiments of the present invention. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)). "Perfluoroalkyl" as used herein refers to alkyl groups having the formula $C_vF_{v+2}$.

The compounds of Formula I can also be quaternized by standard techniques such as alkylation of the piperidine or pyrrolidine with an alkyl halide to yield quaternary piperidinium salt products of Formula I. Such quaternary piperidinium salts would include a counterion. As used herein, "counterion" is used to represent a small, negatively charged species such as chloride, bromide, hydroxide, acetate, sulfate, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S.

Examples of heterocycles include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. Only stable compounds are envisioned for this invention. "Therapeutically effective amount" is intended to include an amount of a compound of the present invention alone or an amount of the combination of compounds claimed or an amount of a compound of the present invention in combination with other active ingredients effective to treat the inflammatory diseases described herein.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

In general compounds described in the scope of this patent application can be synthesized by forming a urea linkage between the amine (II) and the isocyanate or thio-isocyanate (III) or the carbamate (IV).

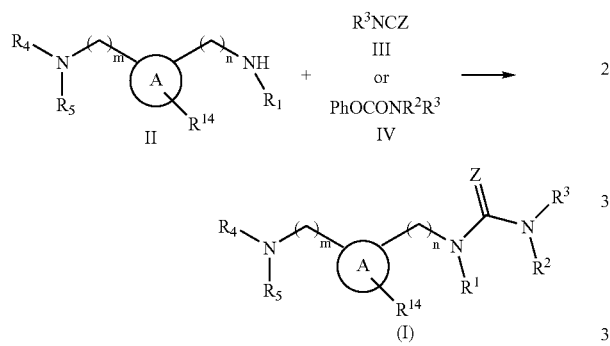

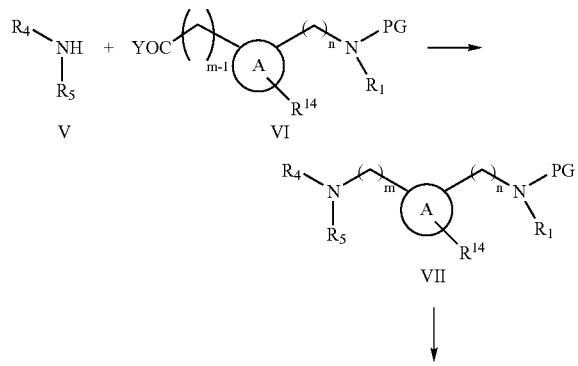

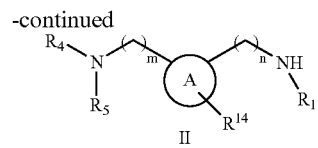

Alternatively the protected amine VII can be prepared by reacting the amine V with a compound of formula VIII, which carries a leaving group (X=Cl, Br, I, —OSO$_2$CH$_3$ or —OTs). The halides, the mesylate and the tosylate of formula VIII can be synthesized from the corresponding alcohol VIII (X=OH), which in turn can be prepared from the amino alcohol IX by a selective protection on the nitrogen. Methods of preparing halides, mesylate or tosylate are well known to one skilled in the art and numerous examples are found in Larock, 'Comprehensive Organic Transformations', 2nd ed., Wiley-VCH Publishers, Inc., New York, 1999, and 'Compendium of Organic Synthetic Methods, Vol 1-8, John Wiley & Sons, New York, 1971-1995.

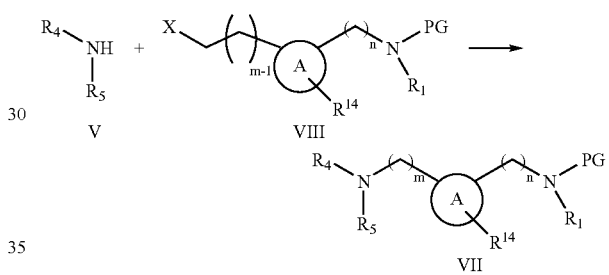

Compounds of formula (I), where m=0, can be prepared from the amino alcohol IX as shown in the following scheme. Amino group of the amino alcohol IX (*J. Am. Chem. Soc.* 1996, 118, 5502-5503 and references therein) is selectively protected with a suitable nitrogen protecting group such as BOC to give an intermediate X. The hydroxy group of the intermediate X is converted to a leaving group such as chloride, bromide, iodide, mesylate or tosylate. The leaving group is then displaced with an azide using an azide salt such as sodium azide or lithium azide in an appropriate solvent such as dimethylformamide or dimethylsulfoxide. The azide is reduced under a reducing condition such as a catalytic hydrogenation with palladium catalyst to give the corresponding amine XI. The amine XI can be converted to a urea or thiourea XII by reacting with an isocynate or thioisocynate III or alternatively with a carbamate IV in a solvent such as tetrahydrofuran or acetonitrile. The amino protecting group of the urea XII is then removed under a suitable condition to yield a free amine intermediate XIII, and the amine XIII is coupled with a corresponding aldehyde by a reductive amination with sodium cyanoborohydride or sodium triacetoxyborohydride in a solvent such as methylene chloride, dichloroethane, or methanol to afford a compound of formula (I). For a compound of formula (I), where R$^4$ is not H, another reductive amination is carried out with the corresponding aldehyde on the product of the first reductive amination with the amine XIII.

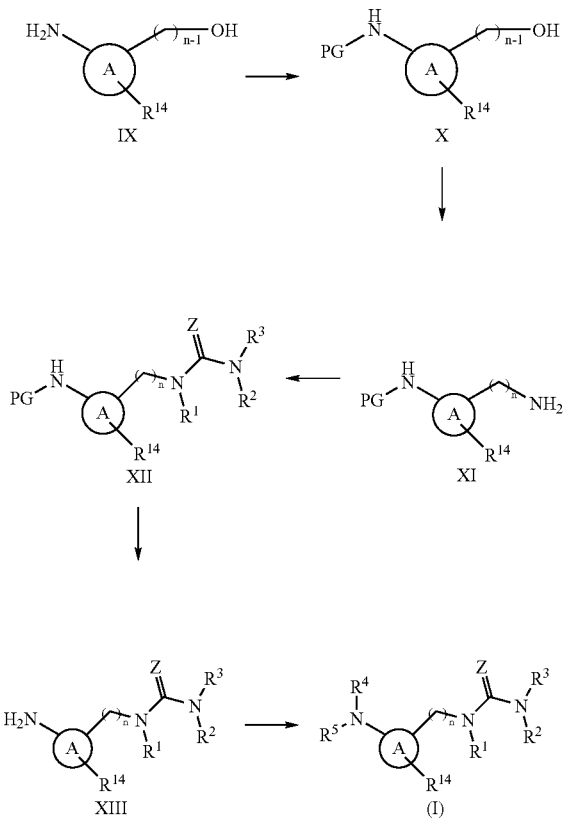

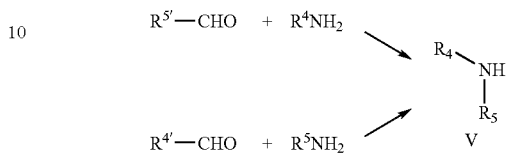

A number of amines of formula V are commercially available, and the non-commercial amines can be prepared by many different methods. The methods described below are two representative examples, however, numerous other methods can be found in Larock, 'Comprehensive Organic Transformations', 2nd ed., Wiley-VCH Publishers, Inc., New York, 1999, and 'Compendium of Organic Synthetic Methods, Vol 1-8, John Wiley & Sons, New York, 1971-1995. The amine V can be made by converting the corresponding carboxylic acid and the amine to an amide and reducing the amide with a reducing agent such as lithium aluminum hydride or diborane and the like in solvent such as tetrahydrofuran. A large number of methods for the amide formation can be found in Larock, 'Comprehensive Organic Transformations', 2nd ed., Wiley-VCH Publishers, Inc., New York, 1999, and 'Compendium of Organic Synthetic Methods, Vol 1-8, John Wiley & Sons, New York, 1971-1995.

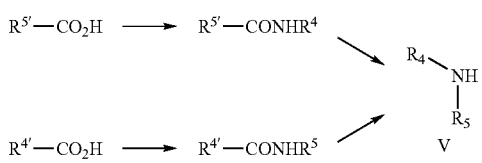

Alternatively the amine V can be prepared by a reductive amination between the corresponding aldehyde and amine with sodium cyanoborohydride or sodium triacetoxyborohydride in a solvent such as methylene chloride, dichloroethane, or methanol. When $R^5$ carries a substitution group in the alkyl chain, the acid or the aldehyde for the amine V preparation may need to be synthesized. Examples of these are described in the Examples section.

A large number of isocyanates and thioisocyanate III are commercially available. When isocyanates are not commercially available, a carbamate IV can be used for the for urea formation. The carbamate IV can be made by reacting the corresponding amine and phenyl chloroformate in the presence of a base such as triethylamine or 2,6-lutidine in an inert solvent.

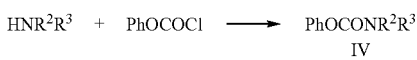

Methods discussed here are merely illustration of some methods by which the compounds of this invention can be synthesized, and various modifications to these schemes can be made including the order of transformations and will be suggested to one skilled in the art having referred to this closure.

Additionally, the synthesis of portions of these molecules is described in PCT publications WO 00/35451 and WO 01/98269, which are both herein incorporated by reference.

EXAMPLES

Compounds described in the scope of this patent application, where $R^{14}$ is H, can be synthesized by the route described in Scheme 1 as exemplified with a cyclohexyl for the ring A of formula (I). It is understood that the same methods with some modifications, if necessary, can be applied to other ring A compounds in the scope of this invention. An appropriately functionalized cyclohexyl compound, such as (1R,2R)-2-hydroxymethylcyclohexylamine 1 (J. Am. Chem. Soc. 1996, 118, 5502-5503 and references therein), is selectively protected on the nitrogen with benzyl chloroformate in the presence of aqueous sodium carbonate to give the CBz-protected amino-alcohol 2. A Swern oxidation of the alcohol gives the corresponding aldehyde 3. It is then coupled with an amine ($R^4R^5NH$) by a reductive amination with sodium triacetoxyborohydride or sodium cyanoborohydride to afford the 2-aminomethyl-cyclohexylamine derivative 4. The CBz-protecting group of the amine is removed by a catalytic hydrogenation to give the free amine 5, which is reacted with an isocyanate, a thioisocyanate or a phenyl carbamate to give the urea 6, a compound of formula (I). Examples 1-8 were prepared according to this scheme or its variation.

SCHEME 1

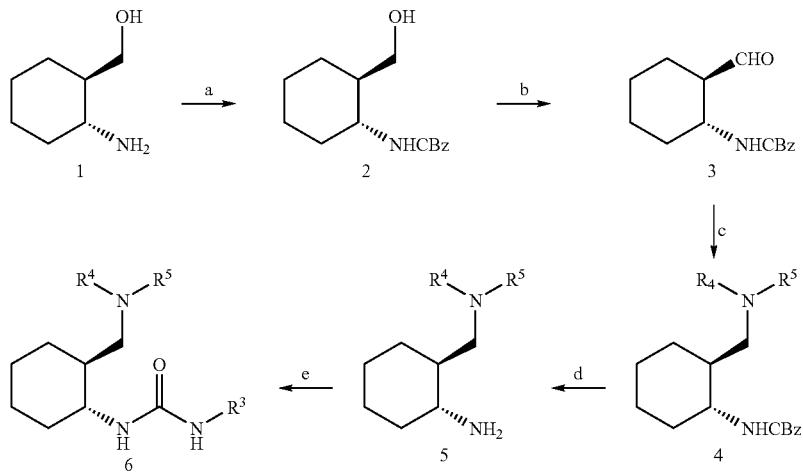

a. Benzyl chloroformate, aq. $Na_2CO_3$, $CH_2Cl_2$. b. DMSO, $(COCl)_2$, $NEt_3$, $CH_2Cl_2$. c. $R^4R^5NH$, $Na(OAc)_3BH$, $CH_2Cl_2$. d. $H_2$, 10% Pd/C, MeOH, e. $R^3NCO$ or $R^3NHCO_2Ph$, THF.

Compounds of formula (I), where $R^{14}$ is not H, can be synthesized as outlined in Schemes 2-5 as exemplified with a cyclohexyl for the ring A of formula (I). It is understood that the same methods with some modifications, if necessary, can be applied to other ring A compounds in the scope of this invention. For 5-substituted cyclohexyl compounds, 3-ethoxy-2-cyclohexen-1-one (7) is acylated with 2 equivalents of diethyl carbonate and 2 equivalents of lithium bis(trimethylsilyl)amide to give the keto-ester 8. The enol ether is hydrolized with 70% aqueous acetic acid to give the diketo-ester 9, which is converted to the ketal-keto-ester 10 with 1.05 equivalent of ethylene glycol and catalytic amount of p-toluenesulfonic acid in benzene. The intermediate 10 is then treated with R-(+)-α-methylbenzylamine in the presence of acetic acid in benzene to give the enamine 11. The enamine is reduced with sodium triacetoxyborohydride in the presence of ethylene glycol and acetic acid in methylene chloride to give the (1R,2S)-cis-amino-ester 12. The ester is then isomerized with sodium tert-butoxide in THF to give the (1R,2R)-trans-amino-ester 13, which is reduced to the corresponding alcohol 14 with lithium aluminum hydride. Removal of the chiral auxiliary under a catalytic hydrogenolysis condition with palladium hydroxide gives the (1R,2R)-amino-alcohol 15.

SCHEME 2

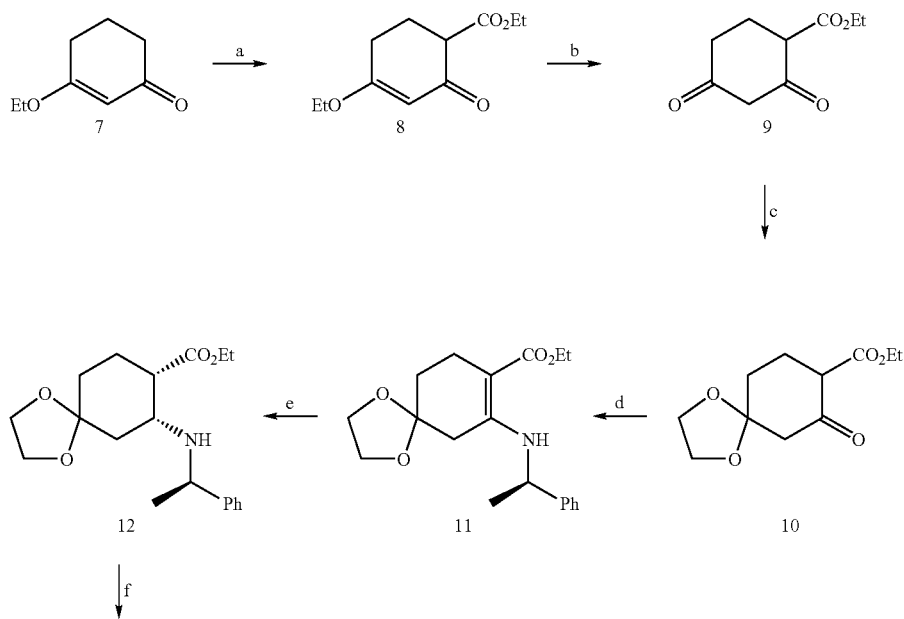

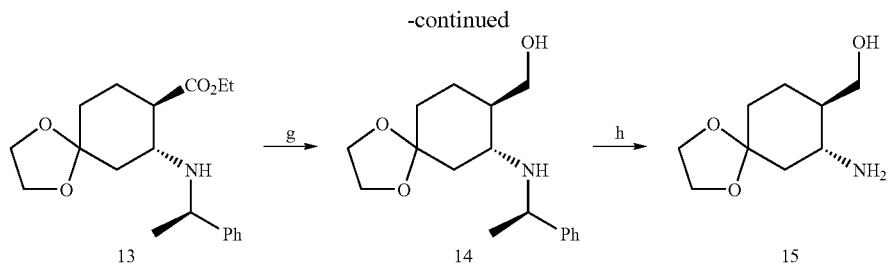

a. 2 eq. LiHMDS, 2 eq. (EtO)₂CO, THF. b. 70% aq. HOAc, 60° C. c. ethylene glycol, p-TsOH, benzene. d. (R)-(+)-α-methylbenzylamine, HOAc, benzene. e. Na(OAc)₃BH, HOAc, ethylene glycol, CH₂Cl₂. f. NaOtBu, THF. g. LiAlH₄, ether. h. H₂, Pd(OH)₂, methanol.

Introduction of the substitution group $R^{14}$ is shown in Scheme 3. (1R,2R)-amino-alcohol 15 is selectively protected on the nitrogen with benzyl chloroformate in the presence of aqueous sodium carbonate to give the CBz-protected amino-alcohol 16. A Swern oxidation of the alcohol gives the corresponding aldehyde 17. It is then coupled with an amine ($R^4R^5NH$) by a reductive amination with sodium triacetoxyborohydride or sodium cyanoborohydride to afford the 2-aminomethyl-cyclohexylamine derivative 18. The ketal of the intermediate 18 is hydrolyzed with 1N HCl in acetonitrile to give the ketone 19. A reductive amination of the ketone 19 with methyl amine or methyl amine hydrochloride and sodium cyanoborohydride or sodium triacetoxyborohydride in methylene chloride, dichloroethane or methanol gives the methyl amine derivative 20 ($R^{14a}$=CH₃, $R^{14b}$=H). The methylamino group can be converted to an amide or an sulfonamide using a suitable acylating or sulfonylating agent. Other $R^{14}$ groups can be introduced either directly through the ketone 19 or through the corresponding alcohol, which can be obtained by a reduction of the ketone 19. The CBz-protecting group of the amine of the intermediate 20 is removed by a catalytic hydrogenation to give the free amine 21, which is reacted with an isocyanate, a thioisocyanate or a phenyl carbamate to give the urea 22, a compound of formula (I). Examples 9-32 were prepared according to this scheme.

SCHEME 3

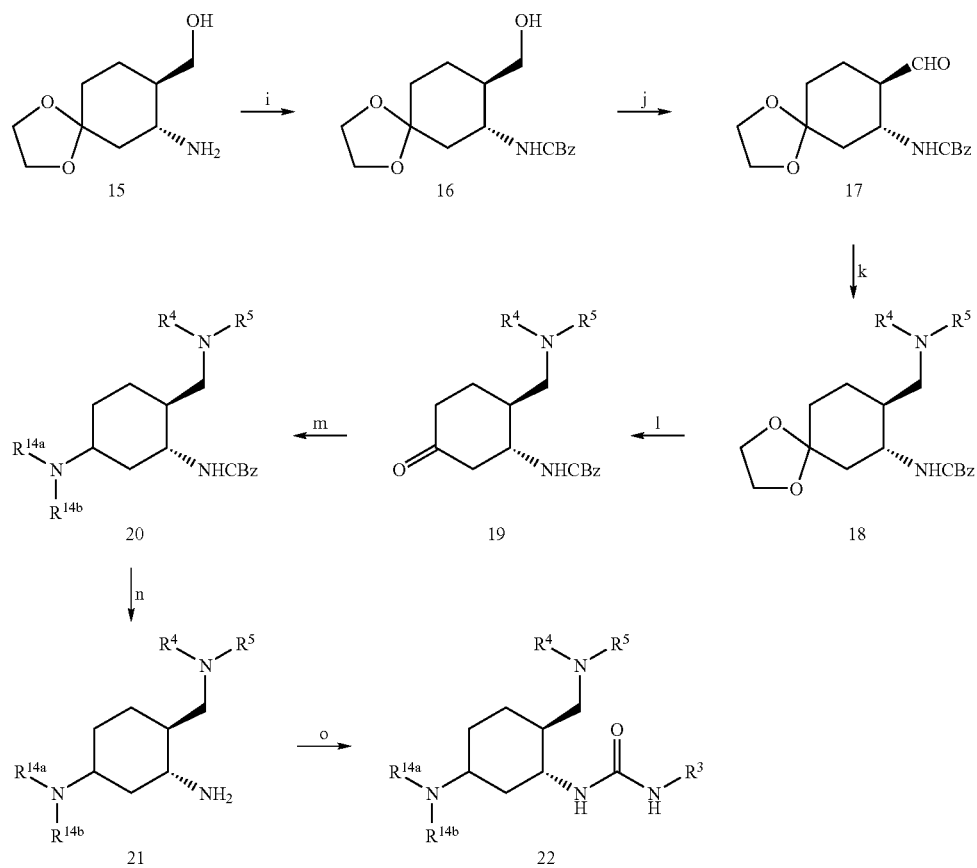

i. Benzyl chloroformate, aq. $Na_2CO_3$, $CH_2Cl_2$. j. DMSO, $(COCl)_2$, $NEt_3$, $CH_2Cl_2$. k. $R^4R^5NH$, $Na(OAc)_3BH$, $CH_2Cl_2$. l. 1N HCl, $CH_3CN$. m. $R^{14a}R^{14b}NH$, $Na(OAc)_3BH$, $CH_2Cl_2$. n. $H_2$, 10% Pd/C, MeOH, o. $R^3NCO$ or $R^3NHCOOPh$, THF.

Compounds of formula (I), where $R^{14}$ is not H at the 4-position of the cyclohexyl urea, can be synthesized as outlined in Schemes 4-5. The mono-protected 1,4-cyclohexane-dione (23) is acylated with excess diethyl carbonate and sodium hydride to give the keto-ester 24. It is then treated with R-(+)-α-methylbenzylamine in the presence of catalytic amount of ytterbium triflate [$Yb(OTf)_3$] in benzene to give the enamine 25. The enamine is reduced with sodium triacetoxyborohydride in acetic acid and acetonitrile to give the (1R,2S)-cis-amino-ester 26. The ester is then isomerized with sodium tert-butoxide in THF to give the (1R,2R)-trans-amino-ester 27, which is reduced to the corresponding alcohol 28 with lithium aluminum hydride. Removal of the chiral auxiliary under a catalytic hydrogenolysis condition with palladium hydroxide gives (1R,2R)-amino-alcohol 29.

a. NaH, $(EtO)_2CO$, THF. b. (R)-(+)-α-methylbenzylamine, $Yb(OTf)_3$, benzene.e. $Na(OAc)_3BH$, $CH_3CO_2H$, $CH_3CN$. f. NaOtBu, THF. g. $LiAlH_4$, ether. h. $H_2$, 20% $Pd(OH)_2$, methanol.

Introduction of the substitution group $R^{14}$ is shown in Scheme 5. (1R,2R)-amino-alcohol 29 is selectively protected on the nitrogen with benzyl chloroformate in the presence of aqueous sodium carbonate to give the CBz-protected amino-alcohol 30. A Swern oxidation of the alcohol gives the corresponding aldehyde 31. It is then coupled with an amine ($R^4R^5NH$) by a reductive amination with sodium triacetoxyborohydride or sodium cyanoborohydride to afford the 2-aminomethyl-cyclohexylamine derivative 32. The ketal of the intermediate 32 is hydrolyzed with 1N HCl in acetonitrile to give the ketone 33. A reductive amination of the ketone 33 with methyl amine or methyl amine hydrochloride and sodium cyanoborohydride or sodium triacetoxyborohydride in methylene chloride, dichloroethane or methanol gives the methyl amine derivative 34 ($R^{14a}=CH_3$, $R^{14b}=H$). The methylamino group can be

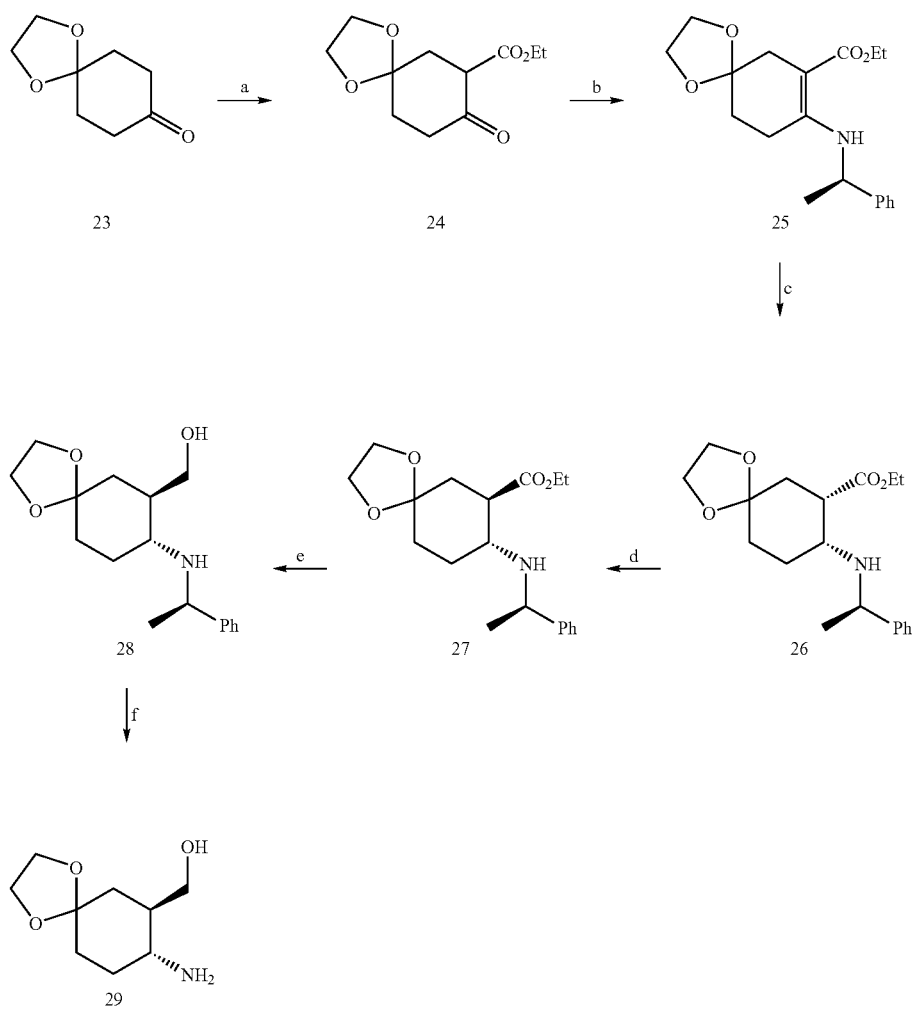

SCHEME 4.

converted to an amide or an sulfonamide using a suitable acylating or sulfonylating agent. Other R¹⁴ groups can be introduced either directly through the ketone 33 or through the corresponding alcohol, which can be obtained by a reduction of the ketone 33. The CBz-protecting group of the amine of the intermediate 34 is removed by a catalytic hydrogenation to give the free amine 35, which is reacted with an isocyanate, a thioisocyanate or a phenyl carbamate to give the urea 36, a compound of formula (I). Examples 33-40 were prepared according to this scheme.

with BOC anhydride in the presence of aqueous sodium carbonate to give the BOC-protected amino-alcohol 37. The alcohol 37 is converted to a leaving group such as a tosylate 38, which is prepared by treating the alcohol with a p-toluenesulfonyl chloride in pyridine. The tosylate 38 is displaced with sodium azide in dimethylformamide to provide the azide 39, which is reduced to the corresponding amine 40 under the catalytic hydrogenation condition with palladium on carbon catalyst. Reaction of the amine 41 with an isocyanate, a thioisocyanate or a phenyl carbamate affords

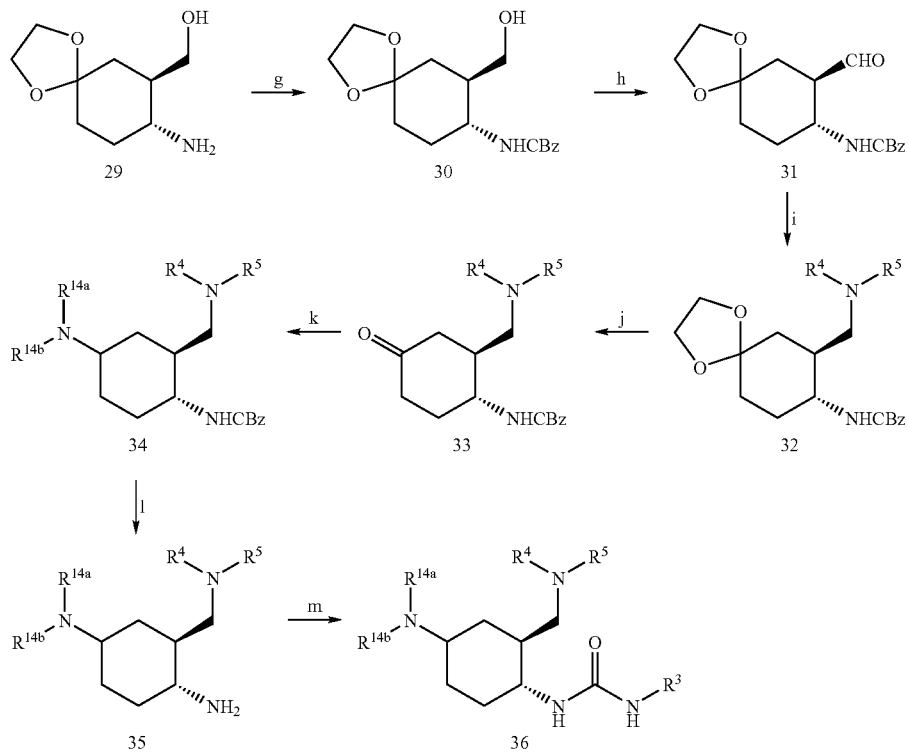

g. Benzyl chloroformate, aq. Na₂CO₃, CH₂Cl₂. h. DMSO, (COCl)₂, NEt₃, CH₂Cl₂. i. R⁴R⁵NH, Na(OAc)₃BH, CH₂Cl₂. j. 1N HCl, CH₃CN. k. R¹⁴ᵃR¹⁴ᵇNH, Na(OAc)₃BH, CH₂Cl₂. l. H₂, 10% Pd/C, MeOH, m. R³NCO or R³NHCO₂Ph, THF.

Compounds of formula (I), where the ring A of E is directly attached to NR⁴R⁵, can be synthesized as outlined in Schemes 6. The (1R,2R)-2-hydroxmethylcyclohexylamine 1 (*J. Am. Chem. Soc.* 1996, 118, 5502-5503 and references therein), is selectively protected on the nitrogen the desired urea 41. The protecting group on the amine of the urea 41, is then deprotected under a suitable condition to give the free amine 42. The R5 is introduced by a reductive amination with the corresponding aldehyde and sodium cyanoborohydride or sodium triacetoxyborohydride to afford a secondary amine 43, a compound of formula (I). Another reductive amination with the amine 43 yields a tertiary amine 44, a compound of formula (I). Examples 41-46 were prepared according to this scheme.

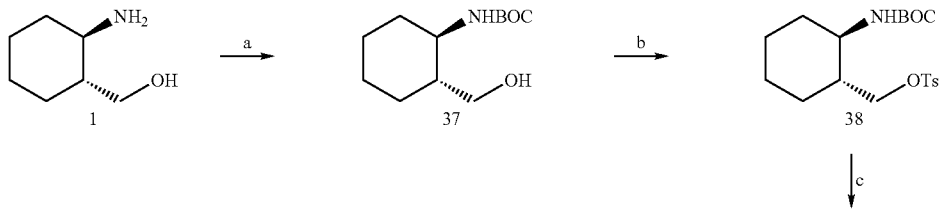

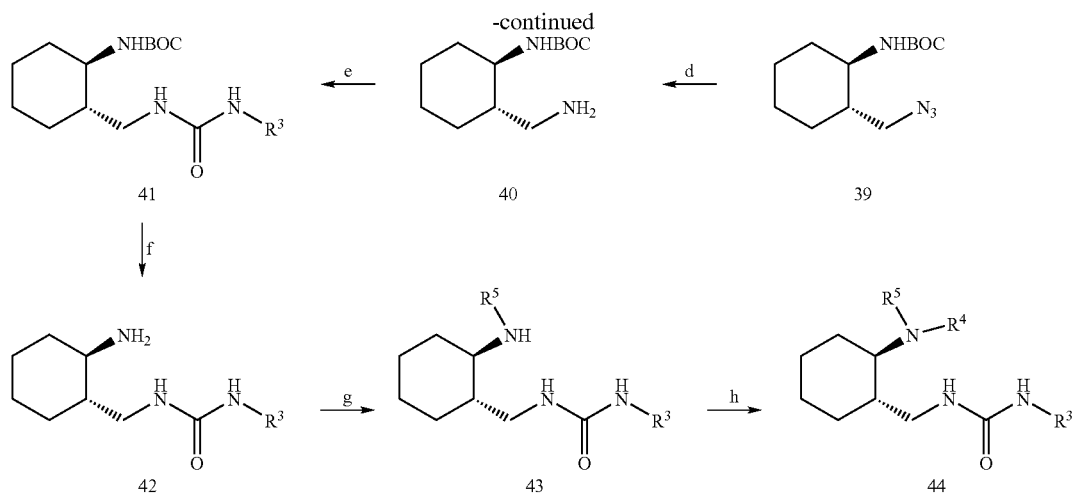

a. (BOC)$_2$O, aq. Na$_2$CO$_3$, CH$_2$Cl$_2$. b. p-TsCl, pyridine. c. NaN$_3$, DMF. d. H$_2$, 10% Pd/C, MeOH. e. R$^3$NCO or R$^3$NHCO$_2$Ph, THF. f. trifluoroacetic acid, CH$_2$Cl$_2$. g. R$^{5'}$CHO, Na(OAc)$_3$BH, CH$_2$Cl$_2$. h. R$^4$ CHO, Na(OAc)$_3$BH, CH$_2$Cl$_2$.

Acyclic linkers between the basic nitrogen and urea nitrogen can be synthesized as shown in Scheme 7. Amine V can be coupled to acrylic acid derivative 45 using a number of coupling reagents such as DCC, PyBOP, etc., by methods which are familiar to one skilled in the art, to yield amide 46. Chiral addition of amine 47 as it's lithium salt under the conditions of Davies (M. E. Bunage, . . . S. G. Davies, et al., J. Chem Soc. P1, (1994) 2373-2384; S. G. Davies, et al., J. Chem Soc. P1, (1994) 1129-1139; S. G. Davies, et al., J. Chem Soc. P1, (1994) 1141-1147; S. G. Davies, et al., Synlett, (1995), 700-702 and references therein) with optional quenching with an electrophile such as oxygen (Davies, ibid.) yields amide 48. Optional alkylation (Davies, ibid.)of 48 (R'=H) using LDA and quenching with an electrophile R"X where X is a leaving group such as halogen, mesylate, tosylate, etc., yields disubstituted linker 49. Reduction of the amide bond with diborane or LAH at room temperature to the refluxing temperature of the solvent yields diamine 50. Reduction of the 2 benzyl groups yields 51 which can be subsequently coupled as previously described to yield ureas and urea isosteres of formula (I).

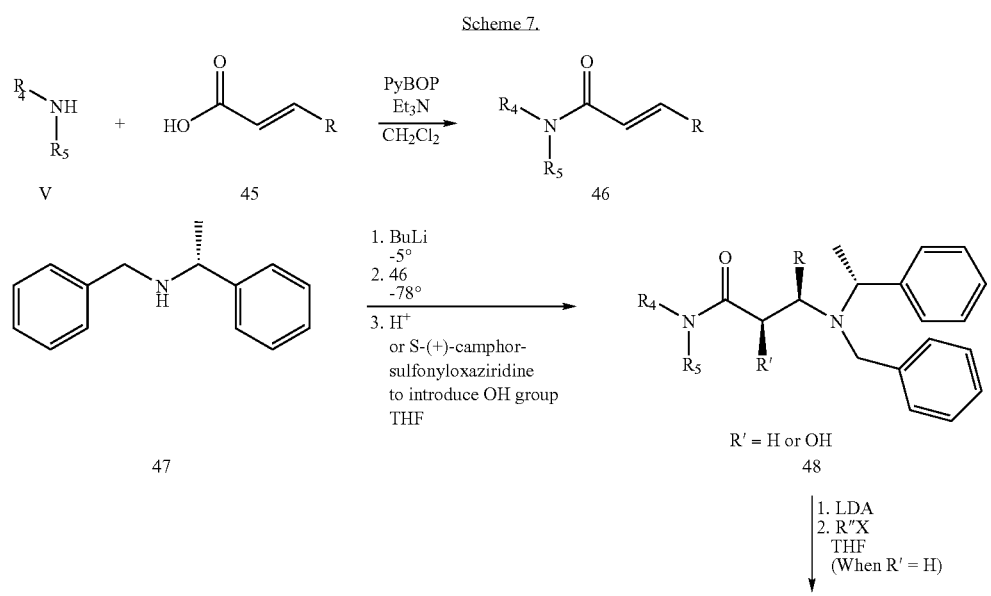

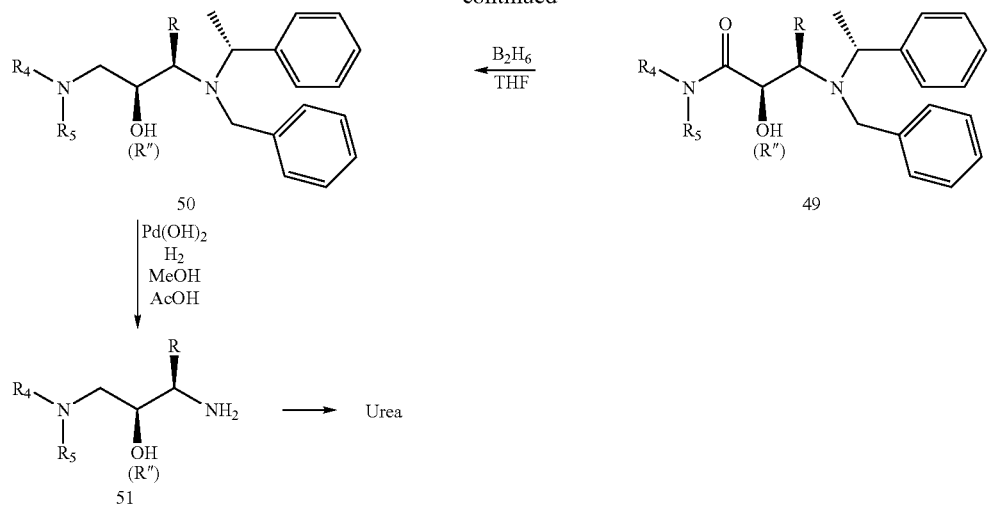

Another route to the acyclic linkers is shown in Scheme 8. Aminoacid 52 can be converted into aminoaldehyde 53 by the method of Beaulieu and Wernic, JOC (1996), 61, 3635-3645. Reaction with bromomethyllithium by the method of Ng (J. S. Ng, et al., Tetrahedron, 1995, 51, 6397-6410) yields epoxide 54. Reaction with amine V yields diaminoalcohol 55. Hydrogenation of the benzyl groups yields deprotected amine 56. Diamine 56 can be coupled to

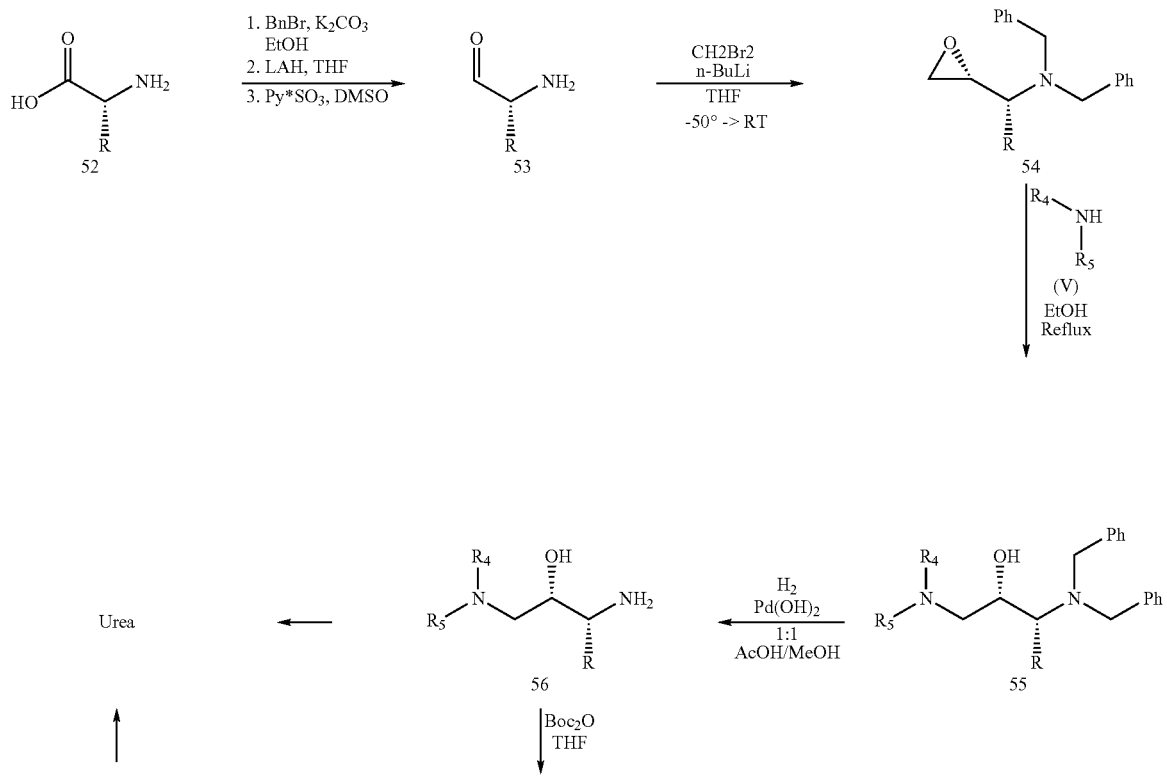

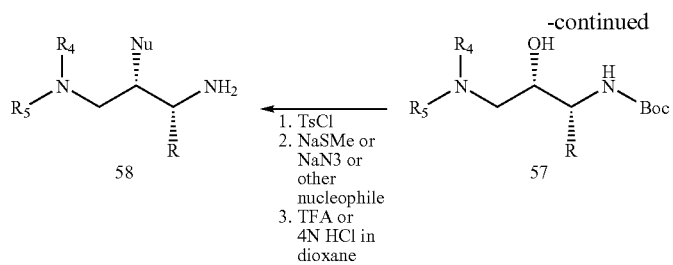

form urea I (or a urea isostere) by methods previously discussed in this application. Alternatively, protection of the amino group 56 with a BOC group (57) and subsequent activation of the hydroxyl group followed by nucleophilic displacement, followed by removal of the BOC group yields compound 58 in which the nucleophile has added with retention of configuration (M. Kossenjans, J. Chem. Soc., Perkin Trans. 1, (1999), 2353-2365). Compound 58 can in turn be converted to urea I (or a urea isostere) by methods discussed previously.

Another route to substituted acyclic linkers is shown in Scheme 9. Aminoester 59 can be reacted with chlor-oiodomethane in the presence of LDA at −65° C. to yield a chloroketone derivative which can be subsequently reduced stereoselectively by a variety of reducing agents, one of which is NaBH$_4$, to yield chlorohydrin 60 (Polniaszak, et. al., Tet. Lett., (1997), 38, 3175). Base promoted ring closure yields epoxide 61. Subsequent reaction with amine V yields diamine 62. Deprotection yields 63 which can be taken on to urea I (or a urea isostere). Alternatively, alcohol 62 can undergo nucleophilic displacement once the hydroxyl is activated to become a leaving group. Nucleophilic displacement occurs with retention of stereochemistry (M. Kossenjans, ibid.)to yield 64. Deprotection of 64 and coupling to form a urea or its isostere leads to compound I.

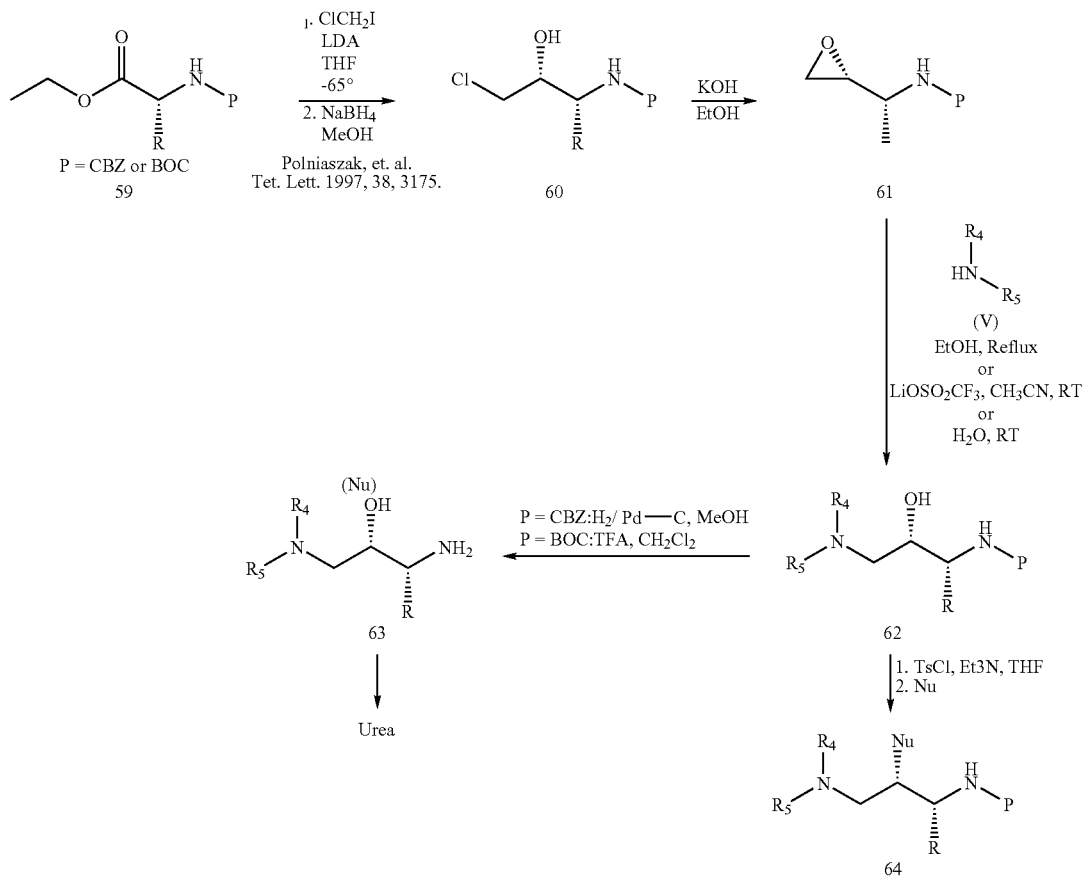

Another synthesis of amines V is shown in Scheme 10. Alcohol 65 can be converted into bromide 66 by methods familiar to one skilled in the art, one of which is using phosphorous tribromide. Subsequent displacement by a nitrogen nucleophile such as potassium phthalimide or sodium azide followed by deprotection with hydrazine or hydrogenation, respectively, yields amine 67 (V, where $R^4$=H). Subsequent reductive amination yields amine V. Alternatively, bromide 66 can react with $R^4NH_2$ to yield V. It is to be understood that bromide 66 can also be in the form of a tosylate or mesylate or chloride or iodide of 65 which can undergo the same nucleophilic displacements by nitrogen nucleophiles.

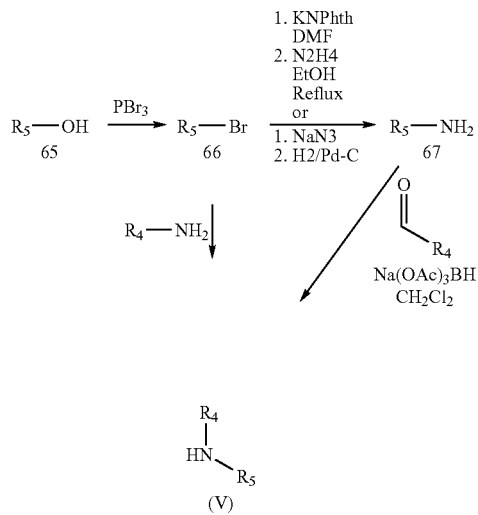

Scheme 10.

Amines V where there is a heteroatom spacer in the linker between the aryl or heterocyclic group and the nitrogen atom can be synthesized by the route shown in Scheme 11.

Alcohol, amine, or thiol 67a is alkylated with bromoalkylphthalimide where n=2-4 with or without base to yield ether, amine, or thioether 67b. If 67b is a phthalimidoamine, then the amine can be reductively aminated at this point. Subsequent removal of the phthalimide protecting group yields ether, amine, or thioether 67c. Reductive amination of the primary amine puts on a $R^4$ group yielding compound V.

Amines V can be synthesized by another route as shown in Scheme 12. Methyl or ethylacetate (or any other ester of acetic acid, or acetic acid coupled with a chiral auxilliary, such as the Evans oxazolidinones) can be alkylated with 3 different R groups to eventually form ester 68. Saponification yields carboxylic acid 69; coupling with $R^4NH_2$ yields amide 72; reduction with LAH or diborane yields amine 73 (V). Acid 69 can undergo Curtis rearrangement to eventually form amine 70. Reductive amination as described elsewhere in this application yields amine 71 (V).

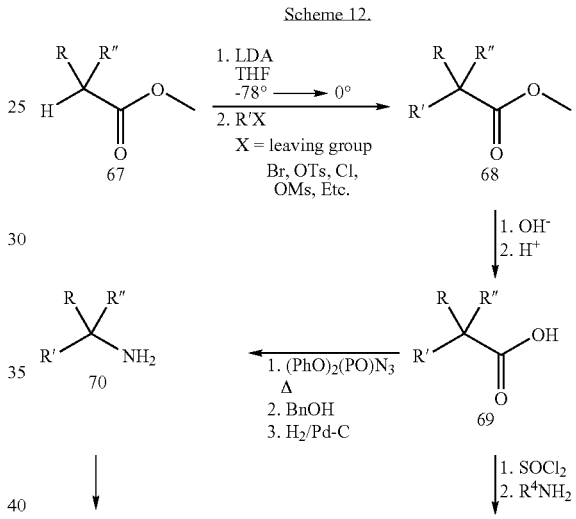

Scheme 12.

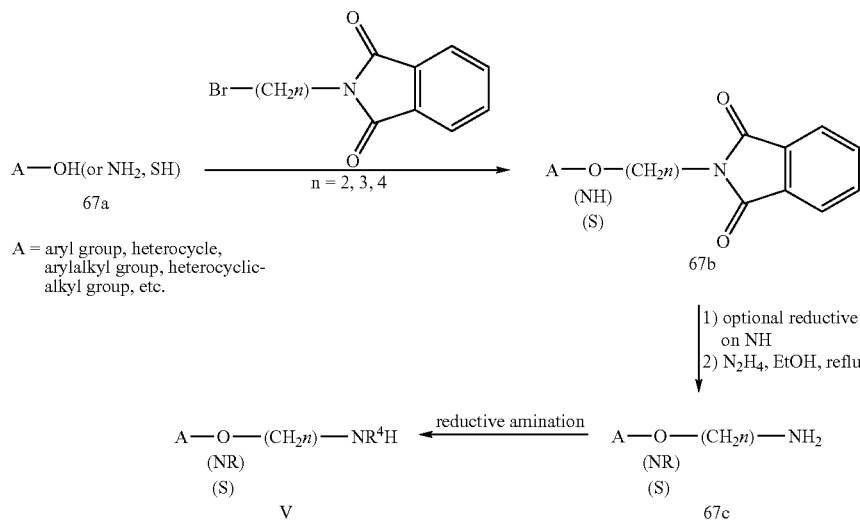

Scheme 11

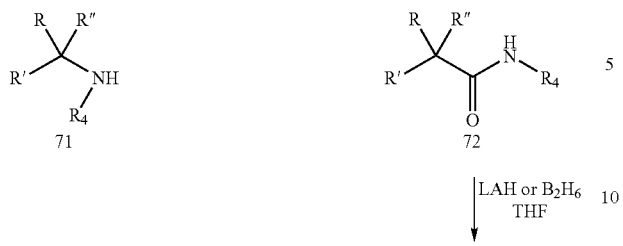

(for a preparation see Beaulieu, ibid.) (only one enantiomer is drawn for the sake of clarity in Scheme 13. Howerver, it is understood that either enantiomer can be used.) undergoes Wittig or Horner-Emmons reactions to yield olefin 86. Selective hydrogenation without acid at one atmosphere for a short while yields protected amine 87. Deprotection and reductive amination yields amine V (89). To introduce a second chiral center the Weinreb amide derivative of a protected aminoacid (90) can react with either Grignard or lithium reagents to yield ketone 91.

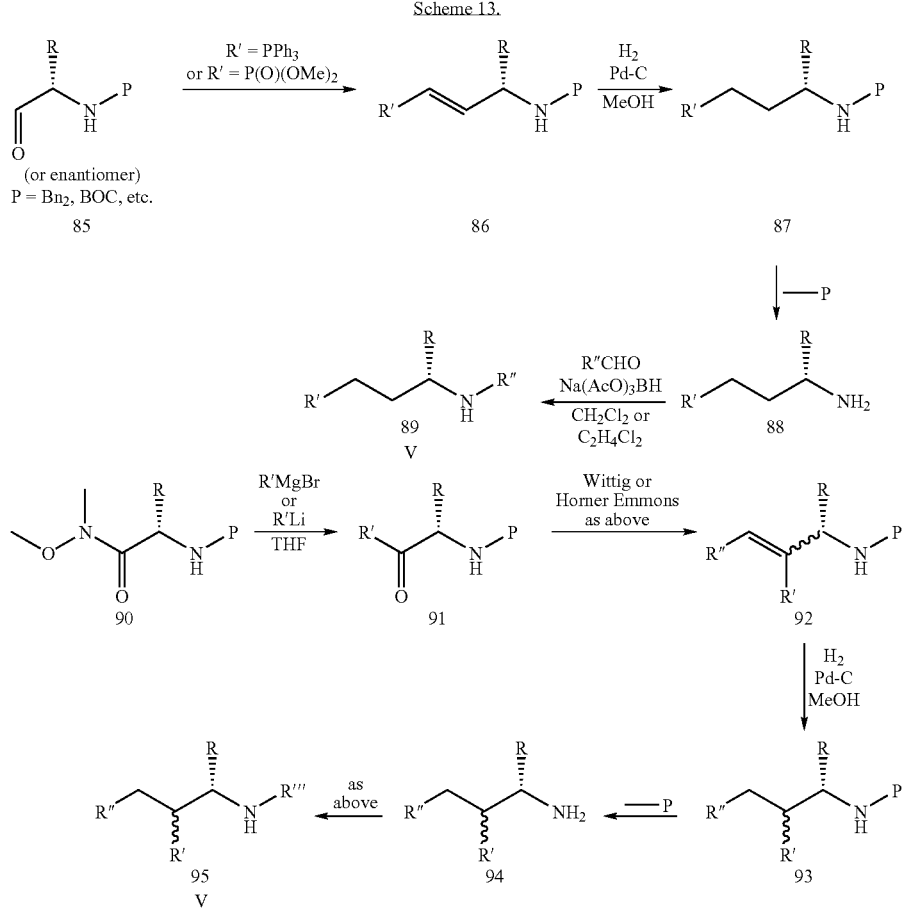

Amines V where there is chiral substitution in the molecule can be synthesized in Scheme 13. Aminoaldehyde 85

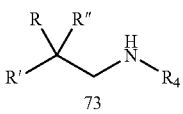

Further elaboration as was done previously yields amine V (95) which now contains 2 chiral centers, one of which is fixed. This mixture of 2 diastereomers can be separated by chromatography or crystallization into discrete isomers by methods familiar to one skilled in the art.

Ureas and thioureas I may be synthesized by the methods shown in Scheme 14. Reaction of 95a with a chloroformate or chlorothioformate 95d (Z=O, S) such as o-, p-nitrophenyl-chloroformate or phenylchloroformate (or their thiocarbonyl equivalents), followed by displacement with an amine 95 g, yields the corresponding urea or thiourea 95b. Likewise, reaction of carbamate 95f (Y=H, or 2- or 4-NO$_2$) with disubstituted amine 95e yields trisubstituted urea or thiourea 95 h. Reaction of the amine 95a with an N,N-disubstituted carbamoyl chloride 95i (or its thiocarbonyl equivalent) yields the corresponding N,N-disubstituted urea or thiourea 95h. Similarly, 95a can react with the phenylcarbamate, o-, p-nitrophenylcarbamate (or the thio equivalent) of an aniline or aminoheterocycle to yield 95b (not shown in Scheme 14). Sometimes $R^4$ or $R^5$ (but not both)=H in 95a. Reaction with isocyanate 95c or with a phenyl carbamate of an aniline or aminoheterocycle (not shown) will yield 95b where $R^4$ or $R^5$=H. Subsequent reductive amination with an aldehyde or ketone introduces the $R^4$ or $R^5$ group in the last step to yield 95b where $R^4$ and $R^5$ are both not equal to H.

such as THF, toluene, DMF, $CH_3CN$, etc., at room temperature to the reflux temperature of the solvent and can optionally employ the use of an acid scavenger or base when necessary such as carbonate and bicarbonate salts, triethylamine, DBU, Huenig's base, DMAP, etc. One can also make ureas (or thioureas) using the phenylcarbamates (or thiocarbamates) of amine 51,56,58,63 or any other amine of formula 95a (and substituted phenylcarbamates such as nitrophenylcarbamates), and reacting them with anilines or aminoheterocycles to yield urea or thiourea I.

The cyanoguanidines (Z=N—CN) can be synthesized by the method of K. S. Atwal, et al. and references contained

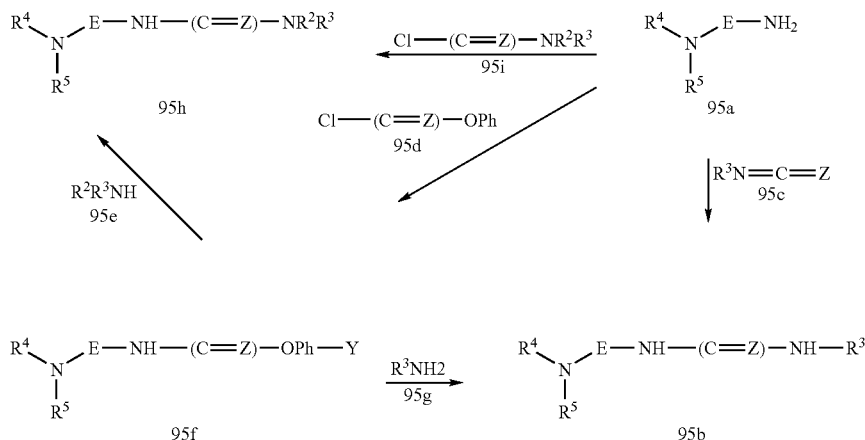

SCHEME 14

Y = H, o- or p-NO2

One can also convert anilines or aminoheterocycles into isocyanates, isothiocyanates, carbamoyl chlorides or its thiocarbonyl equivalent (isocyanate: Nowakowski, J. J Prakt. Chem/Chem-Ztg 1996, 338 (7), 667-671; Knoelker, H.-J. et al., Angew. Chem. 1995, 107 (22), 2746-2749; Nowick, J. S. et al., J. Org. Chem. 1996, 61 (11), 3929-3934; Staab, H. A.; Benz, W.; Angew Chem 1961, 73; isothiocyanate: Strekowski L. et al., J. Heterocycl. Chem. 1996, 33 (6), 1685-1688; Kutschy, Pet al., Synlett. 1997, (3), 289-290) carbamoyl chloride: Hintze, F.; Hoppe, D.; Synthesis (1992) 12, 1216-1218; thiocarbamoyl chloride: Ried, W.; Hillenbrand, H.; Oertel, G.; Justus Liebigs Ann Chem 1954, 590) (these reactions are not shown). These isocyanates, isothiocyantes, carbamoyl chlorides or thiocarbamoyl chlorides can then be reacted with 51,56,58,63 or any other amine of formula 95a to yield ureas or thioureas. An additional urea forming reaction involves the reaction of carbonyldiimidazole (CDI) (Romine, J. L.; Martin, S. W.; Meanwell, N. A.; Epperson, J. R.; Synthesis 1994 (8), 846-850) with an aniline or aminoheterocycle followed by reaction of the intermediate imidazolide with 51,56,58,63 or any other amine of formula 95a, or in the reversed sequence (51,56,58,63 or any other amine of formula 95a+CDI, followed by aniline or aminoheterocycle). Activation of imidazolide intermediates also facilitates urea formation (Bailey, R. A., et al., Tet. Lett. 1998, 39, 6267-6270). The urea forming reactions are done in an aprotic inert solvent therein (J. Med. Chem. (1998) 41, 217-275). The nitroethylene analog (Z=C—$NO_2$) can be synthesized by the method of F. Moimas, et al. (Synthesis 1985, 509-510) and references contained therein. The malononitrile analog (Z=C $(CN)_2$) may be synthesized by the method of S. Sasho, et al. (J. Med. Chem. 1993, 36, 572-579).

Guanidines (Z=$NR^{1a}$) can be synthesized by the methods outlined in Scheme 15. Compound 96 where Z=S can be methylated to yield the methylisothiourea 97. Displacement of the SMe group with amines yields substituted guanidines 98 (see H. King and I. M. Tonkin J. Chem. Soc. 1946, 1063 and references therein). Alternatively, reaction of thiourea 96 with amines in the presence of triethanolamine and "lac sulfur" which facilitates the removal of $H_2S$ yields substituted guanidines 98 (K. Ramadas, Tet. Lett. 1996, 37, 5161 and references therein). Finally, the use of imidoyldichloride 99, or 100 followed by sequential displacements by amines yields the corresponding substituted guanidine 98 (S. Nagarajan, et al., Syn. Comm. 1992, 22, 1191-8 and references therein). In a similar manner, imidoyldichlorides, $R_2$—N=C $(Cl)_2$ (not shown in Scheme 15) and $R^3$—N=C$(Cl)_2$ (not shown) can also be reacted sequentially with amines to yield di- and trisubstituted guanidine 98.

SCHEME 15

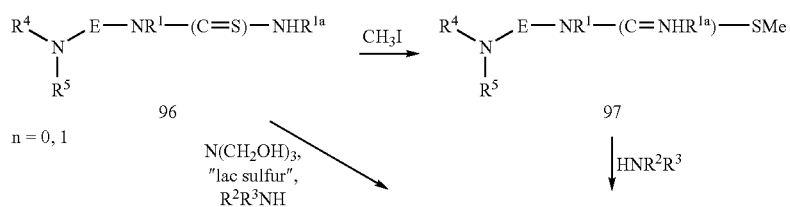

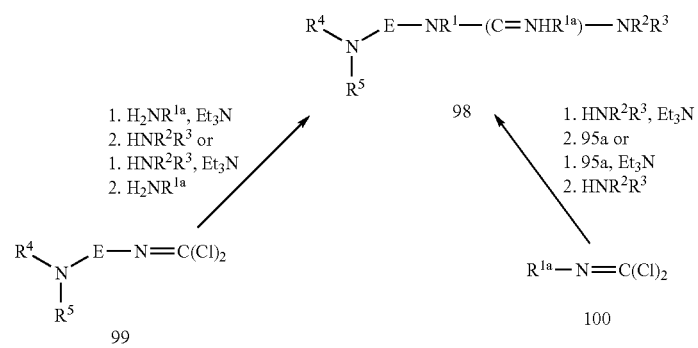

A method for the synthesis of N-(heterocyclic)alkyls at $R^5$ is shown in Scheme 19. The heterocycle can be deprotonated with NaH or by other bases familiar to one skilled in the art, in a solvent such as DMF, THF, or another appropriate aprotic solvent and reacted with 119 at room temperature to the reflux temperature of the solvent. Note that for the sake of clarity, no substitution was drawn on each of the methylene groups of 119 and 120. However, one can have different substituents on those methylene groups which are compatible with reaction conditions. These substituents can be in precursor or final form. They can be transformed into other substituents by methods familiar to one skilled in the art. Deprotection and elaboration as described before yields compounds where $R^5$ contains an N-substituted heterocycle. If the nitrogen atom of the heterocycle is sufficiently nucleophilic, then an acid scavenger, such as $K_2CO_3$, $KHCO_3$, $Na_2CO_3$, $NaHCO_3$, amongst others, can be used in place of NaH, employing THF, DMF, or methyl ethyl ketone as solvents. In this case hydroxylic solvents may be used as well, such as methanol, ethanol, etc. from room temperature to the reflux temperature of the solvent.

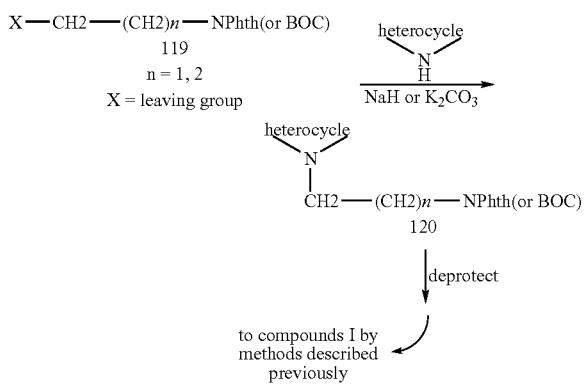

A method for the synthesis of C-substituted heterocyclic alkyls at $R^5$ is shown in Scheme 20. Many heterocycles such as the ones shown in Scheme 20, but not limited thereto, can be metallated with strong bases such as LDA, n-BuLi, sec-BuLi, t-BuLi, etc. to yield the corresponding anionic species. These anions may also be generated via halogen-metal exchange employing n-BuLi, or other alkyllithium reagents. These reactions may be performed in THF, ether, dioxane, DME, benzene, etc. at −78° C. to room temperature.

SCHEME 20

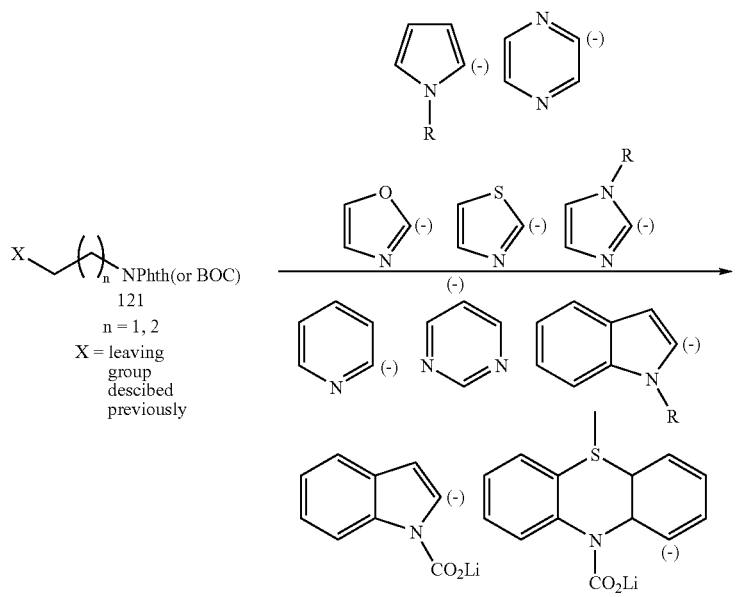

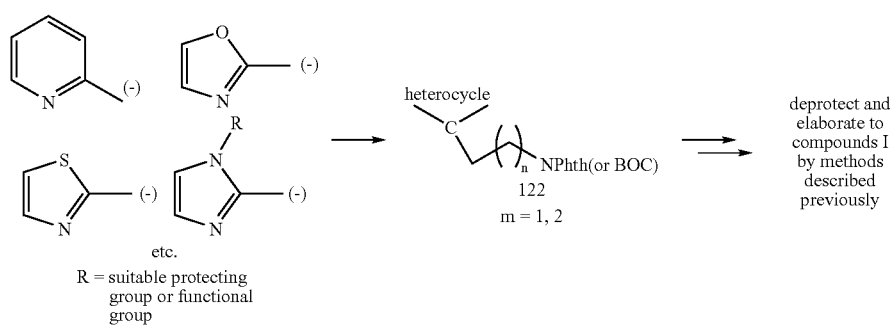

For reviews of these metallations and halogen-metal exchange reactions see Organometallics in Organic Synthesis, FMC Corp., Lithium Division, 1993, pp. 17-39; Lithium Link, FMC Corp., Spring 1993, pp. 2-17; n-Butyllithium in Organic Synthesis, Lithium Corp. of America, 1982, pp. 8-16; G. Heinisch, T. Langer, P. Lukavsky, J. Het. Chem. 1997, 34, 17-19. The anions can then be quenched with electrophile 121. It is to be understood that each methylene group of 121 can be appropriately substituted and that the substituents where omitted for sake of clarity.

SCHEME 21

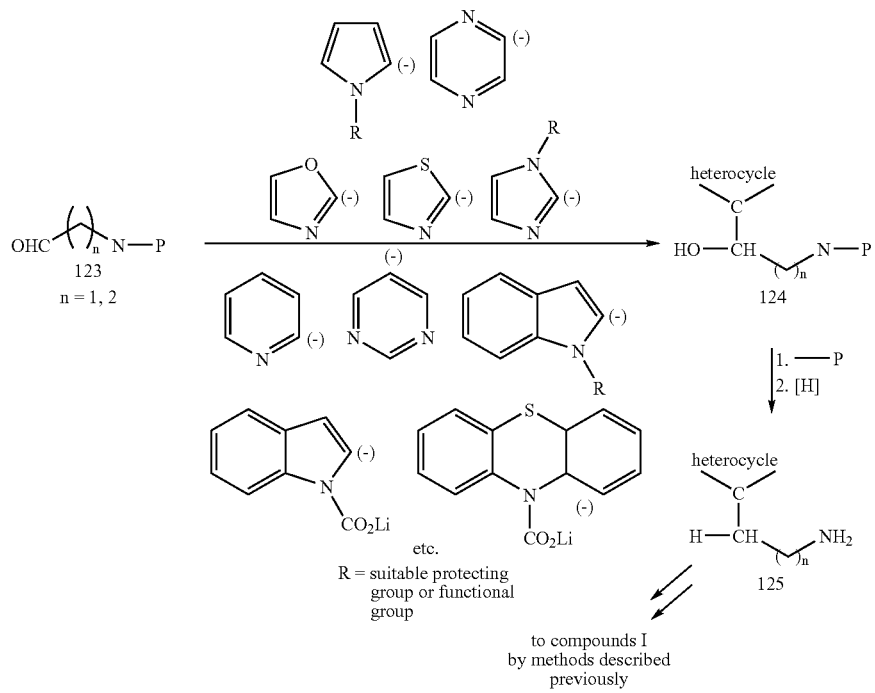

Another method for the synthesis of C-substituted heterocyclic alkyl $R^5$ groups is shown in Scheme 21. The protected aldehyde 123 is reacted with the anion of the heterocycle (its generation as described previously) at −78° C. to room temperature with or without $CeCl_3$ in an inert solvent such as THF, ether, dioxane, DME, benzene, etc. to yield carbinol 124 Catalytic hydrogenation of the alcohol yields the corresponding methylene compound 125. Other reduction methods include $Et_3SiH/TFA$ (J. Org. Chem. 1969, 34, 4; J. Org. Chem. 1987, 52, 2226) amongst others familiar to one skilled in the art. It is to be understood that each methylene group of 123 can be appropriately substituted and that the substituents where omitted for sake of clarity.

The anions of the methyl-substituted heterocycles may also be reacted with 126 to yield alcohols 127 as shown in Scheme 22 (see above reviews on metallations for references). The OH may be reduced by the method of Barton (Barton, D. H. R.; Jaszberenyi, J. C. Tet. Lett. 1989, 30, 2619 and other references therein) to yield 128. These can subsequently be taken on to the compounds of this invention as described previously. It is to be understood that each methylene group of 126 can be appropriately substituted and that the substituents where omitted for sake of clarity.

SCHEME 22

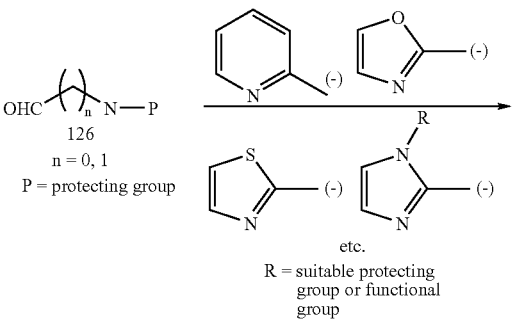

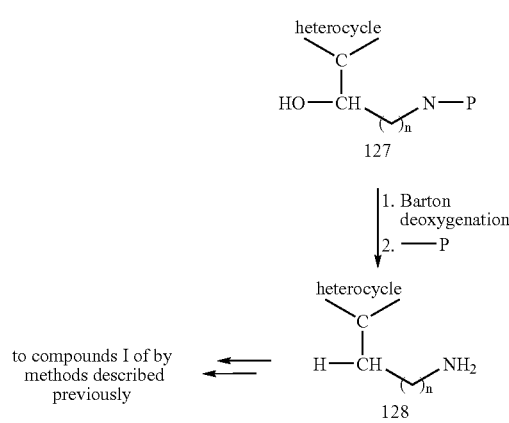

One may also react aryl (phenyl, naphthyl, etc.) anions, generated either by halogen-metal exchange or by ortho-directed metallation (Snieckus, V. Chem. Rev. 1990, 90, 879-933) using n- or s- or t-BuLi in an aprotic solvent such as THF, ether, etc., with or without TMEDA and allow them to react with compounds 121, 123, and 126 with subsequent elaboration to yield the compounds of this invention.

Another method for the preparation of C-substituted heterocycles is shown in Scheme 23. Protected 129 undergoes a Wittig reaction with heterocyclic phosphorous ylides to yield 130. Hydrogenation over a noble metal catalyst such as Pd in an alcoholic solvent or with an optically active transition metal catalyst (see asymmetric hydrogenation references of Parshall and Coleman, op. cit.) yields 131 which can be further elaborated into the compounds of this invention by the procedures described previously. It is to be understood that each methylene group of 129 can be appropriately substituted and that the substituents were omitted for sake of clarity.

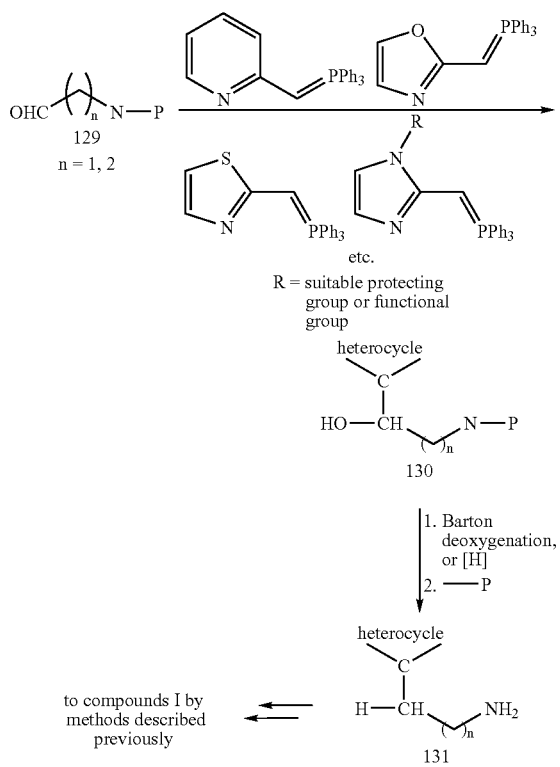

compounds (131a and 133) can then be reduced to the corresponding amines either via catalytic hydrogenation, or via a number of chemical methods such as Zn/CaCl$_2$ (Sawicki, E. J Org Chem 1956, 21). The carbonyl insertion compounds (134) can also undergo reduction of the carbonyl group to either the CHOH or CH2 linkages by methods already discussed (NaBH$_4$ or Et$_3$SiH, TFA, etc.). These amines can then be converted to isocyanates via the following methods (Nowakowski, J. J Prakt Chem/Chem-Ztg 1996, 338 (7), 667-671; Knoelker, H.-J. et al., Angew Chem 1995, 107 (22), 2746-2749; Nowick, J. S. et al., J Org Chem 1996, 61 (11), 3929-3934; Staab, H. A.; Benz, W.; Angew Chem 1961, 73); to isothiocyanates via the following methods (Strekowski L. et al., J Heterocycl Chem 1996, 33 (6), 1685-1688; Kutschy, Pet al., Synlett 1997, (3), 289-290); to carbamoyl chlorides (after 132 or 134 is reductively aminated with an R$^4$ group) (Hintze, F.; Hoppe, D.; Synthesis (1992) 12, 1216-1218); to thiocarbamoyl chlorides (after 132 or 134 is reductively aminated with an R$^4$ group) (Ried, W.; Hillenbrand, H.; Oertel, G.; Justus Liebigs Ann Chem 1954, 590) in synthesizing the compounds of this invention by the methods described previously.

Nitrobenzoic acids are precursors to N-monosubstituted nitrobenzamides which can be converted to tetrazoles by the method of Duncia, J. V. et al., J. Org. Chem., 1991, 56, 2395-2400, or by the method of Thomas, E., Synthesis (1993) 767-768 (and other methods familiar to one skilled in the art). These tetrazole-containing nitrobenzenes can be reduced to the corresponding anilines and coupled to make ureas and urea isosteres (i.e., Z is not oxygen in formula (I)) as in previous discussion to make compounds of the present invention. As in the above synthesis of tetrazole-substituted anilines, one can also make other heterocycle-substituted anilines in a similar de novo fashion using reactions familiar to one skilled in the art.

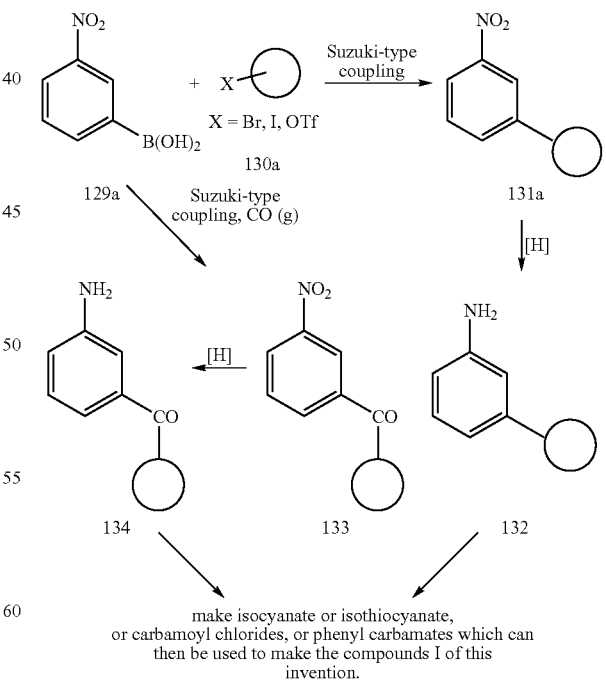

Synthesis of anilines and aminoheterocycles which are precursors to isocyanates, isothiocyanates, phenylcarbamates or thiocarbamates, all of which have been mentioned previously in regards to making ureas and urea isosteres will now be discussed. For example, 3-nitrobenzeneboronic acid (129a: Scheme 24) is commerically available and can undergo Suzuki couplings (Suzuki, A. Pure Appl. Chem. 1991, 63, 419) with a wide variety of substituted iodo- or bromo aryls (aryls such as phenyl, naphthalene, etc.), heterocycles, alkyls, akenyls (Moreno-manas, M., et al., J. Org. Chem., 1995, 60, 2396), or alkynes. It can also undergo coupling with triflates of aryls, heterocycles, etc. (Fu, J.-m, Snieckus, V. Tet. Lett. 1990, 31, 1665-1668). Both of the above reactions can also undergo carbonyl insertion in the presence of an atmosphere of carbon monoxide (Ishiyama, et al., Tet. Lett. 1993, 34, 7595). These nitro-containing Likewise, protected aminobromobenzenes or triflates or protected aminobromoheterocycles or triflates 135 (Scheme 25) may undergo Suzuki-type couplings with arylboronic acids or heterocyclic boronic acids (136). These same bromides or triflates 135 may also undergo Stille-type coupling (Echavarren, A. M., Stille, J. K. J. Am. Chem. Soc., 1987, 109, 5478-5486) with aryl, vinyl, or heterocyclic stannanes 139. Bromides or triflates 135 may also undergo Negishi-type coupling with other aryl or heterocyclic bromides 140 (Negishi E. Accts. Chem. Res. 1982, 15, 340; M. Sletzinger, et al., Tet. Lett. 1985, 26, 2951). Deprotection of the amino group yields an amine which can be coupled to make a urea and other linkers represented by Z as described previously. Amino protecting groups include phthalimide, 2,4-dimethyl pyrrole (S. P. Breukelman, et al. J. Chem. Soc. Perkin Trans. I, 1984, 2801); N-1,1,4,4-Tetramethyldisilyl-azacyclopentane (STABASE) (S. Djuric, J. Venit, and P. Magnus Tet. Lett 1981, 22, 1787) and others familiar to one skilled in the art.

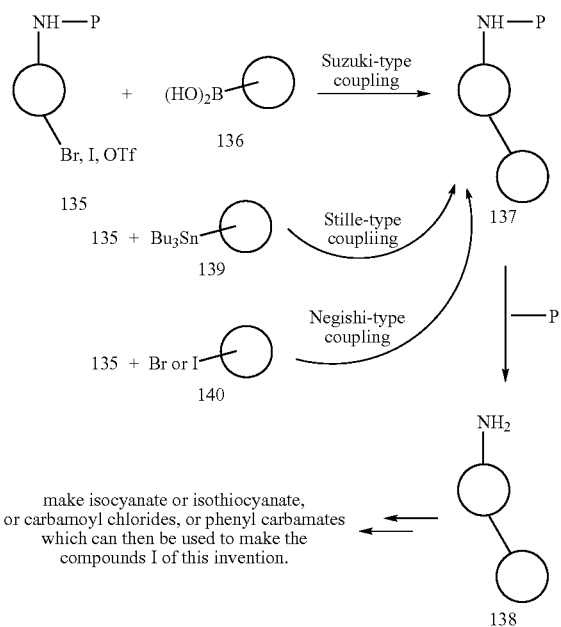

SCHEME 25

Many amines are commercially available and can be converted to isocyanates or isothiocyanates or phenyl carbamates which can be taken on to form ureas and urea isosteres. There are numerous methods for the synthesis of non-commercially available amines familiar to one skilled in the art. For example, aldehydes and ketones may be converted to their O-benzyl oximes and then reduced with LAH to form an amine (Yamazaki, S.; Ukaji, Y.; Navasaka, K.; Bull Chem Soc Jpn 1986, 59, 525). Ketones and trifluoromethylketones undergo reductive amination in the presence of $TiCl_4$ followed by $NaCNBH_4$ to yield amines (Barney, C. L., Huber, E. W., McCarthy, J. R. Tet. Lett. 1990, 31, 5547-5550). Aldehydes and ketones undergo reductive amination with $Na(AcO)_3BH$ as mentioned previously to yield amines (Abdel-Magid, A. F., et al. Tet. Lett. 1990, 31, (39) 5595-5598). Amines may also be synthesized from aromatic and heterocyclic OH groups (for example, phenols) via the Smiles rearrangement (Weidner, J. J., Peet, N. P. J. Het. Chem., 1997, 34, 1857-1860). Azide and nitrile displacements of halides, tosylates, mesylates, triflates, etc. followed by LAH or other types or reduction methods yield amines. Sodium diformyl amide (Yinglin, H., Hongwen, H. Synthesis 1989 122), potassium phthalimide, and bis-BOC-amine anion can all displace halides, tosylates, mesylates, etc., followed by standard deprotection methods to yield amines, procedures which are familiar to one skilled in the art. Other methods to synthesize more elaborate amines involve the Pictet-Spengler reaction, imine/immonium ion Diels-Alder reaction (Larsen, S. D.; Grieco, P. A. J. Am. Chem. Soc. 1985, 107, 1768-69; Grieco, P. A., et al., J. Org. Chem. 1988, 53, 3658-3662; Cabral, J. Laszlo, P. Tet. Lett. 1989, 30, 7237-7238; amide reduction (with LAH or diborane, for example), organometallic addition to imines (Bocoum, A. et al., J. Chem. Soc. Chem. Comm. 1993, 1542-4) and others all of which are familiar to one skilled in the art.

Compounds where Z=N—CN, $CHNO_2$, and $C(CN)_2$ can be synthesized by the methods shown in Scheme 26. Thus amine 142 reacts with malononitrile 141 neat or in an inert solvent at room temperature to the reflux temperature of the solvent, or at the melting point of the solid/solid mixture, to yield malononitrile 143. This in turn can undergo reaction with amine 144 under similar conditions stated just above to yield malononitrile 145. Likewise, a similar reaction sequence may be used to make 148 and 148b [for $Z=C(CN)_2$], see for example P. Traxler, et al., J. Med. Chem. (1997), 40, 3601-3616; for Z=N—CN, see K. S. Atwal, J. Med. Chem. (1998) 41, 271; for $Z=CHNO_2$, see J. M. Hoffman, et al., J. Med. Chem. (1983) 26, 140-144). For all of the above-mentioned urea isosteres in Scheme 26, the reaction sequence can be reversed. For example, malononitrile 141 can react first with 144 followed by 142 to yield 145. The same holds true for nitroethylene 146 and cyanoguanidine intermediate 148c which can also be reacted first with 144 and then secondly with 142.

Scheme 26

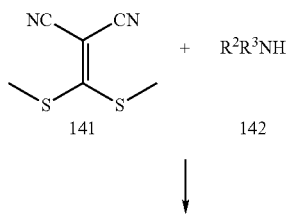

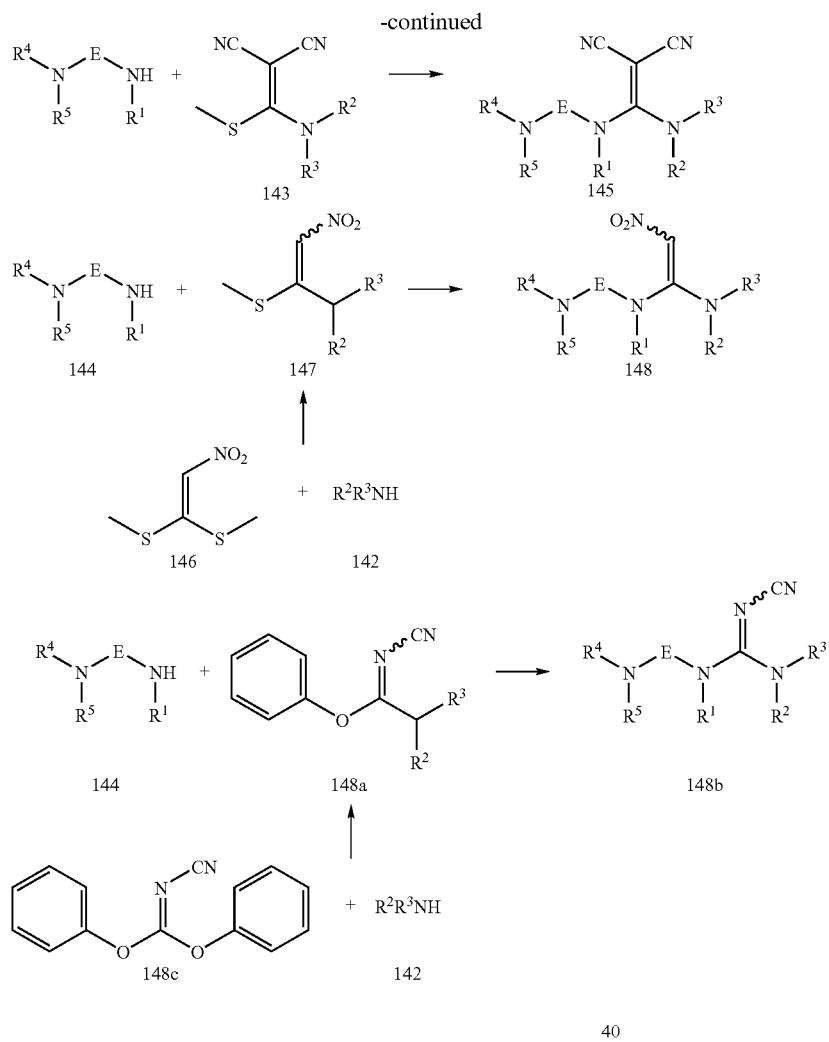
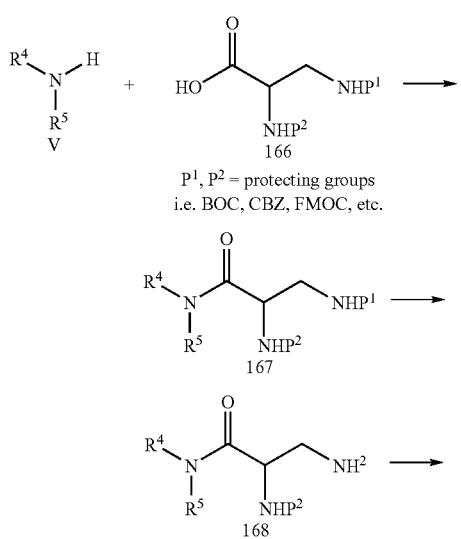
SCHEME 30
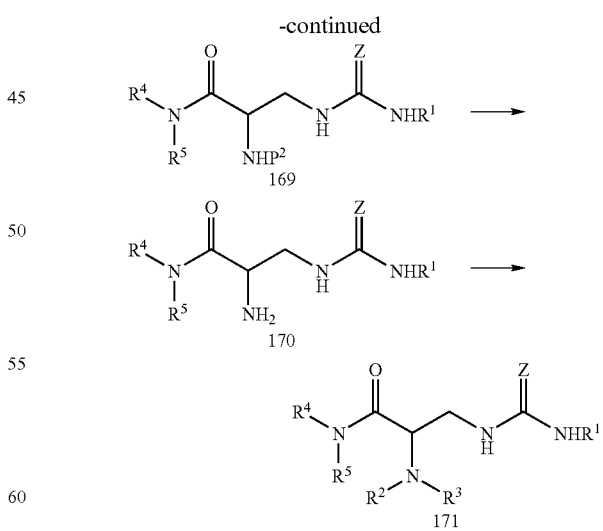
The synthesis of compounds wherein $R^9$ is a modified amino group ($R^{10}$=H) is shown in Scheme 30. Compound V can be coupled to protected diaminopropionic acid 166 using a common amide forming reagent such as PyBOP, HATU or HBTU to furnish the amide 167. Selective removal of protecting group $P^1$ provides amine 168, which can be converted into 169 as urea (Z=O) or thiourea (Z=S) or other urea mimics (Z=N—CN, CHNO$_2$, and C(CN)$_2$) via the general methods described elsewhere in this application. Deprotection of amino group in 169 provides amine 170. The free amine can be then converted into 171 as an amide, sulfonamide, secondary or tertiary amine, etc. by procedures familiar to one skilled in the art.

Note that the numbering of the R groups in Scheme 30 and all of the Schemes in this application do not necessarily correspond to the R groups in the scope and claims of this application. Their numbering system is used to illustrate a synthetic route to the compounds of this invention.

A method for introducing substituents in linkage E is that of A. Chesney et al. (Syn. Comm. 1990, 20 (20), 3167-3180) as shown in Scheme 31. Michael reaction of V with Michael acceptor 172 yields intermediate 173 which can undergo subsequent reactions in the same pot. For example, reduction yields alcohol 174 which can be elaborated to the amine 175 by standard procedures familiar to one skilled in the art. Some of these include mesylation or tosylation followed by displacement with NaN$_3$ followed by reduction to yield amine 175. Another route as depicted in Scheme 31 involves reaction with diphenylphosphoryl azide followed by reduction of the azide to yield amine 175. The mesylate or tosylate can also be displaced by other nucleophiles such as NH$_3$, BOC$_2$N$^-$, potassium phthalimide, etc., with subsequent deprotection where necessary to yield amines 175. Finally, 175 can be converted to urea or thiourea 176 by procedures previously discussed. Similarly, aldehyde 173 may be reacted with a lithium or a Grignard reagent 177 to yield alcohol adduct 178. This in turn can be converted to urea or thiourea 180 in the same way as discussed for the conversion of 174 to 176.

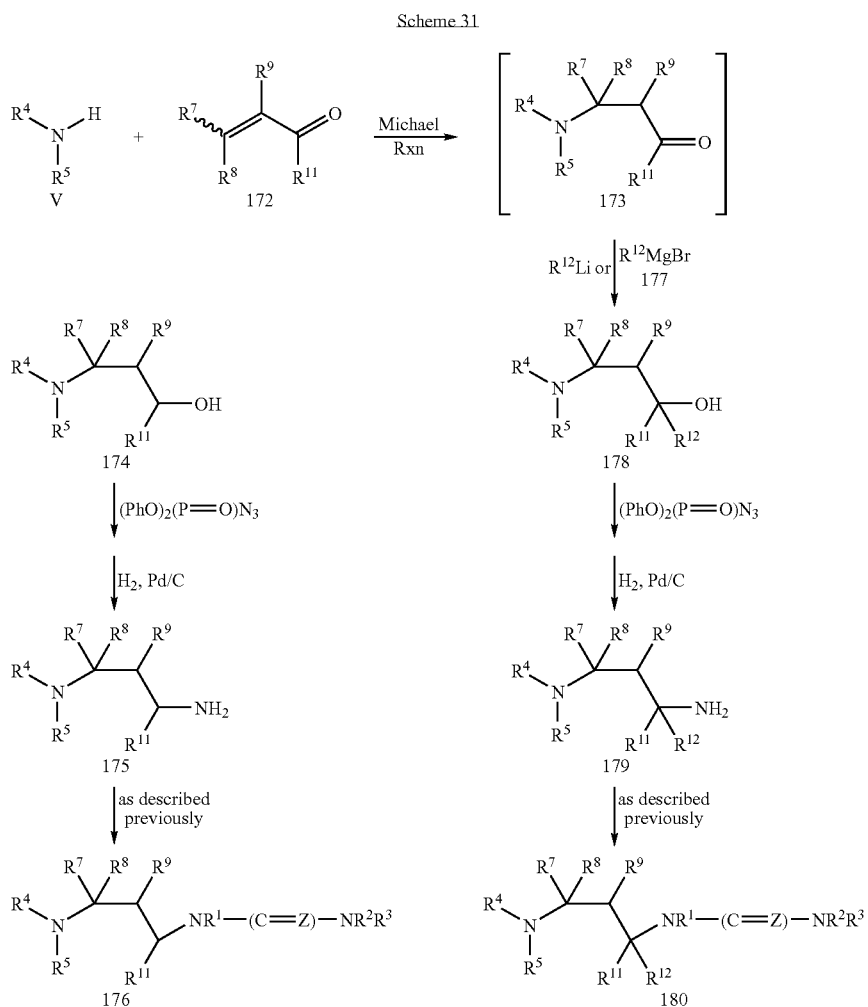

Scheme 31

Scheme 32 shows that intermediate 182 can be extended via a Witting reaction (A. Chesney, et al. Syn. Comm. 1900, 20 (20), 3167-3180) to yield 183. This adduct can be reduced cataytically to yield 184 or by other procedures familiar to one skilled in the art. Alkylation yields 185, followed by saponification and Curtius rearrangement (T. L. Capson and C. D. Poulter Tet. Lett. (1984) 25, 3515-3518) followed by reduction of the benzyl protecting group yields amine 186 which can be elaborated further as was described earlier and elsewhere in this application to make the compounds of this invention. Dialkyllithium cuprate, organo-copper, or copper-catalyzed Grignard addition (for a review, see G. H. Posner, "An Introduction to Synthesis Using Organocopper Reagents", J. Wiley, New York, 1980; Organic Reactions, 19, 1 (1972)) to alpha, beta-unsaturated ester 183 yields 187 which can undergo subsequent transformations just discussed to yield amine 190 which can be elaborated further to the compounds of this invention as was described earlier. The intermediate enolate ion obtained upon cuprate addition to 183 can also be trapped by an electrophile to yield 188 (for a review, see R. J. K. Taylor, Synthesis 1985, 364). Likewise, another 2-carbon homologation is reported by A. Chesney et al. (ibid.) on intermediate 182 which involves reacting 182 with an enolate anion to yield aldol condensation product 188 where $R^{12}$=OH. The OH group can undergo synthetic transformations which are familiar to one skilled in the art and which will be discussed in much detail later on in the application. Chiral auxilliaries can also be used to introduce stereo- and enantioselectivity in these aldol condensations, procedures which are familiar to one skilled in the art (see for example D. A. Evans, et al., J. Am. Chem. Soc. 1981, 103, 2127; D. A. Evans, J. Am. Chem.

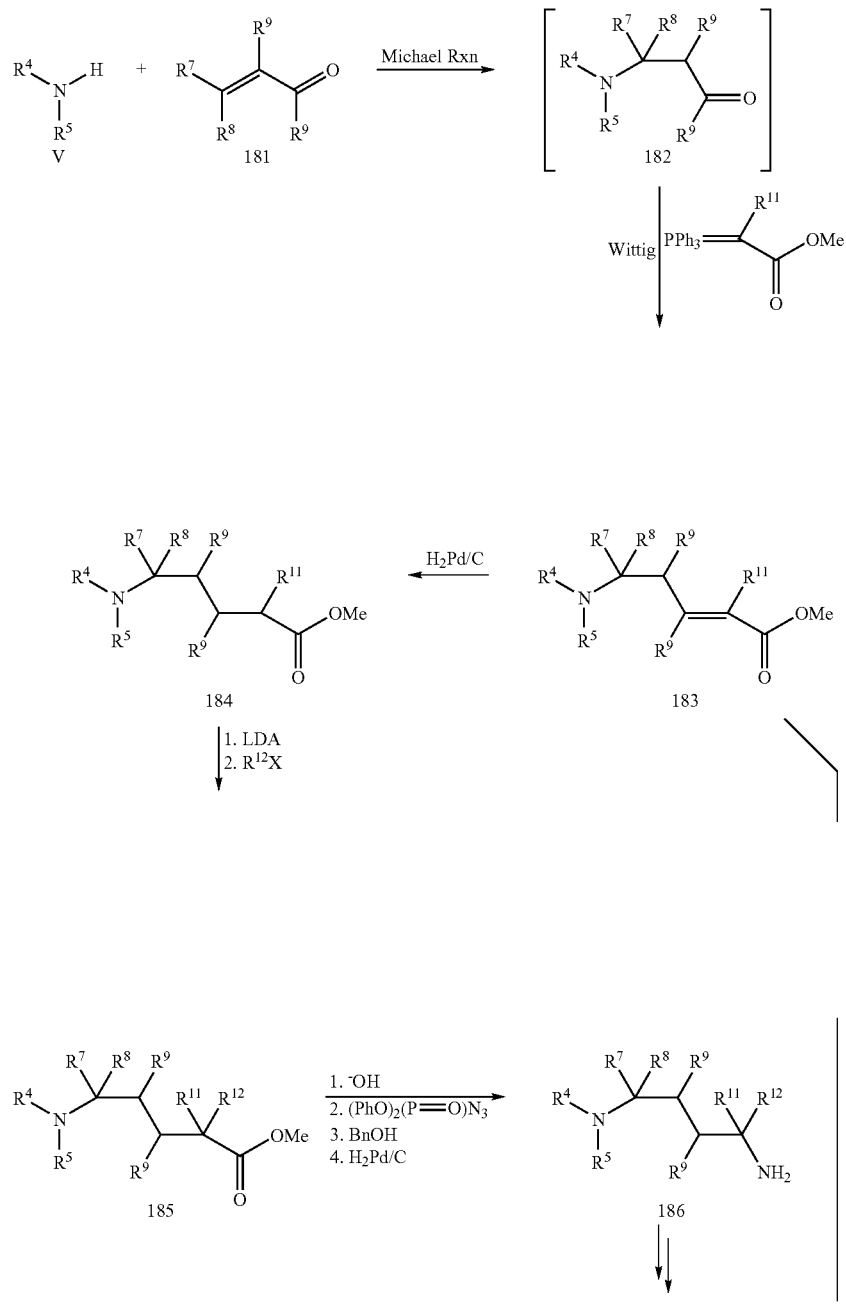

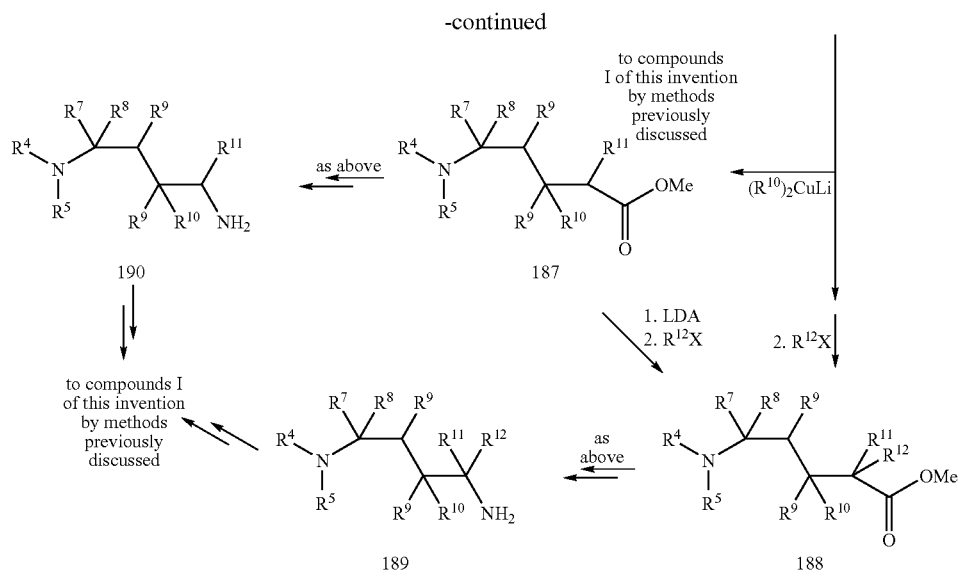

Soc. 1982, 104, 1737; D. A. Evans, J. Am. Chem. Soc. 1986, 108, 2476; D. A. Evans. et al., J. Am. Chem. Soc. 1986, 108, 6757; D. A. Evans, J. Am. Chem. Soc. 1986, 108, 6395; D. A. Evans, J. Am. Chem. Soc. 1985, 107, 4346; A. G. Myers, et al., J. Am. Chem. Soc. 1997, 119, 6496). One can also perform an enantioselective alkylation on esters 184 or 187 with $R^{12}X$ where X is a leaving group as described preveously in this application, provided the ester is first attached to a chiral auxiliary (see above references of Evans, Myers and Mauricio de L. Vanderlei, J. et al., Synth. Commum. 1998, 28, 3047).

Further use of epoxides to synthesize compounds of this invention are shown in Scheme 35. Reaction of V with epoxide 200 yields protected amino-alcohol 201. This reaction works exceptionaly well when $R^7$ and $R^8$ are H but is not limited thereto. The reaction is performed in an inert solvent at room temperature to the reflux temperature of the solvent. Protecting groups on the nitrogen atom of 200 include BOC and CBZ but are not limited thereto. The hydroxyl group can be optionally protected by a variety of protecting groups familiar to one skilled in the art. Deprotection of the nitrogen by methods familiar to one skilled in the art yields 202 which can be elaborated to the compounds of this invention by the procedures previously discussed. If $R^9$=H, then oxidation, for example, by using PCC (Corey E. J. and Suggs, J. W., Tet. Lett. 1975, 31, 2647-2650) or with the Dess-Martin periodinane (Dess, D. B. and Martin, J. C., J. Org. Chem. 1983, 48, 4155-4156) yields ketone 203 which may undergo nucleophilic 1,2-addition with organometallic reagents such as alkyl- or aryllithiums, Grignards, or zinc reagents, with or without $CeCl_3$ (T. Imamoto, et al., Tet. Lett. 1985, 26, 4763-4766; T. Imamoto, et al., Tet. Lett. 1984, 25, 4233-4236) in aprotic solvents such as ether, dioxane, or THF to yield alcohol 204. The hydroxyl group can be optionally protected by a variety of protecting groups Scheme 35

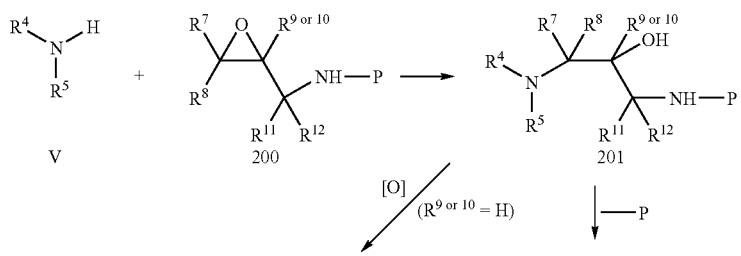

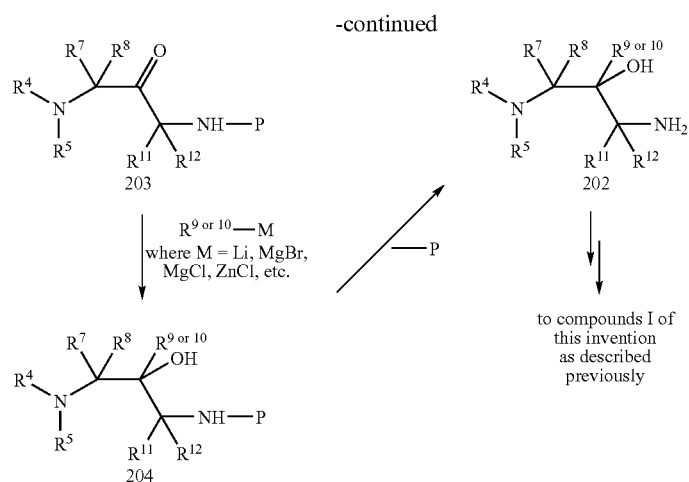

familiar to one skilled in the art. Deprotection of the nitrogen yields 202 which can be finally elaborated to the compounds of this invention as previously discussed. Epoxides disclosed by structure 200 may be synthesized enantioselectively from amino acid starting materials by the methods of Dellaria, et al. J Med Chem 1987, 30 (11), 2137, and Luly, et al. J Org Chem 1987, 52 (8), 1487.

The carbonyl group of ketone 203 in Scheme 35 may undergo Wittig reactions followed by reduction of the double bond to yield alkyl, arylalkyl, heterocyclic-alkyl, cycloalkyl, cycloalkylalkyl, etc. substitution at that position, reactions that are familiar to one skilled in the art. Wittig reagents can also contain functional groups which after reduction of the double bond yield the following functionality: esters (Buddrus, J. Angew Chem., 1968, 80), nitrites (Cativiela, C. et al., Tetrahedron 1996, 52 (16), 5881-5888.), ketene (Stork, G. et al., J Am Chem Soc 1996, 118 (43), 10660-10661), aldehyde and methoxymethyl (Bertram, G. et al., Tetrahedron Lett 1996, 37 (44), 7955-7958.), gamma-butyrolactone Vidari, G. et al., Tetrahedron: Asymmetry 1996, 7 (10), 3009-3020.), carboxylic acids (Svoboda, J. et al., Collect Czech Chem Commun 1996, 61 (10), 1509-1519), ethers (Hamada, Y. et al., Tetrahedron Lett 1984, 25 (47), 5413), alcohols (after hydrogenation and deprotection—Schonauer, K.; Zbiral, E.; Tetrahedron Lett 1983, 24 (6), 573), amines (Marxer, A.; Leutert, T. Helv Chim Acta, 1978, 61) etc., all of which may further undergo transformations familiar to one skilled in the art to form a wide variety of functionality at this position.

Scheme 36 summarizes the displacement chemistry and subsequent elaborations that can be used to synthesize the $R^9$ groups. In Scheme 36 we see that alcohol 204 may be tosylated, mesylated, triflated, or converted to a halogen by methods familiar to one skilled in the art to produce compound 205. (Note that all of the following reactions in this paragraph can be also performed on the compounds, henceforth called carbon homologs of 204 where OH can be $(CH_2)_nOH$ and it is also understood that these carbon homologs may have substituents on the methylene groups as well). For example, a hydroxyl group may be converted to a bromide by $CBr_4$ and $Ph_3P$ (Takano, S. Heterocycles 1991, 32, 1587). For other methods of converting an alcohol to a bromide or to a chloride or to an iodide see R. C. Larock, Comprehensive Organic Transformations, VCH Publishers, New York, 1989, pp. 354-360. Compound 205 in turn may be displaced by a wide variety of nucleophiles as shown in Scheme 36 including but not limited to azide, cyano, malonate, cuprates, potassium thioacetate, thiols, amines, etc., all nucleophilic displacement reactions being familiar to one skilled in the art. Displacement by nitrile yields a one-carbon homologation product. Nitrile 206 can be reduced with DIBAL to yield aldehyde 208. This aldehyde can undergo reduction to alcohol 211 with, for example, $NaBH_4$ which in turn can undergo all of the $S_N2$ displacement reactions mentioned for alcohol 204. Alcohol 211 is a one carbon homolog of alcohol 204. Thus one can envision taking alcohol 211 converting it to a leaving group X as discussed above for compound 204, and reacting it with NaCN or KCN to form a nitrile, subsequent DIBAL reduction to the aldehyde and subsequent $NaBH_4$ reduction to the alcohol resulting in a two carbon homologation product. This alcohol can undergo activation followed by the same $S_N2$ displacement reactions discussed previously, ad infinitum, to result in 3, 4, 5 . . . etc. carbon homologation products. Aldehyde 208 can also be reacted with a lithium or Grignard reagent to form an alcohol 209 which can also undergo the above displacement reactions. Oxidation by methods familiar to one skilled in the art yields ketone 210. Displacement by malonate yields malonic ester 212 which can be saponified and decarboxylated to yield carboxylic acid 213, a two carbon homologation product. Conversion to ester 214 (A. Hassner and V. Alexanian, Tet. Lett, 1978, 46, 4475-8) and reduction with LAH yields alcohol 217 which can undergo all of the displacement reactions discussed for alcohol 204. Alcohols may be converted to the corresponding fluoride 219 by DAST (diethylaminosulfur trifluoride) (Middleton, W. J.; Bingham, E. M.; Org. Synth. 1988, VI, pg. 835). Sulfides 220 can be converted to the corresponding sulfoxides 221 (p=1) by sodium metaperiodate oxidation (N. J. Leonard, C. R. Johnson J. Org. Chem. 1962, 27, 282-4) and to sulfones 221 (p=2) by Oxone® (A. Castro, T. A. Spencer J. Org. Chem. 1992, 57, 3496-9). Sulfones 221 can be converted to the corresponding sulfonamides 222 by the method of H.-C. Huang, E. et al., Tet. Lett. (1994) 35, 7201-7204 which involves first, treatment with base followed by reaction with a trialkylborane yielding a sulfinic acid salt which can be reacted with hydroxylamine-O-sulfonic acid to yield a sulfonamide. Another route to sulfonamides involves reaction of amines with a sulfonyl chloride (G. Hilgetag and A. Martini, Preparative Organic Chemistry, New York: John Wiley and Sons, 1972, p. 679). This sulfonyl chloride (not shown in Scheme 36) can be obtained from the corresponding sulfide (220 where $R^{9d}$=H in Scheme 36, the hydrolysis product after thioacetate displacement), disulfide, or isothiouronium salt by simply reacting with chlorine in water. The isothiouronium salt may be synthesized from the corresponding halide, mesylate or tosylate 205 via reaction with thiourea (for a discussion on the synthesis of sulfonyl chlorides see G. Hilgetag and A. Martini, ibid., p. 670). Carboxylic acid 213 can be converted to amides 215 by standard coupling procedures or via an acid chloride by Schotten-Baumann chemistry or to a Weinreb amide (215: $R^{9a}$=OMe, $R^{9a'}$=Me in Scheme 29) (S. Nahm and S. M. Weinreb, Tet. Lett., 1981, 22, 3815-3818) which can undergo reduction to an aldehyde 216 (R9=H in Scheme 29) with LAH (S. Nahm and S. M. Weinreb, ibid.) or reactions with Grignard reagents to form ketones 216 (S. Nahm and S. M. Weinreb, ibid.). The aldehyde 216 obtained from the Weinreb amide reduction can be reduced to the alcohol with $NaBH_4$. The aldehyde or ketone 216 (or 208 or 210 for that matter) can undergo Wittig reactions as discussed previously followed by optional catalytic hydrogenation of the olefin. This Wittig sequence is one method for synthesizing the carbocyclic and heterocyclic substituted systems at $R^9$ employing the appropriate carbocyclic or heterocyclic Wittig (or Horner-Emmons) reagents. Of course, the Wittig reaction may also be used to synthesize alkenes at $R^9$ and other functionality as well. Ester 214 can also form amides 215 by the method of Weinreb (A. Basha, M. Lipton, and S. M. Weinreb, Tet. Lett. 1977, 48, 4171-74) (J. I. Levin, E. Turos, S. M. Weinreb, Syn. Comm. 1982, 12, 989-993). Alcohol 217 can be converted to ether 218 by procedures familiar to one skilled in the art, for example, NaH, followed by an alkyliodide or by Mitsunobu chemistry (Mitsunobu, O. Synthesis, 1981, 1-28). Alcohol 204, 211, or 217, can be acylated by procedures familiar to one skilled in the art, for example, by Schotten-Baumann conditions with an acid chloride or by an anhydride with a base such as pyridine to yield 227. Halide, mesylate, tosylate or triflate 205 can undergo displacement with azide followed by reduction to yield amine 223 a procedure familiar to one skilled in the art. This amine can undergo optional reductive amination and acylation to yield 224 or reaction with ethyl formate (usually refluxing ethyl formate) to yield formamide 224. Amine 223 can again undergo optional reductive amination followed by reaction with a sulfonyl chloride to yield 225, for example under Schotten-Baumann conditions as discussed previously. This same sequence may be employed for amine 207, the reduction product of nitrile 206. Tosylate 205 can undergo displacement with cuprates to yield 226 (Hanessian, S.; Thavonekham, B.; DeHoff, B.; J. Org. Chem. 1989, 54, 5831). Aldehyde 208 or its homologous extensions can be reacted with a carbon anion of an aryl (phenyl, naphthalene, etc.) or heterocyclic group to yield an aryl alcohol or a heterocyclic alcohol. If necessary, $CeCl_3$ may be added (T. Imamoto, et al., Tet. Lett. 1985, 26, 4763-4766; T. Imamoto, et al., Tet. Lett. 1984, 25, 4233-4236). This alcohol may be reduced with $Et_3SiH$ and TFA (J. Org. Chem. 1969, 34, 4; J. Org. Chem. 1987, 52, 2226) (see discussion of aryl and heterocyclic anions for Schemes 19-22). These aryl and heterocyclic anions may also be alkylated by 205 (or its carbon homolog) to yield compounds where $R^9$ contains an aryl or heterocyclic group. Compound 205 or its carbon homologs may be alkylated by an alkyne anion to produce alkynes at $R^9$ (see R. C. Larock, Comprehensive Organic Transformations, New York, 1989, VCH Publishers, p 297). In addition, carboxaldehyde 208 or its carbon homologs can undergo 1,2-addition by an alkyne anion (Johnson, A. W. The Chemistry of Acetylenic Compounds. V. 1. "Acetylenic Alcohols," Edward Arnold and Co., London (1946)). Nitro groups can be introduced by displacing bromide 205 (or its carbon homologs) with sodium nitrite in DMF (J. K. Stille and E. D. Vessel J. Org. Chem. 1960, 25, 478-490) or by the action of silver nitrite on iodide 205 or its carbon homologs (Org. Syntheses 34, 37-39).

Scheme 36

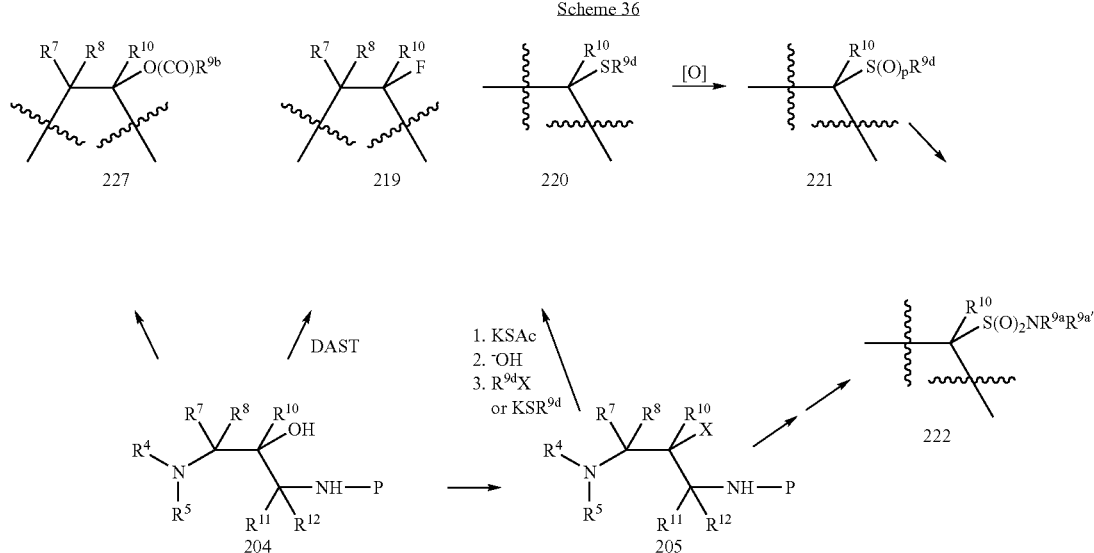

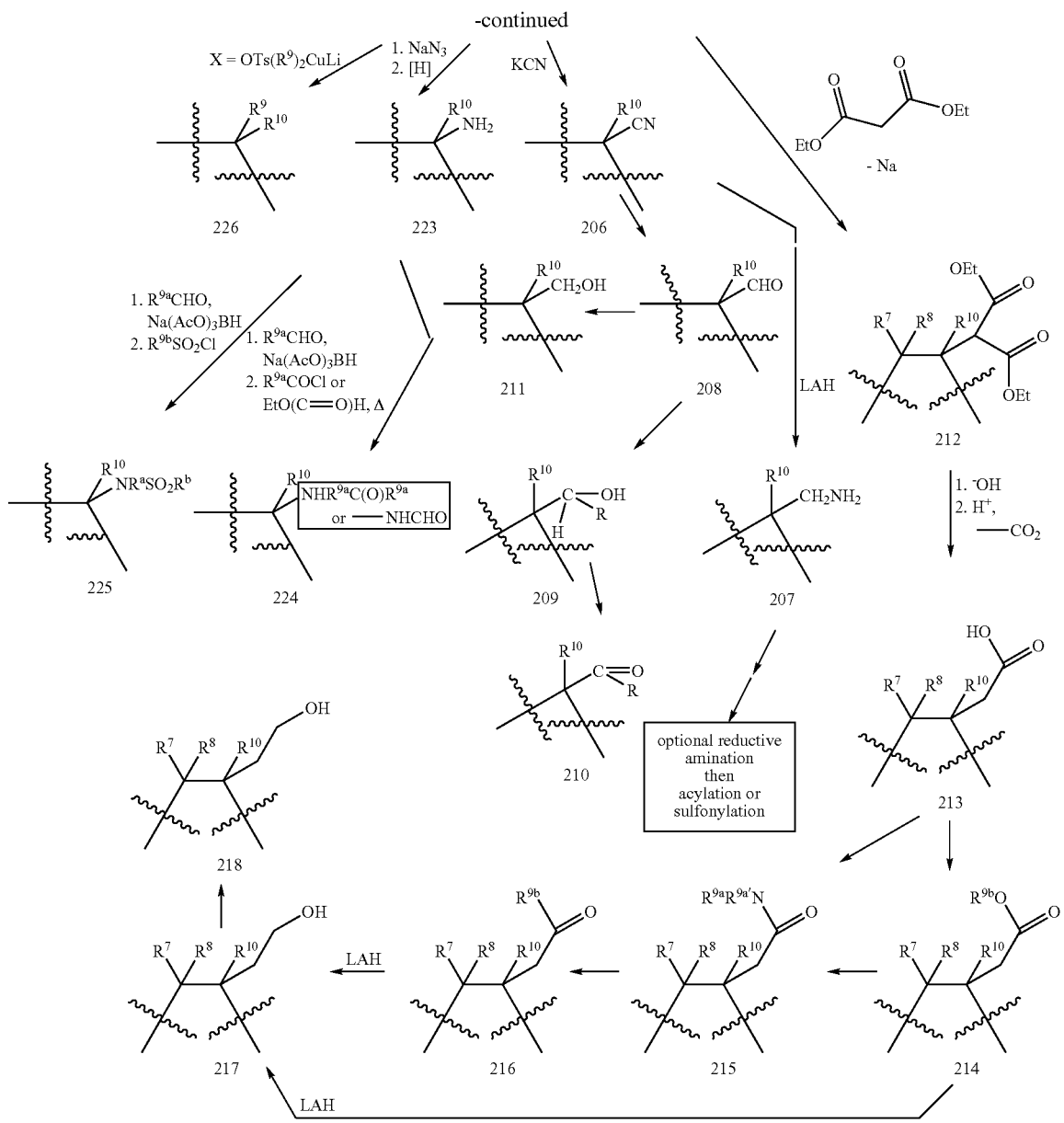

-continued

If an anion is made of V with LDA or n-BuLi, ect., then that anion in a suitable nonhydroxylic solvent such as THF, ether, dioxane, etc., can react in a Michael-type fashion (1,4-addition) with an alpha, beta-unsaturated ester to yield an intermediate enolate which can be quenched with an electrophile ($R^9X$) (where X is a leaving group as described elsewhere in this application) (Uyehara, T.; Asao, N.; Yamamoto, Y.; J Chem Soc, Chem Commun 1987, 1410) as shown in Scheme 37. It is to be understood that $R^9$ is either in its final form or in a suitable protected precursor form. This electrophile can be a carbon-based electrophile, some examples being formaldehyde to introduce a $CH_2OH$ group, an aldehyde or a ketone which also introduces a one-carbon homologated alcohol, ethylene oxide (or other epoxides) which introduces a —$CH_2CH_2OH$ group (a two-carbon homologated alcohol), an alkyl halide, etc., all of which can be later elaborated into $R^9$. It can also be an oxygen-based electrophile such as MCPBA, Davis' reagent (Davis, F. A.; Haque, M. S.; J Org Chem 1986, 51 (21), 4083; Davis, F. A.; Vishwaskarma, L. C.; Billmers, J. M.; Finn, J.; J Org Chem 1984, 49, 3241) or $MoO_5$ (Martin, T. et al., J Org Chem 1996, 61 (18), 6450-6453) which introduces an OH group. These OH groups can undergo the displacement reactions discussed previously in Scheme 36 or protected by suitable protecting groups and deprotected at a later stage when the displacement reactions decribed in Scheme 36 can be performed. In addition, these OH groups can also undergo displacement reactions with heterocycles as described elsewhere in this application to introduce N- or C-substituted heterocycles at this position. Ester 229 can be converted into its Weinreb amide 231 (S. Nahm and S. M. Weinreb, Tet. Lett., 1981, 22, 3815-3818) or Weinreb amide 231 can be synthesized via Michael-type addition of V to alpha, beta-unsaturated Weinreb amide 232. Subsequent reaction with a Grignard reagent forms ketone 234. This ketone can also be synthesized in one step directly from V and alpha, beta-unsaturated ketone 233 using the same procedure. This ketone may be reduced with LAH, NaBH$_4$ or other reducing agents to form alcohol 235. Or else, ketone 234 can be reacted with an organolithium or Grignard reagents to form tertiary alcohol 236. Or else, ester 229 can be directly reduced with LiBH$_4$ or LAH to yield primary alcohol 237. Alcohols 235, 236, and 237 can all be tosylated, mesylated, triflated, or converted to a halogen by methods discussed previously and displaced with an amine nucleophile such as azide, diphenylphosphoryl azide (with or without DEAD and Ph$_3$P), phthalimide, etc. as discussed previously (and which are familiar to one skilled in the art) and after reduction (azide) or deprotection with hydrazine (phthalimide), for example, yield the corresponding amines. These can then be elaborated into the compounds of this invention as discussed previously. Ketone 234 can also be converted into imine 238 which can be reacted with a Grignard reagent or lithium reagent, etc., to form a protected amine 239 which can be deprotected and elaborated into the compounds of this invention as discussed previously. Some protecting groups include benzyl and substituted benzyl which can be removed by hydrogenation, and cyanoethyl, which can be removed with aqueous base, etc. It is to be understood that R$^{7-12}$ in Scheme 37 can be in their final form or in precursor form which can be elaborated into final form by procedures familiar to one skilled in the art.

Scheme 37

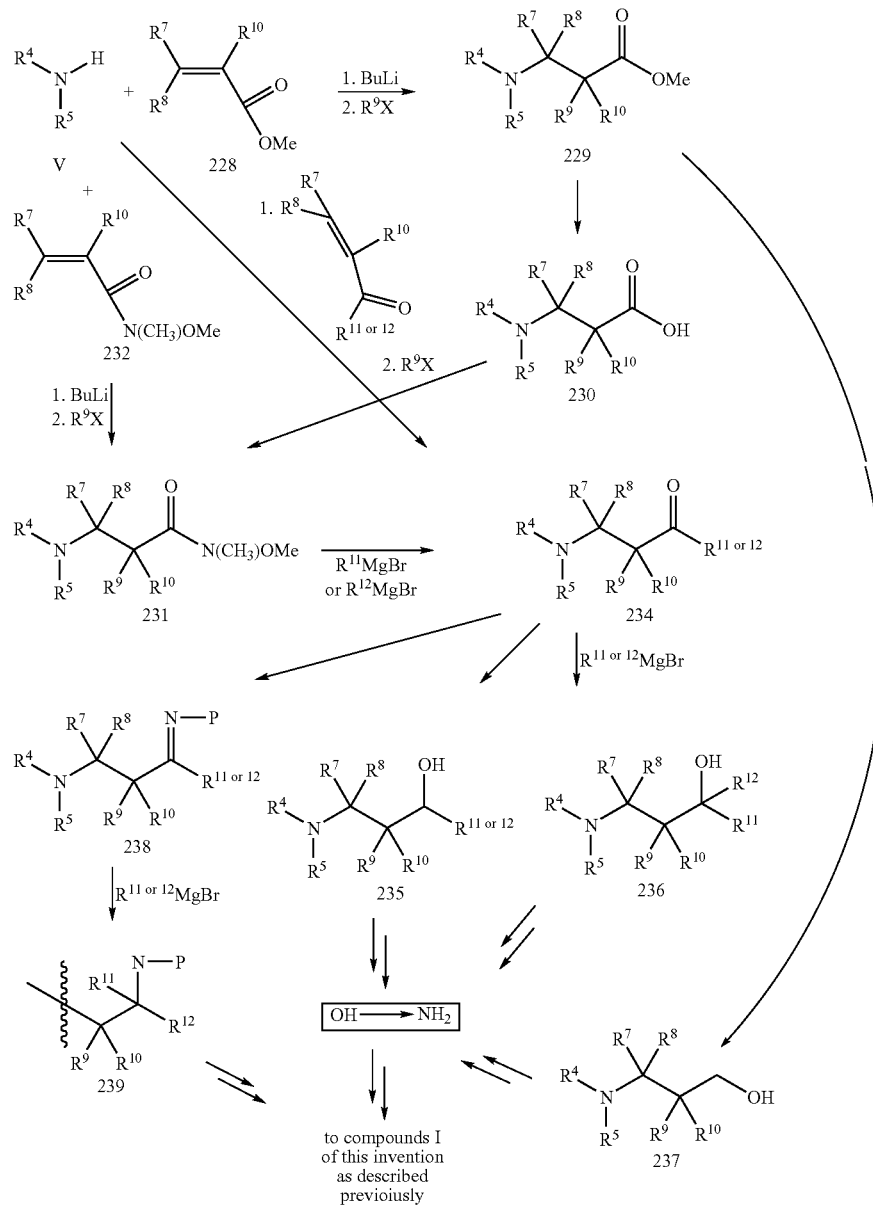

Magnesium amides of amines have been used to add in a Michael-type manner to alpha, beta-unsaturated esters where the substituents at the beta position of the unsaturated ester are tied together to form a cyclopentane ring (for example, compound 228 where $R^7$ and $R^8$ are taken together to be $-(CH_2)_4-$) (Kobayashi, K. et al., Bull Chem Soc Jpn, 1997, 70 (7), 1697-1699). Thus reaction of V with cycloalkylidine esters 228 as in scheme 37 yields esters 229 where $R^7$ and $R^8$ are taken together to form a cycloalkyl ring. Subsequent elaboration yields compounds of this invention where $R^7$ and $R^8$ are taken together to form a cycloalkyl ring. One can also envision this cycloalkyl ring incorporating a heteroatom such as O of N—P where P is a suitable protecting group.

Compounds of structue 245 may also be synthesized from epoxyalcohols which are shown in Scheme 38. Allylic alcohol 240 can be epoxidized either stereoselectively using VO(acac)$_2$ catalyst (for a review, see Evans: Chem. Rev. 1993, 93, 1307) or enantioselectively (Sharpless: J. Am. Chem. Soc. 1987, 109, 5765) to epoxyalcohol 241. $S_N2$ displacement of the alcohol using zinc azide and triphenylphosphine (Yoshida, A. J. Org. Chem. 57, 1992, 1321-1322) or diphenylphosphoryl azide, DEAD, and triphenylphosphine (Saito, A. et al., Tet. Lett. 1997, 38 (22), 3955-3958) yields azidoalcohol 242. Hydrogenation over a Pd catalyst yields aminoalcohol 243. This can be protected in situ or in a subsequent step with BOC$_2$O to put on a BOC protecting group, or with CBZ-Cl and base to put on a CBZ-group or other protecting groups. Alternatively, the amino group can be reacted with an isocyanate, an isothiocyanate, a carbamoyl chloride, or any reagent depicted elsewhere in this application to form 244 which can be alkylated with V to form the compound of this invention. Sometimes amine V might have to be activated with Lewis acids in order to

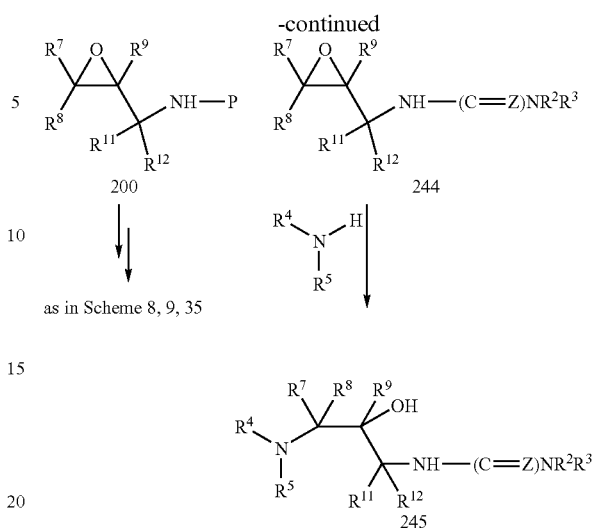

open the epoxide ring (Fujiwara, M.; Imada, M.; Baba, A.; Matsuda, H.; Tetrahedron Lett 1989, 30, 739; Caron, M.; Sharpless, K. B.; J Org Chem 1985, 50, 1557) or V has to be deprotonated and used as a metal amide, for example the lithium amide (Gorzynski-Smith, J.; Synthesis 1984 (8), 629) or MgBr amide (Carre, M. C.; Houmounou, J. P.; Caubere, P.; Tetrahedron Lett 1985, 26, 3107) or aluminum amide (Overman, L. E.; Flippin, L. A.; Tetrahedron Lett 1981, 22, 195).

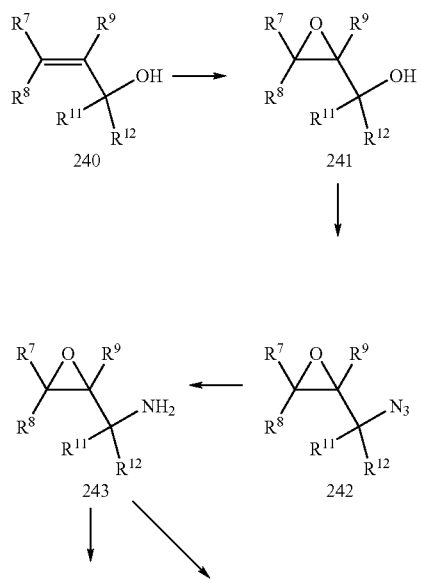

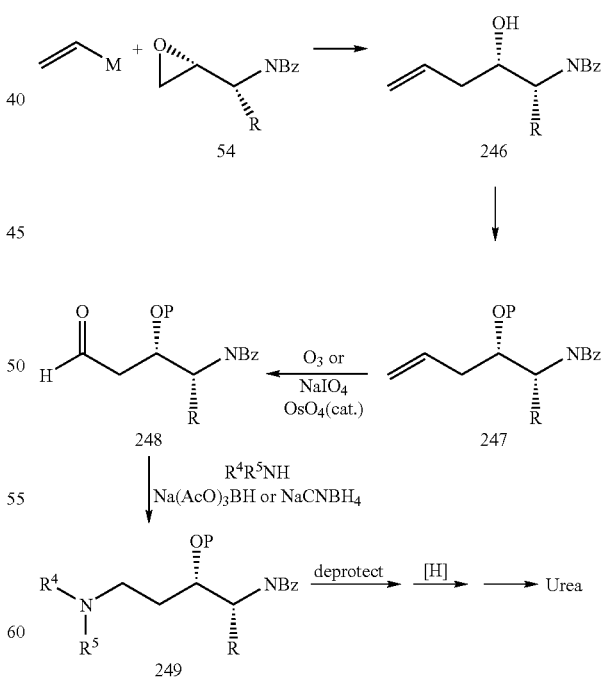

Another method by which a 4 atom linker between the Nitrogen and Urea and or the urea isostere can be synthesized is shown in Scheme 39. Vinyl Grignard or cuprate (M=MgBr, CuLi, resp.) is added to the epoxide 54 to yield homoallyic alcohol 246. Protection of the hydroxyl group with TBDMS, THP, etc., a process familiar to one skilled in the art yields 247. Ozonolytic or osmium tetroxide/sodium periodate cleavage of the olefin yields aldehyde 248 by methods familiar to one skilled in the art. Reductive amination with $R^4R^5NH$ yields 249. Deprotection of the alcohol, hydrogenolysis of the benzyls by methods familiar to one skilled in the art followed by urea formation yields compounds of the present invention. Note that if instead of a reductive work-up one employs an oxidative work-up for the ozonolysis, one obtains a carboxylic acid instead of aldehyde 248. This carboxylic acid can be esterified and then alkylated in the alpha-position to place substituents alpha to the hydroxyl-containing carbon. If instead of an ester a chiral acyloxazolidinone is made, then alkylation alpha to the carbonyl can be done enantioselectively (see Evans, D. A., op. cit.). Hydrolysis of the acyloxazolidinone followed by coupling to $R^4R^5NH$ and reduction with borane by methods familiar to one skilled in the art yields 249 where the methylene alpha to the hydroxyl-containing carbon is now alkylated. Further manipulation as previously disclosed leads to the compound of this invention.

Example 1

N-((1R,2S)-2-{[[3-(4-fluorophenyl)propyl]amino]methyl}cyclohexyl)-N'-[3-(1-methyl-1H-tetrazol-5-yl)phenyl]urea

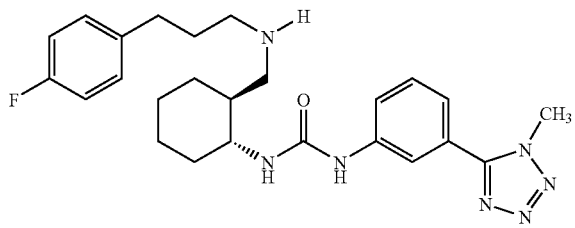

Step a: To a solution of (R,R) amino alcohol 1 [*J. Org. Chem.* 1996, 61, 5557-5563; *J. Am. Chem. Soc.* 1996, 118, 5502-5503] (9.5 g, 73.8 mmol) in $CH_2Cl_2$ (200 mL) is added 200 ml of an aqueous solution of $Na_2CO_3$ (15 g, 141 mmol). While stirring, benzyl chloroformate (12.6 g, 73.8 mmol) is added slowly and the mixture is stirred at room temperature for 1 h. The organic layer is separated and washed with water and brine. The organic solvent is removed on a rotary evaporator to give a white solid. The solid is recrystallized from hexane to give 16.3 g (62 mmol) of the alcohol 2 (Scheme 31a) as a white solid. $^1H$ NMR (300 MHz, $CDCl_3$) δ 7.40-7.29 (m, 5 H), 5.11 (s, 2 H), 4.71 (bd, 1 H), 3.76-3.71 (m, 1 H), 3.53-3.28 (m, 3 H), 2.00-1.95 (m, 1 H), 1.90-1.09 (m, 8 H). MS $AP^+$ $(M+H)^+$=264.3 (100%)

Step b: A solution of DMSO (36 g, 430 mmol) in $CH_2Cl_2$ (200 mL) is cooled to -78° C. To this solution is added drop-wise oxalyl chloride (27.41 g, 216 mmol) and the resulting solution is stirred for an additional 10 min. A solution of alcohol 2 (38 g, 144 mmol) in $CH_2Cl_2$ (150 ml) is added via an addition funnel and stirred for 10 min. Then, $Et_3N$ (58 g, 570 mmol) is added and the solution is stirred for 20 min and the ice bath removed and stirred for an additional 30 min. The solution is diluted with water and the organic layer separated and washed with water, 1 N HCl, and brine. The organic layer is dried over $Na_2SO_4$, filtered, and concentrated to give 38 g of aldehyde 3 as a white solid. The solid is recrystallized from hexane to give 19.7 grams of a first crop of aldehyde 3 as white needles. A second crop gave an additional 11 grams. $^1H$ NMR (300 MHz, $CDCl_3$) δ 9.59 (d, 3.6 Hz, 1 H), 7.38-7.28 (m, 5 H), 5.07 (m, 2 H), 4.69 (m, 1 H), 3.84 (m, 21 H), 2.19-2.11 (m, 1 H), 2.09-2.01 (m, 1 H), 1.86-1.75 (m, 3 H), 1.54-1.17 (m, 4 H).

Step c: Synthesis of 3-(para-fluorophenyl)propanol

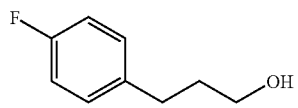

para-Fluorophenylpropionic acid (5.15 g, 31.0 mmol, 1 eq.) was dissolved in THF (150 mL). To this solution a 1.0 M solution of borane in THF was added dropwise (caution—exothermic) at 25° C. under $N_2$. The mixture was refluxed overnight. The reaction was quenched with excess 1N HCl and extracted 3 times with EtOAc. The organic layers were dried ($MgSO_4$), and stripped to yield 5.67 g of a pink oil. Evaporative distillation at 0.05 mmHg and 193-260° C. yielded 2.32 g of product as a clear colorless oil.

NMR (300 MHz, $CDCl_3$) δ 7.10 (t, 2H, J=8 Hz); 6.94 (t, 2H, J=8 Hz); 3.80 (t, 2H, J=7 Hz); 2.64 (t, 2H, J=7 Hz); 1.83 (t of t, 2H, J=7, 7 Hz).

Step d: Synthesis of 1-(para-fluorophenyl)-3-(para-methylphenylsulfonyloxy)propane and 1-(para-fluorophenyl)-3-chloropropane.

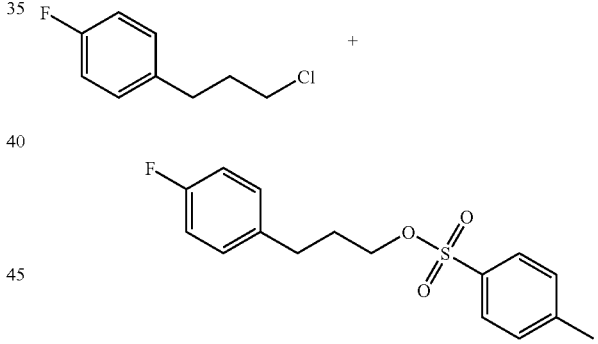

The product from Step c (2.32 g, 15.0 mmol, 1 eq.), para-toluenesulfonyl chloride (2.87 g, 15.0 mmol, 1 eq.), and pyridine (50 mL) were mixed and stirred at room temperature. The reaction after 1 week was dissolved in 300 mL of EtOAc and washed 2× with saturated aqueous $CuSO_4$, 1× with brine, dried ($MgSO_4$) and stripped to yield 2.18 g of a golden oil. Flash chromatography in 1:1 Hexanes/EtOAc yielded 1.36 g of a clear colorless oil. NMR shows a 3:1 mixture of tosylate to chloride and was used as is in the next step.

NMR tosylate (300 MHz, $CDCl_3$) δ 7.79 (d, 2H, J=9 Hz); 7.35 (d, 2H, J=9 Hz); 7.07-6.85 (m, 4H); 4.00 (t, 2H, J=7 Hz); 2.64 (t, 2H, J=7 Hz); 2.45 (s, 3H); 1.92 (t of t, 2H, J=7, 7 Hz).

NMR chloride (300 MHz, $CDCl_3$) δ 7.18-6.95 (m, 4H); 3.50 (t, 2H, J=7 Hz); 2.76 (t, 2H, J=7 Hz); 2.07 (t of t, 2H, J=7, 7 Hz);

Step e: Synthesis of 1-(para-fluorophenyl)-3-azidopropane

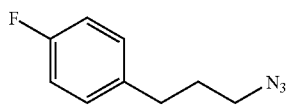

The product from Step d (1.36 g, 7.9 mmol, 1 eq.), sodium azide (1.02 g, 15.8 mmol, 2 eq.), and DMF (100 ml), were mixed and stirred overnight at room temperature. The reaction was worked up by adding 200 mL of EtOAc and washing 3× with H$_2$O (200 mL each time). The organic layers were dried (MgSO$_4$) and stripped to yield 0.79 g of a clear colorless oil. IR (neat) 2098 (cm$^{-1}$).

Step f: Synthesis of 1-(para-fluorophenyl)-3-aminopropane

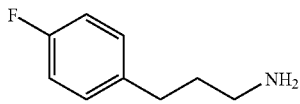

The product from step e (0.79 g, 6.4 mmol) was dissolved in 100 mL of MeOH and added carefully to 0.20 g of 10% Pd/C under N$_2$. The mixture was hydrogenated in a Parr shaker at 50 PSI overnight. Filtration through fiberglass filter paper under N$_2$ and under vacuum yielded 0.56 g of a clear colorless oil.

NMR (300 MHz, CDCl$_3$) δ 7.15 (m, 2H); 6.95 (m, 2H); 2.70 (t, 2H, J=7 Hz); 2.63 (t, 2H, J=7 Hz); 1.73 (t of t, 2H, J=7, 7 Hz); 1.57 (bm, 2H).

Step g: Synthesis of (1R,2S)-[2-({[3-(4-fluoro-phenyl)-propyl]amino}-methyl)-cyclohexyl]-carbamic acid benzyl ester

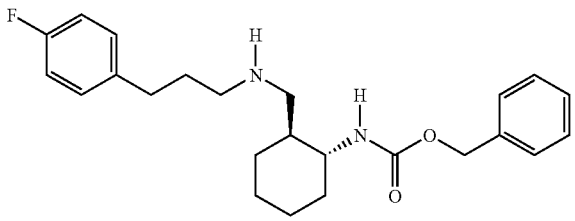

The product from Step f (0.43 g, 2.8 mmol, 1.1 eq.) aldehyde 3 (0.67 g, 2.6 mmol, 1.0 eq.), sodium triacetoxyborohydride (0.60 g, 2.8 mmol, 1.1 eq.) and methylene chloride (100 mL) were mixed and stirred at room temperature for 2 days. The reaction was quenched with water (100 mL) and the layers separated. Further extraction with methylene chloride (2×100 mL) followed by combination of the organic layers, drying (MgSO$_4$) and stripping yielded 1.04 g of a clear colorless oil. Flash chromatography in 1:1 Hexanes/EtOAc followed by 4:1 chloroform/MeOH yielded 0.59 g of a viscous clear oil. MS (AP+) detects (M+H)$^+$ =399.4.

Step h: Synthesis of (1R,2S)-[2-({tert-butoxycarbonyl-[3-(4-fluoro-phenyl)-propyl]amino}-methyl)-cyclohexyl]-carbamic acid benzyl ester

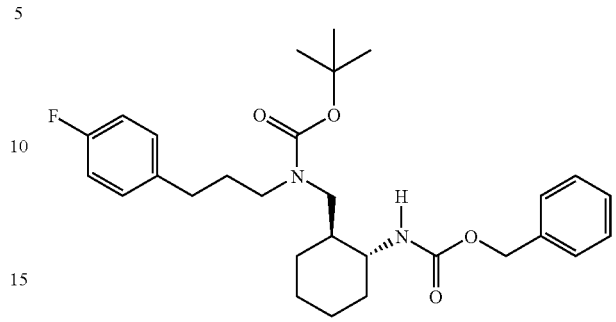

The product of Step g (0.59 g, 1.5 mmol, 1 eq.), di-t-butyl-dicarbonate (0.32 g, 1.5 mmol, 1 eq.) and THF (100 mL) were mixed and stirred overnight. Water (100 mL) was added and the mixture extracted with EtOAc (3×100 mL). The organic layers were dried (MgSO$_4$) and stripped to yield 0.7 g of a clear colorless oil. NMR detects a 1:1 mixture of BOC conformers. NMR (300 MHz, CDCl$_3$) δ 1.55 (s, 4.5H); 1.44 (s, 4.5H).

Step i: Synthesis of (1R,2S)-2-({tert-butoxycarbonyl-[3-(4-fluorophenyl)-propyl]amino}-methyl)-cyclohexylamine

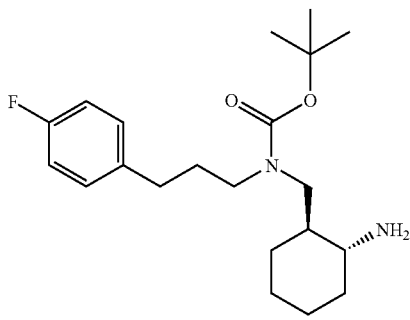

The product from Step h (0.7 g, 1.9 mmol) was dissolved in 100 mL MeOH and added carefully to 0.1 g of 10% Pd/C under N$_2$. The mixture was hydrogenated in a Parr shaker at 50 PSI overnight. Filtration through fiberglass filter paper under N$_2$ and under vacuum yielded 0.45 g of a clear colorless oil.

NMR (key peaks only)(300 MHz, CDCl$_3$) δ 7.10 (m, 2H); 6.90 (m, 2H); 1.47 (s, 9H).

Step j: Synthesis of N-((1R,2S)-2-{[tert-Butoxycarbonyl [3-(4-fluorophenyl)propyl]amino]methyl}cyclohexyl)-N'-[3-(1-methyl-1H-tetrazol-5-yl)phenyl]urea

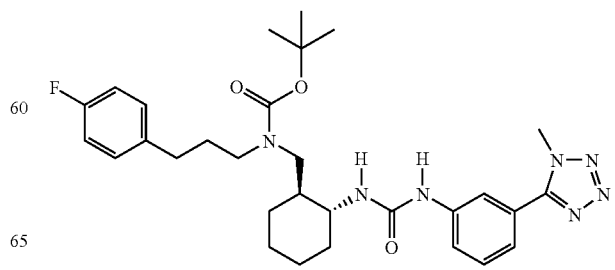

The product of Step i (0.26 g, 0.69 mmol, 1 eq.), and phenyl 3-(1-methyl-1H-tetraazol-5-yl)phenylcarbamate (Example 1a, see below)(0.20 g, 0.69 mmol, 1 eq.) were dissolved in DMF (2 mL) at room temperature and stirred under N$_2$ overnight. The DMF was stripped on the rotary evaporator and EtOAc was added (50 mL). This mixture was washed with water (3×50 mL), dried (MgSO$_4$), stripped, and flash chromatographed in 3:1 Hexanes/EtOAc to 1:1 Hexanes/EtOAc to 100% EtOAc to yield 98 mg of a white glass. MS (AP+) detects (M+H)$^+$=566.6.

Step k: Synthesis of N-((1R,2S)-2-{[[3-(4-fluorophenyl)propyl]amino]methyl}cyclohexyl)-N'-[3-(1-methyl-1H-tetrazol-5-yl)phenyl]urea

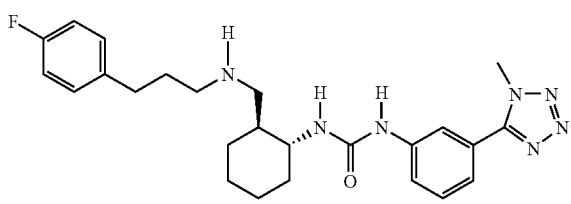

The product of Step j (90 mg) and 4N HCl in dioxane (50 mL) were mixed and stirred at room temperature for 3 hours. The reaction was stripped on the rotary evaporator and restripped twice from isopropanol on the rotary evaporator to yield 76 mg of a glass. MS (ESI) detects (M+H)$^+$=466.3.

$^1$H NMR (300 MHz, d$_6$-DMSO) δ 9.13 (s, 1H); 8.00 (s, 1H); 7.55 (d, 1H, J=9 Hz); 7.50 (t, 1H, J=9 Hz); 7.40 (d, 1H, J=9 Hz); 7.22 (m, 2H); 7.10 (m, 2H); 6.60 (d, 1H, J=9 Hz); 4.13 (s, 3H); 3.40 (m, 1H); 3.07-2.71 (m, 3H); 2.62 (m, 2H); 1.99-1.09 (m, 12H).

Example 1a

Phenyl 3-(1-methyl-1H-tetraazol-5-yl)phenylcarbamate

Phenyl 3-(1-methyl-1H-tetraazol-5-yl)phenylcarbamate was prepared from 3-nitrobenzoic acid using procedures found in Example 25b, parts b, c, e and f.

$^1$H NMR NMR (300 MHz, DMSO-d$_6$) δ 10.60 (bs, 1H), 8.03 (s, 1H), 7.80-7.70 (m, 1H), 7.60-7.50 (m, 2H), 7.50-7.35 (m, 2H), 7.35-7.20 (m, 3H), 4.17 (s, 3H).

Example 2

N-((1R,2S)-2-{[[3-(4-fluorophenyl)propyl](methyl)amino]methyl}cyclohexyl)-N'-[3-(1-methyl-1H-tetrazol-5-yl)phenyl]urea

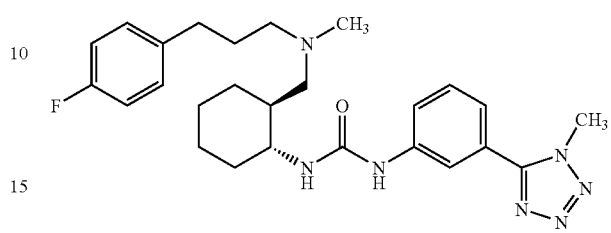

Step a: Preparation of toluene-4-sulfonic acid (1R,2R)-2-benzyloxycarbonylamino-cyclohexylmethyl ester A solution of (1R,2R)-(2-hydroxymethylcyclohexyl)-carbamic acid benzyl ester (6.0 g, 22.8 mmol) in pyridine (35 mL) was stirred on an ice-acetone bath and treated with toluene-4-sulfonyl chloride (4.78 g, 25.1 mmol). The reaction was stirred on an ice-water bath for 3 hours, then ice-cold water (35 mL) was added slowly. The mixture was diluted further with ice water and the resulting slurry was stirred at room temperature for 1 hour. The solid was collected by filtration, washed with water, and dried under vacuum to provide a white powdery solid (9.1 g, 96%).

$^1$H NMR (300 mHz, CDCl$_3$) δ 7.78 (d, J=8 Hz, 2H), 7.37 (m, 5H), 7.30 (d, J=8 Hz, 2H), 5.07 (ab, J=12 Hz, 2H), 4.60 (d, J=9 Hz, 1H), 4.15 (dd, J=10, 4 Hz, 1H), 3.86 (m, 1H), 3.30 (m, 1H), 2.44 (s, 3H), 2.0-1.0 (m, 9H).

Step b: Preparation of (1R,2S)-[2-({[3-(4-fluoro-phenyl)-propyl]-methyl-amino}-methyl)-cyclohexyl]-carbamic acid benzyl ester A solution of toluene-4-sulfonic acid (1R,2R)-2-benzyloxycarbonylamino-cyclohexylmethyl ester (632 mg, 1.51 mmol) in acetone (8 mL) was treated with N-[3-(4-fluorophenyl)-propyl]-methylamine (253 mg, 1.51 mmol) and potassium carbonate (209 mg, 1.51 mmol) and heated at reflux for 23.5 hours. The mixture was cooled and filtered, the solid was rinsed with acetone, and the filtrate was concentrated to provide a yellow-orange oil. Flash chromatography on silica gel, eluting with 50% ethyl acetate in hexane, followed by 50% ethyl acetate in hexane containing 5% ethanol, provided a light yellow viscous oil (400 mg, 64%).

$^1$H NMR (300 mHz, CDCl$_3$) δ 7.32 (m, 5H), 7.07 (m, 2H), 6.94 (m, 2H), 5.08 (s, 2H), 3.14 (m, 1H), 2.6-2.2 (m, 6H), 2.19 (s, 3H), 2.08 (m, 1H), 1.72 (m, 6H), 1.5-0.9 (m, 5H). MS ESI (M+H)$^+$=413.4.

Step c: Preparation of (1R,2S)-2-({[3-(4-fluorophenyl)-propyl]-methyl-amino}-methyl)-cyclohexylamine A mixture of (1R,2S)-[2-({[3-(4-fluoro-phenyl)-propyl]-methyl-amino}-methyl)-cyclohexyl]-carbamic acid benzyl ester (400 mg, 970 μM) and 20% palladium hydroxide on charcoal (Pearlman's catalyst, 200 mg) in methanol (25 mL) was shaken in a pressure bottle under a hydrogen atmosphere (55 psig) for 16.5 hours. The mixture was filtered and the solid was washed with methanol. The combined filtrates were concentrated under vacuum to provide a tan viscous oil (268 mg, quantitative), used without further purification.

$^1$H NMR (300 mHz, CDCl$_3$) δ 7.15 (m, 2H), 6.97 (m, 2H), 2.75 (m, 1H), 2.65-2.20 (m, 6H), 2.25 (s, 3H), 2.05 (m, 1H), 1.80-1.10 (m, 9H), 0.87 (m, 1H). MS ESI (M+H)=279.2.

Step d: Preparation of 1-[(1R,2S)-2-({[3-(4-fluorophenyl)-propyl]-methyl-amino}-methyl)-cyclohexyl]-3-[3-(1-methyl-1H-tetrazol-5-yl)-phenyl]-urea A solution of (1R,2S)-2-({[3-(4-fluorophenyl)-propyl]-methyl-amino}-methyl)-cyclohexylamine (72 mg, 259 µmol) in acetonitrile (2 mL) was treated with triethylamine (72 µL, 517 µmol) and [3-(1-methyl-1H-tetrazol-5-yl)-phenyl]-carbamic acid phenyl ester (76 mg, 259 µmol). The mixture was stirred at room temperature for 15.5 hours and then was concentrated under vacuum. The residue was dissolved in ethyl acetate, and the solution was washed sequentially with 1.0 M aqueous sodium hydroxide, water and saturated aqueous sodium chloride. The organic phase was dried over sodium sulfate and concentrated under vacuum. The residue was purified by flash chromatography, eluting with 4% methanol in dichloromethane containing 0.4% aqueous ammonium hydroxide, to provide a white amorphous solid (75 mg, 60%).

$^1$H NMR (300 mHz, CDCl$_3$) δ 7.99 (s, 1H), 7.50-7.35 (m, 3H), 7.04 (m, 2H), 6.88 (m, 2H), 4.19 (s, 3H), 3.41 (m, 1H), 2.90 (m, 1H), 2.80-2.20 (m, 10H), 2.49 (s, 3H), 1.94 (m, 2H), 1.58 (m, 1H), 1.45-1.10 (m, 4H). MS ESI (M+H)$^+$ =480.6.

Example 3

N-((1R,2S)-2-{[(cyclopropyl) [3-(4-fluorophenyl)-propyl]amino]methyl}cyclohexyl)-N'-[3-(1-methyl-1H-tetrazol-5-yl)phenyl]urea

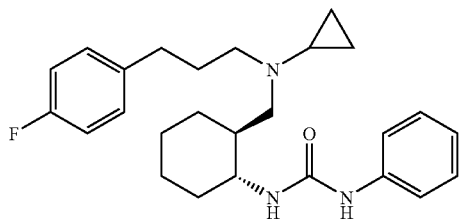

Step a: Preparation of N-cyclopropyl-3-(4-fluorophenyl) propionamide

To a stirred solution of 3-(4-fluorophenyl)propionic acid (5 g, 31 mmoles) and 0.1 mL of dimethylformamide in 50 mL of anhydrous CH$_2$Cl$_2$ at 0° C. was added oxalyl chloride (2.84 mL, 32.6 mmoles) and the mixture was stirred for 1 hour at 0° C. and for 1 hour at room temperature. After cooling to 0° C. were added cyclopropylamine (2.6 mL, 37.2 mmoles) and triethylamine (6.5 mL, 46.5 mmoles), and the mixture was stirred for 1 hour while warming to room temperature gradually. Then water was added and the product was extracted with CH$_2$Cl$_2$. The extract was washed with water, dried over MgSO$_4$ and evaporated to give a solide residue. It was recrystallized from CH$_2$Cl$_2$ and hexane to give 4.94 g of N-cyclopropyl-3-(4-fluorophenyl)propionamide.

Step b: Preparation of N-cyclopropyl-3-(4-fluorophenyl)-propylamine

To a stirred solution of N-cyclopropyl-3-(4-fluorophenyl) propionamide (4.3 g, 20.8 mmoles) in 30 mL of dry tetrahydrofuran at 0° C. was added 1 equivalent of lithium aluminumhydride in tetrahydrofuran dropwise, and the mixture was refluxed for 2 hours. After cooling to room temperature was added sodium sulfate decahydrate slowly and the mixture was stirred for 0.5 hours. It was filtered through a plug of Celite® and evaporated to give an oily residue. It was purified by clolumn chromatography on silica gel with elution by 6:94 methanol-methylene chloride followed by 0.6:5.4:94 cNH$_4$OH-methanol-methylene chloride to give 1.4 g of N-cyclopropyl-3-(4-fluorophenyl)propylamine and 1 g of N-propyl-3-(4-fluorophenyl)propylamine.

Step c: Preparation of (1R,2S)-2-({cyclopropyl-[3-(4-fluoro-phenyl)-propyl]amino}-methyl)-cyclohexyl]-carbamic acid benzyl ester Using the N-cyclopropyl-3-(4-fluorophenyl)propylamine and the aldehyde 3 (Step b of Example 1), the above named compound was made by the methods described in step k of Example 9.

Step d: Preparation of (1R,2S)-2-({cyclopropyl-[3-(4-fluoro-phenyl)-propyl]amino}-methyl)-cyclohexylamine By the methods described in Step i of Example 1, the product of Step c was converted to the named compound.

Step e: Preparation of N-((1R,2S)-2-{[(cyclopropyl)[3-(4-fluorophenyl)propyl]amino]methyl}cyclohexyl)-N'-[3-(1-methyl-1H-tetrazol-5-yl)phenyl]urea To a solution of (1R,2S)-2-({cyclopropyl-[3-(4-fluorophenyl)-propyl]amino}-methyl)-cyclohexylamine in dry tetrahydrofuran was added 1 equivalent of 3-acetyl-phenyl isocyanate, and the mixture was stirred for 5 hours at room temperature. The reaction was quenched with water and the product was extracted with ethyl acetate. The extract was washed with brine, dried over sodium sulfate, and evaporated to give an oily residue. It was purified by column chromatography on silica gel.

$^1$H NMR (300 MHz, CDCl$_3$) δ 7.28-7.21 (m, 5H), 7.12-6.93 (m, 5H), 6.04 (s, 1H), 3.28 (m, 1H), 2.72-2.63 (m, 1H), 2.60-2.17 (m, 6H), 1.82-0.91 (m, 11H), 0.45-0.30 (m, 2H), 0.21 (bs, 2H). MS ESI (M+H)$^+$=424.5.

Example 4

N-((1R,2S)-2-{[[2-(4-fluorophenyl)ethyl](methyl)amino]methyl}cyclohexyl)-N'-[3-(1-methyl-1H-tetrazol-5-yl)phenyl]urea

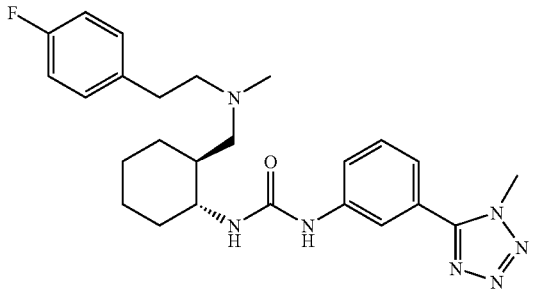

Example 4 was prepared in an analogous manner to Example 2 using N-methyl-2-(4-fluorophenyl)ethylamine in Step b.

$^1$H NMR (300 MHz, CDCl$_3$) δ 7.88 (s, 1H), 7.53 (d, J=7 Hz, 1H), 7.39 (t, J=7 Hz, 1H), 7.29 (d, J=7 Hz, 1H), 7.11 (m, 2H), 7.01 (s, 1H), 6.95 (m, 2H), 4.16 (s, 3H), 3.31 (m, 1H), 2.8-2.6 (m, 3H), 2.6-2.4 (m, 2H), 2.24 (s, 3H), 2.19 (m, 2H), 1.72 (m, 3H), 1.5-0.9 (m, 5H). MS ESI (M+H)$^+$=466.5.

Example 5

N-[3-acetyl-5-(1-methyl-1H-tetrazol-5-yl)phenyl]-N'-((1R,2S)-2-{[[2-(4-fluorophenyl)ethyl](methyl)amino]methyl}cyclohexyl)urea

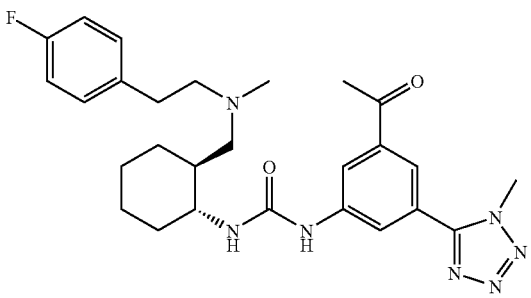

Example 5 was prepared in an analogous manner to Example 4 using [3-acetyl-5-(1-methyl-1H-tetrazol-5yl)-phenyl]-carbamic acid phenyl ester.

$^1$H NMR (300 MHz, CDCl$_3$) δ 8.26 (t, J=2 Hz, 1H), 8.19 (t, J=2 Hz, 1H), 7.91 (t, J=2 Hz, 1H), 7.25 (s, 1H), 7.13 (m, 2H), 6.95 (m, 3H), 4.23 (s, 3H), 3.32 (m, 1H), 2.8-2.6 (m, 3H), 2.65 (s, 3H), 2.6-2.4 (m, 2H), 2.27 (s, 3H), 2.22 (m, 2H), 1.74 (m, 3H), 1.5-0.9 (m, 5H). MS ESI (M+H)$^+$ =507.61.

Example 6

N-[(1R,2S)-2-({[3-(4-fluorophenyl)-2,2-dimethyl-propyl]amino}methyl)cyclohexyl]-N'-[3-(1-methyl-1H-tetrazol-5-yl)phenyl]urea

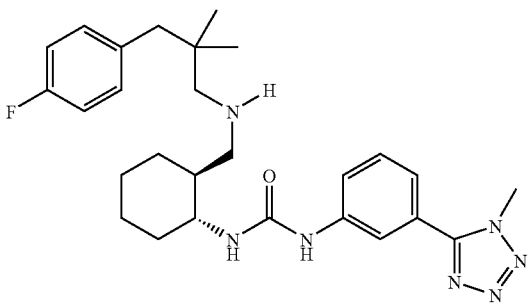

Step a: Preparation of 3-(4-fluorophenyl)-2,2-dimethyl-propionic acid

A mixture of 3-(4-fluorophenyl)-2,2-dimethylpropionic acid ethyl ester (10.0 g, 44.6 mmol, see Part 1 of Example 25a) and a solution of sodium hydroxide (25 g) in water (110 mL) was heated at reflux for 18 h and cooled to room temperature. The solution was stirred on an ice bath and acidified with concentrated aqueous hydrochloric acid. The resulting precipitate was collected by filtration, washed with water and dried under vacuum. The residue was stirred with dichloromethane and filtered, and the filtrate was concentrated to provide an off-white solid (7.60 g, 87%).

$^1$H NMR (300 mHz, CDCl$_3$) δ 7.14 (m, 2H), 6.98 (t, J=9 Hz, 2H), 2.88 (s, 2H), 1.22 (s, 6H); mass spec (ES−) m/z 195.2 (100%, M−H$^+$).

Step b: Preparation of 3-(4-fluorophenyl)-2,2-dimethyl-propionamide

A solution of 3-(4-fluorophenyl)-2,2-dimethylpropionic acid (1.33 g, 6.76 mmol) and N,N-dimethylformamide (1 drop) in dichloromethane (30 mL) was stirred at room temperature and treated over 2 min with oxalyl chloride (658 μL, 7.44 mmol). The solution was stirred at room temperature for 15.5 h, then was concentrated. The residue was added over 1 min to aqueous ammonium hydroxide (40 mL) with rapid stirring and ice cooling. After stirring at room temperature for 45 min, the mixture was extracted with dichloromethane, and the organic extracts were dried (sodium sulfate) and concentrated to provide a viscous oil (1.33 g, 93%) containing about 8% by weight of dichloromethane.

$^1$H NMR (300 mHz, CDCl$_3$) δ 7.15 (m, 2H), 6.96 (t, J=9 Hz, 2H), 5.56 (bs, 1H), 5.50 (bs, 1H), 2.84 (s, 2H), 1.20 (s, 6H).

Step c: Preparation of 3-(4-fluorophenyl)-2,2-dimethyl-propylamine

A solution of 3-(4-fluorophenyl)-2,2-dimethylpropionamide (1.34 g, 6.86 mmol) in tetrahydrofuran (20 mL) was added dropwise over 3 min to a solution of lithium aluminum hydride in tetrahydrofuran (1.0 M; 20.6 mL, 20.6 mmol) and the resulting mixture was heated to reflux. After 17 h, the mixture was cooled, and treated sequentially with water (0.78 mL, added very slowly), 15% aqueous sodium hydroxide (0.78 mL, added very slowly) and water (2.34 mL). The resulting mixture was stirred briefly at room temperature and filtered. The solids were washed with ethyl acetate, and the combined filtrates were concentrated under vacuum to provide a yellow liquid (1.14 g, 92%).

$^1$H NMR (300 mHz, CDCl$_3$) δ 7.10 (m, 2H), 6.97 (t, J=9 Hz, 2H), 2.52 (s, 2H), 2.48 (s, 2H), 1.40 (bs, 2H), 0.85 (s, 6H); mass spec (ES+) m/z 223.0 (100%, M+H+MeCN$^+$).

Step d: Preparation of (2-{[3-(4-fluorophenyl)-2,2-dimethylpropylamino]methyl}cyclohexyl)-carbamic acid benzyl ester 3-(4-Fluorophenyl)-2,2-dimethylpropylamine (253 mg, 1.39 mmol) and (2-formylcyclohexyl)carbamic acid benzyl ester (363 mg, 1.39 mmol) were dissolved in methanol (6 mL) and stirred at room temperature for 4 h. Sodium borohydride (84 mg, 2.22 mmol) was added, and the mixture was stirred for 30 min. 1.0 M aqueous sodium hydroxide was added, and the mixture was extracted with ether. The organic phase was washed with saturated aqueous sodium chloride and dried over sodium sulfate, and concentrated under vacuum. The residue was purified by flash column chromatography on silica gel, eluting with 5% methanol in dichloromethane containing 0.5% aqueous ammonium hydroxide, to provide a colorless gum (450 mg, 76%).

$^1$H NMR (300 mHz, CDCl$_3$) δ 7.28 (m, 5H), 7.03 (m, 2H), 6.95 (t, J=9 Hz, 2H), 5.05 (s, 2H), 3.24 (m, 1H), 2.56 (m, 2H), 2.50 (s, 2H), 2.25 (m, 3H), 1.74 (m, 3H), 1.4-1.0 (m, 6H), 0.83 (s, 3H), 0.81 (s, 3H); mass spec (ES+) m/z 427.5 (100%, M+H$^+$).

Step e: Preparation of (2-{[3-(4-fluorophenyl)-2,2-dimethylpropylamino]methyl}cyclohexyl)amine Using (2-{[3-(4-fluorophenyl)-2,2-dimethylpropylamino]methyl}cyclohexyl)-carbamic acid benzyl ester from step d, the titled compound was made by the methods described in Step c of Example 2.

Step f: Preparation of N-[(1R,2S)-2-({[3-(4-fluorophenyl)-2,2-dimethylpropyl]amino}methyl)cyclohexyl]-N'-[3-(1-methyl-1H-tetrazol-5-yl)phenyl]urea Using the amine from Step e and [3-(1-methyl-1H-tetrazol-5-yl)-phenyl]-carbamic acid phenyl ester, the titled compound was prepared by the methods desribed in Step d of Example 2.

$^1$H NMR (300 MHz, CDCl$_3$) δ 7.86 (s, 1H), 7.68 (bs, 1H), 7.58 (d, J=8 Hz, 1H), 7.37 (t, J=8 Hz, 1H), 7.28 (d, J=8 Hz, 1H), 7.04 (m, 2H), 6.88 (m, 2H), 4.14 (s, 3H), 3.46 (m, 1H), 2.65 (m, 2H), 2.52 (s, 2H), 2.32 (ab, J=12 Hz, 2H), 2.18 (m, 1H), 2.0-1.7 (m, 4H), 1.5-1.1 (m, 5H), 0.86 (s, 3H), 0.84 (s, 3H). MS ESI (M+H)$^+$=494.5.

Example 7

N-((1R,2S)-2-{[[3-(4-fluorophenyl)propyl](2,2,2-trifluoroethyl)amino]methyl}cyclohexyl)-N'-[3-(1-methyl-1H-tetrazol-5-yl)phenyl]urea

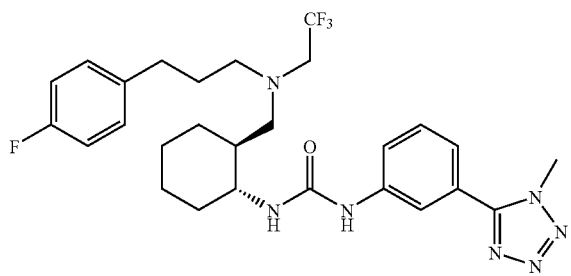

Using the amine from Step c of Example 101, the above named compound was made via the methods disclosed in Example 1.

$^1$H NMR (300 MHz, CDCl$_3$) δ 7.83 (d, 2H, J=7 Hz), 7.40 (t, 1H, J=7 Hz), 7.23 (d, 1H, J=7 Hz), 7.15-7.10 (m, 1H), 6.89 (t, 2H, J=7 Hz), 6.10 (d, 2H, J=7 Hz), 4.15 (s, 3H), 3.60-3.30 (m, 1H), 2.97 (q, 2H, J=7 Hz), 2.86 (m, 1H), 2.70-2.40 (m, 5H), 2.40-2.20 (m, 1H), 2.20-2.00 (m, 1H), 1.80-1.60 (m, 4H), 1.50-1.10 (m, 4H), 1.10-0.90 (m, 1H). MS ESI (M+H)$^+$=548.

Example 8

1-[2-({[2-(1H-Indol-3-yl)-ethyl]-methyl-amino}-methyl)-cyclohexyl]-3-[3-(1-methyl-1H-tetrazol-5-yl)-phenyl]-urea

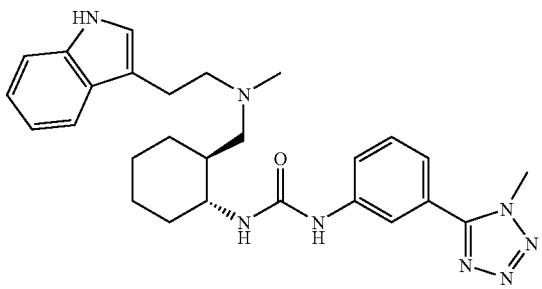

Using commercially available N-methyltryptamine, the above named compound was made via the methods disclosed in Example 1.

$^1$H NMR (300 MHz, CDCl$_3$) δ 7.96 (d, J=8.42 Hz, 1H), 7.56-7.32 (m, 5H), 7.18 (d, J=6.59 Hz, 1H), 7.09 (m, 1H), 6.97 (t, J=7.32 Hz, 1H), 4.14 (s, 1.5H), 4.09 (s, 1.5H), 3.64-3.19 (m, 7H), 2.99 (s, 1.5H), 2.95 (s, 1.5H), 1.99-1.60 (m, 5H), 1.38-1.09 (m, 4H). MS ESI (M+H)$^+$=487

Example 8a

N-[3-ethyl-5-(1-methyl-1H-tetrazol-5-yl)phenyl]-N'-((1R,2S)-2-{[((2RS)-6-fluoro-1,2,3,4-tetrahydronaphthalen-2-yl)amino]methyl}cyclohexyl)urea

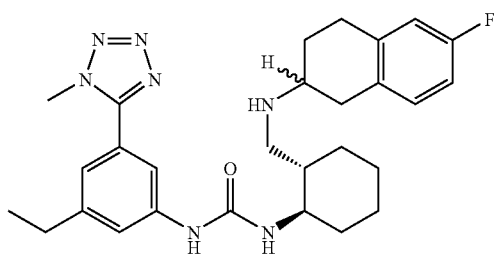

Step a: Preparation of 6-fluoro-3,4-dihydronaphthalen-2(1H)-one oxime

A solution of 6-fluoro-3,4-dihydronaphthalen-2(1H)-one (W. Adcock, P. D. Bettess, S. Q. A. Rizvi, Aust. J. Chem. 1970, 23, 1921-1937; 1.50 g, 9.13 mmol) in ethanol (10 mL) was treated with hydroxylamine hydrochloride (775 mg, 11.14 mmol), sodium acetate (2.01 g, 14.79 mmol) and water (6 mL) and the mixture was stirred at room temperature for 30 min, during which time a dense precipitate formed. The mixture was diluted with water and extracted with ether. The organic phases were dried and concentrated to provide a yellowish solid (1.58 g, 97%) used without further purification.

$^1$H NMR (300 mHz, CDCl$_3$) δ 7.14 (m, 1H), 6.90 (m, 2H), 6.1 (b, 1H), 3.81 (s, 1H), 3.51 (m, 1H), 2.86 (m, 2H), 2.75 (m, 1H), 2.58 (m, 1H); mass spec (ES+) m/z 180.2 (100%, M+H).

Step b: Preparation of (RS)-(6-fluoro-1,2,3,4-tetrahydronaphthalen-2-yl)amine Hydrochloride A mixture of 6-fluoro-3,4-dihydronaphthalen-2(1H)-one oxime (1.58 g, 8.81 mmol), methanol (25 mL), conentrated hydrochloric acid (2 mL) and 10% palladium on charcoal (316 mg) was shaken in a pressure bottle under a hydrogen atmosphere (55 psig). After 18 hours, the mixture was filtered and the solid washed with methanol. The filtrate was concentrated under vacuum, and the residue was washed with ether, dried by concentration from benzene, and dried further under vacuum to provide a white solid (1.48 g, 83%).

$^1$H NMR (300 mHz, CDCl$_3$) δ 7.11 (m, 1H), 6.87 (m, 2H), 4.90 (b, 3H), 3.53 (m, 1H), 3.15 (dd, J=15.8, 4.8 Hz, 1H), 2.94 (m, 2H), 2.79 (dd, J=15.7, 10.2 Hz, 1H), 2.20 (m, 1H), 1.83 (m, 1H); mass spec (ES+) m/z 166.3 (100%, M+H$^+$).

Step c: Preparation of benzyl[(1R,2R)-2-formylcyclohexyl]carbamate

A solution of oxalyl chloride (2.6 mL, 29.4 mmol) in dichloromethane (80 mL) at −78° C. was treated with a solution of dimethyl sulfoxide (4.3 mL, 60.8 mmol) in dichloromethane (10 mL) over 5 minutes. The mixture was stirred for 40 min, then treated with a solution of benzyl [(1R,2R)-2-(hydroxymethyl)cyclohexyl]carbamate (5.0 g, 19 mmol) in dichloromethane (20 mL) over 5 minutes. The mixture was stirred for 45 minutes, then was treated with triethylamine (8.6 mL, 61.7 mmol) and allowed to warm to room temperature. After 60 minutes, the mixture was washed with water, then with brine, and dried over sodium sulfate and concentrated. The residue was purified by flash column chromatography using 30% ethyl acetate in hexane to provide a white solid (4.8 g, 97%).

$^1$H NMR (300 mHz, CDCl$_3$) δ 9.57 (d, J=3.7 Hz, 1H), 7.31 (m, 5H), 5.05 (ab pattern, 2H), 4.78 (bd, J=5.5 Hz, 1H), 3.80 (m, 1H), 2.2-2.0 (m, 2H), 1.9-1.7 (m, 3H), 1.6-1.1 (m, 4H).

Step d: Preparation of benzyl((1R,2S)-2-{[((2RS)-6-fluoro-1,2,3,4-tetrahydronaphthalen-2-yl)amino]methyl}cyclohexyl)carbamate A mixture of (RS)-(6-fluoro-1,2,3,4-tetrahydronaphthalen-2-yl)amine hydrochloride (200 mg, 0.99 mmol) and benzyl [(1R,2R)-2-formylcyclohexyl]carbamate (258 mg, 0.99 mmol) in 1,2-dichloroethane (4 mL) was treated with triethylamine (275 µL, 1.98 mmol) whereupon a clear solution resulted. Sodium triacetoxyborohydride (272 mg, 1.28 mmol) was added and the mixture was stirred at room temperature for 3.5 hours. Aqueous sodium hydroxide (1.0 N) was then added, and the mixture was extracted with ether. The organic phase was dried over sodium sulfate and concentrated. The residue was purified by flash column chromatography, eluting with 5% methanol in dichloromethane, containing 0.5% aqueous ammonia, to provide a colorless oil (280 mg, 69%).

$^1$H NMR (300 mHz, CDCl$_3$) δ 7.35 (m, 5H), 6.97 (m, 1H), 6.78 (m, 2H), 5.98 (b, 1H), 5.10 (m, 2H), 3.30 (m, 1H), 3.0-2.4 (m, 7H), 2.20 (m, 1H), 2.00 (m, 1H), 1.9-1.7 (m, 3H), 1.58 (m, 1H), 1.4-1.0 (m, 5H); mass spec (ES+) m/z 411.3 (100%, M+H$^+$).

Step e: Preparation of N-{[(1S,2R)-2-aminocyclohexyl]methyl}-(2RS)-6-fluoro-1,2,3,4-tetrahydronaphthalen-2-amine A mixture of benzyl((1R,2S)-2-{[((2RS)-6-fluoro-1,2,3,4-tetrahydronaphthalen-2-yl)amino]methyl}cyclohexyl)carbamate (280 mg, 0.68 mmol) and 10% palladium on charcoal (56 mg) in methanol (20 mL) was shaken under an atmosphere of hydrogen (55 psig) for 3.5 hours. The mixture was filtered, the solid was washed with methanol, and the filtrates were concentrated. The residual oil (120 mg, 64%) was used without further purification.

$^1$H NMR (300 mHz, CDCl$_3$) δ 7.01 (m, 1H), 6.80 (m, 2H), 4.8 (b, 4H), 3.1-2.4 (m, 8H), 2.10 (m, 2H), 2.0-0.9 (m, 8H); mass spec (ES+) m/z 277.4 (100%, M+H$^+$).

Step f: Preparation of N-[3-ethyl-5-(1-methyl-1H-tetrazol-5-yl)phenyl]-N'-((1R,2S)-2-{[((2RS)-6-fluoro-1,2,3,4-tetrahydronaphthalen-2-yl)amino]methyl}cyclohexyl)urea A mixture of N-{[(1S,2R)-2-aminocyclohexyl]methyl}-(2RS)-6-fluoro-1,2,3,4-tetrahydronaphthalen-2-amine (60 mg, 217 µmol) and phenyl[3-ethyl-5-(1-methyl-1H-tetrazol-5-yl)phenyl]carbamate (54 mg, 217 µmol) in acetonitrile (2 mL) was treated with triethylamine (75 µL, 540 µmol). After being stirred at room temperature for 18 hours, the mixture was concentrated under vacuum. The residue was purified by flash column chromatography, eluting with 5% methanol in dichloromethane containing 0.5% aqueous ammonia, to provide an amorphous solid (50 mg, 45%).

$^1$H NMR (300 mHz, CDCl$_3$) δ 8.20 (b, 1H), 7.70 (s, 1H), 7.51 (s, 1H), 7.13 (s, 1H), 6.90 (m, 1H), 6.70 (m, 2H), 4.14 (s, 3H), 3.44 (m, 1H), 3.0-2.5 (m, 9H), 2.62 (q, J=7.3 Hz, 2H), 2.2-2.0 (m, 2H), 1.9-1.5 (m, 3H), 1.5-1.1 (m, 5H), 1.20 (t, J=7.3 Hz, 3H); mass spec (ES+) m/z 506.3 (M+H$^+$), HRMS calc. for C$_{28}$H$_{37}$FN$_7$O: 506.3044, found: 506.3020.

Example 8b

N-[3-ethyl-5-(1-methyl-1H-tetrazol-5-yl)phenyl]-N'-((1R,2S)-2-{[((2RS)-6-fluoro-1,2,3,4-tetrahydronaphthalen-2-yl)(methyl)amino]methyl}cyclohexyl)urea

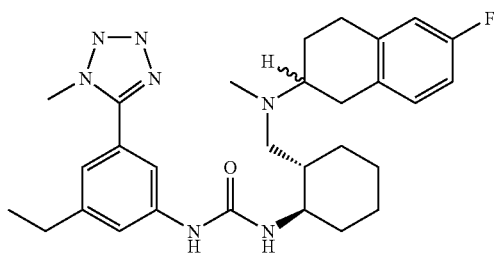

Step a: Preparation of benzyl((1R,2S)-2-{[((2RS)-6-fluoro-1,2,3,4-tetrahydronaphthalen-2-yl)(methyl)amino]methyl}cyclohexyl)carbamate A solution of benzyl((1R,2S)-2-{[((2RS)-6-fluoro-1,2,3,4-tetrahydronaphthalen-2-yl)amino]methyl}cyclohexyl)carbamate (300 mg, 0.73 mmol) in acetonitrile (4 mL) was treated with formaldehyde (37% aqueous, 300 µL), sodium cyanoborohydride (138 mg, 2.19 mmol) and a few drops of acetic acid. After stirring at room temperature, the mixture was treated with aqueous sodium hydroxide (1.0 N) and extracted with dichloromethane. The organic phase was dried over sodium sulfate and concentrated. The residue was purified by flash column chromatography, eluting with 5% methanol in dichloromethane containing 0.5% aqueous ammonia, to provide a gum (280 mg, 90%).

$^1$H NMR (300 mHz, CDCl$_3$) δ 7.32 (m, 5H), 6.88 (m, 1H), 6.77 (m, 2H), 5.2-5.0 (m, 2H), 3.18 (m, 1H), 2.9-2.5 (m, 6H), 2.5-2.2 (m, 2H), 2.30 (s, 3H), 1.98 (m, 1H), 1.8-1.0 (m, 9H); mass spec (ES+) m/z 425.4 (100%, M+H).

Step b: Preparation of N-(2RS)-{[(1S,2R)-2-aminocyclohexyl]methyl}-6-fluoro-N-methyl-1,2,3,4-tetrahydronaphthalen-2-amine A mixture of benzyl((1R,2S)-2-{[((2RS)-6-fluoro-1,2,3,4-tetrahydronaphthalen-2-yl)(methyl)amino]methyl}cyclohexyl)carbamate (280 mg, 0.66 mmol), methanol (20 mL) and 10% palladium on charcoal (56 mg) was shaken under a hydrogen atmosphere (55 psig) for 3.5 hours. The mixture was filtered, the solids were washed with methanol and the filtrate was concentrated under vacuum. The residue (110 mg, 57%) was used without further purification.

$^1$H NMR (300 mHz, CDCl$_3$) δ 7.04 (m, 1H), 6.78 (m, 2H), 0.0-2.5 (m, 7H), 2.44 (s, 3H), 2.25 (m, 1H), 2.1-1.5 (m, 7H), 1.5-1.1 (m, 3H), 0.90 (m, 1H); mass spec (ES+) m/z 291.2 (100%, M+H).

Step c: Preparation of N-[3-ethyl-5-(1-methyl-1H-tetrazol-5-yl)phenyl]-N'-((1R,2S)-2-{[((2RS)-6-fluoro-1,2,3,4-tetrahydronaphthalen-2-yl)(methyl)amino]methyl}cyclohexyl)urea A mixture of N-(2RS)-{[(1S,2R)-2-aminocyclohexyl]methyl}-6-fluoro-N-methyl-1,2,3,4-tetrahydronaphthalen-2-amine (60 mg, 206 µmol), phenyl[3-ethyl-5-(1-methyl-1H-tetrazol-5-yl)phenyl]carbamate (52 mg, 206 µmol), triethylamine (57 µL, 412 µmol) and acetonitrile (2 mL) was stirred at room temperature for 16 hours. The mixture was concentrated, and the residue was dissolved in ethyl acetate. The solution was washed with aqueous sodium hydroxide (1.0 N), dried over sodium sulfate, and concentrated. The residue was purified by flash column chromatography, eluting with 5% methanol in dichloromethane containing 0.5% aqueous ammonia, to provide an amorphous solid (40 mg, 37%) which was a mixture of two diastereomers by NMR.

$^1$H NMR (300 mHz, CDCl$_3$) δ 7.73, 7.69 (2s, 1H), 7.46, 7.42 (2s, 1H), 7.20, 7.16 (2s, 1H), 6.93, 6.84 (2m, 1H), 6.72 (m, 2H), 4.16 (s, 3H), 3.39 (m, 1H), 2.9-2.6 (m, 7H), 2.39, 2.36 (2s, 3H), 2.25 (m, 1H), 2.03 (m, 1H), 1.9-1.4 (m, 4H), 1.4-1.0 (m, 4H), 1.23 (t, 3H); mass spec (ES+) m/z 520.5 (100%, M+H); HRMS calc. for C$_{29}$H$_{39}$FN$_7$O: 520.3200, found: 520.3214.

TABLE 1

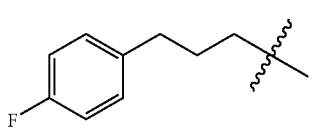

| Ex. No | R5 | R4 | R3 | MS (ESI) (M + H)$^+$ |
|---|---|---|---|---|
| 1 | 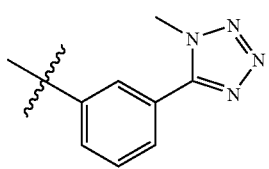 | H | 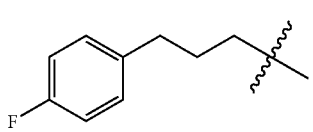 | 466.3 |
| 2 | 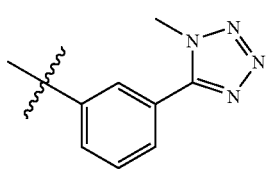 | CH$_3$ | 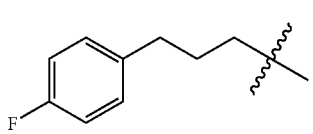 | 480.6 |
| 3 | 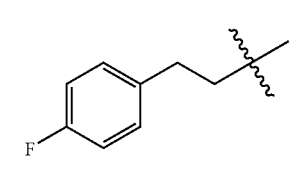 | 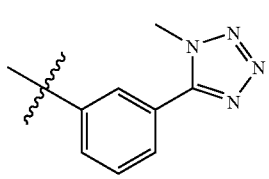 | Ph | 424.5 |
| 4 | 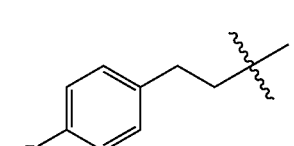 | CH$_3$ | 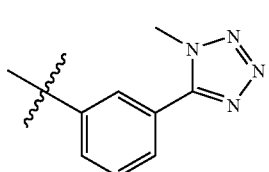 | 466.5 |
| 5 | 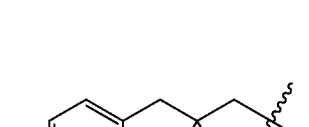 | CH$_3$ | 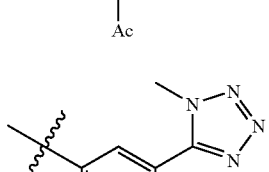 | 507.6 |
| 6 |  | H |  | 494.5 |

TABLE 1-continued

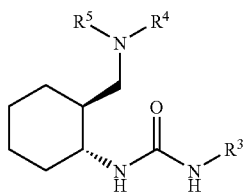

| Ex. No | R5 | R4 | R3 | MS (ESI) (M + H)+ |
|---|---|---|---|---|
| 7 | 4-fluorophenylpropyl | CF₃CH₂ | 3-(1-methyltetrazol-5-yl)phenyl | 548 |
| 8 | indol-3-ylethyl | CH₃ | 3-(1-methyltetrazol-5-yl)phenyl | 487 |
| 8a | 6-fluoro-1,2,3,4-tetrahydronaphthalen-2-yl | H | 3-ethyl-5-(1-methyltetrazol-5-yl)phenyl | 506.3 |
| 8b | 6-fluoro-1,2,3,4-tetrahydronaphthalen-2-yl | CH₃ | 3-ethyl-5-(1-methyltetrazol-5-yl)phenyl | 520.5 |
| 8c | indol-3-ylmethyl | H | 3-(1-methyltetrazol-5-yl)phenyl | |
| 8d | indol-3-ylmethyl | CH₃ | 3-(1-methyltetrazol-5-yl)phenyl | |

TABLE 1-continued
| Ex. No | R5 | R4 | R3 | MS (ESI) (M + H)+ |
|---|---|---|---|---|
| 8e | 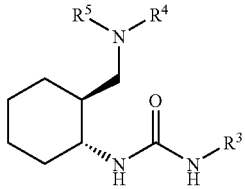 | H | 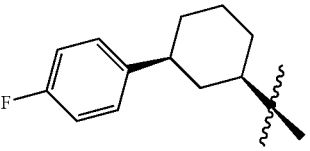 | |
| 8f | 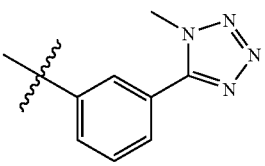 | H | 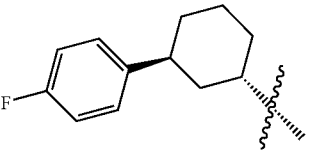 | |
| 8g | 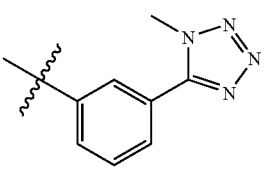 | H | 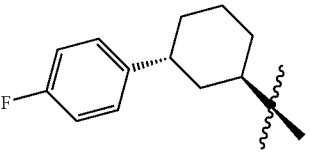 | |
| 8h | 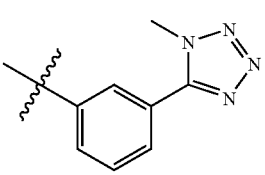 | H | 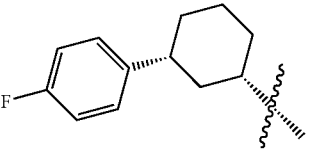 | |
| 8i | 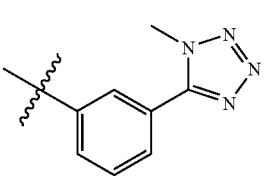 | CH$_3$ | 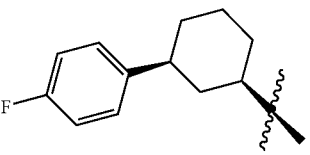 | |
| 8j | 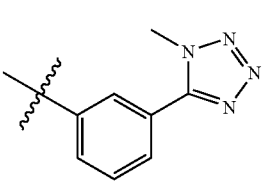 | CH$_3$ | 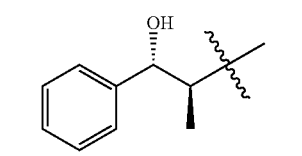 | |

Examples 9 and 10

N-((1R,3R,4S)-3-({[(3-acetylphenyl)amino]carbonyl}amino)-4{[[3-(4-fluorophenyl)propyl](methyl)amino]methyl}cyclohexyl)-N-methylacetamide and N N-((1S,3R,4S)-3-({[(3-acetylphenyl)amino]carbonyl}amino)-4f{[[3-(4-fluorophenyl)propyl](methyl)amino]methyl}cyclohexyl)-N-methylacetamide

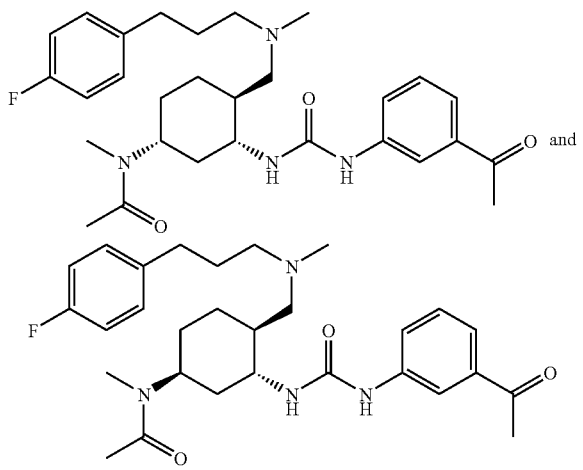

(See Scheme 2 and 3)

Step a: To a stirred solution of 7 (50 g) and diethyl carbonate (86.6 ml, 2 equiv.) in 750 mL of anhydrous THF at −78° C. was added 720 ml of LiHMDS in THF (2 equiv.) dropwise over a period of 1.5 hrs, and then the temperature was raised to room temperature gradually. It was stirred for 2 days at room temperature and poured into a mixture of 1N HCl (1 L) and ice (~700 g) with stirring. The product was extracted with EtOAc (3×) and the combined extracts were washed with brine, sat'd NaHCO$_3$ and brine. It was dried over Na$_2$SO$_4$ and evaporated to give a solid residue. It was crystallized from EtOAc and hexane to give pure keto-ester 8 (65 g, 87% yield).

$^1$H NMR (300 MHz, CDCl$_3$) δ 5.39 (s, 1H), 4.22 (q, 2H, J=7.0 Hz), 3.92 (q, 2H, J=7.0 Hz), 3.32 (dd, 1H, J$_1$=8.8 Hz, J$_2$=5.1 Hz), 2.62-2.12 (m, 4H), 1.37 (t, 3H, J=7.0 Hz), 1.29 (t, 3H, J=7.0 Hz).

Step b: A solution of keto-ester 8 (60.3 g) in 694 mL of 70% aq. acetic acid was stirred for 6 hrs at 60° C. and cooled to room temperature. The acid and water were evaporated off under reduced pressure and the syrupy residue was dried by azeotroping with benzene three times to give crude diketone-ester 9.

Step c: To a solution of diketone-ester 9 in 710 mL of benzene were aded ethylene glycol (16.6 mL, 1.05 equiv.) and p-toluenesulfonic acid monohydrate (0.69 g, 0.013 equiv.), and it was refluxed under a Dean-Stock tarp for 2 hrs. After cooling to room temperature it was made basic with sat'd NaHCO$_3$, and the product was extracted with EtOAc (3×). The combined extracts were washed with brine, dried over Na$_2$SO$_4$, and evaporated to give a syrupy residue. It was purified by column chromatography (silica gel, 15% EtOAc/hexane) to give ketal-keto-ester 10 (35 g, 54% yield for 2 steps) as a light yellow oil.

$^1$H NMR (300 MHz, CDCl$_3$) δ 12.21 (s, 1H), 4.22 (q, 2H, J=7.0 Hz), 4.00 (s, 4H), 2.53 (s, 2H), 2.41 (t, 2H, J=6.6 Hz), 1.77 (t, 2H, J=6.6 Hz, 1.30 (t, 3H, J=7.0 Hz).

Step d: To a solution of ketal-keto-ester 10 (54 g) in 1 L of benzene were added (R)-(+)-α-methylbenzylamine (31.7 mL, 1.04 equiv.) and acetic acid (27 mL, 2 equiv.), and it was refluxed under a Dean-Stock trap for 2 hrs. After cooling to room temperature it was added to 1 L of sat'd NaHCO$_3$ with stirring, and the organic layer was separated. It was washed with brine, dried over Na$_2$SO$_4$, and evaporated to give a syrupy residue of crude enamine 11. It was dried further by azeotroping with benzene three times, and used without purification for next step.

Step e: To a solution of enamine 11 in 1 L of anhydrous CH$_2$Cl$_2$ were added ethylene glycol (69.4 mL, 5 equiv.) and acetic acid (158 mL, 11.1 equiv.) at 0° C., and was also added Na(OAc)$_3$BH (211 g, 4 equiv.) in five equal portions over a period of 2 hrs. The mixture was stirred for 14 hrs at room temperature, and then was made basic with sat'd Na$_2$CO$_3$. The organic layer was separated and the aqueous solution was extracted with CH$_2$Cl$_2$ (2×200 mL). The combined extracts were washed with water, dried over MgSO$_4$, and evaporated to give an oily residue. The residue was dissolved in a 1:1 mixture of EtOAc and hexane (800 mL), and washed with water (4×150 mL) and with brine (2×100 mL) to remove ethylene glycol and excess methylbenzylamine. The solution was dried over Na$_2$SO$_4$ and evaporated to give a syrupy residue of crude cis amino-ester 12 as a ~3:1 mixture of (1R,2S)- and (1S,2R)-diastereomers. It was dried further by azeotroping with benzene three times, and used without purification for next step.

Step f: To a solution of cis amino-ester 12 in 900 mL of anhydrous THF was added sodium t-butoxide (23.8 g, 1 equiv.), and the mixture was stirred for 5.5 hrs at room temperature. It was then poured into a vigorously stirred mixture of 1N HCl (350 mL) and ice (ca. 500 g). After stirring for 5 minutes it was made basic with 250 mL of sat'd NaHCO$_3$, and extracted with 500 mL of EtOAc. The extract was was washed with sat'd NaHCO$_3$ and brine. The combined aquous layers were extracted with 300 mL of EtOAc again and washed with brine. The EtOAc extracts were combined, dried over Na$_2$SO$_4$, and evaporated to give a ~3:1 mixture of trans amino-ester 13 [as a 3:1 mixture of of (1R,2R)- and (1S,2S)-diatereomers] and cis amino-ester 12 [as a 3:1 mixture of of (1S,2R)- and (1R,2S)-diatereomers]. (1S,2S)-Diastereomer of the trans amino-ester (Rf=0.17, 40% EtOAc/hexane) was separaterd out from other diastereomers (Rf>0.3, 40% EtOAc/hexane) by column chromatography (silica gel, 15-40% EtOAc/hexane). Fractions containing the (1R,2R)-trans amino-ester 13 (Rf=0.33, 40% EtOAc/hexane) were combined and evaporated to give a syrupy residue (39.4 g).

$^1$H NMR (300 MHz, CDCl$_3$) δ 7.30-7.20 (m, 5H), 4.18 (q, 2H, J=7.3 Hz), 3.87-3.78 (m, 5H), 3.07 (dt, 1H, J$_1$=9.8 Hz, J$_2$=3.3 Hz), 2.20 (dt, 1H, J$_1$=9.8 Hz, J$_2$=3.3 Hz), 1.92-1.42 (m, 6H), 1.29 (t, 3H, J=6.6 Hz), 1.28 (d, 3H, J=6.6 Hz).

Step g: To a solution of crude (1R,2R)-trans amino-ester 13 (39.4 g) in 600 mL of anhydrous diethyl ether at 0° C. was added dropwise a 1M solution of LiAlH$_4$ in THF (132 mL, 1.1 equiv.), and the mixture was stirred for 1.5 hrs at the same temperature. The reaction was quenched by slow addition of Na$_2$SO$_4$.10H$_2$O (~50 g), and stirring for 45 minutes. It was filtered through a plug of Celite and evaporated to give a crystalline solid. It was recrystallized from EtOAc and hexane to afford (1R,2R)-trans amino-alcohol 14 (28.7 g, 39.7% yield for 4 steps).

$^1$H NMR (300 MHz, CDCl$_3$) δ 7.35-7.23 (m, 5H), 3.92-3.88 (m, 4H), 3.71-3.65 (m, 2H), 2.82 (td, 1H, $J_1$=11.7 Hz, $J_2$=4.0 Hz), 2.08 (dt, 1H, $J_1$=12.7 Hz, $J_2$=2.5 Hz), 1.73-1.12 (m, 7H), 1.41 (d, 3H, J=6.6 Hz).

Step h: To a solution of (1R,2R)-trans amino-alcohol 14 (10 g, 34.3 mmoles) in 100 mL of methanol was added 1 g of Pd(OH)$_2$ under nitrogen, and the mixture was treated with H$_2$ on a Parr hydrogenator (60 psi) for 48 hrs. The catalyst was filtered off and the filtrate was evaporated to give amino-alcohol 15 as an oil, which was used for next reaction without purification.

Step i: To a solution of (1R,2R)-trans amino-alcohol 15 (34.3 mmoles) in 200 mL of CH$_2$Cl$_2$ and 125 mL of sat'd NaHCO$_3$ at 0° C. was added benzyl chloroformate (6.1 mL, 1.25 equiv.) dropwise and the mixture was stirred for 0.5 hrs. Then the CH$_2$CO$_2$ layer was separated and the aqueous layer was extracted with CH$_2$Cl$_2$ once. The extracts were combined, washed with water, dried over MgSO$_4$, and evaporated to give a solid residue. It was crystallized from EtOAc and hexane to give pure CBz-protected amino-alcohol 16 (9.7 g, yield 88% for 2 steps).

$^1$H NMR (300 MHz, CDCl$_3$) δ 7.35 (s, 5H), 5.1 (s, 2H), 4.92 (d, 1H, J=8.4 Hz), 3.94 (s, 4H), 3.80-3.69 (m, 2H), 3.47 (t, 1H, J=10.9 Hz), 3.15 (m, 1H), 2.06-1.20 (m, 6H).

Step j: To a stirred solution of oxalyl chloride (5.51 mL, 1.5 equiv.) in 190 mL of anhydrous CH$_2$Cl$_2$ at −65° C. was added DMSO (4.8 mL, 1.6 equiv.) dropwise over a period of 10 minutes. The mixture was stirred for 20 minutes at −65—60° C. Then a solution of pure CBz-protected amino-alcohol 16 (13.54 g) in 95 mL of anhydrous CH$_2$Cl$_2$ was added dropwise over a period of 20 minutes at −70~−60° C. After stirring for 40 minutes at −60~−50° C. triethylamine (17.6 mL, 3 equiv.) was added dropwise over a period of 10 minutes, and the mixture was continued to stir for 1.25 hrs at −50~0° C. Then 500 mL of diethyl ether was added and the mixture was washed with water (2×150 mL) and brine (100 mL). It was dried over Na$_2$SO$_4$ and evaporated to give a solid residue. Recrystallization from EtOAc and hexane provided aldehyde 17 (13.2 g, 98% yield).

Step k: To a solution of N-methyl-3-(4-fluorophenyl) propylamine (1 g, 1.25 equiv.) in 40 mL of anhydrous CH$_2$Cl$_2$ was added aldehyde 17 (1.3 g), and the solution was stirred for 0.5 hrs at room temperature. Then Na(OAc)$_3$BH (1.8 g, 2 equiv.) was added and the mixture was continued to stir for 16 hrs at room temperature. It was made basic with sat'd Na$_2$CO$_3$ and the product was extracted with CH$_2$Cl$_2$. The extract was washed with brine, dried over MgSO$_4$, and evaporated to give an oily residue. It was purified by column chromatography (silica gel, EtOAc) to give amino-ketal 18 [R$^5$=3-(4-fluorophenyl)propyl, R$^4$=methyl, 1 g, 50% yield].

$^1$H NMR (300 MHz, CDCl$_3$) δ 7.31 (s, 5H), 7.05 (m, 2H), 6.93 (t, 2H, J=8.7 Hz), 5.06 (s, 2H), 3.93 (bs, 4H), 3.56 (m, 1H), 2.55 (t, 2H, J=7.4 Hz), 2.47-1.34 (m, 13H), 2.18 (s, 3H).

Step l: To a solution of amino-ketal 18 [R$^5$=3-(4-fluorophenyl)propyl, R$^4$=methyl, 1 g] in 10 mL of CH$_3$CN was added 20 mL of 1N HCl, and the mixture was stirred for 24 hrs at room temperature. It was then made basic with sat'd Na$_2$CO$_3$ and extracted with EtOAc (2×). The combined extracts were washed with brine, dried over MgSO$_4$, evaporated to give crude amino-ketone 19 [R$^5$=3-(4-fluorophenyl) propyl, R$^4$=methyl, 1 g] as an oil, which was used for next step without purification.

$^1$H NMR (300 MHz, CDCl$_3$) δ 7.30 (s, 5H), 7.05 (m, 2H), 6.93 (t, 2H, J=8.4 Hz), 5.06 (s, 3H), 3.57 (m, 1H), 3.10 (d, 1H, J=14.3 Hz), 2.56 (t, 2H, J=7.3 Hz), 2.53-1.80 (m, 10H), 2.22 (s, 3H), 1.74 (qt, 2H, J=8.1 Hz), 1.40 (m, 1H).

Step m1: To a solution of amino-ketone 19 [R$^5$=3-(4-fluorophenyl)propyl, R$^4$=methyl, 1 g] in 20 mL of CH$_2$Cl$_2$ was added a 33% solution of methylamine in ethanol (1 mL, 10 equiv.), and the mixture was stirred for 0.5 hrs. Then Na(OAc)$_3$BH (2.47 g, 5 equiv.) was added and it was stirred for 2 days at room temperature. The mixture was made basic with sat'd Na$_2$CO$_3$, and extracted with CH$_2$Cl$_2$ (2×). The combined extracts wre washed with brine, dried over Na$_2$SO$_4$, and evaporated to give a ~1:1 diastereomeric mixture of 5-methylamine 20 [R$^5$=3-(4-fluorophenyl)propyl, R$^4$=methyl, R$^{14a}$=methyl, R$^{14b}$=H] as an oil, which was used for next step without purification.

Step m2: To a solution of 5-methylamine 20 [R$^5$=3-(4-fluorophenyl)propyl, R$^4$=methyl, R$^{14a}$=methyl, R$^{14b}$=H, 1:1 mixture of (5R)- and (5S)-isomers, 1 g] in 20 mL of anhydrous CH$_2$Cl$_2$ were added acetic anhydride (0.48 g, 2 equiv.) and triethylamine (0.99 mL, 3 equiv.), and the mixture was stirred for 16 hrs at room temperature. After evaporating off the solvent the product was purified by column chromatography (silica gel, 0.5:2:98 cNH$_4$OH/CH$_3$OH/CH$_2$Cl$_2$) to give 5-N-methylacetamide 20 [R$^5$=3-(4-fluorophenyl)propyl, R$^4$=methyl, R$^{14a}$=methyl, R$^{14b}$=acetyl, 1:1 mixture of (5R)- and (5S)-isomers, 0.45 g] as an oil.

Step n: To a solution of 5-N-methylacetamide 20 [R$^5$=3-(4-fluorophenyl)propyl, R$^4$=methyl, R$^{14a}$=methyl, R$^{14b}$=acetyl, 1:1 mixture of (5R)- and (5S)-isomers, 0.45 g] in 20 mL of methanol was introduced 10% Pd/C (0.1 g) under nitrogen, and the mixture was treated with H$_2$ (1 atm) for 18 hrs. The catalyst was filtered off and the filtrate was evaporated to give disubstituted cyclohexylamine 21 [R$^5$=3-(4-fluorophenyl)propyl, R$^4$=methyl, R$^{14a}$=methyl, R$^{14b}$=acetyl] as a 1:1 mixture of (5R)- and (5S)-isomers (100% yield).

Step o: To a solution of disubstituted cyclohexylamine 21 [R$^5$=3-(4-fluorophenyl)propyl, R$^4$=methyl, R$^{14a}$=methyl, R$^{14b}$=acetyl, a 1:1 mixture of (5R)- and (5S)-isomers, 60 mg] in 1 mL of anhydrous THF were added N-(3-acetylphenyl)-phenylcarbamate (64 mg, 1.5 equiv.) and triethylamine (22 mg, 1.3 equiv.), and the mixture was stirred for 18 hrs at room temperature. After evaporating off the solvent, two diasteromeric ureas were separated by flash chromatography (silica gel, 0.5:3:97 cNH$_4$OH/CH$_3$OH/CH$_2$Cl$_2$) to give N-(3-acetylphenyl)-N'-[(1R,2S,5R)-5-(N-methyl)acetamido-2-[N-methyl-3-(4-fluorophenyl)propylamino]methyl-cyclohexyl]urea (EXAMPLE 9) and N-(3-acetylphenyl)-N'-[(1R,2S,5S)-5-(N-methyl)acetamido-2-[N-methyl-3-(4-fluorophenyl)propylamino]methyl-cyclohexyl]urea (EXAMPLE 10) as amorphous solids.

(5R)-isomer: $^1$H NMR (300 MHz, CDCl$_3$, a 1:1 mixture of conformers) δ 7.81 (d, 1H, J=1.9 Hz), 7.64 (d, 1H, J=8.0 Hz), 7.35 (m, 1H), 7.04 (dd, 2H, $J_1$=8.5 Hz, $J_2$=5.9 Hz), 6.56 (s, 1H), 4.48 (bt, 0.5H), 3.66 (bt, 0.5H), 3.42 (m, 1H), 2.84 (s, 1.5H), 2.80 (s, 1.5H), 2.57 (s, 1.5H), 2.56 (s, 1.5H), 2.19 (s, 1.5H), 2.18 (s, 1.5H), 2.13 (s, 1.5H), 2.06 (s, 1.5H), 2.54-1.10 (m, 15H). MS ESI (M+H)$^+$=511.5.

(5S)-isomer: $^1$H NMR (300 MHz, CDCl$_3$) δ 8.22 (s, 1H), 7.95 (s, 1H), 7.64 (d, 1H, J=6.4 Hz), 7.49 (d, 1H, J=7.7 Hz), 7.27 (t, 1H, J=7.9 Hz), 7.14 (dd, 2H, $J_1$=8.4 Hz, $J_2$=5.5 Hz), 6.94 (t, 2H, J=8.8 Hz), 6.39 (bd, 1H), 4.78 (b, 1H), 4.24 (b, 1H), 2.87 (s, 3H), 2.62 (t, 2H, J=7.7 Hz), 2.56 (s, 3H), 2.35-2.30 (m, 4H), 2.20 (s, 3H), 2.15 (s, 3H), 1.97-1.20 (m, 9H). MS ESI (M+H)=511.5.

Examples 11 and 12

N-((1R,3R,4S)-3-({[(5-acetyl-4-methyl-1,3-thiazol-2-yl)amino]carbonyl}amino)-4{[[3-(4-fluorophenyl)propyl](methyl)amino]methyl}cyclohexyl)-N-methylacetamide and N-((1S,3R,4S)-3-({[(5-acetyl-4-methyl-1,3-thiazol-2-yl)amino]carbonyl}amino)-4{[[3-(4-fluorophenyl)propyl](methyl)amino]methyl}cyclohexyl)-N-methylacetamide

Examples 13 and 14

N-{(1R,3R,4S)-4-{[[3-(4-fluorophenyl)propyl](methyl)amino]methyl}-3-[({[3-(1-methyl-1H-tetrazol-5-yl)phenyl]amino}carbonyl)amino]cyclohexyl}-N-methylacetamide and N-{(1S,3R,4S)-4-{[[3-(4-fluorophenyl)propyl](methyl)amino]methyl}-3-[({[3-(1-methyl-1H-tetrazol-5-yl)phenyl]amino}carbonyl)amino]cyclohexyl}-N-methylacetamide

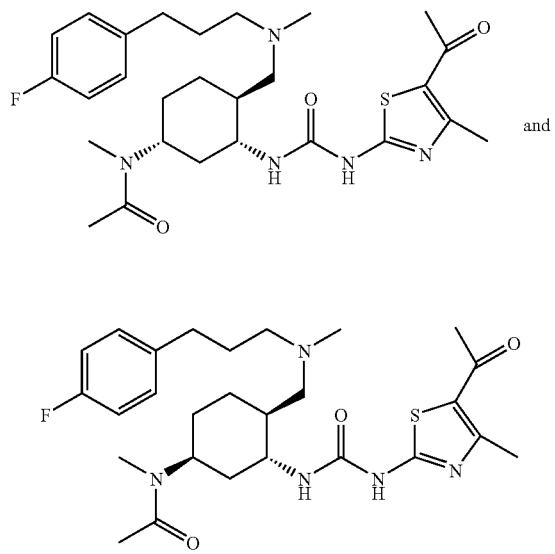

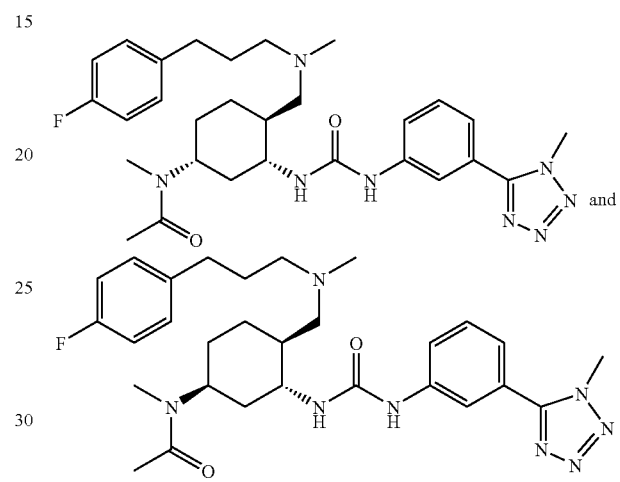

To a solution of disubstituted cyclohexylamine 21 [$R^5$=3-(4-fluorophenyl)propyl, $R^4$=methyl, $R^{14^a}$=methyl, $R^{14^b}$=acetyl, a 1:1 mixture of (5R)- and (5S)-isomers, 60 mg, see Scheme 3] in 1 mL of anhydrous THF were added N-(5-acetyl-4-methyl-thiazol-2-yl)-phenylcarbamate (60 mg, 1.27 equiv.) and triethylamine (22 mg, 1.3 equiv.), and the mixture was stirred for 18 hrs at room temperature. After evaporating off the solvent, two diasteromeric ureas were separated by flash chromatography (silica gel, 0.5:3:97 cNH$_4$OH/CH$_3$OH/CH$_2$Cl$_2$) to give N-(5-acetyl-4-methyl-thiazol-2-yl)-N'-[(1R,2S,5R)-5-(N-methyl)acetamido-2-[N-methyl-3-(4-fluorophenyl)propylamino]methyl-cyclohexyl]urea (EXAMPLE 11) and N-(5-acetyl-4-methyl-thiazol-2-yl)-N'-[(1R,2S,5S)-5-(N-methyl)acetamido-2-[N-methyl-3-(4-fluorophenyl)propylamino]methyl-cyclohexyl]urea (EXAMPLE 12) as amorphous solids.

(5R)-isomer: $^1$H NMR (300 MHz, CDCl$_3$, a 6:4 mixture of conformers) δ 7.10-7.05 (m, 2H), 6.96-6.90 (m, 2H), 4.48 (t, 0.6H, J=11.7 Hz), 3.66 (t, 0.4H, J=11.7 Hz), 3.49-3.40 (m, 1H), 2.85 and 2.80 (s, 3H), 2.61 and 2.60 (s, 3H), 2.53 (t, 2H, J=7.7 Hz), 2.47 and 2.46 (s, 3H), 2.21 and 2.20 (s, 3H), 2.14 and 2.07 (s, 3H), 2.42-1.14 (m, 13H). MS ESI (M+H)$^+$=532.4.

(5S)-isomer: $^1$H NMR (300 MHz, CDCl$_3$) δ 7.14 (dd, 2H, J$_1$=8.4 Hz, J2=5.5 Hz), 6.95 (t, 2H, J=8.7 Hz), 4.75 (b, 1H), 4.33 (b, 1H), 2.87 (s, 3H), 2.63 (t, 2H, J=7.7 Hz), 2.58 (s, 3H), 2.45 (s, 3H), 2.22 (s, 3H), 2.21 (s, 3H), 2.38-1.40 (m, 13H). MS ESI (M+H)$^+$=532.4.

To a solution of disubstituted cyclohexylamine 21 [$R^5$=3-(4-fluorophenyl)propyl, $R^4$=methyl, $R^{14^a}$=methyl, $R^{14^b}$=acetyl, a 1:1 mixture of (5R)- and (5S)-isomers, 60 mg, see Scheme 3] in 1 mL of anhydrous THF were added N-[3-(1-methyl-tetrazol-5-yl)phenyl]-phenylcarbamate (60 mg, 1.2 equiv.) and triethylamine (22 mg, 1.3 equiv.), and the mixture was stirred for 18 hrs at room temperature. After evaporating off the solvent, two diasteromeric ureas were separated by flash chromatography (silica gel, 0.5:3:97 cNH$_4$OH/CH$_3$OH/CH$_2$Cl$_2$) to give N-[3-(1-methyl-tetrazol-5-yl)phenyl]-N'-[(1R,2S,5R)-5-(N-methyl)acetamido-2-[N-methyl-3-(4-fluorophenyl)propylamino]methyl-cyclohexyl]urea (EXAMPLE 13) and N-[3-(1-methyl-tetrazol-5-yl)phenyl]-N'-[(1R,2S,5S)-5-(N-methyl)acetamido-2-[N-methyl-3-(4-fluorophenyl)propylamino]methyl-cyclohexyl]urea (EXAMPLE 14) as amorphous solids.

(5R)-isomer: $^1$H NMR (300 MHz, CDCl$_3$, a 1:1 mixture of conformers) δ 7.87 and 7.81 (t, 1H, J=1.8 Hz), 7.62 and 7.52 (dd, 1H, J$_1$=7.3 Hz, J$_2$=1.1 Hz), 7.43 and 7.41 (t, 1H, J=7.5 Hz), 7.33-7.24 (m, 1H), 7.10-7.03 (m, 2H), 6.88 (t, 2H, J=8.8 Hz), 4.46 and 3.67 (t, 1H, J=12 Hz), 4.18 and 4.17 (s, 3H), 3.53-3.40 (m, 1H), 2.85 and 2.79 (s, 3H), 2.56-1.12 (m, 15H), 2.20 and 2.18 (s, 3H), 2.13 and 2.06 (s, 3H). MS ESI (M+H)$^+$=551.5.

(5S)-isomer: $^1$H NMR (300 MHz, CDCl$_3$) δ 8.37 (s, 1H), 7.90 (s, 1H), 7.47 (d, 1H, J=7.7 Hz), 7.33 (t, 1H, J=8.1 Hz), 7.13 (dd, 2H, J$_1$=8.5 Hz, J$_2$=5.9 Hz), 6.94 (t, 2H, J=8.8 Hz), 6.43 (bd, 1H), 4.77 (b, 1H), 4.21 (b, 1H), 4.15 (s, 3H), 2.87 (s, 3H), 2.62 (d, 2H, J=7.3 Hz), 2.37-2.30 (m, 4H), 2.21 (s, 3H), 2.15 (s, 3H), 1.78-1.30 (m, 11H). MS ESI (M+H)$^+$=551.5.

Examples 15 and 16

N-{(1R,3R,4S)-4-{[[3-(4-fluorophenyl)propyl](methyl)amino]methyl}-3-[({[1-methyl-indazol-5-yl]amino}carbonyl)amino]cyclohexyl}-N-methylacetamide and N-[(1S,3R,4S)-4-{[[3-(4-fluorophenyl)propyl](methyl)amino]methyl}-3-[({[1-methyl-indazol-5-yl]amino}carbonyl)amino]cyclohexyl]-N-methylacetamide

Examples 17 and 18

N-((1R,3R,4S)-3-({[(3-acetylphenyl)amino]carbonyl}amino)-4{[[3-(4-fluorophenyl)propyl](propyl)amino]methyl}cyclohexyl)-N-methylacetamide and N-((1S,3R,4S)-3-({[(3-acetylphenyl)amino]carbonyl}amino)-4 {[[3-(4-fluorophenyl)propyl](propyl)amino]methyl}cyclohexyl)-N-methylacetamide

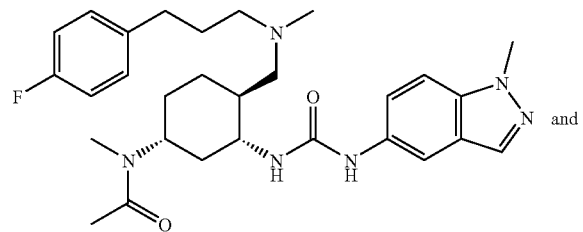 and

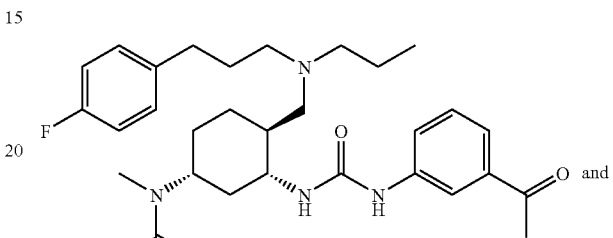 and

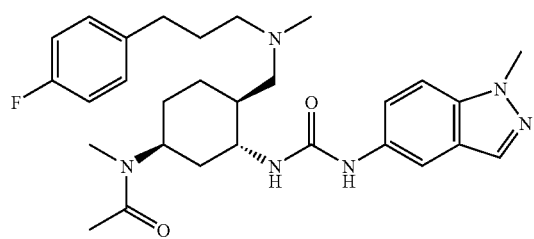

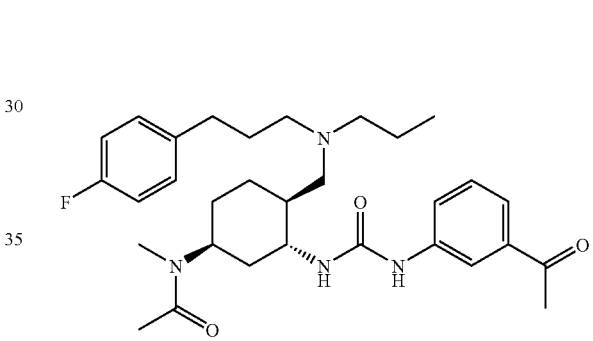

To a solution of disubstituted cyclohexylamine 21 [$R^5$=3-(4-fluorophenyl)propyl, $R^4$=methyl, $R^{14a}$=methyl, $R^{14b}$=acetyl, a 1:1 mixture of (5R)- and (5S)-isomers, 60 mg, see Scheme 3] in 1 mL of anhydrous THF were N-(1-methyl-indazol-5-yl)-phenylcarbamate (42 mg, 1.2 equiv.) and triethylamine (22 mg, 1.3 equiv.), and the mixture was stirred for 18 hrs at room temperature. After evaporating off the solvent, two diasteromeric ureas were separated by flash chromatography (silica gel, 0.5:3:97 cNH$_4$OH/CH$_3$OH/CH$_2$Cl$_2$) to give N-(1-methyl-indazol-5-yl)-N'-[(1R,2S,5R)-5-(N-methyl)acetamido-2-[N-methyl-3-(4-fluorophenyl)propylamino]methyl-cyclohexyl]urea (EXAMPLE 15) and N-(1-methyl-indazol-5-yl)-N'-[(1R,2S,5S)-5-(N-methyl)acetamido-2-[N-methyl-3-(4-fluorophenyl)propylamino]methyl-cyclohexyl]urea (EXAMPLE 16) as amorphous solids.

(5R)-isomer: $^1$H NMR (300 MHz, CDCl$_3$, a ~1:1 mixture of conformers) δ 7.87 (d, 1H, J=3 Hz), 7.61 (s, 1H), 7.24 (s, 1H), 7.04-7.03 (m, 2H), 7.01 (t, 2H, J=12.9 Hz), 6.29 (s, 1H), 4.48 and 3.67 (t, 1H, J=11.7 Hz), 4.00 (s, 3H), 3.47-3.40 (m, 1H), 2.84 and 2.79 (s, 3H), 2.13 and 2.06 (s, 3H), 2.03 and 2.01 (s, 3H), 2.53-1.11 (m, 15H). MS ESI (M+H)$^+$=523.5.

(5S)-isomer: $^1$H NMR (300 MHz, CDCl$_3$) δ 7.83 (s, 1H), 7.81 (d, 1H, J=1.1 Hz), 7.67 (s, 1H), 7.24 (d, 1H, J=1.9 Hz), 7.17 (m, 2H), 6.94 (t, 2H, J=8.4 Hz), 6.09 (b, 1H), 4.77 (b, 1H), 4.23 (b, 1H), 3.96 (s, 3H), 2.84 (s, 3H), 2.61 (t, 2H, J=7.7 Hz), 2.36-2.28 (m, 4H), 2.20 (s, 3H), 2.11 (s, 3H), 1.92-1.40 (m, 11H). MS ESI (M+H)$^+$=523.5.

(See Scheme 3)

Step k: To a solution of N-propyl-3-(4-fluorophenyl)propylamine (1.8 g, 1.25 equiv.) in 40 mL of anhydrous CH$_2$Cl$_2$ was added aldehyde 17 (2.1 g), and the solution was stirred for 0.5 hrs at room temperature. Then Na(OAc)$_3$BH (2.97 g, 2 equiv.) was added and the mixture was continued to stir for 16 hrs at room temperature. It was made basic with sat'd Na$_2$CO$_3$ and the product was extracted with CH$_2$Cl$_2$. The extract was washed with brine, dried over MgSO$_4$, and evaporated to give an oily residue. It was purified by column chromatography (silica gel, EtOAc) to give 1.2 g of amino-ketal 18 [$R^5$=3-(4-fluorophenyl)propyl, $R^4$=propyl].

Step l: To a solution of amino-ketal 18 [$R^5$=3-(4-fluorophenyl)propyl, $R^4$=propyl, 1.2 g] in 10 mL of CH$_3$CN was added 20 mL of 1N HCl, and the mixture was stirred for 24 hrs at room temperature. It was then made basic with sat'd Na$_2$CO$_3$ and extracted with EtOAc (2×). The combined extracts were washed with brine, dried over MgSO$_4$, evaporated to give 1 g of crude amino-ketone 19 [$R^5$=3-(4-fluorophenyl)propyl, $R^4$=propyl] as an oil, which was used for next step without purification.

Step m1: To a solution of amino-ketone 19 [$R^5$=3-(4-fluorophenyl)propyl, $R^4$=propyl, 1 g] in 20 mL of CH$_2$Cl$_2$ was added a 33% solution of methylamine in ethanol (1 mL, 10 equiv.), and the mixture was stirred for 0.5 hrs. Then Na(OAc)$_3$BH (2.4 g, 5 equiv.) was added and it was stirred for 2 days at room temperature. The mixture was made basic with sat'd Na$_2$CO$_3$, and extracted with CH$_2$Cl$_2$ (2×). The combined extracts were washed with brine, dried over Na$_2$SO$_4$, and evaporated to give a ~1:1 diastereomeric mixture of 5-methylamine 20 [R$^5$=3-(4-fluorophenyl)propyl, R$^4$=propyl, R$^{14a}$=methyl, R$^{14b}$=H] as an oil, which was used for next step without purification.

Step m2: To a solution of 5-methylamine 20 [R$^5$=3-(4-fluorophenyl)propyl, R$^4$=propyl, R$^{14a}$=methyl, R$^{14b}$=H, 1:1 mixture of (5R)- and (5S)-isomers, 1 g] in 20 mL of anhydrous CH$_2$Cl$_2$ were added acetic anhydride (0.5 mL, 2 equiv.) and triethylamine (0.99 mL, 3 equiv.), and the mixture was stirred for 16 hrs at room temperature. After evaporating off the solvent the product was purified by column chromatography (silica gel, 0.5:2:98 cNH$_4$OH/CH$_3$OH/CH$_2$Cl$_2$) to give 0.45 g of 5-N-methylacetamide 20 [R$^5$=3-(4-fluorophenyl)propyl, R$^4$=propyl, R$^{14a}$=methyl, R$^{14b}$=acetyl, 1:1 mixture of (5R)- and (5S)-isomers] as an oil.

Step n: To a solution of 5-N-methylacetamide 20 [R$^5$=3-(4-fluorophenyl)propyl, R$^4$=propyl, R$^{14a}$=methyl, R$^{14b}$=acetyl, 1:1 mixture of (5R)- and (5S)-isomers, 0.45 g] in 20 mL of methanol was introduced 10% Pd/C (0.1 g) under nitrogen, and the mixture was treated with H$_2$ (1 atm) for 18 hrs. The catalyst was filtered off and the filtrate was evaporated to give disubstituted cyclohexylamine 21 [R$^5$=3-(4-fluorophenyl)propyl, R$^4$=propyl, R$^{14a}$=methyl, R$^{14b}$=acetyl] as a 1:1 mixture of (5R)- and (5S)-isomers (100% yield).

Step o: To a solution of disubstituted cyclohexylamine 21 [R$^5$=3-(4-fluorophenyl)propyl, R$^4$=propyl, R$^{14a}$=methyl, R$^{14b}$=acetyl, a 1:1 mixture of (5R)- and (5S)-isomers, 60 mg] in 1 mL of anhydrous THF were added N-(3-acetylphenyl)-phenylcarbamate (60 mg, 1.47 equiv.) and triethylamine (22 mg, 1.4 equiv.), and the mixture was stirred for 18 hrs at room temperature. After evaporating off the solvent, two diasteromeric ureas were separated by flash chromatography (silica gel, 0.5:3:97 cNH$_4$OH/CH$_3$OH/CH$_2$Cl$_2$) to give N-(3-acetylphenyl)-N'-[(1R,2S,5R)-5-(N-methyl)acetamido-2-[N-propyl-3-(4-fluorophenyl)propylamino]methyl-cyclohexyl]urea (EXAMPLE 17) and N-(3-acetylphenyl)-N'-[(1R,2S,5S)-5-(N-methyl)acetamido-2-[N-propyl-3-(4-fluorophenyl)propylamino]methyl-cyclohexyl]urea (EXAMPLE 18) as amorphous solids.

(5R)-isomer: $^1$H NMR (300 MHz, CDCl$_3$, a ~6:4 mixture of conformers) δ 7.97 and 7.90 (s, 1H), 7.64 and 7.61 (s, 1H), 7.58 and 7.56 (s, 1H), 7.39-7.31 (m, 1H), 7.05 (bt; 2H), 6.91 (t, 2H, J=8.8 Hz), 4.53 (bt, 1H), 3.60 (b, 2H), 2.&3 and 2.79 (s, 3H), 2.58 (s, 3H), 2.58-1.20 (m, 18H), 2.13 and 2.07 (s, 3H), 0.89(T, 3H, J=6.6 Hz). MS ESI (M+H)$^+$=539.5.

(5S)-isomer: $^1$H NMR (300 MHz, CDCl$_3$) δ 8.11 (s, 1H), 7.95 (S, 1H), 7.64 (d, 1H, J=8 Hz), 7.49 (d, 1H, J=7.7 Hz), 7.13 (dd, 2H, J$_1$=8.4 Hz, J$_2$=5.5 Hz), 6.93 (t, 2H, J=8.8 Hz), 6.33 (br, 1H), 4.76 (br, 1H), 4.21 (br, 1H), 2.87 (s, 3H), 2.60 (m, 2H), 2.56 (s, 3H), 2.14 (s, 3H), 2.44-1.40 (m, 19H), 0.88 (t, 3H, J=7.3 Hz). MS ESI (M+H)$^+$=539.5.

Examples 19 and 20

N-((1R,3R,4S)-3-({[(5-acetyl-4-methyl-1,3-thiazol-2-yl)amino]carbonyl}amino)-4{[[3-(4-fluorophenyl)propyl](propyl)amino]methyl}cyclohexyl)-N-methylacetamide and N-((1S,3R,4S)-3-({[(5-acetyl-4-methyl-1,3-thiazol-2-yl)amino]carbonyl}amino)-4{[[3-(4-fluorophenyl)propyl](propyl)amino]methyl}cyclohexyl)-N-methylacetamide

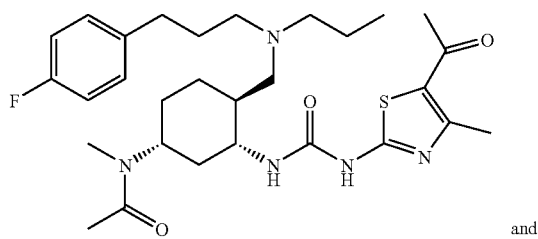

and

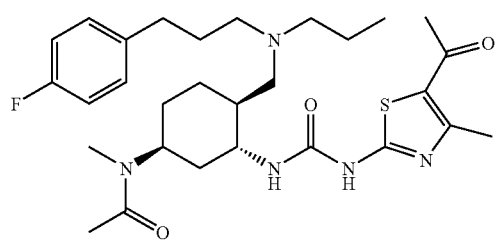

To a solution of disubstituted cyclohexylamine 21 [R$^5$=3-(4-fluorophenyl)propyl, R$^4$=propyl, R$^{14a}$=methyl, R$^{14b}$=acetyl, a 1:1 mixture of (5R)- and (5S)-isomers, 60 mg, see Scheme 3] in 1 mL of anhydrous THF were added N-(5-acetyl-4-methyl-thiazol-2-yl)-phenylcarbamate (60 mg, 1.5 equiv.) and triethylamine (44 mg, 2.93 equiv.), and the mixture was stirred for 18 hrs at room temperature. After evaporating off the solvent, two diasteromeric ureas were separated by flash chromatography (silica gel, 0.5:3:97 cNH$_4$OH/CH$_3$OH/CH$_2$Cl$_2$) to give N-(5-acetyl-4-methyl-thiazol-2-yl)-N'-[(1R,2S,5R)-5-(N-methyl)acetamido-2-[N-propyl-3-(4-fluorophenyl)propylamino]methyl-cyclohexyl]urea (EXAMPLE 19) and N-(5-acetyl-4-methyl-thiazol-2-yl)-N'-[(1R,2S,5S)-5-(N-methyl)acetamido-2-[N-propyl-3-(4-fluorophenyl)propylamino]methyl-cyclohexyl]urea (EXAMPLE 20) as amorphous solids.

(5R)-isomer: $^1$H NMR (300 MHz, CDCl$_3$, a ~6:4 mixture of conformers) δ 7.11-7.06 (m, 2H), 6.93 (t, 2H, J=8.8 Hz), 4.49 and 3.65 (bt, 1H, J=12.1 Hz), 3.48 (bt, 1H, J=8.8 Hz), 2.84 and 2.80 (s, 3H), 2.60 and 2.59 (s, 3H), 2.55 (t, 2H, J=7.7 Hz), 2.60-1.10 (m, 17H), 2.47 and 2.46 (s, 3H), 2.14 and 2.07 (s, 3H), 0.88 (t, 3H, J=7.4 Hz). MS ESI (M+H)$^+$=560.4.

(5S)-isomer: $^1$H NMR (300 MHz, CDCl$_3$) δ 7.13 (dd, 2H, J$_1$=8.8 Hz, J$_2$=5.9 Hz), 6.93 (t, 2H, J=8.8 Hz), 4.74 (br, 1H), 4.31 (br, 1H), 2.87 (s, 3H), 2.60 (t, 2H, J=7 Hz), 2.57 (s, 3H), 2.44 (s, 3H), 2.44-1.39 (m, 17H), 2.23 (s, 3H), 0.89 (t, 3H, J=7.3 Hz). MS ESI (M+H)$^+$=560.4.

Examples 21 and 22

N-{(1R,3R,4S)-4-{[[3-(4-fluorophenyl)propyl](propyl)amino]methyl}-3-[({[3-(1-methyl-1H-tetrazol-5-yl)phenyl]amino}carbonyl)amino]cyclohexyl}-N-methylacetamide and N-{(1S,3R,4S)-4-{[[3-(4-fluorophenyl)propyl](propyl)amino]methyl}-3-[({[3-(1-methyl-1H-tetrazol-5-yl)phenyl]amino}carbonyl)amino]cyclohexyl}-N-methylacetamide

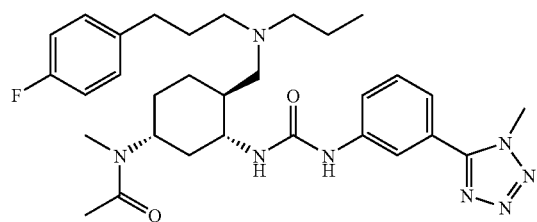
and

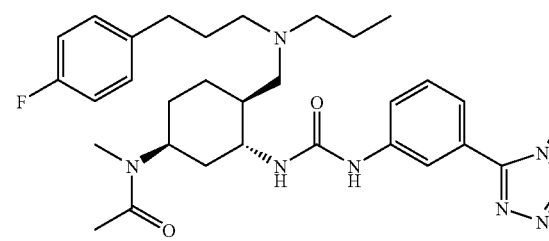

To a solution of disubstituted cyclohexylamine 21 [$R^5$=3-(4-fluorophenyl)propyl, $R^4$=propyl, $R^{14^a}$=methyl, $R^{14^b}$=acetyl, a 1:1 mixture of (5R)- and (5S)-isomers, 60 mg, see Scheme 3] in 1 mL of anhydrous THF were added N-[3-(1-methyl-tetrazol-5-yl)phenyl]-phenylcarbamate (60 mg, 1.36 equiv.) and triethylamine (22 mg, 1.3 equiv.), and the mixture was stirred for 18 hrs at room temperature. After evaporating off the solvent, two diasteromeric ureas were separated by flash chromatography (silica gel, 0.5:3:97 cNH$_4$OH/CH$_3$OH/CH$_2$Cl$_2$) to give N-[3-(1-methyl-tetrazol-5-yl)phenyl]-N'-[(1R,2S,5R)-5-(N-methyl)acetamido-2-[N-propyl-3-(4-fluorophenyl)propylamino]methyl-cyclohexyl]urea (EXAMPLE 21) and N-[3-(1-methyl-tetrazol-5-yl)phenyl]-N'-[(1R,2S,5S)-5-(N-methyl)acetamido-2-[N-propyl-3-(4-fluorophenyl)propylamino]methyl-cyclohexyl]urea (EXAMPLE 22) as amorphous solids.

(5R)-isomer: $^1$H NMR (300 MHz, CDCl$_3$, a ~6:4 mixture of conformers) δ 7.93 and 7.82 (s, 1H), 7.61-7.32 (m, 3H), 7.07 (dd, 2H, J$_1$=8.4 Hz, J$_2$=5.8 Hz), 6.90 (t, 2H, J=8.8 Hz), 4.51 and 3.66 (t, 1H, J=7.7 Hz), 4.20 and 4.19 (s, 3H), 3.51 (br, 1H), 2.81 and 2.78 (s, 3H), 2.78-1.10 (m, 17H), 2.56 (t, 2H, J=7.7 Hz), 2.13 and 2.06 (s, 3H), 0.89 (t, 3H, J=7.3 Hz). MS ESI (M+H)$^+$=579.5.

(5S)-isomer: $^1$H NMR (300 MHz, CDCl$_3$) δ 8.42 (s, 1H), 7.90 (s, 1H), 7.46 (d, 1H, J=8.4 Hz), 7.32 (t, 1H, J=7.7 Hz), 7.13 (dd, 2H, J$_1$=8.4 Hz, J$_2$=5.5 Hz), 6.93 (t, 2H, J=8.8 Hz), 6.46 (br, 1H), 4.77 (br, 1H), 4.20 (br, 1H), 4.14 (s, 3H), 2.87 (s, 3H), 2.60 (t, 2H, J=7.3 Hz), 2.45-1.40 (m, 17H), 2.15 (s, 3H), 0.89 (t, 3H, J=7.2 Hz). MS ESI (M+H)$^+$=579.5.

Examples 23 and 24

N-{(1R,3R,4S)-4-{[[3-(4-fluorophenyl)propyl](propyl)amino]methyl}-3-[({[4-methyl-1,3-thiazol-2-yl]amino}carbonyl)amino]cyclohexyl}-N-methylacetamide and N-{(1S,3R,4S)-4-{[[3-(4-fluorophenyl)propyl](propyl)amino]methyl}-3-[({[4-methyl-1,3-thiazol-2-yl]amino}carbonyl)amino]cyclohexyl}-N-methylacetamide

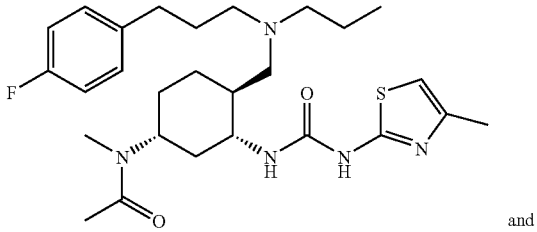
and

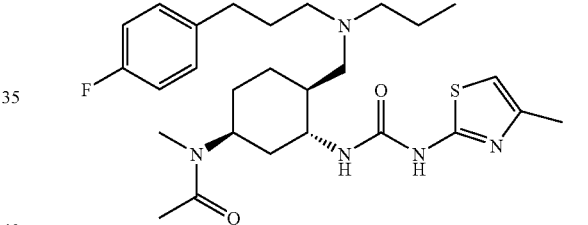

To a solution of disubstituted cyclohexylamine 21 [$R^5$=3-(4-fluorophenyl)propyl, $R^4$=propyl, $R^{14^a}$=methyl, $R^{14^b}$=acetyl, a 1:1 mixture of (5R)- and (5S)-isomers, 60 mg, see Scheme 3] in 1 mL of anhydrous THF were added N-(4-methyl-thiazol-2-yl)-phenylcarbamate (60 mg, 1.7 equiv.) and triethylamine (22 mg, 1.3 equiv.), and the mixture was stirred for 18 hrs at room temperature. After evaporating off the solvent, two diasteromeric ureas were separated by flash chromatography (silica gel, 0.5:3:97 cNH$_4$OH/CH$_3$OH/CH$_2$Cl$_2$) to give N-(4-methyl-thiazol-2-yl)-N'-[(1R,2S,5R)-5-(N-methyl)acetamido-2-[N-propyl-3-(4-fluorophenyl)propylamino]methyl-cyclohexyl]urea (EXAMPLE 23) and N-(4-methyl-thiazol-2-yl)-N'-[(1R,2S,5S)-5-(N-methyl)acetamido-2-[N-propyl-3-(4-fluorophenyl)propylamino]methyl-cyclohexyl]urea (EXAMPLE 24) as amorphous solids.

(5R)-isomer: MS ESI$^+$ (M+H)$^+$=518.5.

(5S)-isomer: $^1$H NMR (300 MHz, CDCl$_3$) δ 7.16-7.11 (m, 2H), 6.93 (t, 2H, J=8.7 Hz), 6.31 (s, 1H), 4.73 (br, 1H), 4.26 (br, 1H), 2.83 (s, 3H), 2.60 (br, 2H), 2.40-1.40 (m, 17H), 2.30 (s, 3H), 2.13 (s, 3H), 0.88 (t, 3H, J=7.4 Hz). MS ESI (M+H)$^+$=518.5.

Example 25

N-{(1R,3R,4S)-4-{[[2,2-dimethyl-3-(4-fluorophenyl)propyl](methyl)amino]methyl}-3-[({[3-ethyl-5-(1-methyl-1H-tetrazol-5-yl)phenyl]amino}carbonyl)amino]cyclohexyl}-N-methylacetamide

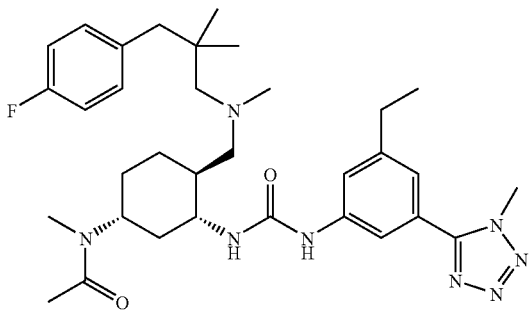

(See Scheme 3)

Step k: According to the procedure described in Step k of Example 9, the amino-ketal 18 [$R^4$=methyl, $R^5$=2,2-dimethyl-3-(4-fluorophenyl)propyl] was prepared from the aldehyde 17 and N-methyl-2,2-dimethyl-3-(4-fluorophenyl)propylamine. Synthesis of the N-methyl-2,2-dimethyl-3-(4-fluorophenyl)propylamine is described in Example 25a below.

Step l-m1: According to the procedure described in Steps 1 and m1 of Example 7, the amino-ketal 18 [$R^4$=methyl, $R^5$=2,2-dimethyl-3-(4-fluorophenyl)propyl] was converted to a diastereomeric mixture of the methylamine 20 [$R^4$=methyl, $R^5$=2,2-dimethyl-3-(4-fluorophenyl)propyl, $R^{14a}$=Me, $R^{14b}$=H]. The (5R)- and (5S)-isomers of the methylamine 20 were separated by chromatotran (silica gel).

Step m2-n: According to the procedure described in Steps m2 and n of Example 7, the (5R)-isomer of the methylamine 20 [$R^4$=methyl, $R^5$=2,2-dimethyl-3-(4-fluorophenyl)propyl, $R^{14a}$=Me, $R^{14b}$=H] was converted to the disubsituted cyclohexylamine 21 [$R^4$=methyl, $R^5$=2,2-dimethyl-3-(4-fluorophenyl)propyl, $R^{14a}$=Me, $R^{14b}$=acetyl] as an oil.

Step o: To a solution of the (5R)-isomer of the disubstituted cyclohexylamine 21 [$R^4$=methyl, $R^5$=2,2-dimethyl-3-(4-fluorophenyl)propyl, $R^{14a}$=Me, $R^{14b}$=acetyl, 54 mg] in 5 mL of anhydrous tetrahydrofuran were added phenyl 3-ethyl-5-(1-methyl-tetrazol-5-yl)phenylcarbamate (61 mg, synthesis of the carbamate is described in Example 25b below) and triethylamine (0.13 mL), and the mixture was stirred for 18 hrs at room temperature. It was diluted with EtOAc and washed with brine. The EtOAc solution was dried over $Na_2SO_4$, and the solvet was evaporated off to give an oily residue. It was purified by chromatotran (silicagel, 0.5:4.5:95 to 1:9:90 cNH$_4$OH/MeOH/CH$_2$Cl$_2$) to give pure N-[3-ethyl-5-(1-methyl-tetrazol-5-yl)phenyl]-N'-[(1R,2S,5R)-5-(N-methyl)acetamido-2-[N-methyl-2,2-dimethyl-3-(4-fluorophenyl)propylamino]methyl-cyclohexyl]urea as a white amorphous solid (48 mg).

$^1$H NMR (300 MHz, CDCl$_3$) δ 7.61-7.4 (m, 3H), 7.15 (d, 1H, J=5 Hz), 7.04-6.96 (m, 2H), 6.92-6.85 (m, 2H), 4.42-4.35 (m, 1H), 4.17 (d, 3H, J=1.9 Hz), 3.7-3.4 (m, 2H), 2.87 (s, 1H), 2.80 (s, 1H), 2.68-2.62 (m, 3H), 2.47 (d, 2H, J=4.1 Hz), 2.26-2.05 (m, 10H), 1.80-1.40 (m, 6H), 1.25-1.19 (m, 4H), (d, 6H, J=3.4 Hz). MS ESI (M+H)=607.7.

Example 25a

Preparation of N-methyl-2,2-dimethyl-3-(4fluorophenyl)propylamine

Part a. To a mixture of 1M LiHMDS in THF (91 mL) and 90 mL of anhydrous THF at −78° C. was added a solution of ethyl isobutyrate (10 g) in 68 mL of anhydrous THF drop wise over a period of 15 minutes, and the solution was stirred for 45 minutes. Then a solution of 4-fluorobenzylbromide (15.8 g) in 22 mL of THF was added drop wise over a period of 5 minutes, and the mixture was allow to stir at room temperature for 18 hrs. The reaction was quenched with 1N HCl and the product was extracted with diethyl ether twice. The combined extracts were washed with 1N HCl and brine, dried over $Na_2SO_4$, and evaporated to give ethyl 2,2-dimethyl-3-(4-fluoro)phenylpropionate as a brown oil (18.5 g, 99% yield).

Part b. To a solution of ethyl 2,2-dimethyl-3-(4-fluoro)phenylpropionate (10 g) in 200 mL of anhydrous THF at 0° C. was added a 1M solution of lithium aluminum hydride in THF (53.6 mL, 1.2 equiv.) drop wise, and the mixture was stirred for 1.5 hrs at the same temperature. The reaction was quenched by slow addition of sodium sulfate decahydrate. After stirring for additional 0.5 hrs, it was filtered through Celite, and the filtrate was concentrated to give 2,2-dimethyl-3-(4-fluoro)phenylpropanol as an oil (97% yield).

Part c. To a stirred solution of oxalyl chloride (1.06 mL, 1.6 equiv.) in 28 mL of anhydrous CH$_2$Cl$_2$ at −65° C. was added DMSO (1.72 mL, 1.72 equiv.) drop wise over a period of 10 minutes. The mixture was stirred for 20 minutes at −65~−60° C. Then a solution of 2,2-dimethyl-3-(4-fluoro)phenylpropanol (1.38 g) in 18 mL of anhydrous CH$_2$Cl$_2$ was added drop wise over a period of 20 minutes at −70~−60° C. After stirring for 40 minutes at −60~−50° C. triethylamine (3.43 mL, 3.25 equiv.) was added drop wise over a period of 10 minutes, and the mixture was continued to stir for 1.25 hrs at −50~0° C. Then 100 mL of diethyl ether was added and the mixture was washed with water and brine. It was dried over $Na_2SO_4$ and evaporated to give 2,2-dimethyl-3-(4-fluoro)phenylpropanal as an oil.

Part d. To a solution of 2,2-dimethyl-3-(4-fluoro)phenylpropanal (1.13 g) in 50 mL of CH$_2$Cl$_2$ was added 33% methylamine in ethanol (2.35 mL, 3 equiv.), and the mixture was stirred for 0.5 hrs. Then sodium triacetoxyborohydride (6.65 g, 5 equiv.) was added and the mixture was stirred overnight at room temperature. It was diluted with EtOAc, and washed with water. The aqueous layer was extracted with EtOAc and the combined extracts were washed with brine. After drying over $Na_2SO_4$, solvent was evaporated off to give a solid residue. It was recrystallized from EtOAc to give 0.6 g of N-methyl-2,2-dimethyl-3-(4-fluoro)phenylpropylamine.

$^1$H NMR (300 MHz, CDCl$_3$) δ 7.18 (dd, 2H, J$_1$=5.5 Hz, J$_2$=2.2 Hz), 7.16 (t, 2H, J=3.3 Hz), 2.78 (s, 2H), 2.75 (s, 3H), 2.73 (s, 2H), 1.14 (s, 6H).

Example 25b

Preparation of Phenyl 3-ethyl-5-(1-methyl-1H-tetrazole-5-yl)phenylcarbamate

Part a. Preparation of 3-Bromo-5-nitrobenzoic acid

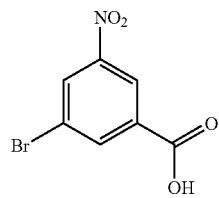

3-Nitrobenzoic acid (16.7 g, 100 mmol, 1 equiv.) was stirred in 50 ml of trifluoroacetic and 20 ml of sulfuric at at 50° C. Added N-Bromosuccinimde (26.7 g, 150 mmol, 1.5 equiv.) in 3 portions over 3 hours. Stirred for 16 hours then cooled to 25° C. Poured the reaction into 200 ml of ice water and extracted with ethyl acetate (3×100 ml). The organic layers were combined, dried over $Na_2SO_4$, and stripped in vacuo to give a white solid. Purified by recrystallization in methylene chloride to give 17.7 g of a white solid as product. NMR (300 MHz, DMSO-$d_6$) δ 14.30-13.30 (m, 1H), 8.60 (t, 1H, J=3 Hz), 8.55 (s, 1H, J=3 Hz), 8.37 (s, 1H, J=3 Hz).

Part b. Preparation of 3-bromo-N-methyl-5-nitrobenzamide

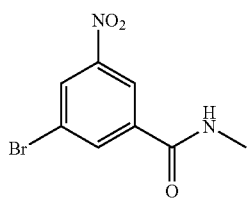

To a solution of 3-bromo-5-nitrobenzoic acid (17.7 g) and oxalyl chloride (2 equiv.) in 250 mL of anhydrous $CH_2Cl_2$ was added a few drops of DMF, and the mixture was stirred for 2 hrs at room temperature. It was concentrated in vacuo, then reconcentrated in vacuo twice from 400 mL of toluene to remove excess oxalyl chloride. The residue was dissolved in 100 mL of anhydrous THF. In a separated flask methylamine (3 equiv.) was dissolved in 100 ml of anhydrous THF and cooled to 0° C. Then the acid chloride solution was added dropwise, causing a white solid to precipitate. The mixture was allowed to stir at room temperature for 16 hrs, and the solids were removed by filtration. The filtrate was concentrated in vacuo to provide a white solid, which was triturated with diethyl ether, collected by filtration to yield 3-bromo-N-methyl-5-nitrobenzamide. NMR (300 MHz, DMSO-$d_6$) δ 9.92 (m, 1H), 8.64 (s, 1H), 8.53 (s, 1H), 8.43 (s, 1H), 2.81 (d, 3H, J=7 Hz).

Part c. Preparation of 5-(3-bromo-5-nitrophenyl)-1-methyl-1H-tetraazole

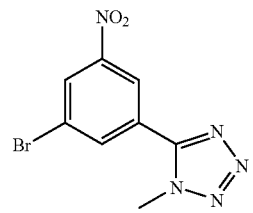

3-bromo-N-methyl-5-nitrobenzamide (23.20 g, 90 mmol, 1 equiv.) was suspended in 200 ml of acetonitrile at 25° C. under nitrogen then sodium azide (5.82 g, 90 mmol, 1 equiv.) was added. Cooled to 0° C. then very slowly added triflic anhydride (15.07 ml, 90 mmol, 1 equiv.) dropwise via an addition funnel. The reaction became an amber solution. Worked up after 4 hours by adding 200 ml of sat'd $NaHCO_3$ and stirred 10 minutes. Then added ethyl acetate and separated the layers. The ethyl acetate was rinsed twice with sat'd $NaHCO_3$ then once with brine. The ethyl acetate was dried over MgSO4 then stripped in vacuo to give a dark amber oil which was stirred in 25 ml of ethyl acetate. After stirring 5 minutes, solids which precipitated were filtered off, and pumped under high vacuum to give 10.5 g of tan solids. The filtrate was stripped then purified over silica gel in 100% methylene chloride to obtain an additional 9.0 g of solids. By NMR both solids were identical for product and were combined.

NMR (300 MHz, $CDCl_3$) δ 8.60 (s, 1H), 8.55 (s, 1H), 8.32 (s, 1H), 7.26 (s, 1H), 4.29 (s, 3H).

Part d. Preparation of 1-methyl-5-(3-nitro-5-vinylphenyl)-1H-tetraazole

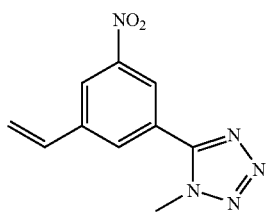

5-(3-bromo-5-nitrophenyl)-1-methyl-1H-tetraazole from Part 3 (19.50 g, 68.6 mmol, 1 equiv.), tributylvinyl tin (Aldrich, 20.06 ml, 68.6 mmol, 1 equiv.), and tetrakis(triphenylphosphine)palladium(0)(Aldrich, 1.59 g, 1.37 mmol, 0.02 equiv.) were mixed at 25° C. under nitrogen then refluxed for 2 hours. Worked up by stripping the reaction then purified over silica gel in 100% methylene chloride to 1:1 methylene chloride/ethyl acetate. Obtained 22.0 g of product and a tributyltin impurity.

NMR of product (300 MHz, $CDCl_3$) δ 8.49 (d, 2H, J=7 Hz), 8.19 (s, 1H), 6.86 (m, 1H), 6.05 (d, 1H, J=15 Hz), 5.60 (d, 1H, J=7 Hz), 4.28 (s, 3H).

Part e. Preparation of
3-ethyl-5-(1-methyl-1H-tetraazol-5-yl)aniline

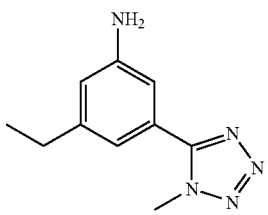

Pd(OH)$_2$(3.0 g) was carefully wetted down under nitrogen with methanol then 1-methyl-5-(3-nitro-5-vinylphenyl)-1H-tetraazole (17.0 g) dissolved in 50 ml of methanol was added. Hydrogenated at 50 PSI for 4 hours. Worked up by filtering the reaction under nitrogen through fiberglass filter paper. The filtrate was stripped in vacuo to give 14.3 g of amber solids as product. NMR (300 MHz, CDCl$_3$) δ 6.90 (s, 1H), 6.87 (s, 1H), 6.73 (s, 1H), 4.16 (s, 3H), 3.95 (bs, 2H), 2.65 (q, 2H, J=7 Hz), 1.22 (t, 3H, J=7 Hz).

Part f. Preparation of Phenyl 3-ethyl-5-(1-methyl-1H-tetraazol-5-yl)phenylcarbamate

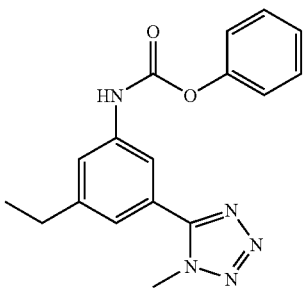

3-Ethyl-5-(1-methyl-1H-tetraazol-5-yl)aniline (3.83 g, 19 mmol, 1 equiv.), was dissolved in THF at 25° C. under nitrogen then 2,6-lutidine (Aldrich, 2.17 ml, 19 mmol, 1 equiv.) was added. Cooled the reaction to 0° C. Added a THF solution of phenyl chloroformate (2.36 ml, 19 mmol, 1 equiv.) dropwise via an addition funnel. Worked up after 1 hour by adding ethyl acetate and 0.1 N HCl. Separated the layers and rinsed the organic layer twice more with 0.1 N HCl and once with brine. The organic layer was dried over MgSO$_4$ then stripped in vacuo to give 6.00 g of tan solids as product. NMR (300 MHz, CDCl$_3$) δ 7.86 (s, 1H), 7.50-7.30 (m, 5H), 7.30-7.10 (m, 3H), 4.17 (s, 3H), 2.71 (q, 2H, J=7 Hz), 1.27 (t, 3H, J=7 Hz).

Example 26

N-{(1S,3R,4S)-4-{[[2,2-dimethyl-3-(4-fluorophenyl)propyl](methyl)amino]methyl}-3-[({[3-ethyl-5-(1-methyl-1H-tetrazol-5-yl)-phenyl]amino}carbonyl)amino]cyclohexyl}-N-methylacetamide

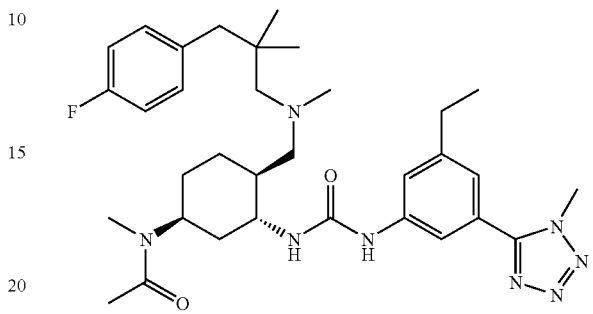

Example 26 was prepared in an analogous manner to Example 25 using (5S)-isomer of the methylamine 20 [R$^4$=methyl, R$^5$=2,2-dimethyl-3-(4-fluorophenyl)propyl, R$^{14a}$=Me, R$^{14b}$=H] in Step m2.

$^1$H NMR (300 MHz, CDCl$_3$) δ 8.20 (s, 1H), 7.69 (s, 1H), 7.36 (s, 1H), 7.14 (s, 1H), 7.09-7.04 (m, 2H), 6.94 (t, 2H, J=8.8 Hz), 4.8-4.70 (m, 1H), 4.3-4.25 (m, 1H), 4.15 (s, 3H), 2.85 (s, 3H), 2.64 (q, 3H, J=7.43), 2.55-2.4 (m, 3H), 2.29 (s, 3H), 2.23 (s, 2H), 2.12 (s, 3H), 1.95-1.40 (m, 9H), 1.22 (t, 2H, J=10.0 Hz) 0.83(s, 6H). MS ESI (M+H)$^+$=607.7.

Example 27

N-{(1R,3R,4S)-4-{[[2,2-dimethyl-3-(4-fluorophenyl)propyl](methyl)amino]methyl}-3-[({[3-(1-methyl-1H-tetrazol-5-yl)phenyl]amino}carbonyl)amino]cyclohexyl}-N-methylacetamide

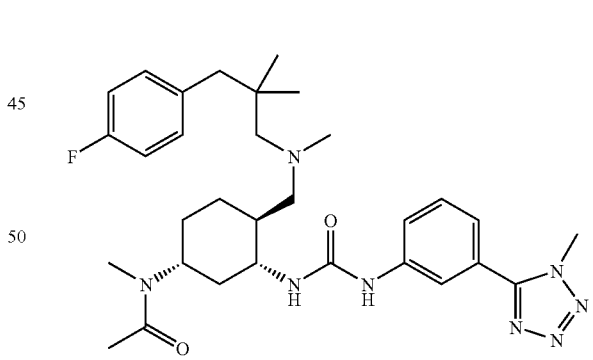

Example 27 was prepared in an analogous manner to Example 25 using phenyl 3-(1-methyl-tetrazol-5-yl)phenylcarbamate in Step 0.

$^1$H NMR (300 MHz, CDCl$_3$) δ 8.08 (d, 1H, J=33 Hz), 7.54 (d, 1H, J=11.3 Hz), 7.72 (dd, 1H, J=5.5 Hz, J=2.5 Hz), 7.40 (q, 1H, J=2.6 Hz), 7.04-6.98 (m, 2H), 6.92-6.85 (m, 2H), 4.42-4.38 (m, 1H), 4.17 (s, 3H), 3.75-3.45 (m, 2H), 2.87 (s, 1H), 2.80 (s, 1H), 2.70-2.65 (m, 1H), 2.45 (d, 2H, J=7.3 Hz), 2.28-2.08 (m, 12H), 1.80-1.65 (m, 2H), 1.6-1.4 (m, 3H), 1.22-1.05 (m, 1H), 0.77 (d, 6H, J=5.8 Hz). MS ESI (M+H)$^+$=579.6.

Example 28

N-{(1S,3R,4S)-4-{[[2,2-dimethyl-3-(4-fluorophenyl)propyl](methyl)amino]methyl}-3-[({[3-(1-methyl-1H-tetrazol-5-yl)phenyl]amino}carbonyl)amino]cyclohexyl}-N-methylacetamide

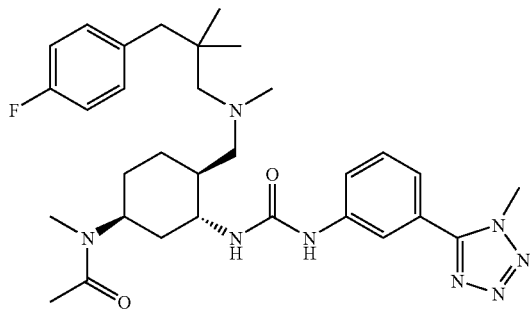

Example 28 was prepared in an analogous manner to Example 25 using phenyl 3-(1-methyl-tetrazol-5-yl)phenylcarbamate in Step 0.

$^1$H NMR (300 MHz, CDCl$_3$) δ 8.15 (s, 1H), 7.87 (s, 1H), 7.47 (d, 1H, J=7 Hz), 7.34 (t, 1H, J=7.85 Hz), 7.09-7.04 (m, 2H), 6.94 (t, 2H, J=8.8 Hz), 4.8-4.70 (m, 1H), 4.3-4.25 (m, 1H), 4.16 (s, 3H), 2.85 (s, 3H), 2.55-2.4 (m, 4H), 2.29 (s, 3H), 2.23 (s, 2H), 2.12 (s, 3H), 1.95-1.40 (m, 9H), 0.83(s, 6H). MS ESI (M+H)$^+$=579.6.

Example 29

N-((1R,3R,4S)-3-({[(5-acetyl-4-methyl-1,3-thiazol-2-yl)amino]carbonyl}amino)-4{[[2,2-dimethyl-3-(4-fluorophenyl)propyl](methyl)amino]methyl}cyclohexyl)-N-methylacetamide

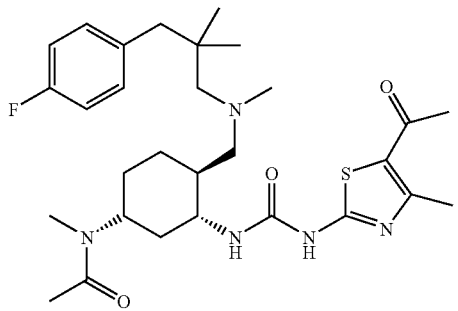

Example 29 was prepared in an analogous manner to Example 25 using phenyl 5-acetyl-4-methyl-thiazol-2-ylcarbamate in Step 0.

$^1$H NMR (300 MHz, CDCl$_3$) δ 7.03-6.99 (m, 2H), 6.91 (t, 2H, J=11.1 Hz), 4.4-4.2 (m, 1H), 3.75-3.5 (m, 2H), 2.90 (s, 1H), 2.83 (s, 1H), 2.66-2.56 (m, 5H), 2.51-2.42 (m, 5H), 2.35-2.05 (m, 12H), 1.80-1.45 (m, 4H), 1.20-1.05 (m, 1H), 0.79(s, 6H). MS ESI (M+H)$^+$=560.5.

Example 30

N-((1S,3R,4S)-3-({[(5-acetyl-4-methyl-1,3-thiazol-2-yl)amino]carbonyl}amino)-4{[[2,2-dimethyl-3-(4-fluorophenyl)propyl](methyl)amino]methyl}cyclohexyl)-N-methylacetamide

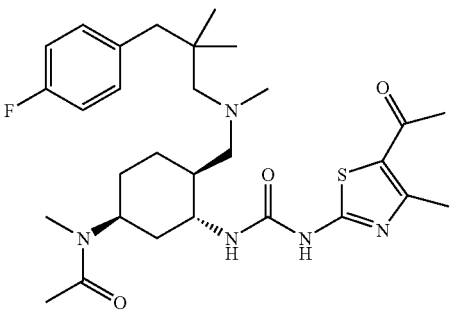

Example 30 was prepared in an analogous manner to Example 25 using phenyl 5-acetyl-4-methyl-thiazol-2-ylcarbamate in Step 0.

$^1$H NMR (300 MHz, CDCl$_3$) δ 7.09-7.05 (m, 2H), 6.95 (t, 2H, J=6 Hz), 4.8-4.71 (m, 1H), 4.4-4.35 (m, 1H), 2.65-2.4 (m, 10H), 2.38 (s, 3H), 2.29 (s, 2H), 2.19 (s, 3H), 1.87-1.47 (m, 12H), 0.81(s, 6H). MS ESI (M+H)=560.5.

Example 31

N-((1R,3R,4S)-4-{[[2,2-dimethyl-3(4-fluorophenyl)propyl](methyl)amino]methyl}-3-({[(4-methyl-1,3-thiazol-2-yl)amino]carbonyl}amino) cyclohexyl)-N-methylacetamide

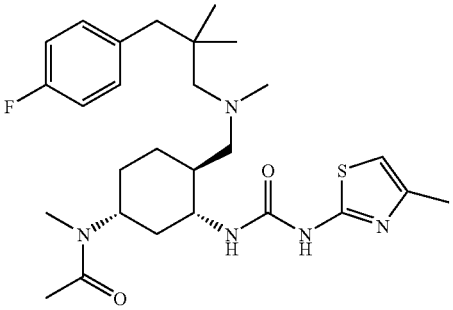

Example 30 was prepared in an analogous manner to Example 25 using phenyl 4-methyl-thiazol-2-ylcarbamate in Step 0.

$^1$H NMR (300 MHz, CDCl$_3$) δ 7.03-6.99 (m, 2H), 6.91 (t, 2H, J=6.7 Hz), 6.34 (d, 1H, 2.5 Hz), 4.6-4.45 (m, 1H), 3.7-3.5 (m, 2H), 2.86 (s, 1H), 2.82 (s, 1H), 2.7-2.64 (m, 2H), 2.51 (s, 2H), 2.3-2.02 (m, 14H), 1.80-1.40 (m, 6H), 1.25-1.10 (m, 1H), (s, 6H). MS ESI (M+H)$^+$=518.6.

Example 32

N-((1S,3R,4S)-4-{[[2,2-dimethyl-3(4-fluorophenyl)propyl](methyl)amino]methyl}-3-({[(4-methyl-1,3-thiazol-2-yl)amino]carbonyl}amino) cyclohexyl)-N-methylacetamide

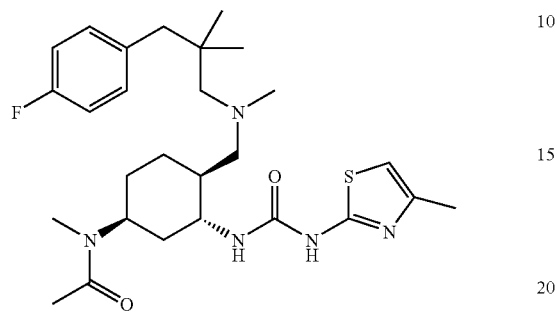

Example 32 was prepared in an analogous manner to Example 25 using phenyl 4-methyl-thiazol-2-ylcarbamate in Step 0.

$^1$H NMR (300 MHz, CDCl$_3$) δ 7.09-7.05 (m, 2H), 6.94 (t, 2H, J=5.87 Hz), 6.32 (s, 1H), 4.8-4.70 (m, 1H), 4.4-4.35 (m, 1H), 2.82 (s, 3H), 2.78 (s, 1H), 2.55-2.4 (m, 5H), 2.35-2.05 (m, 10H), 2.0-1.45 (m, 8H), 0.82(s, 6H). MS ESI (M+H)$^+$ =518.9.

TABLE 2

| Ex. No | R5 | R4 | R14 | R3 | MS(ESI) (M + H)$^+$ |
|---|---|---|---|---|---|
| 9 | 4-F-phenyl-(CH$_2$)$_3$- | CH$_3$ | N(Me)Ac (R)* | 3-Ac-phenyl- | 511.5 |
| 10 | 4-F-phenyl-(CH$_2$)$_3$- | CH$_3$ | N(Me)Ac (S)* | 3-Ac-phenyl- | 511.5 |
| 11 | 4-F-phenyl-(CH$_2$)$_3$- | CH$_3$ | N(Me)Ac (R)* | 4-methyl-5-Ac-thiazol-2-yl | 532.4 |

TABLE 2-continued
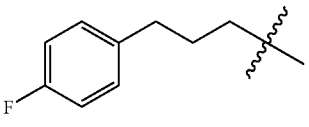
| Ex. No | R5 | R4 | R14 | R3 | MS(ESI) (M + H)+ |
|---|---|---|---|---|---|
| 12 | 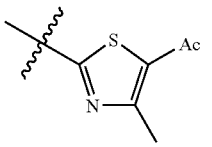 | CH₃ | N(Me)Ac (S)* | 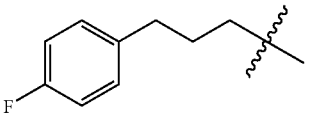 | 532.4 |
| 13 | 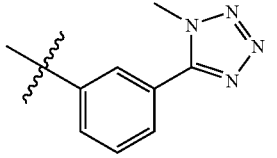 | CH₃ | N(Me)Ac (R)* | 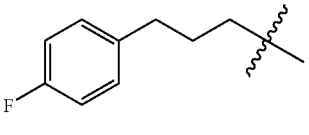 | 551.5 |
| 14 | 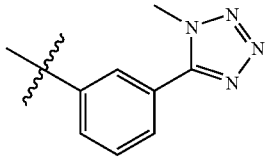 | CH₃ | N(Me)Ac (S)* | 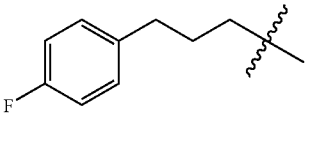 | 551.5 |
| 15 | 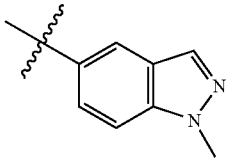 | CH₃ | N(Me)Ac (R)* | 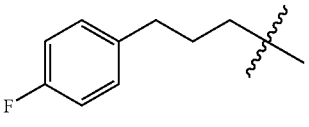 | 523.5 |
| 16 | 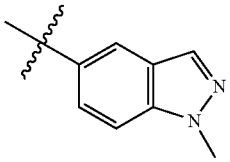 | CH₃ | N(Me)Ac (S)* | 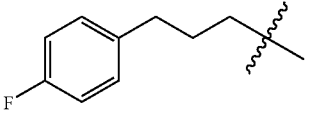 | 523.5 |
| 17 | 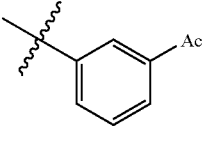 | nPr | N(Me)Ac (R)* | 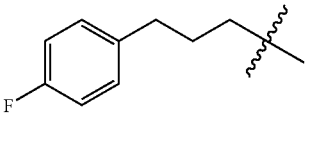 | 539.5 |
| 18 | 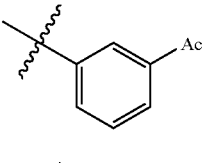 | nPr | N(Me)Ac (S)* | 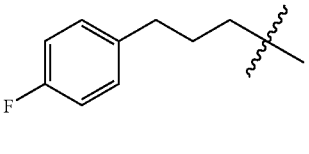 | 539.5 |
| 19 | 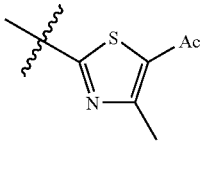 | nPr | N(Me)Ac (R)* | | 560.4 |

TABLE 2-continued
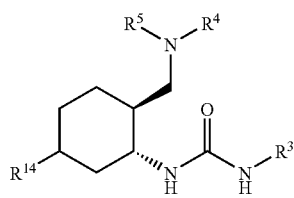
| Ex. No | R5 | R4 | R14 | R3 | MS(ESI) (M + H)+ |
|---|---|---|---|---|---|
| 20 | 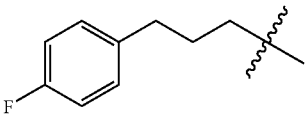 | nPr | N(Me)Ac (S)* | 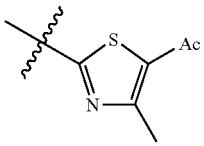 | 560.4 |
| 21 | 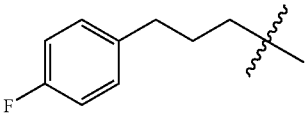 | nPr | N(Me)Ac (R)* | 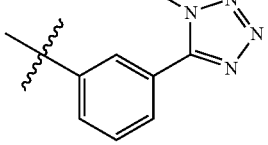 | 579.5 |
| 22 | 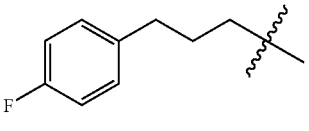 | nPr | N(Me)Ac (S)* | 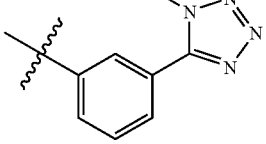 | 579.5 |
| 23 | 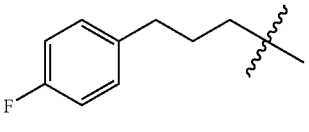 | nPr | N(Me)Ac (R)* | 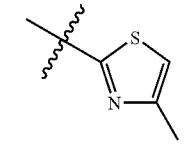 | 518.5 |
| 24 | 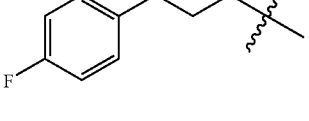 | nPr | N(Me)Ac (S)* | 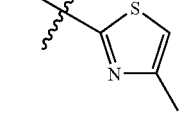 | 518.5 |
| 25 | 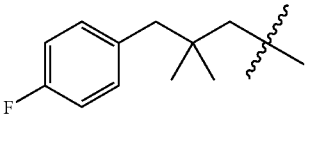 | CH₃ | N(Me)Ac (R)* | 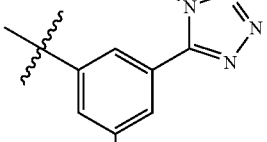 | 607.7 |
| 26 | 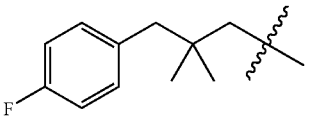 | CH₃ | N(Me)Ac (S)* | 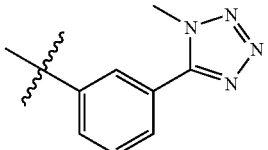 | 607.7 |

TABLE 2-continued

| Ex. No | R5 | R4 | R14 | R3 | MS(ESI) (M + H)+ |
|---|---|---|---|---|---|
| 27 | 4-F-C6H4-CH2-C(CH3)2-CH2- | CH3 | N(Me)Ac (R)* | 3-(1-methyltetrazol-5-yl)phenyl | 579.6 |
| 28 | 4-F-C6H4-CH2-C(CH3)2-CH2- | CH3 | N(Me)Ac (S)* | 3-(1-methyltetrazol-5-yl)phenyl | 579.6 |
| 29 | 4-F-C6H4-CH2-C(CH3)2-CH2- | CH3 | N(Me)Ac (R)* | 5-acetyl-4-methylthiazol-2-yl | 560.5 |
| 30 | 4-F-C6H4-CH2-C(CH3)2-CH2- | CH3 | N(Me)Ac (S)* | 5-acetyl-4-methylthiazol-2-yl | 560.5 |
| 31 | 4-F-C6H4-CH2-C(CH3)2-CH2- | CH3 | N(Me)Ac (R)* | 4-methylthiazol-2-yl | 518.6 |
| 32 | 4-F-C6H4-CH2-C(CH3)2-CH2- | CH3 | N(Me)Ac (S)* | 4-methylthiazol-2-yl | 518.9 |
| 32a | 4-F-C6H4-(CH2)3- | CH3 | N(Me)Ac (R)* | 5-methyl-1,3,4-thiadiazol-2-yl | 491.5 |
| 32b | 4-F-C6H4-(CH2)3- | Et | N(Me)Ac (R)* | 3-(1-methyltetrazol-5-yl)phenyl | 593.3 |

TABLE 2-continued

| Ex. No | R5 | R4 | R14 | R3 | MS(ESI) (M + H)+ |
|---|---|---|---|---|---|
| 32c | 4-F-phenyl-(CH2)3- | Et | N(Me)Ac (R)* | 3-Et-5-(1-methyltetrazol-5-yl)phenyl | 565.2 |
| 32d | 4-F-phenyl-(CH2)3- | Et | N(Me)Ac (R)* | 5-Ac-4-methylthiazol-2-yl | 546.2 |
| 32e | 4-F-phenyl-(CH2)3- | Et | N(Me)Ac (R)* | 4-methylthiazol-2-yl | 504.1 |
| 32f | 4-F-phenyl-(CH2)3-cyclopropyl- | | N(Me)Ac (R)* | 3-(1-methyltetrazol-5-yl)phenyl | 577.5 |
| 32g | 4-F-phenyl-(CH2)3-cyclopropyl- | | N(Me)Ac (S)* | 3-(1-methyltetrazol-5-yl)phenyl | 577.6 |
| 32h | 4-F-phenyl-(CH2)3-cyclopropyl- | | N(Me)Ac (R)* | 3-Et-5-(1-methyltetrazol-5-yl)phenyl | 605.7 |
| 32i | 4-F-phenyl-(CH2)3-cyclopropyl- | | N(Me)Ac (S)* | 3-Et-5-(1-methyltetrazol-5-yl)phenyl | 605.7 |

TABLE 2-continued
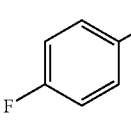
| Ex. No | R5 | R4 | R14 | R3 | MS(ESI) (M + H)+ |
|---|---|---|---|---|---|
| 32j | 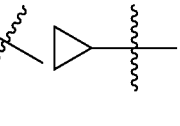 |  | N(Me)Ac (R)* | 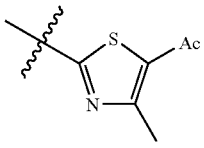 | 558.5 |
| 32k | 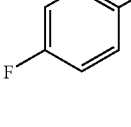 | 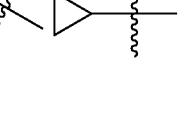 | N(Me)Ac (S)* |  | 558.5 |
| 32l | 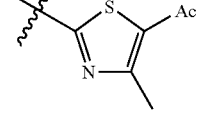 | 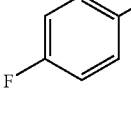 | N(Me)Ac (R)* | 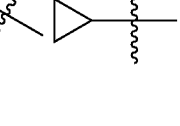 | 516.5 |
| 32m |  | 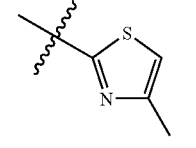 | N(Me)Ac (S)* | 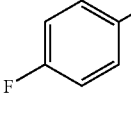 | 516.5 |
| 32n | 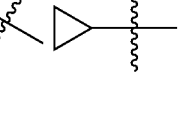 |  | N(Me)Ac (R)* | 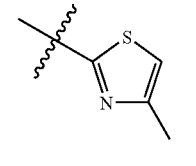 | 563.6 |
| 32o | 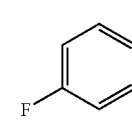 | 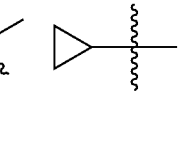 | N(Me)Ac (S)* |  | 563.6 |

TABLE 2-continued
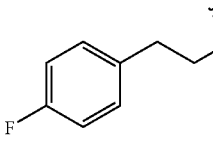
| Ex. No | R5 | R4 | R14 | R3 | MS(ESI) (M + H)+ |
|---|---|---|---|---|---|
| 32p | 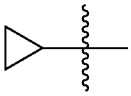 |  | N(Me)Ac (R)* | 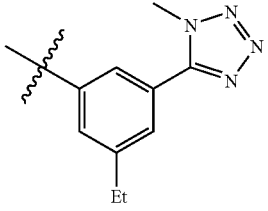 | 591.6 |
| 32q | 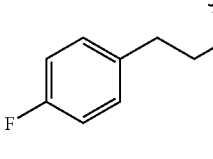 | 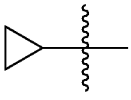 | N(Me)Ac (S)* |  | 591.6 |
| 32r | 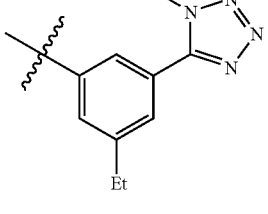 | 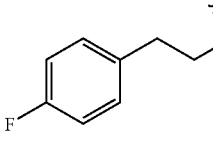 | N(Me)Ac (R)* | 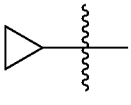 | 544.5 |
| 32s |  | 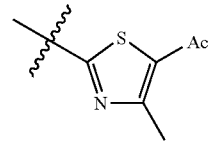 | N(Me)Ac (S)* | 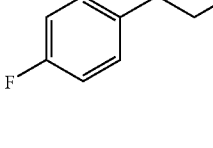 | 544.5 |
| 32t | 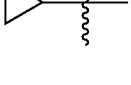 |  | N(Me)Ac (R)* | 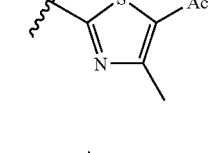 | 502.5 |
| 32u | 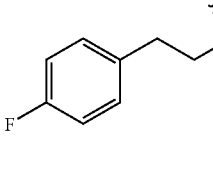 | 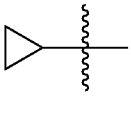 | N(Me)Ac (S)* |  | 502.5 |

Examples 33 and 34

N-((1R,3S,4R)-4-({[(5-acetyl-4-methyl-1,3-thiazol-2-yl)amino]carbonyl}amino)-3-{[[3-(4-fluorophenyl)propyl](methyl)amino]methyl}cyclohexyl)-N-methylacetamide and N-((1S,3S,4R)-4-({[(5-acetyl-4-methyl-1,3-thiazol-2-yl)amino]carbonyl}amino)-3-{[[3-(4-fluorophenyl)propyl](methyl)amino]methyl}cyclohexyl)-N-methylacetamide

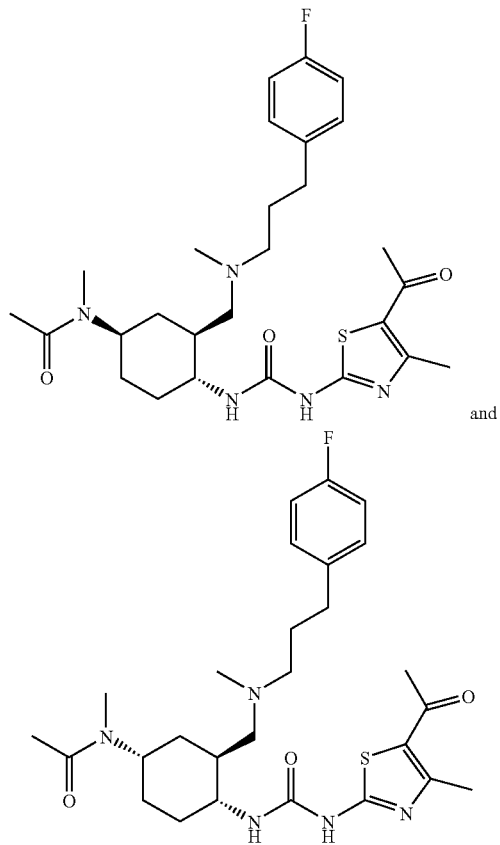

and (See Scheme 4)

Step a: Into a 2-L 3-neck flask was added NaH 60% dispersion (60 g, 1.56 mol) and washed with 700 mL of hexane (2×), suspended in 1 L of THF and treated with diethylcarbonate (150 g, 1.25 mol). The suspension was heated to reflux and treated dropwise with a solution of ketone 23 (80.0 g, 0.51 mol) in THF (300 mL). After the addition was complete the suspension was heated to reflux for an additional 4 hours. The mixture was cooled in an ice bath to 0° C. and then poured, while vigorously stirring, into a mixture of ice (1.5 L), water (100 ml) and acetic acid (150 mL). The resulting mixture is extracted into hexane (3 L total) and the extract washed with water and brine. The hexane extract is dried over Na$_2$SO$_4$, filtered and concentrated to give the ester product 24 as a pale yellow oil. This was used without further purification.

$^1$H NMR (300 MHz, CDCl$_3$) δ 12.25 (s, 1 H), 4.20 (q, J=7 Hz, 2 H), 4.06-3.96 (m, 4 H), 2.53-2.48 (m, 4 H), 1.84 (t, J=6.6 Hz, 2 H), 1.29 (t, J=7 Hz, 3 H).

Step b: A solution of crude ester 24 in benzene (500 mL) was treated with (R)-1-Phenyl-ethylamine (61.8 g, 0.51 mol) and Yb(OTf)$_3$ catalyst (0.8 g) and heated to reflux for 2-3 hours with the removal of water with a Dean-Stark trap. The resulting solution is concentrated on a rotary evaporator to give a yellow solid. This is titurated with 300 mL of 20% isopropyl alcohol in hexane to give a nearly white solid. The solid is recrystallized from 300 mL of hexane to give 108 grams of crystalline ene-amine 25.

$^1$H NMR (300 MHz, CDCl$_3$) δ 9.41 (d, J=7.4 Hz, 1 H), 7.35-7.20 (m, 5 H), 4.64-4.58 (m, 1 H), 4.14 (q, J=7 Hz, 2 H), 4.02-3.88 (m, 4 H), 2.57-2.49 (m, 3 H), 2.25-2.15 (m, 1 H), 1.72-1.65 (m, 2 H), 1.48 (d, J=7.4 Hz, 3 H), 1.28 (t, J=7 Hz, 3 H).

Step c: A solution of ene-amine 25 (380 g, 1.14 mol) in 700 ml of acetonitrile and 350 ml of acetic acid is cooled in an ice bath and treated with NaBH(OAc)$_3$ (360 g, 1.71 mol) powder and stirred 30 min—removed ice bath and stirred overnight at room temperature. The solution is concentrated on a rotory evaporator and the residue dissolved in CH$_2$Cl$_2$ and concentrated on a rotary evaporator a couple of times to removed as much acetic acid as possible. The residue is dissolved in 2 L of CH$_2$Cl$_2$ and divided in 2 equal parts. While cooling in an ice bath and by adding ice into the solution, each part of the solution was neutralized by the slow addition of 50% NaOH (205 g) while vigorously stirring. The resulting mixture was separated and the organic phase washed with water and brine, dried over Na$_2$SO$_4$, filtered and concentrated on a rotory evaporator to give 380 g of the cis ester amine 26 as a thick oil. The crude product was used without further purification.

$^1$H NMR (300 MHz, CDCl$_3$) δ 7.34-7.21 (m, 5 H), 4.18 (q, J=7 Hz, 2 H), 3.95-3.88 (m, 4 H), 3.73 (q, J=7 Hz, 1 H), 3.14 (m, 1 H), 2.81 (m, 1 H), 2.08 (m, 1 H), 1.80-1.38 (m, 6 H), 1.32-1.25 (m, 6 H).

Step d: A solution of sodium t-butoxide (185 g, 1.92 mol) in THF (1 L) was prepared and cooled to 0° C. and added to a solution of the crude cis amino ester 26 while cooling in ice bath. After mixing the ice bath is removed and the mixture is stirred at room temperature for 4 hours. The mixture is then poured into a mixture of cold 1 N HCl (2 L) and Ethyl acetate (2 L) while stirring vigorously. The pH is adjusted to slightly basic with 1 N NaOH and the organic layer separated. The aqueous layer is extracted with ethyl acetate and the combine ethyl acetate extracts are washed with water, brine, and then concentrated on a rotory evaporator to give 380 grams of thick oil. This was chromatographed in two equal portions on 2.5 Kg of silica gel eluting with 50% ethyl acetate/hexane to give a total of 280 g of mostly trans isomer 27 as an oil which slowly solidified on standing. This was further purified by recrystallization from hexane after cooling in freezer to give 210 grams of a crystalline solid.

$^1$H NMR (300 MHz, CDCl$_3$) δ 7.30-7.21 (m, 5 H), 4.22-4.14 (m, 2 H), 3.93-3.87 (m, 4 H), 3.80 (q, J=7 Hz, 1 H), 2.82-2.77 (m, 1 H), 2.56-2.47 (m, 1 H), 1.86-1.32 (m, 7 H), 1.32-1.25 (m, 6 H).

Step e: A solution of the trans amino ester 27 (397 g, 1.19 mol) in ether (1.5 L) is cooled to 0° C. in an ice bath and treated slowly first with LAH pellets (25 g, one at a time), and then with LAH powder (41 g, portion-wise; total 66 g, 1.73 mol). After the addition is complete the mixture is stirred for an additional 45 mins and then quenched by drop-wise addition of 66 ml of water followed by 264 ml of 1 N NaOH (caution: vigorous foaming). The resultant suspension is stirred in the ice bath for 1-2 hours to give a granular white suspension which is filtered on a buchner funnel. The solid is washed with ether and the combine ether filtrates are concentrated to give 346 g of the alcohol 28 as a colorless syrup. This is used without further purification.

$^1$H NMR (300 MHz, CDCl$_3$) δ 7.35-7.25 (m, 5 H), 3.95-3.90 (m, 4 H), 3.60-3.47 (m, 3 H), 2.61-2.48 (m, 1 H), 2.12-2.04 (m, 1 H), 1.87-1.42 (m, 4 H), 1.39 (d, J=6 Hz, 3 H), 1.25-1.16 (m, 2 H).

Step f: A solution of crude amino alcohol 28 (347 g, 1.19 mol) in 500 ml of MeOH was treated with 50 g of 20% Pd(OH)$_2$/C and hydrogenated overnight at 55 psi. The mixture was filtered through Celite and concentrated on a rotory evaporator to give the amino alcohol 29 as a syrup. This was used without further purification.

$^1$H NMR (300 MHz, CDCl$_3$) δ 3.96 (bs, 4 H), 3.58 (d, J=7 Hz, 2 H), 2.94 (bs, 3 H), 2.57 (m, 1 H), 1.84-1.48 (m, 6 H), 1.20 (t, J=13 Hz, 1 H).

Step g: A solution of crude amino alcohol 29 (223 g, 1.19 mol) in 1 L of CH$_2$Cl$_2$ was treated with a 1 L aqueous solution of K$_2$CO$_3$ (200 g, 1.45 mol) and cooled in a ice bath. The mixture is stirred vigorously while benzyl chloroformate (225 g, 1.3 mol) is added slowly. After the addition is complete the mixture is stirred an additional 30 min. The organic layer is separated and washed with water, brine and concentrated to give 390 g of crude solid. This is recrystallized from hexane to give 270 g of N-CBZ amino alcohol 30.

$^1$H NMR (300 MHz, CDCl$_3$) δ 7.36-7.32 (s, 5 H), 5.11 (s, 2 H), 4.82 (d, J=8 Hz, 1 H), 3.96-3.88 (m, 4 H), 3.72 (m, 1 H), 3.53 (m, 1 H), 3.32 (m, 2 H), 1.95-1.52 (m, 7 H).

Step h: To a stirred solution of oxalyl chloride (3.64 mL, 2.5 equiv.) in 75 mL of anhydrous CH$_2$CO$_2$ at −60° C. was added DMSO (3.55 mL, 3 equiv.) drop wise over a period of 10 minutes. The mixture was stirred for 15 minutes at −60~−50° C. Then a solution of pure CBz-protected aminoalcohol 30 (5.36 g) in 35 mL of anhydrous CH$_2$Cl$_2$ was added drop wise over a period of 10 minutes at −70~−60° C. After stirring for 30 minutes at −60~−40° C. triethylamine (11.6 mL, 5 equiv.) was added drop wise over a period of 10 minutes, and the mixture was continued to stir for 0.75 hrs at −60~10° C. Then 300 mL of diethyl ether was added and the mixture was washed with water (2×100 mL) and brine (100 mL). It was dried over Na$_2$SO$_4$ and evaporated to give aldehyde 31 as an oil (~100% yield).

Step i: To a solution of N-methyl-3-(4-fluorophenyl) propylamine (0.79 g, 1.2 equiv.) in 20 mL of anhydrous CH$_2$Cl$_2$ was added aldehyde 31 (1.26 g), and the solution was stirred for 20 minutes at room temperature. Then Na(OAc)$_3$BH (1.67 g, 2 equiv.) was added and the mixture was continued to stir for 16 hrs at room temperature. It was made basic with 20 mL of 1N—NaOH and stirred for 0.5 hrs. The product was extracted with EtOAc, washed with brine and dried over MgSO$_4$. Evaporation of the solvent under reduced pressure gave an oily residue. It was purified by column chromatography (silica gel, EtOAc) to give amino-ketal 32 [R$^5$=3-(4-fluorophenyl)propyl, R$^4$=methyl, 1.12 g, 60.4% yield].

Step j: To a solution of amino-ketal 32 [R$^5$=3-(4-fluorophenyl)propyl, R$^4$=methyl, 1.12 g] in 25 mL of CH$_3$CN was added 40 mL of 1N HCl, and the mixture was stirred for 18 hrs at room temperature. It was then made basic with sat'd Na$_2$CO$_3$ and extracted with EtOAc (2×). The combined extracts were washed with brine, dried over Na$_2$SO$_4$, evaporated to give crude amino-ketone 33 [R$^5$=3-(4-fluorophenyl) propyl, R$^4$=methyl] as an oil, which was used for next step without purification.

Step k1: To a solution of amino-ketone 33 [R$^5$=3-(4-fluorophenyl)propyl, R$^4$=methyl] in 10 mL of methanol was added methylamine hydrochloride (1.6 g, 10 equiv.), and the mixture was stirred for 15 minutes. Then NaCNBH$_3$ (0.3 g, 2 equiv.) was added and it was stirred for 18 hrs at room temperature. The mixture was made basic with sat'd Na$_2$CO$_3$, and extracted with EtOAc (2×). The combined extracts wre washed with brine, dried over Na$_2$SO$_4$, and evaporated to give a ~1:1 diastereomeric mixture of 4-methylamine 34 [R$^5$=3-(4-fluorophenyl)propyl, R$^4$=methyl, R$^{14a}$=methyl, R$^{14b}$=H] as an oil, which was used for next step without purification.

Step k2: To a solution of 4-methylamine 34 [R$^5$=3-(4-fluorophenyl)propyl, R$^4$=methyl, R$^{14a}$=methyl, R$^{14b}$=H, 1:1 mixture of (4R)- and (4S)-isomers] in 20 mL of anhydrous CH$_2$Cl$_2$ were added acetic anhydride (0.27 g, 1.2 equiv.) and triethylamine (0.66 mL, 2 equiv.), and the mixture was stirred for 6 hrs at room temperature. The reaction was quenched with several drops of methanol, and the mixture was diluted with EtOAc. The solution was washed with brine, dried over Na$_2$SO$_4$, and evaporated to give an oily residue. It was purified by column chromatography (silica gel, 5% CH$_3$OH/CH$_2$Cl$_2$) to give 4-N-methylacetamide 34 [R$^5$=3-(4-fluorophenyl)propyl, R$^4$=methyl, R$^{14a}$=methyl, R$^{14b}$=acetyl, 1:1 mixture of (4R)- and (4S)-isomers, 0.66 g] as an oil.

Step l: To a solution of 4-N-methylacetamide 34 [R$^5$=3-(4-fluorophenyl)propyl, R$^4$=methyl, R$^{14a}$=methyl, R$^{14b}$=acetyl, 1:1 mixture of (4R)- and (4S)-isomers, 0.54 g] in 20 mL of methanol was introduced 10% Pd/C (0.085 g) under nitrogen, and the mixture was treated with H$_2$ on a Parr hydrogenator for 7 hrs. The catalyst was filtered off and the filtrate was evaporated to give disubstituted cyclohexylamine 35 [R$^5$=3-(4-fluorophenyl)propyl, R$^4$=methyl, R$^{14a}$=methyl, R$^{14b}$=acetyl] as a 1:1 mixture of (4R)- and (4S)-isomers (100% yield).

Step m: To a solution of disubstituted cyclohexylamine 35 [R$^5$=3-(4-fluorophenyl)propyl, R$^4$=methyl, R$^{14a}$=methyl, R$^{14}$=acetyl, a 1:1 mixture of (4R)- and (4S)-isomers, 97 mg] in 2.5 mL of anhydrous THF were added N-(5-acetyl-4-methyl-thiazol-2-yl)-phenylcarbamate (85 mg, 1.1 equiv.) and triethylamine (0.1 mL), and the mixture was stirred for 18 hrs at room temperature. After addition of several drops of methanol the solvent was evaporated off, and two diasteromeric ureas were separated by flash chromatography (silica gel, 0.6:5.4:94 cNH$_4$OH/CH$_3$OH/CH$_2$Cl$_2$) to give N-(5-acetyl-4-methyl-thiazol-2-yl)-N'-[(1R,2S,4R)-5-(N-methyl)acetamido-2-[N-methyl-3-(4-fluorophenyl)propylamino]methyl-cyclohexyl]urea (EXAMPLE 33) and N-(5-acetyl-4-methyl-thiazol-2-yl)-N'-[(1R,2S,4S)-5-(N-methyl) acetamido-2-[N-methyl-3-(4-fluorophenyl)propylamino] methyl-cyclohexyl]urea (EXAMPLE 34) as amorphous solids.

(4R)-isomer: $^1$H NMR (300 MHz, CDCl$_3$) δ 7.07 (dd, 2H, J$_1$=8.5 Hz, J2=5.5 Hz), 6.92 (t, 2H, J=8.5 Hz), 4.46 (bt, 1H), 3.46 (bt, 1H), 2.88 (s, 3H), 2.59 (s, 3H), 2.46 (s, 3H), 2.24 (s, 3H), 2.11 (s, 3H), 2.90-1.20 (m, 15H). MS ESI (M+H)$^+$ =532

(4S)-isomer: $^1$H NMR (300 MHz, CDCl$_3$) δ 7.11 (t, 2H, J=8 Hz), 6.93 (dt, 2H, J$_1$=8.8 Hz, J$_2$=2.9 Hz), 4.38 (b, 1H), 4.04 (b, 1H), 3.71 (B, 1S), 2.89 (s, 3H), 2.60 (s, 3H), 2.43 (s, 3H), 2.23 (s, 3H), 2.10 (s, 3H), 2.90-1.20 (m, 14H).

MS ESI$^+$ (M+H)$^+$=532

Examples 35 and 36

N-{(1R,3S,4R)-3-{[[3-(4-fluorophenyl)propyl](methyl)amino]methyl}-4-[({[3-(1-methyl-1H-tetrazol-5-yl)phenyl]amino}carbonyl)amino]cyclohexyl}-N-methylacetamide and N-{(1S,3S,4R)-3-{[[3-(4-fluorophenyl)propyl](methyl)amino]methyl}-4-[({[3-(1-methyl-1H-tetrazol-5-yl)phenyl]amino}carbonyl)amino]cyclohexyl}-N-methylacetamide

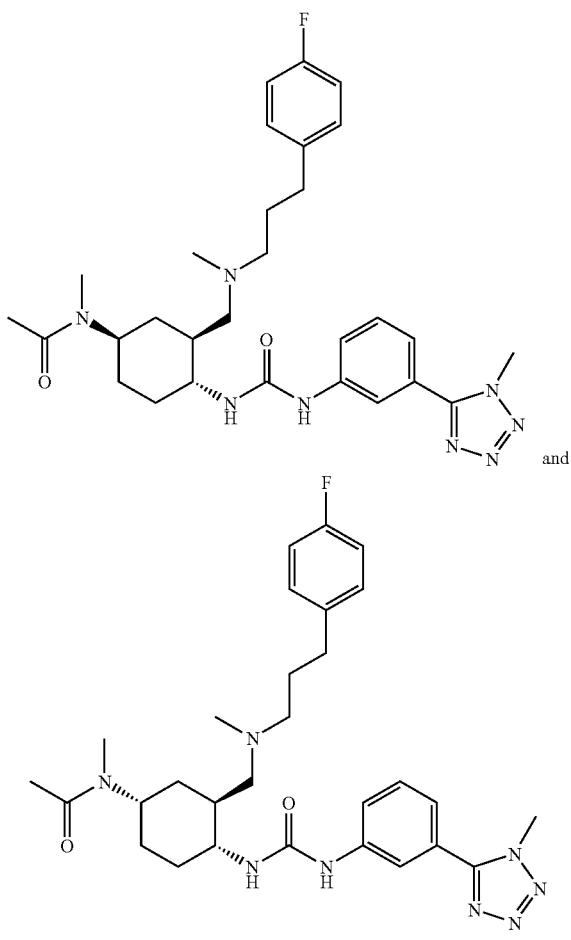

(See Scheme 5)

To a solution of disubstituted cyclohexylamine 35 [$R^5$=3-(4-fluorophenyl)propyl, $R^4$=methyl, $R^{14a}$=methyl, $R^{14b}$=acetyl, a 1:1 mixture of (4R)- and (4S)-isomers, 97 mg] in 2.5 mL of anhydrous THF were added N-[3-(1-methyl-tetrazol-5-yl)phenyl]-phenylcarbamate (90.5 mg, 1.1 equiv.) and triethylamine (0.1 mL), and the mixture was stirred for 18 hrs at room temperature. After addition of several drops of methanol the solvent was evaporated off, and two diasteromeric ureas were separated by flash chromatography (silica gel, 0.6:5.4:94 cNH$_4$OH/CH$_3$OH/CH$_2$Cl$_2$) to give N-[3-(1-methyl-tetrazol-5-yl)phenyl]-N'-[(1R,2S,4R)-5-(N-methyl)acetamido-2-[N-methyl-3-(4-fluorophenyl)propylamino]methyl-cyclohexyl]urea (EXAMPLE 35) and N-[3-(1-methyl-tetrazol-5-yl)phenyl]-N'-[(1R,2S,4S)-5-(N-methyl)acetamido-2-[N-methyl-3-(4-fluorophenyl)propylamino]methyl-cyclohexyl]urea (EXAMPLE 36) as amorphous solids.

(4R)-isomer: MS ESI$^+$ (M+H)$^+$=551
(4S)-isomer: MS ESI$^+$ (M+H)$^+$=551

Examples 37 and 38

N-{(1R,3S,4R)-3-{[[3-(4-fluorophenyl)propyl](methyl)amino]methyl}-4-[({[1-methyl-indazol-5-yl]amino}carbonyl)amino]cyclohexyl}-N-methylacetamide and N-{(1S,3S,4R)-3-{[[3-(4-fluorophenyl)propyl](methyl)amino]methyl}-4-[({[1-methyl-indazol-5-yl]amino}carbonyl)amino]cyclohexyl}-N-methylacetamide

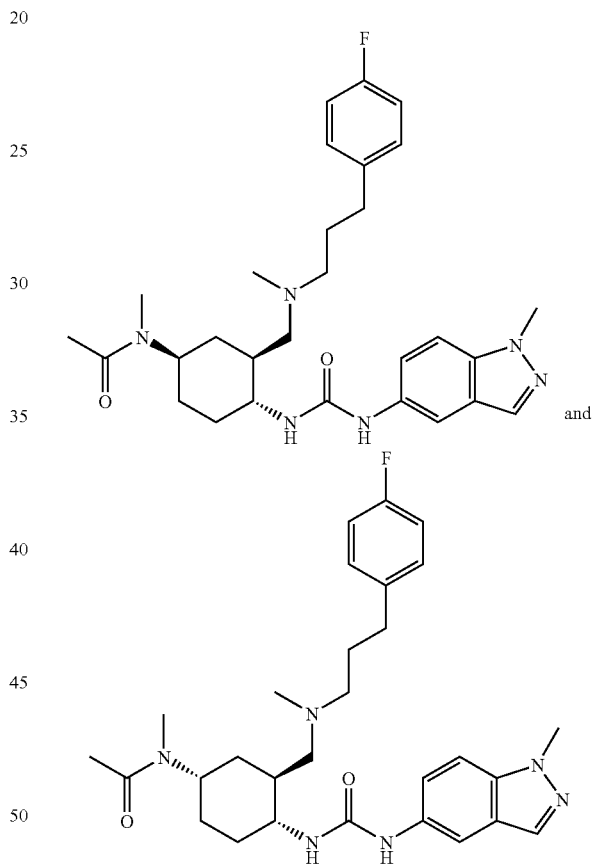

To a solution of disubstituted cyclohexylamine 35 [$R^5$=3-(4-fluorophenyl)propyl, $R^4$=methyl, $R^{14a}$=methyl, $R^{14b}$=acetyl, a 1:1 mixture of (4R)- and (4S)-isomers, 97 mg, see Scheme 5] in 2.5 mL of anhydrous THF were added N-(1-methyl-indazol-5-yl)-phenylcarbamate (82 mg, 1.1 equiv.) and triethylamine (0.1 mL), and the mixture was stirred for 18 hrs at room temperature. After addition of several drops of methanol the solvent was evaporated off, and two diasteromeric ureas were separated by flash chromatography (silica gel, 0.6:5.4:94 cNH$_4$OH/CH$_3$OH/CH$_2$Cl$_2$) to give N-(1-methyl-indazol-5-yl)-N'-[(1R,2S,4R)-5-(N-methyl)acetamido-2-[N-methyl-3-(4-fluorophenyl)propylamino]methyl-cyclohexyl]urea (EXAMPLE 37) and N-(1-methyl-indazol-5-yl)-N'-[(1R,2S,4S)-5-(N-methyl)acetamido-2-[N-methyl-3-(4-fluorophenyl)propylamino]methyl-cyclohexyl]urea (EXAMPLE 38) as amorphous solids.

(4R)-isomer: $^1$H NMR (300 MHz, CDCl$_3$) δ 7.86 (s, 1H), 7.69 (s, 1H), 7.25 (s, 2H), 7.08 (m, 2H), 6.92 (t, 2H, J=8.8 Hz), 4.53 (bt, 1H), 4.0 (s, 3H), 3.33 (bt, 1H), 2.81 (s, 3H), 2.11 (s, 3H), 2.02 (s, 3H), 2.90-1.10 (m, 15H). MS ESI$^+$ (M+H)$^+$=523.

(4S)-isomer: $^1$H NMR (300 MHz, CDCl$_3$) δ 7.88 (s, 1H), 7.74 (s, 1H), 7.36 (s, 1H), 7.25 (s, 1H), 7.02 (m, 2H), 6.92 (t, 2H, J=8.8 Hz), 4.35 (b, 1H), 4.04 (s, 3H), 3.90 (b, 1H), 3.59 (b, 1H), 2.77 (s, 3H), 2.10 (s, 3H), 2.05 (s, 3H), 2.90-1.10 (m, 14H). MS ESI$^+$ (M+H)$^+$=523.

Examples 39 and 40

N-{(1R,3S,4R)-3-{[[3-(4-fluorophenyl)propyl](methyl)amino]methyl}-4-[({[4-methyl-1,3-thiazol-2-yl]amino}carbonyl)amino]cyclohexyl}-N-methylacetamide and N-{(1S,3S,4R)-3-{[[3-(4-fluorophenyl)propyl](methyl)amino]methyl}-4-[({[4-methyl-1,3-thiazol-2-yl]amino}carbonyl)amino]cyclohexyl}-N-methylacetamide

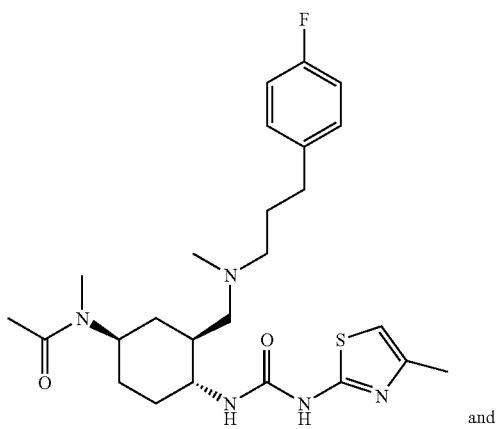

and

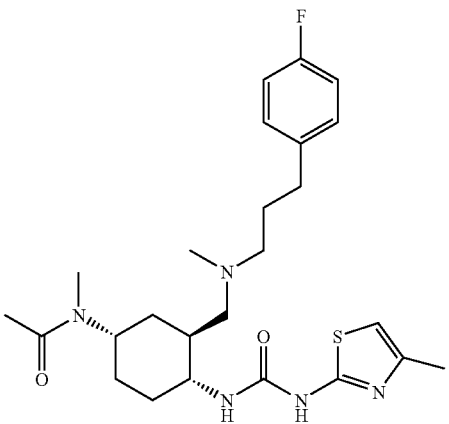

To a solution of disubstituted cyclohexylamine 35 [R$^5$=3-(4-fluorophenyl)propyl, R$^4$=methyl, R$^{14a}$=methyl, R$^{14b}$=acetyl, a 1:1 mixture of (4R)- and (4S)-isomers, 97 mg, see Scheme 5] in 2.5 mL of anhydrous THF were N-(4-methyl-thiazol-2-yl)-phenylcarbamate (72 mg, 1.1 equiv.) and triethylamine (0.1 mL), and the mixture was stirred for 18 hrs at room temperature. After addition of several drops of methanol the solvent was evaporated off, and two diasteromeric ureas were separated by flash chromatography (silica gel, 0.6:5.4:94 cNH$_4$OH/CH$_3$OH/CH$_2$Cl$_2$) to give N-(4-methyl-thiazol-2-yl)-N'-[(1R,2S,4R)-5-(N-methyl)acetamido-2-[N-methyl-3-(4-fluorophenyl)propylamino]methyl-cyclohexyl]urea (EXAMPLE 39) and N-(4-methyl-thiazol-2-yl)-N'-[(1R,2S,4S)-5-(N-methyl)acetamido-2-[N-methyl-3-(4-fluorophenyl)propylamino]methyl-cyclohexyl]urea (EXAMPLE 40) as amorphous solids.

(4R)-isomer: MS ESI$^+$ (M+H)$^+$=490.
(4S)-isomer: MS ESI$^+$ (M+H)$^+$=490.

TABLE 3

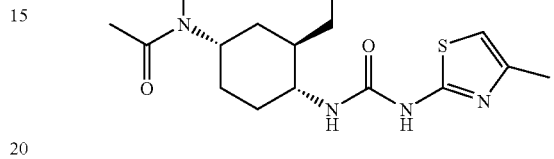

| Ex. No | R5 | R4 | R14 | R3 | MS (ESI) (M + H)$^+$ |
|---|---|---|---|---|---|
| 33 | 4-F-C$_6$H$_4$-(CH$_2$)$_3$-CH(-)- | CH$_3$ | N(Me)Ac (R)* | 2-(4-methyl-5-acetyl-thiazolyl) | 532 |

TABLE 3-continued

| Ex. No | R5 | R4 | R14 | R3 | MS (ESI) (M + H)+ |
|---|---|---|---|---|---|
| 34 | 4-F-phenyl-(CH₂)₃-C(CH₃)- | CH₃ | N(Me)Ac (S)* | 4-methyl-5-acetyl-thiazol-2-yl | 532 |
| 35 | 4-F-phenyl-(CH₂)₃-C(CH₃)- | CH₃ | N(Me)Ac (R)* | 3-(1-methyl-tetrazol-5-yl)phenyl | 551 |
| 36 | 4-F-phenyl-(CH₂)₃-C(CH₃)- | CH₃ | N(Me)Ac (S)* | 3-(1-methyl-tetrazol-5-yl)phenyl | 551 |
| 37 | 4-F-phenyl-(CH₂)₃-C(CH₃)- | CH₃ | N(Me)Ac (R)* | 1-methyl-indazol-5-yl | 523 |
| 38 | 4-F-phenyl-(CH₂)₃-C(CH₃)- | CH₃ | N(Me)Ac (S)* | 1-methyl-indazol-5-yl | 523 |
| 39 | 4-F-phenyl-(CH₂)₃-C(CH₃)- | CH₃ | N(Me)Ac (R)* | 4-methyl-thiazol-2-yl | 490 |
| 40 | 4-F-phenyl-(CH₂)₃-C(CH₃)- | CH₃ | N(Me)Ac (S)* | 4-methyl-thiazol-2-yl | 490 |

Example 41

N-({(1S,2R)-2-[[3-(4-orophenyl)propyl]amino]cyclohexyl}methyl)-N'-[3-(1-methyl-1H-tetrazol-5-yl)phenyl]urea

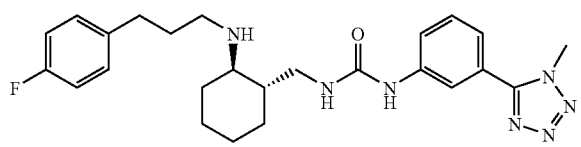

Step a: To a solution of the BOC-protected amino-alcohol 37 (5 g) in 30 mL of anhydrous pyridine was added p-toluenesulfonyl chloride (4.16 g, 1 equiv.), and the mixture was stirred at room temperature for 1.75 hrs. After evaporating off pyridine under the reduced pressure the residue was dissolved in EtOAc, and washed with water and brine. The organic layer was dried over Na2SO4 and evaporated to give a syrupy residue of the tosylate 38.

Step b: To a solution of tosylate 38 in 50 mL of anhydrous dimethylformamide was added sodium azide (4.25 g, 3 equiv.), and the mixture was stirred for 1 hr at 90° C. After cooling it was diluted with diethyl ether, and washed with water and brine. It was dried over Na2SO4 and evaporated to give a solid residue, which was purified by column chromatography (silica gel, 20% EtOAc/hexane) to give pure azide 39 as a white crystalline solid (3.63 g).

Step c: The azide 39 (3.63 g) was dissolved in 50 mL of methanol and 0.7 g of 10% palladium on carbon (50% wet) was added to the solution. The mixture was treated with hydrogen on a Parr hydrogenator (60 psi) for 6 hrs. After removal of the catalyst by filtration through a plug of Celite, the filtrate was evaporated to give the amine 40 as a white solid (~100% yield).

Step d: To a solution of the amine 40 (533 mg) in 10 mL of anhydrous acetonitrile were added phenyl 3-(1-methyl-tetrazol-5-yl)phenyl carbamate (680 mg, 1 equiv.) and 0.5 mL of triethylamine, and the mixture was stirred for 18 hrs at room temperature. The solvent and triethylamine were evaporated off, and the residue was purified by column chromatography (silica gel, 50% EtOAc/hexane followed by 10% MeOH/CH$_2$Cl$_2$) to give pure urea 41 [R$^3$=3-(1-methyl-tetrazol-5-yl)phenyl, 670 mg].

Step e: To a solution of the urea 41 [R$^3$=3-(1-methyl-tetrazol-5-yl)phenyl, 670 mg] in 7 mL of CH$_2$Cl$_2$ was added trifluoroacetic acid (1.2 mL, 10 equiv.), and the mixture was stirred for 7 hrs at room temperature. After evaporation off the solvent and the residue was dissolved in EtOAc, washed with saturated NaHCO$_3$ and brine, dried over Na$_2$SO$_4$, and evaporated to give the crude amine 42 [R$^3$=3-(1-methyl-tetrazol-5-yl)phenyl] as an oil.

Step f: To a solution of the amine 42 [R$^3$=3-(1-methyl-tetrazol-5-yl)phenyl, 237 mg] in 5 mL of 1,2-dichloroethane were added 3-(4-fluorophenyl)propanal (220 mg, 2 equiv.) and sodium triacetoxyborohydride (458 mg, 3 equiv.), and the mixture was stirred for 2 days at room temperature. At the end of the stirring 3 mL of saturated Na$_2$CO$_3$ was added, and it was extracted with EtOAc. The extract was washed with brine, dried over Na$_2$SO$_4$, and evaporated to give a solid residue. It was purified by column chromatography (silica gel, 0.5:4.5:95 cNH$_4$OH/MeOH/CH$_2$Cl$_2$) to give pure N-[3-(1-methyl-tetrazol-5-yl)phenyl]-N'-[(1S,2R)-2-[3-(4-fluorophenyl)propylamino]-cyclohexylmethyl]urea (163 mg).

$^1$H NMR (300 MHz, CDCl$_3$) δ 7.88 (s, 1H), 7.54 (d, 1H, J=8 Hz), 7.35 (t, 1H, J=7.7 Hz), 7.26 (d, 1H, J=8 Hz), 7.04 (dd, 2H, J$_1$=8 Hz, J$_2$=6 Hz), 6.89 (t, 2H, J=8.8 Hz), 4.13 (s, 3H), 3.5 (bd, 1H, J=13.5 Hz), 3.09 (dd, 1H, J$_1$=13.9 Hz, J$_2$=5.5 Hz), 2.74 (m, 1H), 2.59-2.46 (m, 3H), 2.27 (bt, 1H), 2.04 (bd, 1H, J=11.7 Hz), 1.8-1.6 (m, 4H), 1.37-0.80 (m, 6H). MS ESI (M+H)=466.

Example 42

N-[3-Ethyl-5-(1-methyl-1H-tetrazol-5-yl)phenyl]-N'-({(1S,2R)-2-[[3-(4-fluorophenyl)propyl]amino]cyclohexyl}methyl)urea

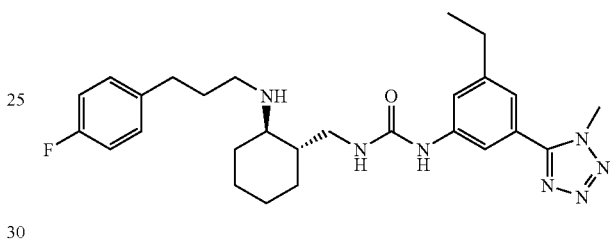

Example 42 was prepared in an analogous manner to Example 41 using phenyl 3-ethyl-5-(1-methyl-tetrazol-5-yl)phenyl carbamate in Step d.

$^1$H NMR (300 MHz, CDCl$_3$) δ 7.67 (S, 1H), 7.38 (S, 1H), 1.12 (s, 1H), 7.05 (dd, 2H, J$_1$=7.7 Hz, J$_2$=6.8 Hz), 6.89 (t, 2H, J=8.8 Hz), 4.12 (s, 3H), 3.50 (bd, 1H, J=13.1 Hz), 3.10 (dd, 1H, J$_1$=13.6 Hz, J$_2$=4.4 Hz), 2.74 (m, 1H), 2.63-2.40 (m, 3H), 2.58 (q, 2H, J=7.7 Hz), 2.25 (bd, 1H, J=13.5 Hz), 2.05 (bt, 1H), 1.80-1.60 (m, 4H), 1.40-0.80 (m, 6H), 1.18 (t, 3H, J=7.7 Hz). MS ESI (M+H)$^+$=494.

Example 43

N-(5-acetyl-4-methyl-1,3-thiazol-2-yl)-N'-[{(1S,2R)-2-[[3-(4-fluorophenyl)propyl]amino]cyclohexyl}methyl)urea

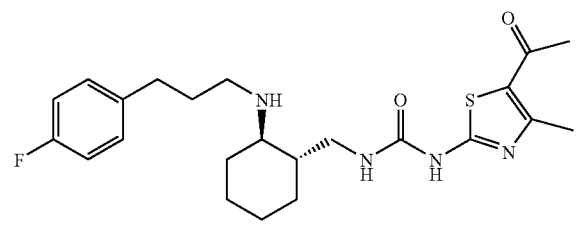

Example 43 was prepared in an analogous manner to Example 41 using phenyl 5-acetyl-4-methyl-thiazol-2-yl carbamate in Step d.

$^1$H NMR (300 MHz, CDCl$_3$) δ 7.11 (b, 2H), 6.94 (t, 2H, J=8.1 Hz), 5.87 (bs, 1H), 3.70-3.45 (m, 2H), 3.19 (b, 1H), 3.00 (b, 1H), 2.80-2.40 (m, 3H), 2.55 (s, 3H), 2.46 (s, 3H), 2.15-2.00 (m, 2H), 1.80-1.60 (m, 4H), 1.40-1.00 (m, 6H). MS ESI (M+H)$^+$=447.3.

Example 44

N-({(1S,2R)-2-[[3-(4-fluorophenyl)propyl](methyl)amino]cyclohexyl}methyl)-N'-[3-(1-methyl-1H-tetrazol-5-yl)phenyl]urea

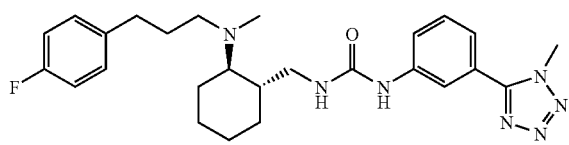

To a solution of N-[3-(1-methyl-tetrazol-5-yl)phenyl]-N'-[(1S,2R)-2-[3-(4-fluorophenyl)propylamino]-cyclohexylmethyl]urea (98 mg), the product of Step g of Example 31, in 4 mL of CH$_2$Cl$_2$ was added a solution of formaldehyde in THF (excess), and the mixture was stirred for 15 minutes. Then excess amount of sodium cyanoborohydride was added, and the mixture was continued to stir for 5 hrs at room temperature. After quenching the reaction with saturated Na$_2$CO$_3$, it was extracted with CH$_2$Cl$_2$. The extract was washed with water, dried over MgSO$_4$ and evaporated to give an oily residue. It was purified by column chromatography (silica gel, 0.6:5.494 cNH$_4$OH/CH$_3$OH/CH$_2$Cl$_2$) to give pure N-[3-(1-methyl-tetrazol-5-yl)phenyl]-N'-[(1S,2R)-2-[N-methyl-3-(4-fluorophenyl)propylamino]-cyclohexylmethyl]urea.

$^1$H NMR (300 MHz, CDCl$_3$) δ 7.93 (s, 1H), 7.53 (d, 1H, J=8.1 Hz), 7.38 (t, 1H, J=8.1 Hz), 7.30 (d, 1H, J=7.3 Hz), 7.06 (t, 2H, J=7.7 Hz), 6.91 (t, 2H, J=8.8 Hz), 4.15 (s, 3H), 3.69 (bt, 1H), 3.44 (bt, 1H), 3.10 (m, 1H), 2.56 (t, 2H, J=6.9 Hz), 2.60-2.10 (m, 3H), 2.26 (s, 3H), 1.85-0.80 (m, 10H). MS ESI (M+H)=480.4.

Example 45

N-[3-Ethyl-5-(1-methyl-1H-tetrazol-5-yl)phenyl]-N'-({(1S,2R)-2-[[3-(4-fluorophenyl)propyl](methyl)amino]cyclohexyl}methyl)urea

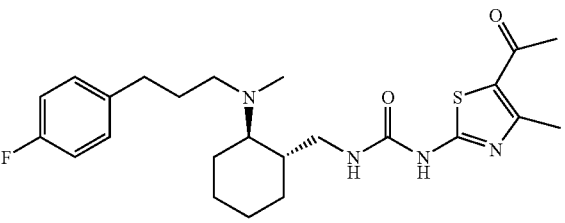

Example 45 was prepared in an analogous manner to Example 44 using phenyl 3-ethyl-5-(1-methyl-tetrazol-5-yl)phenyl carbamate in Step d.

$^1$H NMR (300 MHz, CDCl$_3$) δ 7.79 (s, 1H), 7.33 (s, 1H), 7.19 (s, 1H), 7.06 (t, 2H, J=7.7 Hz), 6.91 (m, 2H), 4.14 (s, 3H), 3.70 (t, 1H, J=5.1 Hz), 3.46 (bt, 1H), 3.05 (m, 1H), 2.67-2.40 (m, 7H), 2.32 (s, 3H), 1.80-0.8 (m, 10H), 1.21 (t, 3H, J=7.7 Hz). MS ESI (M+H)$^+$=508.5.

Example 46

N-(5-acetyl-4-methyl-1,3-thiazol-2-yl)-N'-[{(1S,2R)-2-[[3-(4-fluorophenyl)-propyl](methyl)amino]cyclohexyl}methyl)urea Example 46 was prepared in an analogous manner to Example 44 using phenyl 5-acetyl-4-methyl-thiazol-2-yl carbamate in Step d.

$^1$H NMR (300 MHz, CDCl$_3$) δ 7.77 (b, 2H), 6.93 (t, 2H, J=8.4 Hz), 5.76 (b, 1H), 3.60 (b, 1H), 3.37 (b, 1H), 2.90-0.80 (m, 18H), 2.58 (s, 3H), 2.46 (s, 3H). MS ESI (M+H)$^+$=461.3.

TABLE 4
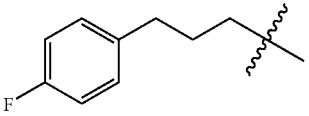
| Ex. No | R5 | R4 | R3 | MS (ESI) (M + H)+ |
|---|---|---|---|---|
| 41 | 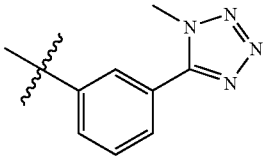 | H | 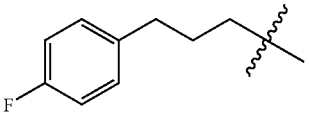 | 466 |
| 42 | 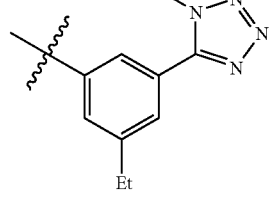 | H | 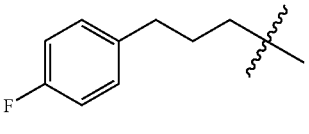 | 494 |
| 43 | 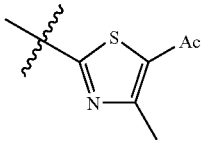 | H | 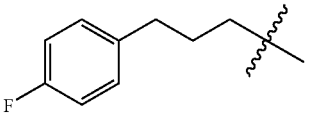 | 447 |
| 44 | 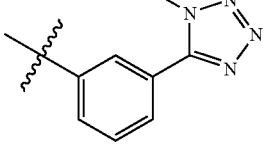 | CH3 | 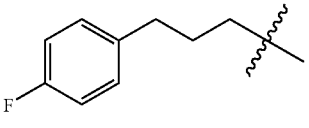 | 480.4 |
| 45 | 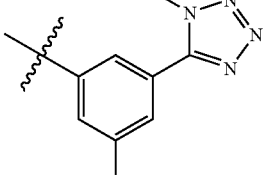 | CH3 | 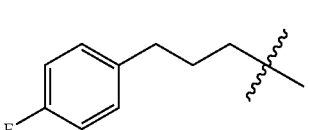 | 508.5 |
| 46 | 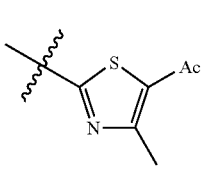 | CH3 | | 461.3 |

Example 47

1-((1R,2S,4R)-2-(((3-(4-fluorophenyl)propyl)(propyl)amino)methyl)-4-pivalamidocyclohexyl)-3-(1,3,4-thiadiazol-2-yl)urea

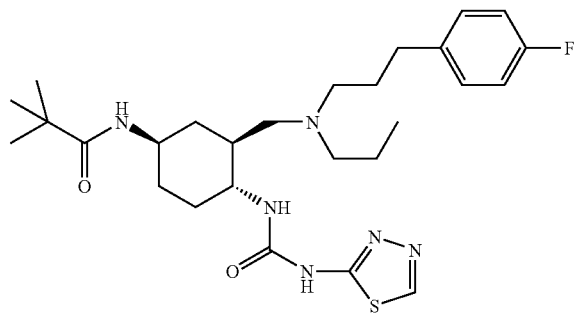

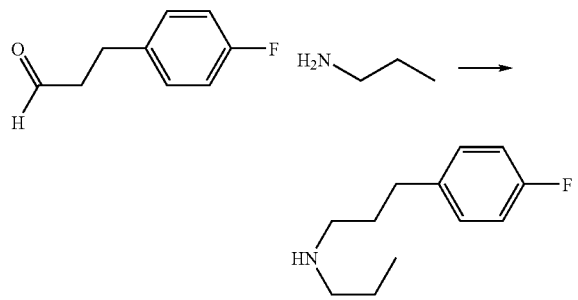

Synthesis of 3-(4-fluorophenyl)-N-propylpropan-1-amine

A solution of 3-(4-fluorophenyl)propanoic acid (5.0 g, 30 mmol) in THF is cooled in an ice bath and treated with N-methyl morpholine (NMM) (3.0 g, 30 mmol), isobutylchloroformate (4.04 g, 30 mmol) and stirred for few mins. This was then treated with a solution of N,O-Dimethyl hydroxylamine hydrochloride (3.0 g, 30 mmol) in THF/water (neutralized with 3.0 g of NMM) and stirred for 30 minutes. The reaction mixture is diluted with $CH_2Cl_2$ and washed successively with 1 N NaOH, water and brine. The solvent was evaporated under vacuum to give 6.2 g of 3-(4-fluorophenyl)-N-methoxy-N-methylpropanamide as oil.

The crude amide was dissolved in ether and cooled in an ice bath and treated with LAH (1.35 g, 35 mmol) and stirred for 1 hour. The reaction was quenched with 1 N HCl, extracted with ethyl acetate and washed successively with water and brine, dried over $MgSO_4$. The extract was filtered and evaporated under vacuum to give 4.3 g of 3-(4-fluorophenyl)propanal.

A solution of the crude 3-(4-fluorophenyl)propanal and propylamine (3.0 g, 51 mmol) in $CH_2Cl_2$ and was treated with $NaBH(OAc)_3$ and stirred at room temperature overnight. The reaction was quenched with 1 N NaOH, and washed successively with water and brine. The solvent was evaporated under vacuum to give 4.3 g of 3-(4-fluorophenyl)-N-propylpropan-1-amine.

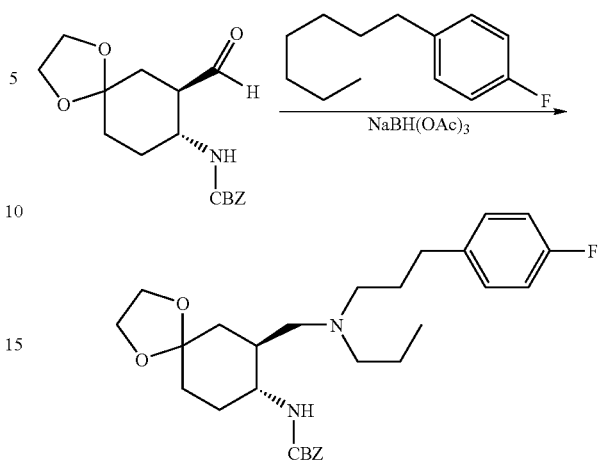

Synthesis of benzyl {((7S,8R)-7-[(3-(4-fluorophenyl)propyl)(propyl)amino)methyl)]-1,4-dioxa-spiro[4.5]dec-8-yl}-carbamate A solution of aldehyde 5.0 g, 0.016 mol) and 3-(4-fluorophenyl)-N-propylpropan-1-amine (4.3 g, 0.022 mol) in 70 ml of methylene chloride was cooled in an ice bath and treated with $NaBH(OAc)_3$ (4.9 g, 0.023 mol). The resulting mixture was then stirred at room temperature overnight. Reaction was quenched with 1 N NaOH and stirred at room temperature for 1 hour. The organic layer was separated and washed with water and brine. The solvent is removed on a rotary evaporator and the residue obtained was chromatographed on silica gel (2-5% $NH_4OH/MeOH/CH_2Cl_2$) to give 4.2 g of benzyl {((7S,8R)-7-[(3-(4-fluorophenyl)propyl)(propyl)amino)methyl)]-1,4-dioxa-spiro[4.5]dec-8-yl}-carbamate as an oil. MS: $(M+H)^+=499.34$.

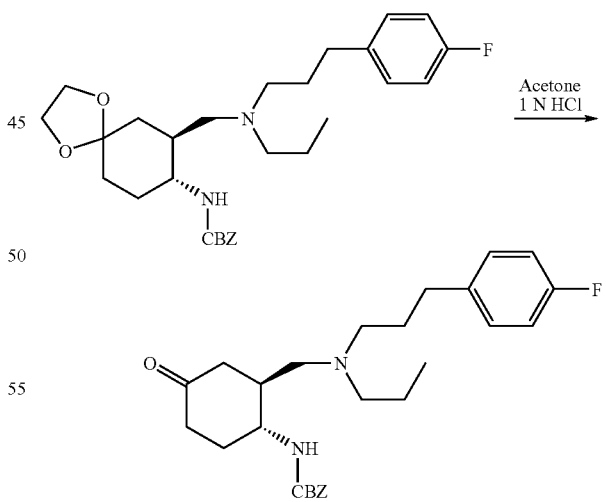

Synthesis of benzyl(1R,2S)-2-(((3-(4-fluorophenyl)propyl)(propyl)amino)methyl)-4-oxocyclohexylcarbamate A solution of ketal (4.2 g, 0.008 mol) in 50 ml acetone was treated with 1 N HCl (50 ml) and heated to reflux for 4 hours. Most of the acetone was removed on a rotary evaporator and the aqueous residue was made basic with 1 N NaOH. The resulting suspension was extracted into CH₂Cl₂ and the organic extract was washed with water and brine. The solvent was removed on a rotary evaporator to give 3.8 g of ketone as a thick oil. MS: (M+H)⁺=455.32.

Synthesis of benzyl(1R,2S,4R)-2-(((3-(4-fluorophenyl)propyl)(propyl)amino)methyl)-4-pivalamidocyclohexylcarbamate A solution of benzyl(1R,2S,4R)-4-amino-2-(((3-(4-fluorophenyl)propyl)(propyl)-amino)methyl)-cyclohexylcarbamate (1.1 g, 2.4 mmol) and Et₃N (0.3 g, 3 mmol) in CH₂Cl₂ (50 ml) was cooled in an ice bath and treated drop-wise with pivaloyl chloride (0.32 g, 2.6 mmol). The solution is stirred for 30 minutes and then washed successively with saturated sodium bicarbonate, 0.5 N NaOH, and brine. The solution was dried over sodium sulfate, filtered and the solvent removed on a rotary evaporator. This chromatographed on silica gel to (0.3:2.7:97 NH₄OH/MeOH/CH₂Cl₂) to give 0.85 g of white solid. MS: (M+H)⁺=540.38.

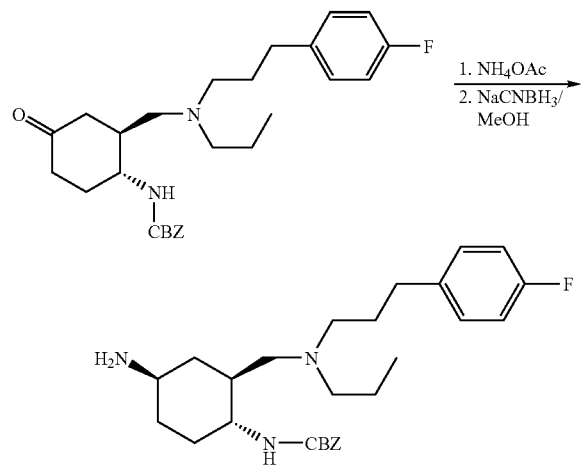

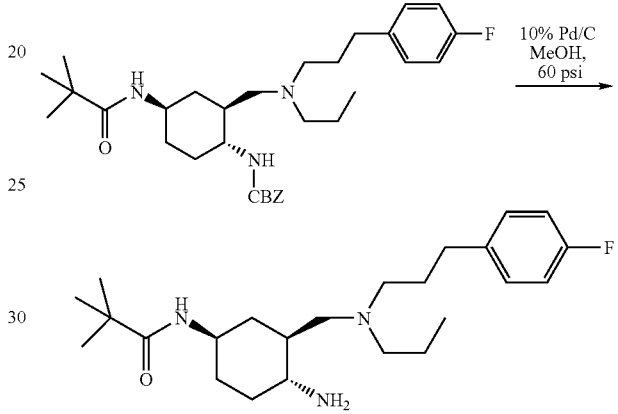

Synthesis of benzyl(1R,2S,4R)-4-amino-2-(((3-(4-fluorophenyl)propyl)(propyl)amino)methyl)-cyclohexylcarbamate A solution of ketone (3.8 g, 8.4 mmol) in methanol (25 ml) was treated with ammonium acetate (6.0 g, 80 mmol) and stirred until all the salt dissolved. The solution was treated with NaCNBH₃ (0.6 g, 9.6 mmol) and stirred at room temperature overnight. The solution was concentrated on a rotary evaporator and the residue treated with 1 N NaOH and extracted into CH₂Cl₂, and washed with water and brine. The solvent is removed on a rotary evaporator and the residue was chromatographed on silica gel (2-5% NH₄OH/MeOH/CH₂Cl₂) to give two isomers. The S isomer eluted first, then mixed fractions, and R isomer eluted last to give 1.1 g of the desired amine.

Synthesis of N-((1R,3S,4R)-4-amino-3-(((3-(4-fluorophenyl)propyl)(propyl)amino)methyl)-cyclohexyl) pivalamide A solution of carbamate (0.85 g, 1.5 mmol) in methanol (30 ml) was treated with 10% Pd/C (0.4 g) and hydrogenated at 60 psi of hydrogen for 20 hours at room temperature. The catalyst was filtered and the solvent evaporated on a rotary evaporator to give 4.6 g of amine as an oil that was used without further purification. MS: (M+H)⁺=406.39.

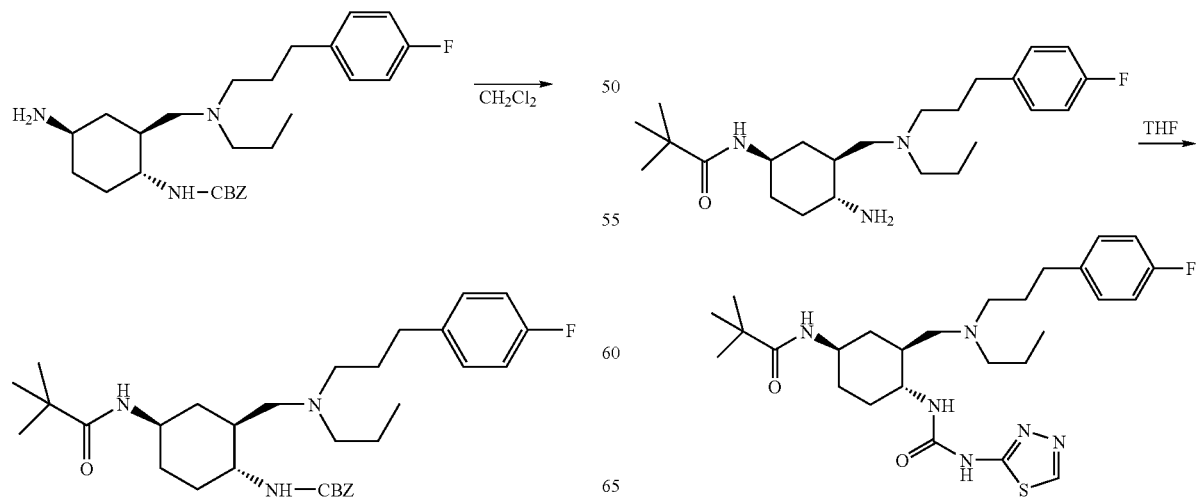

Synthesis of 1-((1R,2S,4R)-2-(((3-(4-fluorophenyl)propyl)(propyl)amino)methyl)-4-pivalamidocyclohexyl)-3-(1,3,4-thiadiazol-2-yl)urea A solution of crude amine (42 mg, 0.10 mmol) in THF (10 ml) was treated with phenyl 1,3,4-thiadiazol-2-ylcarbamate (26 mg, 0.11 mmol) and stirred at room temperature overnight. The solvent was removed on a rotary evaporator and the resulting solid dissolved in $CH_2Cl_2$ and chromatographed on silica gel eluting first with 0.2:1.8:98 $NH_4OH$/MeOH/$CH_2Cl_2$ to remove unreacted carbamate and phenol. Then eluted with 0.5:4.5:95 $NH_4OH$/MeOH/$CH_2Cl_2$ to give 40 mg of desired urea. MS ESI $(M+H)^+$=533.31.

Example 48

1-((1R,2S,4R)-2-(((3-(4-fluorophenyl)propyl)(propyl)amino)methyl)-4-pivalamidocyclohexyl)-3-(5-methyl-1,3,4-thiadiazol-2-yl)urea

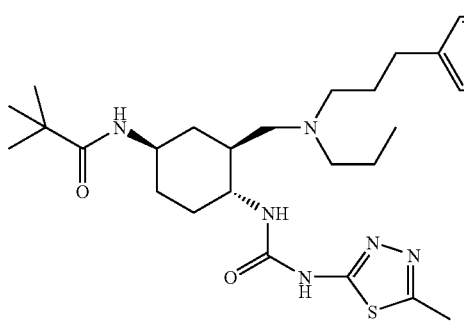

A solution of N-((1R,3S,4R)-4-amino-3-(((3-(4-fluorophenyl)propyl)(propyl)-amino)methyl)cyclohexyl)pivalamide (42 mg, 0.10 mmol) in THF (10 ml) was treated with phenyl(5-methyl-1,3,4-thiadiazol-2-yl)carbamate (28 mg, 0.11 mmol) and stirred at room temperature overnight. The solvent was removed on a rotary evaporator and the resulting solid dissolved in $CH_2Cl_2$ and chromatographed on silica gel eluting first with 0.2:1.8:98 $NH_4OH$/MeOH/$CH_2Cl_2$ to remove unreacted carbamate and phenol. Then eluted with 0.5:4.5:95 $NH_4OH$/MeOH/$CH_2Cl_2$ to give 40 mg of desired urea. MS ESI $(M+H)^+$=547.34.

Example 49

1-((1R,2S, 4R)-2-(((3-(4-fluorophenyl)propyl)(propyl)amino)methyl)-4-pivalamidocyclohexyl)-3-(5-ethyl-1,3,4-thiadiazol-2-yl)urea

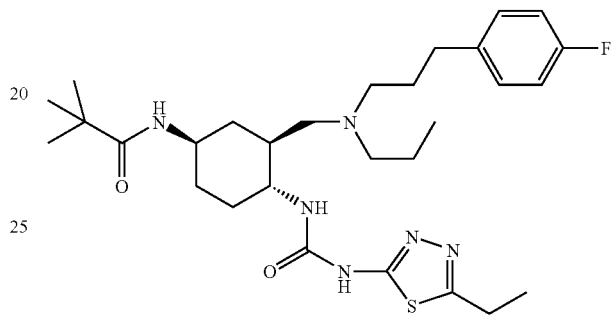

A solution of N-((1R,3S,4R)-4-amino-3-(((3-(4-fluorophenyl)propyl)(propyl)-amino)methyl)cyclohexyl)pivalamide (42 mg, 0.10 mmol) in THF (10 ml) was treated with phenyl(5-ethyl-1,3,4-thiadiazol-2-yl)carbamate (30 mg, 0.11 mmol) and stirred at room temperature overnight. The solvent was removed on a rotary evaporator and the resulting solid dissolved in $CH_2Cl_2$ and chromatographed on silica gel eluting first with 0.2:1.8:98 $NH_4OH$/MeOH/$CH_2Cl_2$ to remove unreacted carbamate and phenol. Then eluted with 0.5:4.5:95 $NH_4OH$/MeOH/$CH_2Cl_2$ to give 40 mg of desired urea. MS ESI $(M+H)^+$=561.40.

TABLE 4a

| Ex. No | R5 | R4 | R3 | MS (ESI) $(M+H)^+$ |
|---|---|---|---|---|
| 47 | 4-fluorophenylpropyl | propyl | 1,3,4-thiadiazol-2-yl | 533.31 |
| 42 | 4-fluorophenylpropyl | propyl | 5-methyl-1,3,4-thiadiazol-2-yl | 547.34 |

TABLE 4a-continued

| Ex. No | R5 | R4 | R3 | MS (ESI) (M + H)+ |
|---|---|---|---|---|
| 43 | 4-fluorophenylpropyl | propyl | 2-ethyl-1,3,4-thiadiazol-5-yl | 561.40 |

Example 100

N-((1R,2S)-3-{ethyl[3-(4-fluorophenyl)propyl]amino}-2-hydroxy-1-methylpropyl)-N'-[3-(1-methyl-1H-tetrazol-5-yl)phenyl]urea Step a: Synthesis of 1-(para-fluorophenyl)propionic acid.

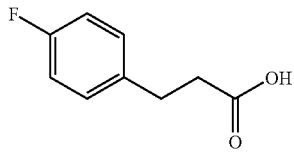

The product from Example 102 Step b (23.4 g, 119 mmol, 1 eq.), 10N NaOH (119.4 mL, 1.19 mol, 10 eq.), and methanol (50 mL) were mixed and refluxed overnight. The mixture was stripped, dissolved in water (250 mL), and adjusted to pH=1 with conc. HCl. This aqueous mixture was extracted with ethyl acetate (3×250 mL), the organic layers collected and dried (MgSO4), and stripped to yield 19.4 g of a light yellow solid. NMR (300 MHz, D₆DMSO) a 12.15 (s, 1H); 7.25 (m, 2H); 7.05 (m, 2H); 2.78 (t, 2H, J=7 Hz); 2.50 (t, 2H, J=7 Hz).

Step b: Synthesis of 1-(para-fluorophenyl)propionamide.

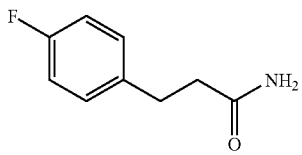

The product from Step a (19.4 g, 115 mmol, 1 eq.), thionyl chloride (42.0 mL, 576 mmol, 5 eq.) and chloroform (100 mL) were mixed and stirred overnight. The contents were stripped and then restripped twice from toluene to yield an oil. This oil was dissolved in THF (100 mL) and slowly dripped into a mixture of conc. NH₄OH (200 mL) and water (100 mL) at 0° C. After 2 hours of stirring, the contents were stripped, dissoved in ethyl acetate (300 mL), and washed with water (3×200 mL), brine (1×200 mL), dried (MgSO4) and stripped to yield 13.8 g of a white solid. MS (AP+) detects (M+H)+=168.2.

Step c: Synthesis of 1-(para-fluorophenyl)-3-(amino)propane

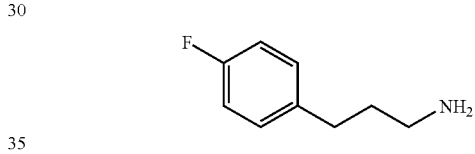

The product from Step b (13.8 g, 83 mmol, 1 eq.), was dissloved in 100 mL of THF and cooled to 0° C. Lithium aluminum hydride (1.0 N, 82.9 mL, 83 mmol, 1 eq.), was slowly added dropwise. The resultant mixture was stirred at room temperature for 3 days. Workup entailed the extremely slow addition of water (3.15 ml), followed by 1N NaOH (12.6 mL). The alumina solids were filtered off and the filtrate stripped to yield 11.8 g of a yellow oil. MS (ESI) detects (M+H+CH₃CN)+=195.2.

Step d: Synthesis of 1-(para-fluorophenyl)-3-(acetamido)propane

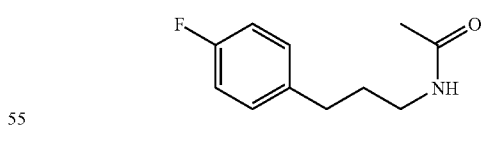

1-(para-fluorophenyl)-3-aminopropane (1.00 g, 6.53 mmol, 1 eq.) and triethylamine (0.91 mL, 6.53 mmol, 1 eq.) were dissoved in THF (10 mL) at 25° C. under N₂. Then a THF solution (5 mL) of acetyl chloride (0.46 mL, 6.53 mmol, 1 eq.) was added dropwise via an addition funnel over 10 minutes. Worked up after 20 minutes by filtering off the solids then stripping the filtrate to obtain an amber oil. The oil was purified over silica gel in 1:1 Hexanes/EtOAc to 100% EtOAc to 4:1 EtOAc/MeOH. Obtained 1.10 g of an amber oil as product. MS (ESI) detects (M+H)+=196.

Step e: Synthesis of 1-(para-fluorophenyl)-3-(ethylamino)propane

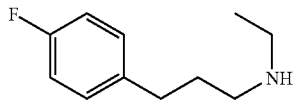

The product of Step d (1.10 g, 5.63 mmol, 1 eq.) was dissolved in THF at 25° C. under $N_2$ then 1.0M LAH in THF (22.54 mL, 22.50 mmol, 4 eq.) was added dropwise via an addition funnel over 10 minutes. After the addition was complete, refluxed for 1 hour. Worked up by carefully adding water (0.86 mL)(Caution—lots of foaming and gas evolution were observed) dropwise via an addition funnel followed by 1N NaOH (3.42 mL). Stirred 20 minutes then filtered off the solids. The filtrate was stripped to give 0.90 g of a colorless oil as product. MS (ESI) detects $(M+H)^+ = 182$.

Step f: Synthesis of (2S,3R)-3-(dibenzylamino)-1-{ethyl[3-(4-fluorophenyl)propyl]amino}butan-2-ol

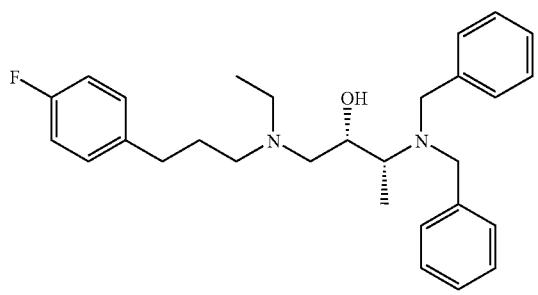

Part 1. Synthesis (1R)-N,N-dibenzyl-1-[(2S)-oxiran-2-yl]ethanamine.

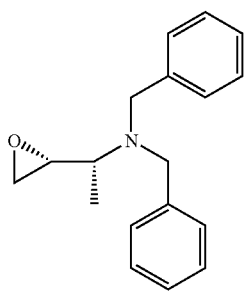

N,N-dibenzyl-R-2-aminopropanal was obtained from D-Alanine by the method of Beaulieu, Pierre L.; Wernic, Dominik,. Journal of Organic Chemistry (1996), 61(11), 3635-3645. To a flame-dried 3-neck flask at 25° C. under $N_2$ was added N,N-dibenzyl-R-2-aminopropanal (292.5 g, 1.15M, 1 eq.), dibromomethane (107.8 mL, 1.54M, 1.33 eq) and THF (2000 mL). Cooled to −55° C. then added 1.6M n-BuLi (721.6 mL, 1.15M, 1 eq.) dropwise via an addition funnel keeping the temperature below −45° C. After 15 minutes added dibromomethane (16.1 mL, 0.23 mmol, 0.2 eq.) followed by 1.6M n-BuLi (144.4 mL, 0.23 mmol, 0.2 eq.). After 30 minutes added dibromomethane (8.05 mL, 0.115 mmol, 0.1 eq.) followed by 1.6M n-BuLi (72.2 mL, 0.115 mmol, 0.1 eq.). After 10 minutes added dibromomethane (8.05 mL, 0.115 mmol, 0.1 eq.) followed by 1.6M n-BuLi (72.2 mL, 0.115 mmol, 0.1 eq.). After 10 minutes added dibromomethane (16.1 mL, 0.23 mmol, 0.2 eq.) followed by 1.6M n-BuLi (144.4 mL, 0.23 mmol, 0.2 eq.). After 10 minutes added dibromomethane (16.1 mL, 0.23 mmol, 0.2 eq.) followed by 1.6M n-BuLi (144 mL, 0.23 mmol, 0.2 eq.). Allowed the reaction to slowly warm to 25° C. overnight. Worked up by cooling the reaction to 10° C. then adding 1500 mL of a $NH_4Cl$ solution which contained 400 g of $NH_4Cl$, keeping the temperature below 20° C. Stirred for 10 minutes then extracted 3 times with hexanes. The organic layers were combined, dried ($MgSO_4$) then stripped to give 307.0 g of an amber oil as product. NMR shows diastereoisomer ratio to be 8.7:1. MS (ESI) detects $(M+H)^+ = 268$.

Part 2. Coupling

The product of Step e (0.90 g, 4.97 mmol, 1 eq.), epoxide from Part 1 above (1.33 g, 4.97 mmol, 1 eq.) and ethanol (10 mL) were mixed at 25° C. under $N_2$ then refluxed overnight. Worked up by stripping off the ethanol then purifying the residue over silica gel in 1:1 Hexanes/EtOAc to 100% EtOAc to 4:1 EtOAc/MeOH. Obtained 0.95 g of an amber oil as product. MS (ESI) detects $(M+H)^+ = 449$.

Step g: Synthesis of (2S,3R)-3-amino-1-{ethyl[3-(4-fluorophenyl)propyl]amino}butan-2-ol.

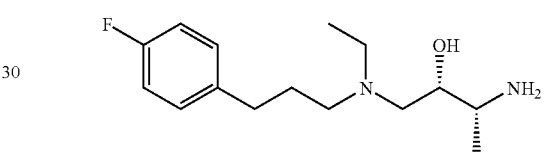

$Pd(OH)_2$ was carefully wetted down under $N_2$ with 5 mL of MeOH then the product of Step f (0.95 g) dissolved in 5 mL of MeOH was added followed by 5 mL of HOAc. The mixture was hydrogenated overnight on a Parr shaker at 50 psi. Worked up by filtering off the catalyst under $N_2$ through a fiberglass filter paper and vacuum. The filtrate was stripped to obtain white glass. To white glass was added $Et_2O$/saturated $NaHCO_3$ (25 mL) The layers were separated. The aqueous was basified further with 1N NaOH to pH=12 and extracted 3 times with $Et_2O$. The $Et_2O$ extracts from the 1N NaOH layer were combined, dried ($Na_2SO_4$) and stripped to give 0.40 g of and amber oil as product. MS (ESI) detects $(M+H)^+ = 269$.

Step h: Synthesis of N-((1R,2S)-3-{ethyl[3-(4-fluorophenyl)propyl]amino}-2-hydroxy-1-methylpropyl)-N'-[3-(1-methyl-1H-tetrazol-5-yl)phenyl]urea.

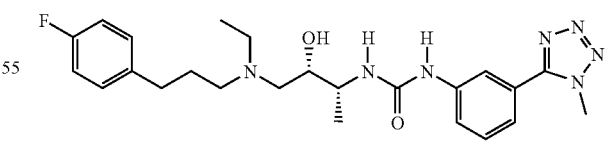

The product of Step g (50 mg, 0.19 mmol, 1 eq.), phenyl 3-(1-methyl-1H-tetraazol-5-yl)phenylcarbamate (55 mg, 0.19 mmol, 1 eq.) and acetonitrile (3 mL) were mixed at 25° C. under $N_2$ overnight. Worked up by stripping off the solvents then purifying the residue over silica gel in 100% EtOAc to 4:1 EtOAc/MeOH. Obtained 70 mg of a white glass as product. NMR (300 MHz, $CDCl_3$) δ 7.86 (s, 1H); 7.6 (d, 1H, J=7 Hz); 7.38 (t, 1H, J=7 Hz); 7.29 (d, 1H, J=7

Hz); 7.20-7.00 (m, 2H); 6.92 (t, 2H, J=7 Hz); 4.13 (s, 3H) 4.05-3.85 (m, 1H); 3.80-3.60(m, 1H); 2.80-2.40 (m, 8H); 1.85-1.60 (m, 2H); 1.18 (d, 3H, J=7 Hz); 1.00 (t, 3H, J=7 Hz).

Example 101

Synthesis of N-{(1R,2S)-3-[[3-(4-fluorophenyl)propyl](2,2,2-trifluoroethyl)amino]-2-hydroxy-1-methylpropyl}-N'-[3-(1-methyl-1H-tetrazol-5-yl)phenyl]urea Step a: Synthesis of 3-(para-Fluorophenyl)propionyl chloride

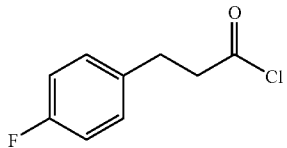

3-(para-Fluorophenyl)propionic acid (25.00 g, 150.0 mmol, 1 eq.) was dissolved in methylene chloride (100 mL) at 25° C. under N₂ and thionyl chloride (54.2 mL, 740.0 mmol, 5 eq.) added dropwise via an addition funnel. Worked up after 24 hours by stripping off the solvent then rerotovaping 2 times from toluene (25 mL) to obtain 24.3 g of a yellow oil.

Step b: Synthesis of 3-(4-fluorophenyl)-N-(2,2,2-trifluoroethyl)-propanamide.

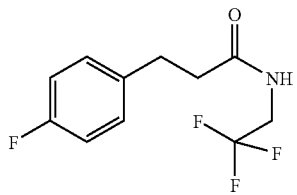

2,2,2-trifluoroethylamine (5.0 g, 50.0 mmol, 1 eq.), triethylamine (7.0 mL, 50.0 mmol, 1 eq.) and methylene chloride were mixed at 25° C. under N₂. The product of Step a (9.42 g, 50.0 mmol, 1 eq.) in methylene chloride (25 mL) was added dropwise via an addition funnel. Worked up after 24 hours by adding water (100 mL) and extracting 3 times with methylene chloride. The organic layers were combined, dried (MgSO4) and stripped to give 10.5 g of a white solid. MS (ESI) detects (M+H)⁺=250.

Step c: Synthesis of [3-(4-fluorophenyl)propyl](2,2,2-trifluoroethyl)amine.

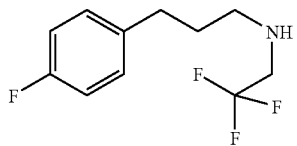

The product of Step b (10.5 g, 42.0 mmol, 1 eq.) was dissolved in THF at 25° C. under N₂ then 1.0M LAH in THF (169.0 mL, 170.0 mmol, 4 eq.) was added dropwise via an addition funnel over 10 minutes. After the addition was complete, the reaction mixture was refluxed for 3 hours. Worked up by carefully adding water (6.5 g)(Caution—lots of foaming and gas evolution were observed) dropwise via an addition funnel followed by 1N NaOH (25.8 mL). Stirred 20 minutes then filtered off the solids. The filtrate was stripped to give 9.80 g of a colorless oil as product. MS (ESI) detects (M+H+CH₃CN)⁺=277.

Step d: Synthesis of (2S,3R)-3-(dibenzylamino)-1-[[3-(4-fluorophenyl)propyl](2,2,2-trifluoroethyl)amino]butan-2-ol.

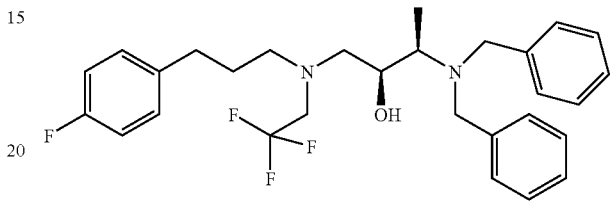

The product of Step c (3.48 g, 15.0 mmol, 1 eq.), (1R)-N,N-dibenzyl-1-[(2S)-oxiran-2-yl]ethanamine (the synthesis of which is described in Example 100) (3.96 g, 15.0 mmol, 1 eq.) and ethanol (20 mL) were mixed at 25° C. under N₂ then refluxed for 4 days. Worked up by stripping off the ethanol then purifying the residue by flash chromatography in 3:1 Hexanes/EtOAc. Obtained to 3.78 g of a yellow oil. By NMR, the oil is product and some minor impurities and was carried on to the next step. MS (ESI) detects (M+H)⁺=503.

Step e: Synthesis of (2S,3R)-3-amino-1-[[3-(4-fluorophenyl)propyl](2,2,2-trifluoroethyl)amino]butan-2-ol.

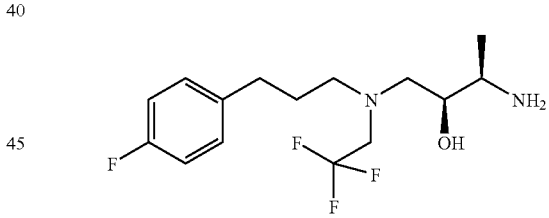

Pd(OH)₂ was carefully wetted down under N₂ with 20 mL of MeOH and the product of Step d (3.78 g) dissolved in 50 mL of MeOH was added followed by 70 mL of HOAc. The mixture was hydrogenated for 3 days on a Parr shaker at 50 PSI. Worked up by filtering off the catalyst under N₂ and vacuum through a fiberglass filter paper to obtain an oil. To the oil was added Et₂O/saturated NaHCO₃ (100 mL) The layers were separated. The aqueous was basified further with 1N NaOH to pH=12 then extracted 3 times with Et₂O. The Et₂O extracts from the 1N NaOH layer were combined, dried (Na₂SO₄) and stripped to give 2.46 g of and amber oil. The oil was purified by flash chromatography in 9:1 Hexanes/EtOAc to 100% EtOAc. Obtained 192 mg of an oil. MS (ESI) detects (M+H)⁺=323.

Step f: Synthesis of N-{(1R,2S)-3-[[3-(4-fluorophenyl)propyl](2,2,2-trifluoroethyl)amino]-2-hydroxy-1-methylpropyl}-N'-[3-(1-methyl-1H-tetrazol-5-yl)phenyl]urea.

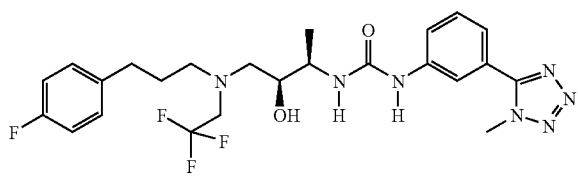

The product of Step e (192 mg, 0.60 mmol, 1 eq.), phenyl 3-(1-methyl-1H-tetraazol-5-yl)phenylcarbamate (176 mg, 0.60 mmol, 1 eq.) and acetonitrile (4 mL) were mixed at 25° C. under $N_2$ overnight. Worked up by stripping off the solvents then purifying the residue over silica gel in 9:1 Hexanes/EtOAc to 100% EtOAc. Obtained 21 mg of a viscous oil. NMR (300 MHz, $CDCl_3$) δ 8.35-8.20 (M, 1H); 7.79 (s, 1H); 7.70 (d, 1H, J=7 Hz); 7.45-7.20 (m, 2H); 7.10 (t, 2H, J=7 Hz); 6.93 (t, 2H, J=7 Hz); 6.20-5.80 (m, 1H); 4.05 (s, 3H); 3.93 (m, 1H); 3.80-3.40 (m, 2H); 3.25-3.05 (m, 2H); 2.85-2.40 (m, 4H); 1.85-1.60 (m, 2H); 1.20 (d, 3H, J=7 Hz); 1.00-0.70 (m, 1H).

Example 102

N-{(1R,2S)-3-[[3-(4-fluorophenyl)propyl](methyl)amino]-2-hydroxy-1-methylpropyl}-N'-[3-(1-methyl-1H-tetrazol-5-yl)phenyl]urea Step a: Synthesis of Ethyl-3-(4-Fluorophenyl)propenoate.

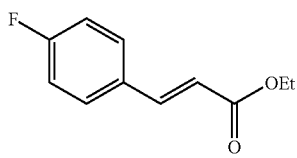

4-Fluorobenzaldehyde (27.2 ml, 0.23 Mol) and carboethoxymethylenetriphenylphosphorane (88.38 g, 0.23 Mol) were disolved in toluene (500 ml), and the mixture was heated overnight at reflux. The reaction was stripped then purified by flash chromatography in 25% EtOAc/Hexanes yielded 44.55g of a crystalline solid as product. NMR (300 MHz, $CDCl_3$) δ 7.65 (d, 1H, J=16 Hz); 7.60-7.40 (m, 2H); 7.08 (t, 2H, J=7 Hz); 6.35 (d, 1H, J=16 Hz); 4.26 (q, 2H, J=7 Hz); 1.34 (t, 3H, J=7 Hz).

Step b: Synthesis of Ethyl-3-(4-Fluorophenyl)propionate.

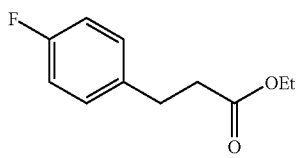

10% palladium on carbon (1.0 g) was carefully wetted down under $N_2$ with 10 mL of ethanol then the product of Step a (44.55 g, 0.23 mol) in ethanol (200 ml) was added. The mixture was placed on a Parr shaker and hydrogenated overnight at 50 psi. The catalyst was removed by filtration and rinsed, under nitrogen, with two 50 ml portions of ethanol. The combined filtrates were concentrated in-vacuo to yield 44.0 g of a colorless oil. This material was used as-is in the next step. NMR (300 MHz, $CDCl_3$) δ 7.25 (m, 2H); 6.97 (t, 2H, J=7 Hz); 4.10 (q, 2H, J=7 Hz); 2.90 (t, 2H, J=7 Hz); 2.60 (t, 2H, J=7 Hz); 1.24 (t, 3H, J=7 Hz).

Step c: Synthesis of 3-(4-Fluorophenyl)propanol.

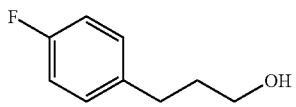

The product of Step b (20.0 g, 102 mmol) was dissolved in anhydrous THF (500 ml), and the mixture was cooled to 0° C. To this solution, 1M LAH in THF (100 ml) was added dropwise, then the mixture was allowed to come to room temperature and stirred for three days. The reaction was quenched by the careful sequential addition of water (3.8 ml), 15% NaOH (3.8 ml), and water (11.4 ml). The resulting slurry was stirred for 1 hour, the solids were removed by filtration and rinsed with EtOAc, and the combined filtrates were stripped to yield 15.4 g of a colorless oil. This material was used as-is in the next step. NMR (300 MHz, $CDCl_3$) δ 7.20-7.05 (m, 2H); 6.97 (t, 2H, J=7 Hz); 3.69 (q, 2H, J=7 Hz); 2.70 (t, 2H, J=7 Hz); 1.88 (t of t, 2H, J=7, 7 Hz); 1.31 (t, 1H, J=7 Hz).

Step d: Synthesis of 1-Bromo-3-(4-Fluorophenyl)propane.

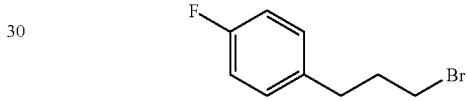

The product of Step c (15.4 g, 100.0 mmol, 1 eq.) dissolved in $CCl_4$ (10 mL) at 25° C. under $N_2$ was added dropwise via an addition funnel to a refluxing solution of phosphourus tribromide in $CCl_4$ (100 mL). Refluxed for 15 minutes and stirred overnight at 25° C. Worked up by washing 2 times with water (100 mL), 1 time with saturated $NaHCO_3$ (100 mL) and 1 time with water (100 mL). Used a little brine to help separate the layers. The organic layers were combined, dried ($MgSO_4$) and stripped to give 13.7 g of a clear colorless oil. Purified by Kugelrohr distillation at 0.5 mmHg at 60-70° C. Obtained 10.6 g of a clear colorless oil. NMR (300 MHz, $CDCl_3$) δ 7.20-7.05 (m, 2H); 6.98 (t, 2H, J=7 Hz); 3.99 (t, 2H, J=7 Hz); 2.74 (t, 2H, J=7 Hz); 2.14 (t of t, 2H, J=7, 7 Hz).

Step e: Synthesis of 1-(methylamino)-3-(4-Fluorophenyl)propane.

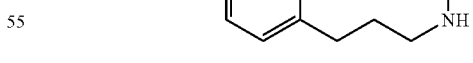

The product of Step d (2.0 g, 9.2 mmol, 1 eq.), 2.0M methylamine in THF (100 mL, 20.0 mmol, 10 eq.) and THF (100 mL) were mixed at 25° C. under $N_2$ and stirred overnight. Worked up by stripping to obtain a solid. Dissolved in 150 mL of 1N $NaOH/Et_2O$. Separated the layers. Extracted 2 times more with $Et_2O$. The organic layers were combined, dried ($MgSO_4$) and stripped to give 1.38 g of a yellow oil. MS (ESI) detects $(M+H)^+$168.

Step f: Synthesis of (2S,3R)-3-(dibenzylamino)-1-[[3-(4-fluorophenyl)propyl](methyl)amino]butan-2-ol.

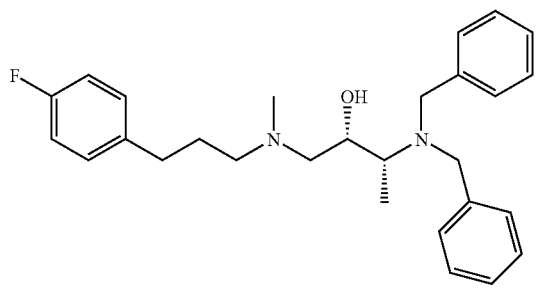

The product of Step e (1.30 g, 7.80 mmol, 1 eq.), (1R)-N,N-dibenzyl-1-[(2S)-oxiran-2-yl]ethanamine (the synthesis of which is described in Example 100) (2.08 g, 7.80 mmol, 1 eq.) and ethanol (10 mL) were mixed at 25° C. under $N_2$ then refluxed overnight. Worked up by stripping off the ethanol then purifying the residue over silica gel in 1:1 Hexanes/EtOAc to 100% EtOAc. Obtained 1.16 g of an amber oil. MS (ESI) detects (M+H)$^+$=435.

Step g: Synthesis of (2S,3R)-3-amino-1-[[3-(4-fluorophenyl)propyl](methyl)amino]butan-2-ol.

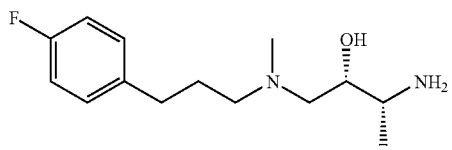

Pd(OH)$_2$ was carefully wetted down under $N_2$ with 10 mL of MeOH then the product of Step f (1.15 g) dissolved in 40 mL of MeOH was added followed by 50 mL of HOAc. The mixture was hydrogenated overnight on a Parr shaker at 50 PSI. Worked up by filtering off the catalyst under $N_2$ through a fiberglass filter paper and vacuum. The filtrate was stripped to obtain an oily residue which was dissolved in 25 mL of Et$_2$O and washed 2 times with 1N NaOH, 1 time with brine, dried (Na$_2$SO$_4$) and stripped to give 0.57 g of a light yellow oil. MS (ESI) detects (M+H)$^+$=255.

Step h: Synthesis of N-{(1R,2S)-3-[[3-(4-fluorophenyl)propyl](methyl)amino]-2-hydroxy-1-methylpropyl}-N'-[3-(1-methyl-1H-tetrazol-5-yl)phenyl]urea.

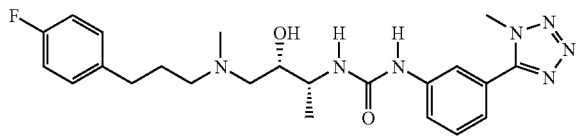

The product of Step g (186 mg, 7.3 mmol, 1 eq.), phenyl 3-(1-methyl-1H-tetraazol-5-yl)phenylcarbamate (220 mg, 7.3 mmol, 1 eq.) and acetonitrile (10 mL) were mixed at 25° C. under N$_2$ overnight. Worked up by stripping off the solvents then purifying the residue over silica gel in 1:1 Hexanes/EtOAc to 100% EtOAc to 4:1 EtOAc/MeOH. Obtained 123 mg of an amorphous solid. NMR (300 MHz, CDCl$_3$) δ 7.88 (s, 1H); 7.60 (d, 1H, J=7 Hz); 7.42 (t, 1H, J=7 Hz); 7.30 (d, 1H, J=7 Hz); 7.20-7.00 (m, 2H); 6.91 (t, 2H, J=7 hz); 4.17 (s, 3H); 3.97 (m, 1H); 3.80 (m, 1H); 2.70-2.40 (m, 6H); 2.34 (s, 3H); 1.90-1.70 (m, 2H); 1.18 (d, 3H, J=7 Hz).

Example 103

N-((1R,2S)-3-{cyclohexyl[3-(4-fluorophenyl)propyl]amino}-2-hydroxy-1-methylpropyl)-N'-[3-ethyl-5-(1-methyl-1H-tetrazol-5-yl)phenyl]urea Step a: Synthesis of Boc-D-alanine ethyl ester.

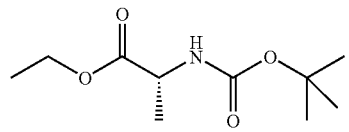

Boc-D-alanine (5.0 g, 26.4 mmol), dimethylaminopyridine (161 mg, 1.3 mMol), and ethanol (1.34 g, 29.1 mMol) were dissolved in methylene chloride (300 ml), and the solution was cooled to 0° C. To this solution was added 1,3-dicyclohexylcarbodiimide (6.0 g, 29.1 mMol). The mixture was allowed to slowly come to room temperature, and stirred under nitrogen overnight, during which time a white solid precipitated. The precipitate was removed by filtration, rinsed with methylene chloride, and the filtrate was concentrated to a pale yellow oil. Flash chromatography in 10-30% EtOAc/Hexanes yielded 4.9 g of a colorless oil as product. NMR (300 MHz, CDCl$_3$) δ 5.05 (b, 1H), 4.28 (q, 1H, J=7 Hz), 4.20 (q, 2H, J=7 Hz), 1.45 (s, 9H), 1.38 (d, 3H, J=7 Hz), 1.28 (t, 3H, J=7 Hz).

Step b: Synthesis of tert-butyl [(1R,2R)-3-chloro-2-hydroxy-1-methylpropyl]carbamate.

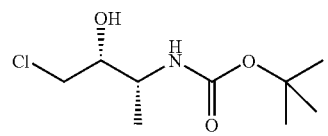

Boc-D-alanine ethyl ester (4.9 g, 22.6 mMol) and iodochloromethane (15.9 g, 90.2 mMol) were dissolved in dry THF (50 ml), and the mixture was cooled to −70° C. To this solution was added dropwise a solution of freshly prepared LDA (115 mMol, 5.1 eq) in 1:1 THF/Hexanes (150 ml) at a rate which did not allow the temperature to rise above −65° C. After the addition was completed, the mixture was stirred for an additional 15 minutes, then a 1:1 solution of acetic acid/THF was added dropwise, at a rate which did not allow the temperature to rise above −65° C. After the addition was completed, the mixture was stirred for an additional 20 minutes, then allowed to warm to −20° C. The solution was diluted with toluene (60 ml) followed by an ice-cold aqueous 1% HCl solution (60 ml). The resulting mixture was stirred until all salts had dissolved, then the phases were separated. The organic phase was combined with an ice-cold aqueous 5% sodium bicarbonate solution, and the mixture was stirred for 10 minutes. The phases were separated, ethanol (60 ml) was added to the organic phase, and the mixture was cooled to −70° C. To this solution was added dropwise a solution of sodium borohydride (2.2 g, 58.6 mMol) in MeOH (60 ml), and the resulting mixture was stirred for two days at −70° C. The solution was allowed to come to 0° C., stirred for 3 hours, then carefully quenched with saturated sodium bicarbonate (30 ml) and water (30 ml). The mixture was stirred at 0° C. for 30 minutes, the organic solvents were stripped, the residue was diluted with 100 ml water, and the slurry was vigorously stirred for ten minutes. The resulting brown solids were collected by filtration, rinsed with water followed by hexanes, then dried under vacuum to yield 4.1 g of a brown solid, which was a 6:1 diasteromeric mixture by NMR. These solids were crystallized from methylcyclohexane to yield 2.1 g of brown needles containing only the desired diastereomer. NMR (300 MHz, CDCl₃) δ 4.77 (b, 1H), 3.83-3.81 (m, 2H), 3.61 (dd, 1H, J=4, 7 Hz), 3.55-3.48 (m, 1H), 2.99 (b, 1H), 1.45 (s, 9H), 1.18 (d, 3H, J=7 Hz).

Step c: Preparation of tert-butyl {(1R)-1-[(2R)-oxiran-2-yl]ethyl}carbamate.

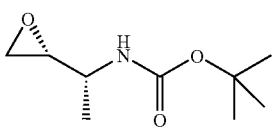

The product from step b (2.1 g, 9.34 mMol) was dissolved in ethanol (50 ml), a 1.0 M ethanolic solution of potassium hydroxide (11.2 ml) was added, and the mixture was stirred overnight at room temperature. The ethanol was stripped, the residue was taken up in EtOAc (100 ml), and the organic solution was washed with saturated ammonium chloride (2×20 ml) followed by water (20 ml). The organic phase was dried over sodium sulfate and concentrated in-vacuo to 1.65 g of an amber oil. The oil was dissolved in hexanes (50 ml), a small amount of dark colored solids were removed by filtration, and the filtrate was concentrated to 15 ml. This solution was cooled in a dry ice/acetone bath until a solid began to precipitate. The mixture was allowed to stand at room temperature for 2 hours, after which the mother liquor was decanted from the resulting solids. The crystals were dried under vacuum to yield 1.1 g of colorless crystals as product. NMR (300 MHz, CDCl₃) δ 4.54 (b, 1H), 3.67 (b, 1H), 2.95 (m, 1H), 2.78 (d, 1H, J=4, 5 Hz), 2.73-2.71 (m, 1H), 1.45 (s, 9H), 1.15 (d, 3H, J=7 Hz).

Step d: Preparation of tert-butyl((1R,2S)-3-{[3-(4-fluorophenyl)propyl]amino}-2-hydroxy-1-methylpropyl)carbamate.

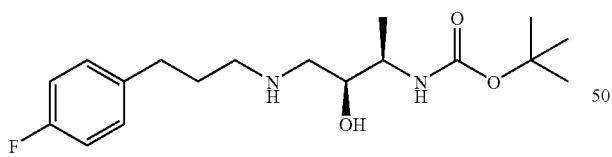

The product from step c (823 mg, 4.39 mMol) and 3-(4-fluorophenyl)propylamine (674 mg, 4.39 mMol) were dissolved in anhydrous acetonitrile (10 ml). To this solution, lithium trifluoromethanesulfonate (1.44 g, 9.23 mMol) was added, and the solution was stirred overnight. The mixture was concentrated in-vacuo, then the residue was dissolved in EtOAc (60 ml), washed with saturated sodium bicarbonate (2×20 ml), followed by water (20 ml). The organic phase was dried over sodium sulfate and concentrated to a yellow oil. Purified via flash chromatography, eluting with EtOAc, 2.5% 7N NH₄ in MeOH/EtOAc, 5% 7N NH₄ in MeOH/EtOAc to yield 1.2 g of a colorless oil as product. ESI+MS detects 341 (M+H).

Step e: Preparation of tert-butyl((1R,2S)-3-{cyclohexyl[3-(4-fluorophenyl)propyl]amino}-2-hydroxy-1-methylpropyl)carbamate.

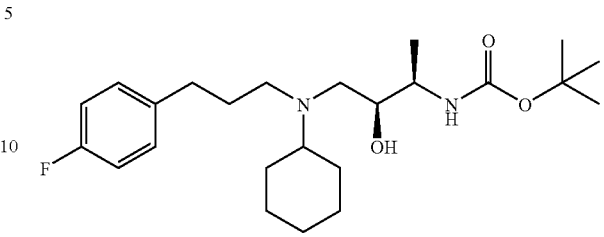

The material from step d (623 mg, 1.83 mMol) and cyclohexanone (179 mg, 1.83 mMol) were dissolved in methanol (5 ml), 4 A molecular sieves were added, and the mixture was stirred at room temperature for 2 hours. To this mixture, sodium cyanoborohydride (173 mg, 2.75 mMol) was added, and the mixture was stirred overnight. Analysis of the reaction mixture by ESI MS showed an M+H which was two AMU higher than that of the desired product, indicating that the imine or aminal hadn't been reduced by sodium cyanoborohydride. The reaction mixture was filtered, the solids were rinsed with EtOAc, and the combined filtrates were concentrated in-vacuo. The residue was dissolved in EtOAc (30 ml), washed with water (2×10 ml), dried over sodium sulfate, and concentrated in-vacuo. The residue was dissolved in methylene chloride (5 ml), sodium triacetoxyborohydride (583 mg, 2.75 mMol) followed by two drops of glacial acetic acid were added, and the mixture was stirred at room temperature for three days. The reaction was worked up by diluting with water (50 ml), adjusting the pH of the mixture to >10 with 1N NaOH, and extracting with EtOAc (3×30 ml). The combined organic phases were dried over sodium sulfate, and concentrated to a yellow oil. This oil was purified via flash chromatography, eluting with EtOAc to yield 310 mg of a colorless oil as product. ESI+MS detects 423 (M+H).

Step f: Preparation of (2S,3R)-3-amino-1-{cyclohexyl[3-(4-fluorophenyl)propyl]amino}butan-2-ol.

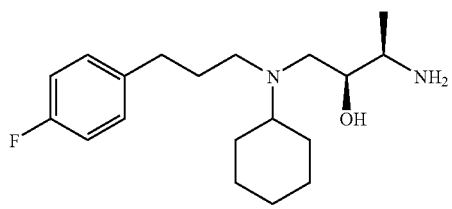

The product from step e (310 mg, 0.73 mMol) was dissolved in a 1:1 mixture of methylene chloride/trifluoroacetic acid (10 ml), and the solution was stirred at room temperature for 3 hours. The reaction mixture was concentrated in-vacuo, the residue was diluted with 1N NaOH (30 ml) and this mixture was stirred at room temperature for 30 minutes. The resulting cloudy aqueous mixture was extracted with EtOAc (3×30 ml), the combined organic phases were washed with 1N NaOH (20 ml), water (20 ml), and brine (20 ml), then dried over sodium sulfate and concentrated in-vacuo. The resulting colorless oil was used as-is in the next step. ES+MS detects 323 (M+H).

Step g: Preparation of N-((1R,2S)-3-{cyclohexyl[3-(4-fluorophenyl)propyl]amino}-2-hydroxy-1-methylpropyl)-N'-[3-ethyl-5-(1-methyl-1H-tetrazol-5-yl)phenyl]urea.

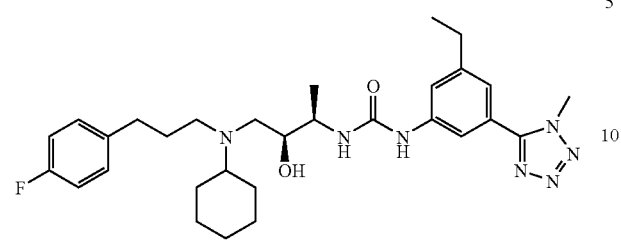

The product from step f (105 mg, 0.33 mMol) and phenyl 3-ethyl-5-(1-methyl-1H-tetraazol-5-yl)phenylcarbamate (106 mg, 0.33 mMol) were dissolved in 1 ml of acetonitrile, and the mixture was stirred at room temperature overnight. The reaction mixture was directly purified via preparative HPLC using a 3" reverse-phase $C_{18}$ column, and eluting with 10%-90% acetonitrile (0.05% TFA)/water (0.05% TFA) over 40 minutes. Lyophilization of the fractions which contained the product peak yielded 153 mg of the product as the TFA salt. NMR (300 MHz, CD$_3$OD) δ 7.75 (s, 1H), 7.40 (s, 1H), 7.26-7.20 (m, 3H), 6.99-6.95 (m, 2H), 4.16 (s, 3H), 3.89-3.68 (m, 2H), 3.48-3.02 (m, 5H), 2.71-2.65 (m, 4H), 2.15-1.81 (m, 6H), 1.77-1.12 (m, 12H). ES+MS detects 552 (M+H).

Example 104

N-((1R,2S)-3-{cyclohexyl[3-(4-fluorophenyl)propyl]amino}-2-hydroxy-1-methylpropyl)-N'-[3-(1-methyl-1H-tetrazol-5-yl)phenyl]urea

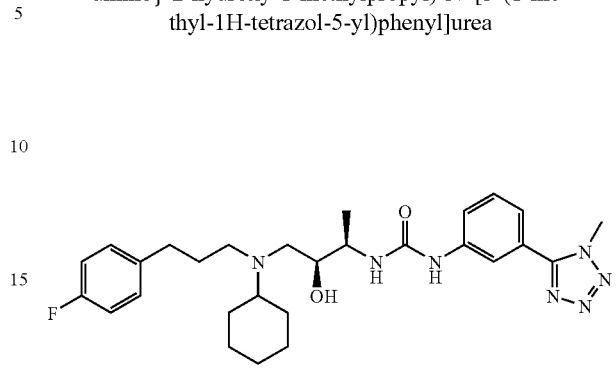

The title compound was prepared from the material from step f of Example 103 and phenyl 5-(1-methyl-1H-tetrazol-5-yl)phenylcarbamate as in step h in Example 102 to yield 96 mg of the product as the TFA salt. NMR (300 MHz, CD$_3$OD) δ 7.95 (d, 1H, J=2 Hz), 7.58-7.45 (m, 2H), 7.40 (ddd, 1H, J=2, 2, 7 Hz), 7.25-7.16 (m, 2H), 6.9-6.93 (m, 2H), 4.17 (s, 3H), 3.89-3.69 (m, 2H), 3.45-3.04 (m, 5H), 2.66 (q, 2H, J=7 Hz), 2.09-1.87 (m, 6H), 1.70-1.16 (m, 9H). ES+MS detects 524 (M+H).

TABLE 5

| Ex. No | R5 | R4 | R3 | MS (ESI) (M + H)+ |
|---|---|---|---|---|
| 100 | 4-fluorophenylpropyl | Et | 3-(1-methyl-1H-tetrazol-5-yl)phenyl | 470 |
| 101 | 4-fluorophenylpropyl | CF$_3$CH$_2$ | 3-(1-methyl-1H-tetrazol-5-yl)phenyl | 524 |
| 102 | 4-fluorophenylpropyl | CH$_3$ | 3-(1-methyl-1H-tetrazol-5-yl)phenyl | 456 |

TABLE 5-continued
| Ex. No | R5 | R4 | R3 | MS (ESI) (M + H)+ |
|---|---|---|---|---|
| 103 | 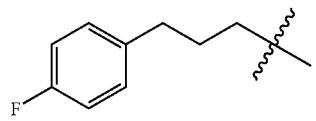 | 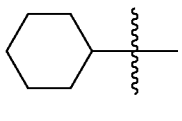 | 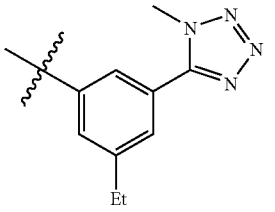 | 552 |
| 104 | 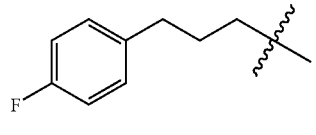 | 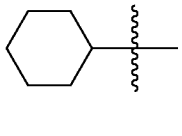 | 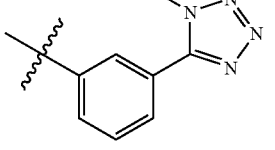 | 524 |
| 105 | 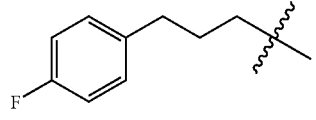 | CH₃ | 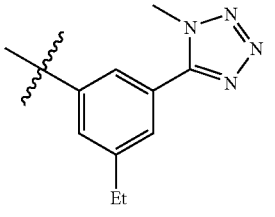 | |
| 106 | 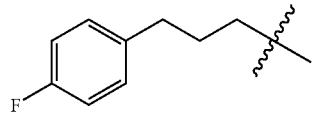 | Et | 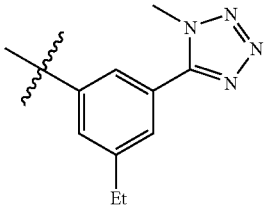 | |
| 107 | 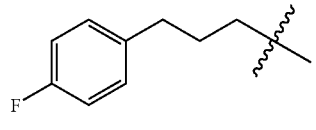 | Et | 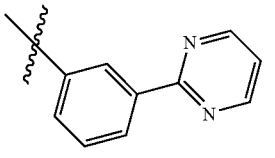 | |
| 108 | 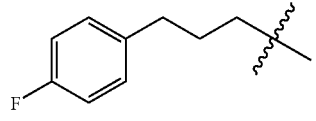 | Et | 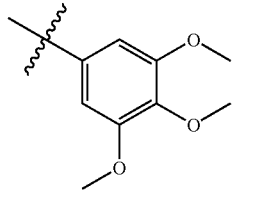 | |
| 109 | 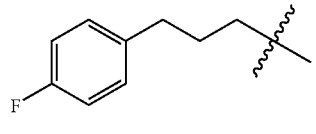 | Et | 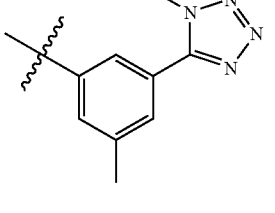 | |

TABLE 5-continued

| Ex. No | R5 | R4 | R3 | MS (ESI) (M + H)+ |
|---|---|---|---|---|
| 110 | 4-F-C6H4-(CH2)3- | Et | benzo[1,3]dioxol-5-yl | |
| 111 | 4-F-C6H4-(CH2)3- | Et | 7-methoxy-benzo[1,3]dioxol-5-yl | |
| 112 | 4-F-C6H4-(CH2)3- | Et | 3,5-dimethoxyphenyl | |
| 113 | 4-F-C6H4-(CH2)3- | Et | 3-cyano-5-(1-methyl-1H-tetrazol-5-yl)phenyl | |
| 114 | 4-F-C6H4-(CH2)3- | Et | 3-(1-methyl-1H-tetrazol-5-yl)phenyl | |
| 115 | 4-F-C6H4-(CH2)3- | Et | 3-ethyl-5-(1-methyl-1H-tetrazol-5-yl)phenyl | |
| 116 | 4-F-C6H4-(CH2)3- | iPr | 3-ethyl-5-(1-methyl-1H-tetrazol-5-yl)phenyl | |

TABLE 5-continued
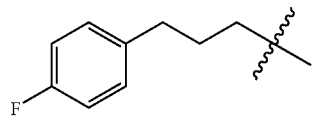
| Ex. No | R5 | R4 | R3 | MS (ESI) (M + H)+ |
|---|---|---|---|---|
| 117 | 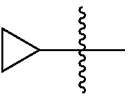 | 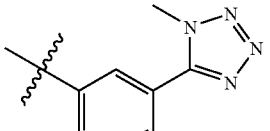 | 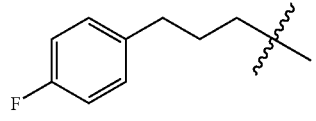 | |
| 118 | 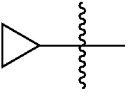 | 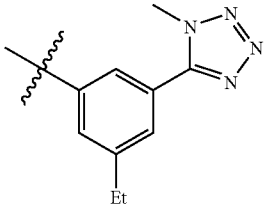 | 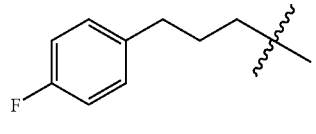 | |
| 119 | 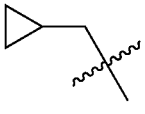 | 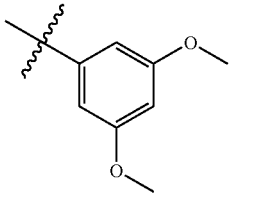 | 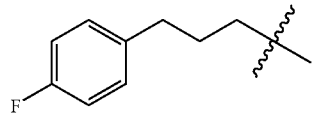 | |
| 120 | 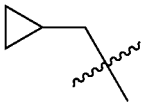 | 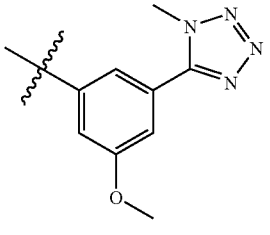 | 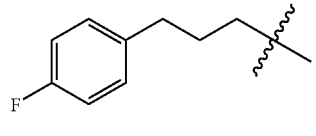 | |
| 121 |  | 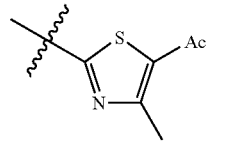 | 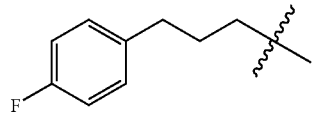 | |
| 122 |  | 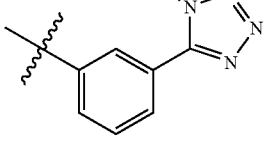 | 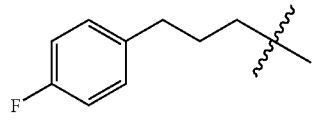 | |
| 123 | 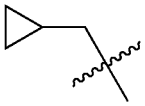 | 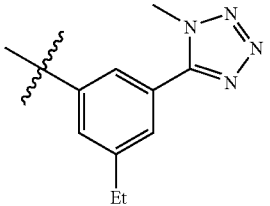 | | |

TABLE 5-continued

| Ex. No | R5 | R4 | R3 | MS (ESI) (M + H)+ |
|---|---|---|---|---|
| 124 | 4-F-C6H4-(CH2)3-CH(-)- | H | 3-(1-methyltetrazol-5-yl)-5-ethylphenyl | |
| 125 | 4-F-C6H4-(CH2)3-CH(-)- | CF3CH2 | 3-(1-methyltetrazol-5-yl)-5-ethylphenyl | |
| 126 | 4-F-C6H4-(CH2)3-CH(-)- | 1-adamantyl | 3-(1-methyltetrazol-5-yl)phenyl | |
| 127 | 4-F-C6H4-(CH2)3-CH(-)- | 1-adamantyl | 3-(1-methyltetrazol-5-yl)-5-ethylphenyl | |
| 128 | 4-F-C6H4-(CH2)3-CH(-)- | Bn | 3-(1-methyltetrazol-5-yl)-5-ethylphenyl | |
| 129 | 4-F-C6H4-(CH2)3-CH(-)- | CH3CO | 3-(1-methyltetrazol-5-yl)-5-ethylphenyl | |

TABLE 5-continued

| Ex. No | R5 | R4 | R3 | MS (ESI) (M + H)+ |
|---|---|---|---|---|
| 130 | 4-F-C6H4-(CH2)3- | CH3SO2 | 3-(1-methyltetrazol-5-yl)-5-ethyl-phenyl | |
| 131 | 4-F-C6H4-CH2-C(CH3)2-CH2- | CH3 | 3-(1-methyltetrazol-5-yl)-phenyl | |
| 132 | 4-F-C6H4-CH2-C(CH3)2-CH2- | CH3 | 3-(1-methyltetrazol-5-yl)-5-ethyl-phenyl | |
| 133 | 4-F-C6H4-CH2-C(CH3)2-CH2- | CH3 | 5-acetyl-4-methyl-thiazol-2-yl | |
| 134 | 4-F-C6H4-CH2-C(CH3)2-CH2- | Et | 3-(1-methyltetrazol-5-yl)-phenyl | |
| 135 | 4-F-C6H4-CH2-C(CH3)2-CH2- | Et | 3-(1-methyltetrazol-5-yl)-5-ethyl-phenyl | |
| 136 | 2-pyridyl-(CH2)3- | CH3 | 3-(1-methyltetrazol-5-yl)-phenyl | |

TABLE 5-continued
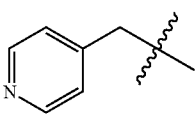
| Ex. No | R5 | R4 | R3 | MS (ESI) (M + H)+ |
|---|---|---|---|---|
| 137 | 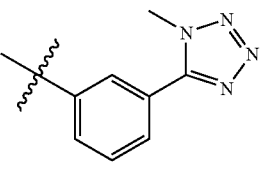 | Et | 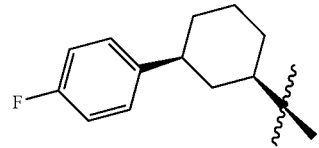 | |
| 138 | 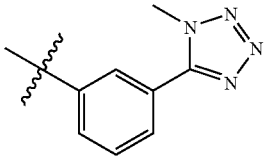 | H | 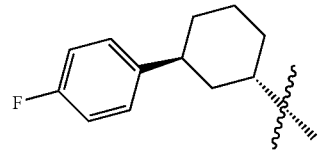 | |
| 139 | 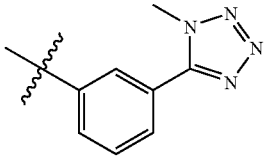 | H | 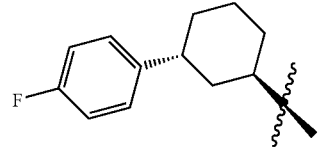 | |
| 140 | 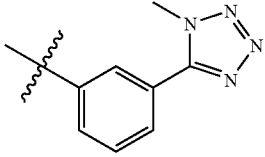 | H | 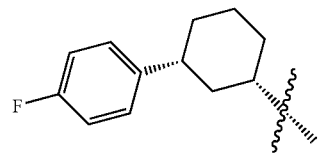 | |
| 141 | 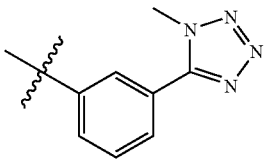 | H | 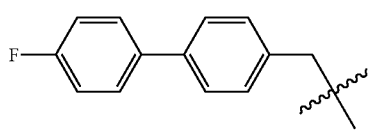 | |
| 142 | 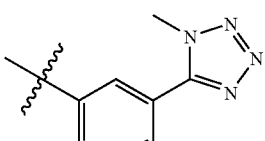 | Et | 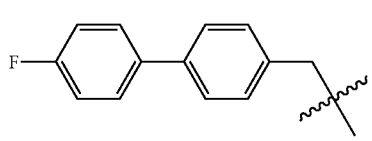 | |
| 143 | 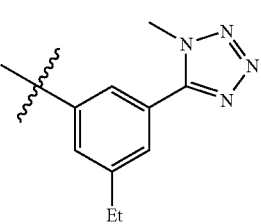 | Et | | |

TABLE 5-continued

| Ex. No | R5 | R4 | R3 | MS (ESI) (M + H)+ |
|---|---|---|---|---|
| 144 | 4'-fluorobiphenyl-2-ylmethyl | Et | 3-(1-methyltetrazol-5-yl)phenyl | |
| 145 | 4'-fluorobiphenyl-2-ylmethyl | Et | 3-ethyl-5-(1-methyltetrazol-5-yl)phenyl | |
| 146 | 4'-fluorobiphenyl-3-ylmethyl | Et | 3-(1-methyltetrazol-5-yl)phenyl | |
| 147 | 4'-fluorobiphenyl-3-ylmethyl | Et | 3-ethyl-5-(1-methyltetrazol-5-yl)phenyl | |
| 148 | (1R,2S)-1-hydroxy-2-methyl-1-phenylpropyl | CH3 | 3-(1-methyltetrazol-5-yl)phenyl | |
| 149 | (1R,2R)-1-hydroxy-2-methyl-1-phenylpropyl | CH3 | 3-(1-methyltetrazol-5-yl)phenyl | |
| 150 | (1S,2S)-1-hydroxy-2-methyl-1-phenylpropyl | CH3 | 3-(1-methyltetrazol-5-yl)phenyl | |

TABLE 5-continued

| Ex. No | R5 | R4 | R3 | MS (ESI) (M + H)+ |
|---|---|---|---|---|
| 151 | (phenyl-CH(OH)-CH(CH3)-) | CH3 | (3-(1-methyltetrazol-5-yl)phenyl) | |
| 152 | (phenyl-CH(OH)-CH(CH3)-) | CH3 | (3-(1-methyltetrazol-5-yl)-5-ethylphenyl) | |
| 153 | (phenyl-CH(OH)-CH(CH3)-) | CH3 | (3,4,5-trimethoxyphenyl) | |
| 154 | (indol-3-yl-CH2CH2-) | CH3 | (3-(1-methyltetrazol-5-yl)phenyl) | |

Utility

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966-974 (1988). In particular, the compound of the present invention have activity in inhibition of the migration of eosinophils in the aforementioned assays. As used herein, "activity" is intended to mean a compound demonstrating an IC50 of 10 μM or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at 1×10⁶ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 μl volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30-45 seconds. The filter is rinsed with distilled water for 7 minutes, rinsed once with water briefly, and allowed to dry. Migrated cells are enumerated by microscopy.

The utility of the compounds in accordance with the present invention as modulators of chemokine receptor activity may be demonstrated by methodology known in the art, such as the assays for CCR-1 ligand binding. In particular, the compound of the present invention have activity in binding to the CCR-1 receptor in the aforementioned assays. As used herein, "activity" is intended to mean a compound demonstrating an IC50 of 10 µM or lower in concentration when measured in the aforementioned assays. Such a result is indicative of the intrinsic activity of the compounds as modulators of chemokine receptor activity. A general binding protocol is described below.

A, Cells

CCR1 Expressing Cells a. THP-1 Cells

THP-1 cells are obtained from ATCC (Manassas, Va.) and cultured as a suspension in RPMI-1640 medium supplemented with 2 mM L-glutamine, penicillin/streptomycin, and 10% FBS. Cells are grown under 5% $CO_2$/95% air, 100% humidity at 37° C. and subcultured twice weekly at 1:5 and harvested at $1 \times 10^6$ cells/ml. THP-1 cells express CCR1 and can be used in CCR1 binding and functional assays.

b. CCR1-Transfected CHO Cells

Human CCR1 cDNA is purchased from ATCC and cloned into the pcDNA3 expression vector (Introgen, San Diego, Calif.). CCR1-pcDNA3 is introduced into CHO cells (ATCC) by electroporation and stable integrants are selected by growth in G418-containg media. High-expressing cell lines are identified by radioligand binding assays and then subsequently maintained in DMEM with 10% FBS and 200 µg/ml G418.

c. Isolated Human Monocytes

Monocytes are isolated from the peripheral blood of human healthy donors using magnetic bead separation. Briefly, following Ficoll gradient separation to isolate a mononuclear fraction, cells are washed with PBS and the red blood cells lysed using standard procedures. Remaining cells are labeled with anti-CD14 antibodies coupled to magnetic beads (Miltenyi Biotech, Auburn, Calif.). Labeled cells are passed through an AutoMACS (Miltenyi, Auburn, Calif.) and the positive fraction collected. Monocytes express CCR1 and can be used in CCR1 binding and functional assays.

B. Assays

Inhibition of CCR1 Ligand Binding

A. Whole Cell Binding

CCR1-expressing cells are centrifuged and resuspended in assay buffer (RPMI 1640, 20 mM HEPES pH 7.4, with 0.1% bovine serum albumin) to a concentration of $1.7 \times 10^6$ cells/mL. Compound is diluted in assay buffer and 0.05 mL are added to the assay plate. An equivalent volume of cell suspension is then added to give a final density of $2.5 \times 10^5$ THP-1 cells/well. 0.05 mL of $^{125}$I, labeled human MIP-1α (NEN/Perkin Elmer; Boston, Mass.) diluted in assay buffer to a final concentration of 40 pM, yielding 30,000 cpm per well, is added and the plates incubated for approximately 60 minutes at room temperature. Reactions are aspirated onto GF/B glass filters pre-soaked in 0.3% polyethyleneimine (PEI) solution, on a vacuum cell harvester (Packard Instruments; Meriden, Conn.). Scintillation fluid (50µl; Microscint 20, Packard Instruments) is added to each well, the plates sealed and radioactivity measured in a Top Count scintillation counter (Packard Instruments). Control wells contain either diluent only (for total binding) or excess MIP-1a (for non-specific binding). The percent inhibition of specific binding is calculated from duplicate wells. If a graded series of compound concentrations has been used, the percent inhibition is plotted against compound concentration using computer software (GraphPad Prism, San Diego, Calif.) and the $IC_{50}$ obtained.

B. Membrane Binding

The procedure is similar to that for whole cells, but utilizes membranes from CHO cells stably transfected with human CCR1 (Amersham, Piscataway, N.J.). To wells containing diluted compound, 0.05 mL of membrane are added to a final concentration of 950 µg/mL. $^{125}$I labeled MIP-1α is added at the same concentration as for whole cells and the plates incubated for approximately 60 minutes at room temperature. After incubation, the plates are washed with buffer (RPMI 1640, 20 mM HEPES with 0.1% bovine serum albumin and 0.4 M NaCl), aspirated and air-dried. The plates are counted in gamma counter (Packard Instruments).

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966-974 (1988). In particular, the compound of the present invention have activity in inhibition of the migration of eosinophils in the aforementioned assays. As used herein, "activity" is intended to mean a compound demonstrating an IC50 of 10 µM or lower in concentration when measured in the aforementioned assays. Such a result is indicative of the intrinsic activity of the compounds as modulators of chemokine receptor activity. A human eosinophil chemotaxis assay protocol is described below.

Chemotaxis Assay

THP-1 cells ($3 \times 10^7$) are loaded with Calcein-AM fluorescent dye (Molecular Probes; Eugene, Oreg.) in cell medium for 30 minutes at 37° C. and washed with prewarmed chemotaxis buffer (RPMI 1640 phenol red-free, with 0.1% bovine serum albumin). The assay is performed in a 96-well chemotaxis plate (BD Falcon Fluoroblok, Bedford, Mass.) in which each well contains upper and lower chambers separated by a polycarbonate, polyvinylpyrrolidone-coated filter containing pores of 8 micron diameter. Lower chambers are each loaded with 225 µL of buffer containing MIP-1α (i.e., 1-100 ng/mL) and compound. Top chambers are each loaded with 50 µL of buffer containing $5 \times 10^4$ cells. The plates are incubated for 30-60 minutes at 37° C. The chemotactic migration of cells through the filter is quantified either by determining the levels of fluorescence in the lower chamber, using a Cytofluor at an excitation wavelength of 485 nm and emission wavelength of 530 nm (PE Biosystems, Stafford, Tex.), or by directly counting the cells on the undersurface of the filter using a microscope.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 μm or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (*Trichuriasis, Enterobiasis, Ascariasis*, Hookworm, *Strongyloidiasis, Trichinosis, filariasis*); trematodes (flukes) (*Schistosomiasis, Clonorchiasis*), cestodes (tape worms) (*Echinococcosis, Taeniasis saginata, Cysticercosis*); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

It is desirable to find new compounds with improved pharmacological characteristics compared with known CCR-3 inhibitors. For example, it is desirable to find new compounds with improved CCR-3 inhibitory activity and selectivity for CCR-3 versus other G protein-coupled receptors (i.e. 5HT2A receptor). It is also desirable to find compounds with advantageous and improved characteristics in one or more of the following categories:

(a) pharmaceutical properties (i.e. solubility, permeability, amenability to sustained release formulations); (b) dosage requirements (e.g., lower dosages and/or once-daily dosing); (c) factors which decrease blood concentration peak-to-trough characteristics (i.e. clearance and/or volume of distribution); (d) factors that increase the concentration of active drug at the receptor (i.e. protein binding, volume of distribution); (e) factors that decrease the liability for clinical drug-drug interactions (cytochrome P450 enzyme inhibition or induction, such as CYP 2D6 inhibition, see GK Dresser, JD Spence, DG Bailey Clin. Pharmacokinet. 2000, 38, 41-57, which is hereby incorporated by reference); (f) factors that decrease the potential for adverse side-effects (i.e. pharmacological selectivity beyond G protein-coupled receptors, potential chemical or metabolic reactivity, limited CNS penetration) (g) factors that improve manufacturing costs or feasibility (i.e. difficulty of synthesis, number of chiral centers, chemical stability, ease of handling).

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

As will be appreciated by one of skill in the art, numerous modifications and variations of the present invention are possible in light of the above teachings. It is therefore to be understood that within the scope of the appended claims, the invention may be practiced otherwise than as specifically described herein.

What is claimed is:

1. A compound of formula (I):

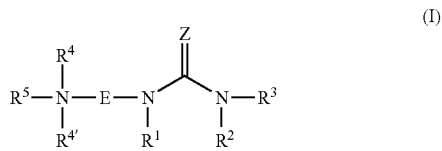

or stereoisomers or pharmaceutically acceptable salts thereof, wherein:

Z is selected from O and S;

E is —$(CH_2)$—$(CHR^9)$—$(CHR^{11})$—;

$R^1$ and $R^2$ are independently selected from H, $C_{1-8}$ alkyl, $C_{3-8}$ alkenyl, $C_{3-8}$ alkynyl, $(CH_2)_r C_{3-6}$ cycloalkyl, and a $(CH_2)_r$—$C_{3-10}$ carbocyclic residue substituted with 0-5 $R^a$;

$R^a$, at each occurrence, is selected from $C_{1-4}$ alkyl, $C_{3-8}$ alkenyl, $C_{3-8}$ alkynyl, $(CH_2)_r C_{3-6}$ cycloalkyl, Cl, Br, I, F, $(CF_2)_r CF_3$, $NO_2$, CN, $(CH_2)_r NR^b R^b$, $(CH_2)_r OH$, $(CH_2)_r OR^c$, $(CH_2)_r SH$, $(CH_2)_r SR^c$, $(CH_2)_r C(O)R^b$, $(CH_2)_r C(O)NR^b R^b$, $(CH_2)_r NR^b C(O)R^b$, $(CH_2)_r C(O)OR^b$, $(CH_2)_r OC(O)R^c$, $(CH_2)_r CH(=NR^b)NR^b R^b$, $(CH_2)_r NHC(=NR^b)NR^b R^b$, $(CH_2)_r S(O)_p R^c$, $(CH_2)_r S(O)_2 NR^b R^b$, $(CH_2)_r NR^b S(O)_2 R^c$, and $(CH_2)_r$phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

$R^3$ is selected from a $(CR^{3'}R^{3'})_r$—$C_{3-10}$ carbocyclic residue substituted with 0-5 $R^{15}$ and a $(CR^{3'}R^{3'})_r$-5-10 membered heterocyclic system containing 1-4 heteroatoms selected from N, O, and S, substituted with 0-3 $R^{15}$;

$R^{3'}$, at each occurrence, is selected from H, $C_{1-6}$ alkyl, $(CH_2)_r C_{3-6}$ cycloalkyl, and phenyl;

$R^4$ is selected from H, $C_{1-6}$ alkyl, $(CH_2)_r$—$C_{1-3}$ perfluoroalkyl, —C(O)—$C_{1-4}$ alkyl, —$SO_2$—$C_{1-14}$ alkyl, and a $(CH_2)_r$—$C_{3-10}$ carbocyclic residue substituted with 0-3 $R^{4c}$;

$R^{4'}$ is absent, taken with the nitrogen to which it is attached to form an N-oxide, or selected from $C_{1-8}$ alkyl, $C_{3-8}$ alkenyl, $C_{3-8}$ alkynyl, $(CH_2)_q C_{3-6}$ cycloalkyl, $(CH_2)_q C(O)R^{4b}$, $(CH_2)_q C(O)NR^{4a}R^{4a}$, $(CH_2)_q C(O)OR^{4b}$, and a $(CH_2)_r$—$C_{3-10}$ carbocyclic residue substituted with 0-3 $R^{4c}$;

$R^{4a}$, at each occurrence, is selected from H, $C_{1-6}$ alkyl, $(CH_2)_r C_{3-6}$ cycloalkyl, and phenyl;

$R^{4b}$, at each occurrence, is selected from $C_{1-6}$ alkyl, $C_{3-8}$ alkenyl, $(CH_2)_r C_{3-6}$ cycloalkyl, $C_{3-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, $(CH_2)_r OH$, $(CH_2)_r SC_{1-5}$ alkyl, $(CH_2)_r NR^{4a}R^{4a}$, and $(CH_2)_r$phenyl;

$R^5$ is selected from

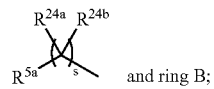

and ring B;

ring B is 1,2,3,4-tetrahydronaphthylenyl substituted with 0-3 $R^{16}$;

alternatively, ring B is selected from a $C_{3-10}$ carbocyclic residue substituted with 1-5 $R^{5a}$;

$R^{5a}$ is selected from a $(CR^{5'}R^{5'})_r$—$C_{3-10}$ carbocyclic residue substituted with 0-5 $R^{16}$, and a $(CR^{5'}R^{5'})_r$-5-10 membered heterocyclic residue containing 1-4 heteroatoms selected from N, O, and S, substituted with 0-3 $R^{16}$;

$R^{5'}$, at each occurrence, is selected from H, $C_{1-6}$ alkyl, $(CH_2)_r C_{3-6}$ cycloalkyl, and phenyl;

$R^9$, is selected from $C_{1-6}$ alkyl, $C_{2-8}$ alkenyl, $C_{2-8}$ alkynyl, F, Cl, Br, I, $NO_2$, CN, $(CH_2)_r OH$, $(CH_2)_r SH$, $(CH_2)_r OR^{9d}$, $(CH_2)_r SR^{9d}$, $(CH_2)_r NR^{9a}R^{9a}$, $(CH_2)_r C(O)OH$, $(CH_2)_r C(O)R^{9b}$, $(CH_2)_r C(O)NR^{9a}R^{9a}$, $(CH_2)_r NR^{9a}C(O)R^{9a}$, $(CH_2)_r NR^{9a}C(O)H$, $(CH_2)_r NR^{9a}C(O)NHR^{9a}$, $(CH_2)_r C(O)OR^{9b}$, $(CH_2)_r OC(O)R^{9b}$, $(CH_2)_r OC(O)NHR^{9a}$, $(CH_2)_r S(O)_p R^{9b}$, $(CH_2)_r S(O)_2 NR^{9a}R^{9a}$, $(CH_2)_r NR^{9a}S(O)_2 R^{9b}$, $C_{1-6}$ haloalkyl, a $(CH_2)_r$—$C_{3-10}$ carbocyclic residue substituted with 0-5 $R^{9c}$, and a $(CH_2)_r$-5-10 membered heterocyclic system containing 1-4 heteroatoms selected from N, O, and S, substituted with 0-3 $R^{9c}$;

$R^{9a}$, at each occurrence, is selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{9e}$, and a $(CH_2)_r$-5-10 membered heterocyclic system containing 1-4 heteroatoms selected from N, O, and S, substituted with 0-3 $R^{9e}$;

$R^{9b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0-2 $R^{9e}$, and a $(CH_2)_r$-5-6 membered heterocyclic system containing 1-4 heteroatoms selected from N, O, and S, substituted with 0-3 $R^{9e}$;

$R^{9c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{9f}R^{9f}$, $(CH_2)_r OH$, $(CH_2)_r OC_{1-4}$ alkyl, $(CH_2)_r SC_{1-4}$ alkyl, $(CH_2)_r C(O)OH$, $(CH_2)_r C(O)R^{9b}$, $(CH_2)_r C(O)NR^{9f}R^{9f}$, $(CH_2)_r NR^{9f}C(O)R^{9a}$, $(CH_2)_r C(O)OC_{1-4}$ alkyl, $(CH_2)_r OC(O)R^{9b}$, $(CH_2)_r C(=NR^{9f})NR^{9f}R^{9f}$, $(CH_2)_r S(O)_p R^{9b}$, $(CH_2)_r NHC(=NR^{9f})NR^{9f}R^{9f}$, $(CH_2)_r S(O)_2 NR^{9f}R^{9f}$, $(CH_2)_r NR^{9f}S(O)_2 R^{9b}$, and $(CH_2)_r$phenyl substituted with 0-3 $R^{9e}$;

$R^{9d}$, at each occurrence, is selected from $C_{1-6}$ alkyl, $C_{3-6}$ alkenyl, $C_{3-6}$ alkynyl, a $C_{3-10}$ carbocyclic residue substituted with 0-3 $R^{9c}$, and a 5-6 membered heterocyclic system containing 1-4 heteroatoms selected from the group consisting of N, O, and S substituted with 0-3 $R^{9c}$;

$R^{9e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{9f}R^{9f}$, and $(CH_2)_r$phenyl;

$R^{9f}$, at each occurrence, is selected from H, $C_{1-6}$ alkyl, and $C_{3-6}$ cycloalkyl;

$R^{11}$, is selected from $C_{1-6}$ alkyl, $C_{2-8}$ alkenyl, $C_{2-8}$ alkynyl, $(CR'R')_q OH$, $(CH_2)_q SH$, $(CR'R')_q OR^{11d}$, $(CH_2)_q SR^{11d}$, $(CR'R')_q NR^{11a}R^{11a}$, $(CH_2)_r C(O)OH$, $(CH_2)_r C(O)R^{11b}$, $(CH_2)_r C(O)NR^{11a}R^{11a}$, $(CH_2)_q NR^{11a}C(O)R^{11a}$, $(CH_2)_q OC(O)NR^{11a}R^{11a}$, $(CH_2)_q NR^{11a}C(O)OR^{11b}$, $(CH_2)_q NR^{11a}C(O)NHR^{11a}$, $(CH_2)_q C(O)OR^{11b}$, $(CH_2)_q OC(O)R^{11b}$, $(CH_2)_q S(O)_p R^{11b}$, $(CH_2)_q S(O)_2 NR^{11a}R^{11a}$, $(CH_2)_q NR^{11a}S(O)_2 R^{11b}$, $C_{1-6}$ haloalkyl, a $(CR'R')_r$—$C_{3-10}$ carbocyclic residue substituted with 0-5 $R^{11c}$, and a $(R'R')_r$-5-10 membered heterocyclic system containing 1-4 heteroatoms selected from N, O, and S, substituted with 0-3 $R^{11c}$;

$R^{11a}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{11e}$, and a $(CH_2)_r$-5-10 membered heterocyclic system containing 1-4 heteroatoms selected from N, O, and S, substituted with 0-3 $R^{11e}$;

alternatively, $R^{11a}$ and $R^{11a}$ along with the N to which they are attached, join to form a 5-6 membered heterocyclic system containing 1-2 heteroatoms selected from $NR^{11g}$, O, and S and optionally fused with a benzene ring or a 6-membered aromatic heterocycle;

$R^{11b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0-2 $R^{11e}$, and a $(CH_2)_r$-5-6 membered heterocyclic system containing 1-4 heteroatoms selected from N, O, and S, substituted with 0-3 $R^{11e}$;

$R^{11c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11f}R^{11f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{11b}$, $(CH_2)_rC(O)NR^{11f}R^{11f}$, $(CH_2)_rNR^{11f}C(O)R^{11a}$, $(CH_2)_rC(O)OC_{1-4}$ alkyl, $(CH_2)_rOC(O)R^{11b}$, $(CH_2)_rC(=NR^{11f})NR^{11f}R^{11f}$, $(CH_2)_rNHC(=NR^{11f})NR^{11f}R^{11f}$, $(CH_2)_rS(O)_pR^{11b}$, $(CH_2)_rS(O)_2NR^{11f}R^{11f}$, $(CH_2)_rNR^{11f}S(O)_2R^{11b}$, and $(CH_2)_r$phenyl substituted with 0-3 $R^{11e}$;

$R^{11d}$, at each occurrence, is selected from $C_{1-6}$ alkyl, $C_{3-6}$ alkenyl, $C_{3-6}$ alkynyl, and a $C_{3-10}$ carbocyclic residue substituted with 0-3 $R^{11c}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{11f}R^{11f}$, and $(CH_2)_r$phenyl, wherein the phenyl on the $(CH_2)_r$phenyl is substituted with 0-5 substituents selected from F, Cl, Br, I, $NO_2$, $C_{1-6}$alkyl, OH, and $NR^{11f}R^{11f}$;

$R^{11f}$, at each occurrence, is selected from H, $C_{1-6}$ alkyl, and $C_{3-6}$ cycloalkyl;

$R^{11g}$ is selected from H, $C_{1-6}$ alkyl, $C_{3-6}$ cycloalkyl, $(CH_2)_r$phenyl, $C(O)R^{11f}$, $C(O)OR^{11h}$, and $SO_2R^{11h}$;

$R^{11h}$, at each occurrence, is selected from $C_{1-6}$ alkyl, and $C_{3-6}$ cycloalkyl;

$R^{15}$, at each occurrence, is selected from $C_{1-8}$ alkyl, (CR'R')$_rC_{3-6}$ cycloalkyl, Cl, Br, I, F, $NO_2$, CN, (CR'R')$_r$$NR^{15a}R^{15a}$, (CR'R')$_r$OH, (CR'R')$_r$O(CHR')$_r$$R^{15d}$, (CR'R')$_r$SH, (CR'R')$_r$C(O)H, (CR'R')$_r$S(CHR')$_r$$R^{15d}$, (CR'R')$_r$C(O)OH, (CR'R')$_r$C(O) (CHR')$_r$$R^{15b}$, (CR'R')$_r$C(O)NR$^{15a}$R$^{15a}$, (CR'R')$_r$NR$^{15f}$C(O) (CHR')$_r$$R^{15b}$, (CR'R')$_r$OC(O)NR$^{15a}$R$^{15a}$, (CR'R')$_r$NR$^{15f}$C(O)O (CHR')$_r$$R^{15b}$, (CR'R')$_r$NR$^{15f}$C(O)NR$^{15f}$R$^{15f}$, (CR'R')$_r$C(O)O(CHR')$_r$$R^{15d}$, (CR'R')$_r$OC(O) (CHR')$_r$$R^{15b}$, (CR'R')$_r$C(=NR$^{15f}$)NR$^{15a}$R$^{15a}$, (CR'R')$_r$NHC(=NR$^{15f}$)NR$^{15f}$R$^{15f}$, (CR'R')$_r$S(O)$_p$(CHR')$_r$$R^{15b}$, (CR'R')$_r$S(O)$_2$NR$^{15a}$R$^{15a}$, (CR'R')$_r$NR$^{15f}$S(O)$_2$(CHR')$_r$$R^{15b}$, $C_{1-6}$ haloalkyl, $C_{2-8}$ alkenyl substituted with 0-3 R', $C_{2-8}$ alkynyl substituted with 0-3 R', (CR'R')$_r$phenyl substituted with 0-3 $R^{15e}$, and a $(CH_2)_r$-5-10 membered heterocyclic system containing 1-4 heteroatoms selected from N, O, and S, substituted with 0-3 $R^{15e}$;

R', at each occurrence, is independently selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{15e}$;

$R^{15a}$, at each occurrence, is selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{15e}$, and a $(CH_2)_r$-5-10 membered heterocyclic system containing 1-4 heteroatoms selected from N, O, and S, substituted with 0-2 $R^{15e}$;

alternatively, two $R^{15a}$, along with the N to which they are attached, join to form a 5-6 membered non-aromatic heterocyclic system containing 1-2 heteroatoms selected from $NR^{15g}$, O, and S and optionally fused with a benzene ring or a 6-membered aromatic heterocycle;

$R^{15b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0-3 $R^{15e}$, and $(CH_2)_r$-5-6 membered heterocyclic system containing 1-4 heteroatoms selected from N, O, and S, substituted with 0-2 $R^{15e}$;

$R^{15d}$, at each occurrence, is selected from $C_{3-8}$ alkenyl, $C_{3-8}$ alkynyl, methyl, $CF_3$, $C_{2-6}$ alkyl substituted with 0-3 $R^{15e}$, a $(CH_2)_r$—$C_{3-10}$ carbocyclic residue substituted with 0-3 $R^{15e}$, and a $(CH_2)_r$-5-6 membered heterocyclic system containing 1-4 heteroatoms selected from N, O, and S, substituted with 0-3 $R^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, and $(CH_2)_r$phenyl;

$R^{15f}$, at each occurrence, is selected from H, $C_{1-6}$ alkyl, $C_{3-6}$ cycloalkyl, and phenyl;

$R^{15g}$ is selected from H, $C_{1-6}$ alkyl, $C_{3-6}$ cycloalkyl, $(CH_2)_r$phenyl, $C(O)R^{15f}$, $C(O)OR^{15h}$, and $SO_2R^{15h}$;

$R^{15h}$, at each occurrence, is selected from $C_{1-5}$ alkyl, and $C_{3-6}$ cycloalkyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, (CHR')$_r$NR$^{16a}$R$^{16a}$, (CHR')$_r$OH, (CHR')$_r$O(CHR')$_r$$R^{16d}$, (CHR')$_r$SH, (CHR')$_r$C(O)H, (CHR')$_r$S(CHR')$_r$$R^{16d}$, (CHR')$_r$C(O)OH, (CHR')$_r$C(O) (CHR')$_r$$R^{16b}$, (CHR')$_r$C(O)NR$^{16a}$R$^{16a}$, (CHR')$_r$NR$^{16f}$C(O) (CHR')$_r$$R^{16b}$, (CHR')$_r$C(O)O(CHR')$_r$$R^{16d}$, (CHR')$_r$OC(O) (CHR')$_r$$R^{16b}$, (CHR')$_r$C(=NR$^{16f}$)NR$^{16a}$R$^{16a}$, (CHR')$_r$NHC(=NR$^{16f}$)NR$^{16f}$R$^{16f}$, (CHR')$_r$S(O)$_p$(CHR')$_r$$R^{16b}$, (CHR')$_r$S(O)$_2$NR$^{16a}$R$^{16a}$, (CHR')$_r$NR$^{16f}$S(O)$_2$(CHR')$_r$$R^{16b}$, $C_{1-6}$ haloalkyl, $C_{2-8}$ alkenyl substituted with 0-3 R', $C_{2-8}$ alkynyl substituted with 0-3 R', and (CHR')$_r$phenyl substituted with 0-3 $R^{16e}$;

$R^{16a}$, at each occurrence, is selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{16e}$, and a $(CH_2)_r$-5-10 membered heterocyclic system containing 1-4 heteroatoms selected from N, O, and S, substituted with 0-2 $R^{16e}$;

$R^{16b}$, at each occurrence, is selected from $C_{1-6}$ alkyl, $C_{3-8}$ alkenyl, $C_{3-8}$ alkynyl, a $(CH_2)_rC_{3-6}$ carbocyclic residue substituted with 0-3 $R^{16e}$, and a $(CH_2)_r$-5-6 membered heterocyclic system containing 1-4 heteroatoms selected from N, O, and S, substituted with 0-2 $R^{16e}$;

$R^{16d}$, at each occurrence, is selected from $C_{3-8}$ alkenyl, $C_{3-8}$ alkynyl, methyl, $CF_3$, $C_{2-6}$ alkyl substituted with 0-3 $R^{16e}$, a $(CH_2)_r$—$C_{3-10}$ carbocyclic residue substituted with 0-3 $R^{16e}$, and a $(CH_2)_r$-5-6 membered heterocyclic system containing 1-4 heteroatoms selected from N, O, and S, substituted with 0-3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is selected from H, $C_{1-5}$ alkyl, and $C_{3-6}$ cycloalkyl, and phenyl;

$R^{18}$ at each occurrence is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-15}$ alkyl, $(CH_2)_rS(O)C_{1-5}$ alkyl, $(CH_2)_rS(O)_2C_{1-5}$ alkyl, $(CH_2)_rS(O)_2N(R^{18a})R^{18b}$, $(CH_2)_rN(R^{18c})C(O)C_{1-5}$ alkyl $(CH_2)_rN(R^{18c})S(O)_2C_{1-5}$ alkyl, $(CH_2)_rC(O)N(R^{18a})R^{18b}$, $(CH_2)_rC(O)OC_{1-5}$ alkyl, $(CH_2)_rC(O)C_{1-5}$ alkyl, and $(CH_2)_rN(R^{18a})R^{18b}$;

$R^{18a}$, $R^{18b}$, and $R^{18c}$ at each occurrence are independently selected from H, $C_{1-6}$ alkyl, and $C_{3-6}$ cycloalkyl;

$R^{19}$ at each occurrence is independently selected from $C_{1-6}$ alkyl, $C_{3-6}$ cycloalkyl, and phenyl substituted with 0-3 $R^{18}$;

alternatively, $R^{18a}$ and $R^{18b}$ along with the nitrogen to which both are attached form a pyrrolidine, piperidine, piperazine or morpholine ring;

$R^{24a}$ and $R^{24b}$, at each occurrence, are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_r C(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_t OC(O)R^{19}$, $(CH_2)_rS(O)R^{19}$, $(CH_2)_rS(O)_2R^{19}$, $(CH_2)_rS(O)_2N(R^{18a})R^{18b}$, $(CH_2)_rN(R^{18c})S(O)_2R^{19}$, and $(CH_2)_r$phenyl substituted with 0-3 $R^{18}$;

t is selected from 0, 1, 2, 3, 4, and 5, with the proviso that when s is 1, then t can not be 0;

s is selected from 1, 2, 3, 4, and 5;

r is selected from 0, 1, 2, 3, 4, and 5;

q is selected from 1, 2, 3, 4, and 5; and p is selected from 0, 1, and 2.

2. The compound of claim 1, wherein:

$R^{4'}$ is absent, taken with the nitrogen to which it is attached to form an N-oxide, or selected from $C_{1-8}$ alkyl, $(CH_2)_rC_{3-6}$ cycloalkyl, and $(CH_2)_r$-phenyl substituted with 0-3 $R^{4c}$;

$R^1$ and $R^2$ are independently selected from H and $C_{1-4}$ alkyl;

$R^{24a}$ and $R^{24b}$, at each occurrence, are independently selected from H, $C_{1-6}$ alkyl, $C_{2-8}$ alkenyl, $C_{2-8}$ alkynyl, $(CH_2)_rC_{3-6}$ cycloalkyl, $(CF_2)_rCF_3$, $(CH_2)_rN(R^{18a})R^{18b}$, $(CH_2)_rOH$, $(CH_2)_rOR^{19}$, $(CH_2)_rSH$, $(CH_2)_rSR^{19}$, $(CH_2)_r C(O)OH$, $(CH_2)_rC(O)R^{19}$, $(CH_2)_rC(O)N(R^{18a})R^{18b}$, $(CH_2)_rN(R^{18c})C(O)R^{19}$, $(CH_2)_rC(O)OR^{19}$, $(CH_2)_r OC(O)R^{19}$, and $(CH_2)_r$phenyl substituted with 0-3 $R^{18}$;

q is selected from 1, 2, and 3; and r is selected from 0, 1, 2, and 3.

3. The compound of claim 2, wherein:

$R^3$ is selected from a $(CR^{3'}H)_r$-carbocyclic residue substituted with 0-5 $R^{15}$, wherein the carbocyclic residue is selected from phenyl, $C_{3-6}$ cycloalkyl, naphthyl, and adamantyl; and a $(CR^{3'}H)_r$-heterocyclic system substituted with 0-3 $R^{15}$, wherein the heterocyclic system is selected from pyridinyl, thiophenyl, furanyl, indazolyl, benzothiazolyl, benzo[1,3]dioxolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{5a}$ is selected from $(CR^{5'}H)_r$-phenyl substituted with 0-5 $R^{16}$; and a $(CR^{5'}H)_r$-heterocyclic system substituted with 0-3 $R^{16}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

4. The compound of claim 3, wherein $R^{18}$ at each occurrence is independently selected from $C_{1-6}$ alkyl, $C_{3-6}$ cycloalkyl, Cl, F, Br, I, CN, $NO_2$, $(CF_2)_rCF_3$, $OC_{1-5}$ alkyl, $(CH_2)_rOH$, $SC_{1-5}$ alkyl, $N(R^{18c})C(O)C_{1-5}$ alkyl, $C(O)N(R^{18a})R^{18b}$, $C(O)OC_{1-5}$ alkyl, $C(O)C_{1-5}$ alkyl, and $N(R^{18a})R^{18b}$;

$R^{18a}$, $R^{18b}$, and $R^{18c}$ at each occurrence are independently selected from H, methyl, ethyl, propyl, i-propyl, butyl, i-butyl, t-butyl, cyclopropyl, cyclopentyl, and cyclohexyl;

$R^{19}$ at each occurrence is independently selected from methyl, ethyl, propyl, i-propyl, butyl, i-butyl, t-butyl, cyclopropyl, cyclopentyl, and cyclohexyl, and phenyl substituted with 0-3 $R^{18}$;

alternatively, $R^{18a}$ and $R^{18b}$ along with the nitrogen to which both are attached form a pyrrolidine, piperidine, piperazine or morpholine ring.

5. The compound of claim 4, wherein:

$R^5$ is selected from

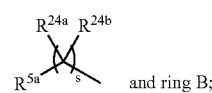

and ring B;

ring B is 1,2,3,4-tetrahydronaphthylenyl substituted with 0-3 $R^{16}$;

alternatively, ring B is selected from a $C_{3-10}$ carbocyclic residue substituted with 1-5 $R^{5a}$, wherein the carbocyclic residue is selected from phenyl and cyclohexyl r is selected from 0, 1, and 2.

6. The compound of claim 5, wherein:

$R^3$ is a $C_{3-10}$ carbocyclic residue substituted with 0-3 $R^{15}$, wherein the carbocyclic residue is selected from cyclopropyl, cyclopentyl, cyclohexyl, phenyl, naphthyl and adamantyl, and a $(CR^{3'}H)_r$-heterocyclic system substituted with 0-3 $R^{15}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{11}$, is selected from $C_{1-6}$ alkyl, $(CH_2)_qOH$, $(CH_2)_qSH$, $(CH_2)_qOR^{11d}$, $(CH_2)_qSR^{11d}$, $(CH_2)_qNR^{11a}R^{11a}$, $(CH_2)_rC(O)R^{11b}$, $(CH_2)_rC(O)NR^{11a}R^{11a}$, $(CH_2)_qNR^{11a}C(O)R^{11a}$, $(CH_2)_qOC(O)NR^{11a}R^{11a}$, $(CH_2)_qNR^{11a}C(O)OR^{11b}$, $(CH_2)_qNR^{11a}C(O)NHR^{11a}$, $(CH_2)_rC(O)OR^{11b}$, $(CH_2)_qOC(O)R^{11b}$, $C_{1-6}$ haloalkyl, a $(CH_2)_r$—$C_{3-10}$ carbocyclic residue substituted with 0-5 $R^{11c}$, and a $(CH_2)_r$-5-10 membered heterocyclic system containing 1-4 heteroatoms selected from N, O, and S, substituted with 0-3 $R^{11c}$;

$R^{11a}$, at each occurrence, is selected from H, methyl, ethyl, propyl, i-propyl, butyl, pentyl, hexyl, a $(CH_2)_r$—$C_{3-10}$ carbocyclic residue substituted with 0-5 $R^{11e}$, wherein the carbocyclic residue is selected from cyclopropyl, cyclopentyl, cyclohexyl, and phenyl;

$R^{11b}$, at each occurrence, is selected from methyl, ethyl, propyl, i-propyl, butyl, pentyl, hexyl, a $(CH_2)_r$—$C_{3-6}$ carbocyclic residue substituted with 0-2 $R^{11e}$, wherein the carbocyclic residue is selected from cyclopropyl, cyclopentyl, cyclohexyl, and phenyl;

$R^{11d}$, at each occurrence, is selected from methyl, ethyl, propyl, i-propyl, butyl, pentyl, hexyl, and a $C_{3-10}$ carbocyclic residue substituted with 0-3 $R^{11c}$ wherein the carbocyclic residue is selected from cyclopropyl, cyclopentyl, cyclohexyl, and phenyl;

$R^{11e}$, at each occurrence, is selected from methyl, ethyl, propyl, i-propyl, butyl, pentyl, hexyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{11f}R^{11f}$, and $(CH_2)_r$phenyl, wherein the phenyl on the $(CH_2)_r$phenyl is substituted with 0-5 substituents selected from F, Cl, Br, I, $NO_2$, $C_{1-6}$alkyl, OH, and $NR^{11f}R^{11f}$;

$R^{15}$, at each occurrence, is selected from $C_{1-8}$ alkyl, $(CH_2)_rC_{3-6}$ cycloalkyl, $CF_3$, Cl, Br, I, F, $(CH_2)_rNR^{15a}R^{15a}$, $NO_2$, CN, OH, $(CH_2)_rOR^{15d}$, $(CH_2)_rC(O)R^{15b}$, $(CH_2)_rC(O)NR^{15a}R^{15a}$, $(CH_2)_rNR^{15f}C(O)R^{15b}$, $(CH_2)_rOC(O)NR^{15a}R^{15a}$, $(CH_2)_rNR^{15f}C(O)OR^{15b}$, $(CH_2)_rS(O)_pR^{15b}$, $(CH_2)_rS(O)_2NR^{15a}R^{15a}$, $(CH_2)_rNR^{15f}S(O)_2R^{15b}$, $C_{1-6}$ haloalkyl, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$;

$R^{15a}$, at each occurrence, are selected from H, $C_{1-6}$ alkyl, $C_{3-6}$ cycloalkyl, and $(CH_2)_r$phenyl substituted with 0-3 $R^{15e}$;

alternatively, $R^{15a}$, along with the N to which they are attached, join to form a 5-6 membered heterocyclic system containing 1-2 heteroatoms selected from $NR^{15g}$, O, and S and optionally fused with a benzene ring or a 6-membered aromatic heterocycle;

$R^{15b}$, at each occurrence, is selected from H, $C_{1-6}$ alkyl, $C_{3-6}$ cycloalkyl, and $(CH_2)_r$phenyl substituted with 0-3 $R^{15e}$;

$R^{15d}$, at each occurrence, is selected from $C_{1-6}$ alkyl, $CF_3$, and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl.

7. The compound of claim 6, wherein:

$R^1$ is H;

$R^2$ is H;

$R^3$ is a $C_{3-10}$ carbocyclic residue substituted with 0-3 $R^{15}$, wherein the carbocyclic residue is phenyl, and a $(CR^{3'}H)_r$-heterocyclic system substituted with 0-3 $R^{15}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{5a}$ is selected from a $(CH_2)_r$—$C_{3-10}$ carbocyclic residue substituted with 1-5 $R^{16}$ and a heterocyclic system substituted with 0-3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

8. A compound of formula (I):

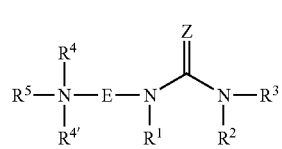

(I)

or stereoisomers or pharmaceutically acceptable salts thereof, wherein:

Z is selected from O and S;

E is selected from

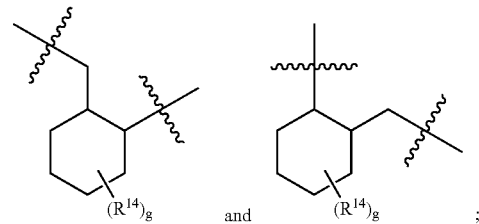

$R^1$ and $R^2$ are independently selected from H, $C_{1-8}$ alkyl, $C_{3-8}$ alkenyl, $C_{3-8}$ alkynyl, $(CH_2)_rC_{3-6}$ cycloalkyl, and a $(CH_2)_r$—$C_{3-10}$ carbocyclic residue substituted with 0-5 $R^a$;

$R^a$, at each occurrence, is selected from $C_{1-4}$ alkyl, $C_{3-8}$ alkenyl, $C_{3-8}$ alkynyl, $(CH_2)_rC_{3-6}$ cycloalkyl, Cl, Br, I, F, $(CF_2)_rCF_3$, $NO_2$, CN, $(CH_2)_rNR^bR^b$, $(CH_2)_rOH$, $(CH_2)_rOR^c$, $(CH_2)_rSH$, $(CH_2)_rSR^c$, $(CH_2)_rC(O)R^b$, $(CH_2)_rC(O)NR^bR^b$, $(CH_2)_rNR^bC(O)R^b$, $(CH_2)_rC(O)OR^b$, $(CH_2)_rOC(O)R^c$, $(CH_2)_rCH(=NR^b)NR^bR^b$, $(CH_2)_rNHC(=NR^b)NR^bR^b$, $(CH_2)_rS(O)_pR^c$, $(CH_2)_rS(O)_2NR^bR^b$, $(CH_2)_rNR^bS(O)_2R^c$, and $(CH_2)_r$phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

$R^3$ is selected from a $(CR^{3'}R^{3'})_r$—$C_{3-10}$ carbocyclic residue substituted with 0-5 $R^{15}$ and a $(CR^{3'}R^{3'})_r$-5-10 membered heterocyclic system containing 1-4 heteroatoms selected from N, O, and S, substituted with 0-3 $R^{15}$;

$R^{3'}$, at each occurrence, is selected from H, $C_{1-6}$ alkyl, $(CH_2)_rC_{3-6}$ cycloalkyl, and phenyl;

$R^4$ is selected from H, $C_{1-6}$ alkyl, $(CH_2)_r$—$C_{1-3}$ perfluoroalkyl, —C(O)—$C_{1-4}$ alkyl, —$SO_2$—$C_{1-4}$ alkyl, and a $(CH_2)_r$—$C_{3-10}$ carbocyclic residue substituted with 0-3 $R^{4c}$;

$R^{4'}$ is absent, taken with the nitrogen to which it is attached to form an N-oxide, or selected from $C_{1-8}$ alkyl, $C_{3-8}$ alkenyl, $C_{3-8}$ alkynyl, $(CH_2)_rC_{3-6}$ cycloalkyl, $(CH_2)_qC(O)R^{4b}$, $(CH_2)_qC(O)NR^{4a}R^{4a}$, $(CH_2)_qC(O)OR^{4b}$, and a $(CH_2)_r$—$C_{3-10}$ carbocyclic residue substituted with 0-3 $R^{4c}$;

$R^{4a}$, at each occurrence, is selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{3-8}$ alkenyl, $(CH_2)_rC_{3-6}$ cycloalkyl, $C_{3-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$ SC$_{1-5}$ alkyl, (CH$_2$)$_r$NR$^{4a}$R$^{4a}$, and (CH$_2$)$_r$phenyl;

R$^5$ is selected from

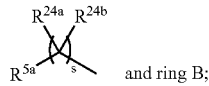

and ring B;

ring B is 1,2,3,4-tetrahydronaphthylenyl substituted with 0-3 R$^{16}$;

alternatively, ring B is selected from a C$_{3-10}$ carbocyclic residue substituted with 1-5 R$^{5a}$;

R$^{5a}$ is selected from a (CH$_2$)$_r$—C$_{3-10}$ carbocyclic residue substituted with 0-5 R$^{16}$, and a (CH$_2$)$_r$-5-10 membered heterocyclic residue containing 1-4 heteroatoms selected from N, O, and S, substituted with 0-3 R$^{16}$;

R$^{14}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{14a}$R$^{14a}$, (CHR')$_r$OH, (CHR')$_r$O(CHR')$_r$R$^{14d}$, (CHR')$_r$SH, (CHR')$_r$C(O)H, (CHR')$_r$S(CHR')$_r$R$^{14d}$, (CHR')$_r$C(O)OH, (CHR')$_r$C(O) (CHR')$_r$R$^{14b}$, (CHR')$_r$C(O)NR$^{14a}$R$^{14a}$, (CHR')$_r$NR$^{14f}$C(O)(CHR')$_r$R$^{14b}$, (CHR')$_r$C(O)O(CHR')$_r$R$^{14d}$, (CHR')$_r$OC(O) (CHR')$_r$R$^{14b}$, (CHR')$_r$C(=NR$^{14f}$)NR$^{14a}$R$^{14a}$, (CHR')$_r$NHC(=NR$^{14f}$)NR$^{14f}$R$^{14f}$, (CHR')$_r$S(O)$_p$(CHR')$_r$R$^{14b}$, (CHR')$_r$S(O)$_2$NR$^{14a}$R$^{14a}$, (CHR')$_r$NR$^{14f}$S(O)$_2$(CHR')$_r$R$^{14b}$, C$_{1-6}$ haloalkyl, C$_{2-8}$ alkenyl substituted with 0-3 R', C$_{2-8}$ alkynyl substituted with 0-3 R', (CHR')$_r$phenyl substituted with 0-3 R$^{14e}$, and a (CH$_2$)$_r$-5-10 membered heterocyclic system containing 1-4 heteroatoms selected from N, O, and S, substituted with 0-2 R$^{14e}$, or two R$^{14}$ substituents on adjacent atoms on ring A form to join a 5-6 membered heterocyclic system containing 1-3 heteroatoms selected from N, O, and S substituted with 0-2 R$^{14e}$;

R$^{14a}$, at each occurrence, is selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0-5 R$^{14e}$, and a (CH$_2$)$_r$-5-10 membered heterocyclic system containing 1-4 heteroatoms selected from N, O, and S, substituted with 0-2 R$^{14e}$;

R$^{14b}$, at each occurrence, is selected from C$_{1-6}$ alkyl, C$_{3-8}$ alkenyl, C$_{3-8}$ alkynyl, a (CH$_2$)$_r$—C$_{3-6}$ carbocyclic residue substituted with 0-3 R$^{14e}$, and (CH$_2$)$_r$-5-6 membered heterocyclic system containing 1-4 heteroatoms selected from N, O, and S, substituted with 0-2 R$^{14e}$;

R$^{14d}$, at each occurrence, is selected from C$_{3-8}$ alkenyl, C$_{3-8}$ alkynyl, C$_{1-6}$ alkyl substituted with 0-3 R$^{14e}$, a (CH$_2$)$_r$—C$_{3-10}$ carbocyclic residue substituted with 0-3 R$^{14e}$, and a (CH$_2$)$_r$-5-6 membered heterocyclic system containing 1-4 heteroatoms selected from N, O, and S, substituted with 0-3 R$^{14e}$;

R$^{14e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{14f}$R$^{14f}$, and (CH$_2$)$_r$phenyl;

R$^{14f}$, at each occurrence, is selected from H, C$_{1-6}$ alkyl, C$_{3-6}$ cycloalkyl, and phenyl;

R$^{15}$, at each occurrence, is selected from C$_{1-8}$ alkyl, (CR'R')$_r$C$_{3-6}$ cycloalkyl, Cl, Br, I, F, NO$_2$, CN, (CR'R')$_r$NR$^{15a}$R$^{15a}$, (CR'R')$_r$OH, (CR'R')$_r$O(CHR')$_r$R$^{15d}$, (CR'R')$_r$SH, (CHR')$_r$C(O)H, (CR'R')$_r$S(CHR')$_r$R$^{15d}$, (CR'R')$_r$C(O)OH, (CR'R')$_r$C(O) (CHR')$_r$R$^{15b}$, (CR'R')$_r$C(O)NR$^{15a}$R$^{15a}$, (CR'R')$_r$NR$^{15f}$C(O) (CHR')$_r$R$^{15b}$, (CR'R')$_r$OC(O)NR$^{15a}$R$^{15a}$, (CR'R')$_r$NR$^{15f}$C(O)O(CHR')$_r$R$^{15b}$, (CR'R')$_r$NR$^{15f}$C(O)NR$^{15f}$R$^{15f}$, (CR'R')$_r$C(O)O(CHR')$_r$R$^{15d}$, (CR'R')$_r$OC(O) (CHR')$_r$R$^{15b}$, (CR'R')$_r$C(=NR$^{15f}$)NR$^{15a}$R$^{15a}$, (CR'R')$_r$NHC(=NR$^{15f}$)NR$^{15f}$R$^{15f}$, (CR'R')$_r$S(O)$_p$(CHR')$_r$R$^{15b}$, (CR'R')$_r$S(O)$_2$NR$^{15a}$R$^{15a}$, (CR'R')$_r$NR$^{15f}$S(O)$_2$(CHR')$_r$R$^{15b}$, C$_{1-6}$ haloalkyl, C$_{2-8}$ alkenyl substituted with 0-3 R', C$_{2-8}$ alkynyl substituted with 0-3 R', (CR'R')$_r$phenyl substituted with 0-3 R$^{15e}$, and a (CH$_2$)$_r$-5-10 membered heterocyclic system containing 1-4 heteroatoms selected from N, O, and S, substituted with 0-2 R$^{15e}$;

R', at each occurrence, is independently selected from H, C$_{1-6}$ alkyl, C$_{2-8}$ alkenyl, C$_{2-8}$ alkynyl, (CH$_2$)$_r$C$_{3-6}$ cycloalkyl, and (CH$_2$)$_r$phenyl substituted with R$^{15e}$;

R$^{15a}$, at each occurrence, is selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0-5 R$^{15e}$, and a (CH$_2$)$_r$-5-10 membered heterocyclic system containing 1-4 heteroatoms selected from N, O, and S, substituted with 0-2 R$^{15e}$;

alternatively, two R$^{15a}$, along with the N to which they are attached, join to form a 5-6 membered non-aromatic heterocyclic system containing 1-2 heteroatoms selected from NR$^{15g}$, O, and S and optionally fused with a benzene ring or a 6-membered aromatic heterocycle;

R$^{15b}$, at each occurrence, is selected from C$_{1-6}$ alkyl, C$_{3-8}$ alkenyl, C$_{3-8}$ alkynyl, a (CH$_2$)$_r$—C$_{3-6}$ carbocyclic residue substituted with 0-3 R$^{15e}$, and (CH$_2$)$_r$-5-6 membered heterocyclic system containing 1-4 heteroatoms selected from N, O, and S, substituted with 0-2 R$^{15e}$;

R$^{15d}$, at each occurrence, is selected from C$_{3-8}$ alkenyl, C$_{3-8}$ alkynyl, methyl, CF$_3$, C$_{2-6}$ alkyl substituted with 0-3 R$^{15e}$, a (CH$_2$)$_r$—C$_{3-10}$ carbocyclic residue substituted with 0-3 R$^{15e}$, and a (CH$_2$)$_r$5-6 membered heterocyclic system containing 1-4 heteroatoms selected from N, O, and S, substituted with 0-3 R$^{15e}$;

R$^{15e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{15f}$R$^{15f}$, and (CH$_2$)$_r$phenyl;

R$^{15f}$, at each occurrence, is selected from H, C$_{1-6}$ alkyl, C$_{3-6}$ cycloalkyl, and phenyl;

R$^{15g}$ is selected from H, C$_{1-6}$ alkyl, C$_{3-6}$ cycloalkyl, (CH$_2$)$_r$phenyl, C(O)R$^{15f}$, C(O)OR$^{15h}$, and SO$_2$R$^{15h}$;

R$^{15h}$, at each occurrence, is selected from C$_{1-5}$ alkyl, and C$_{3-6}$ cycloalkyl;

R$^{16}$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{16a}$R$^{16a}$, (CHR')$_r$OH, (CHR')$_r$O(CHR')$_r$R$^{16d}$, (CHR')$_r$SH, (CHR')$_r$C(O)H, (CHR')$_r$S(CHR')$_r$R$^{16d}$, (CHR')$_r$C(O)OH, (CHR')$_r$C(O) (CHR')$_r$R$^{16b}$, (CHR')$_r$C(O)NR$^{16a}$R$^{16a}$, (CHR')$_r$NR$^{16f}$C(O)(CHR')$_r$R$^{16b}$, (CHR')$_r$C(O)O(CHR')$_r$R$^{16d}$, (CHR')$_r$OC(O) (CHR')$_r$R$^{16b}$, (CHR')$_r$C(=NR$^{16f}$)NR$^{16a}$R$^{16a}$, (CHR')$_r$NHC(=NR$^{16f}$)NR$^{16f}$R$^{16f}$, (CHR')$_r$S(O)$_p$(CHR')$_r$R$^{16b}$, (CHR')$_r$S(O)$_2$NR$^{16a}$R$^{16a}$, (CHR')$_r$NR$^{16f}$S(O)$_2$ (CHR')$_r$R$^{16b}$, C$_{1-6}$ haloalkyl, C$_{2-8}$ alkenyl substituted with 0-3 R', C$_{2-8}$ alkynyl substituted with 0-3 R', and (CHR')$_r$phenyl substituted with 0-3 R$^{16e}$;

R$^{16a}$, at each occurrence, is selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0-5 R$^{16e}$, and a (CH$_2$)$_r$-5-10 membered heterocyclic system containing 1-4 heteroatoms selected from N, O, and S, substituted with 0-2 $R^{16e}$;

$R^{16b}$, at each occurrence, is selected from $C_{1-6}$ alkyl, $C_{3-8}$ alkenyl, $C_{3-8}$ alkynyl, a $(CH_2)_r C_{3-6}$ carbocyclic residue substituted with 0-3 $R^{16e}$, and a $(CH_2)_r$-5-6 membered heterocyclic system containing 1-4 heteroatoms selected from N, O, and S, substituted with 0-2 $R^{16e}$;

$R^{16d}$, at each occurrence, is selected from $C_{3-8}$ alkenyl, $C_{3-8}$ alkynyl, methyl, $CF_3$, $C_{2-6}$ alkyl substituted with 0-3 $R^{16e}$, a $(CH_2)_r$—$C_{3-10}$ carbocyclic residue substituted with 0-3 $R^{16e}$, and a $(CH_2)_r$-5-6 membered heterocyclic system containing 1-4 heteroatoms selected from N, O, and S, substituted with 0-3 $R^{16e}$;

$R^{16e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{16f} R^{16f}$, and $(CH_2)_r$phenyl;

$R^{16f}$, at each occurrence, is selected from H, $C_{1-5}$ alkyl, and $C_{3-6}$ cycloalkyl, and phenyl;

$R^{18}$ at each occurrence is independently selected from $C_{1-6}$ alkyl, $C_{3-6}$ cycloalkyl, Cl, F, Br, I, CN, $NO_2$, $(CF_2)_r CF_3$, $(CH_2)_r OC_{1-5}$ alkyl, $(CH_2)_r OH$, $(CH_2)_r SC_{1-5}$ alkyl, $(CH_2)_r S(O) C_{1-5}$ alkyl, $(CH_2)_r S(O)_2 C_{1-5}$ alkyl, $(CH_2)_r S(O)_2 N(R^{18a})R^{18b}$, $(CH_2)_r N(R^{18c})C(O)C_{1-5}$ alkyl $(CH_2)_r N(R^{18c})S(O)_2 C_{1-5}$ alkyl, $(CH_2)_r C(O)N(R^{18a})R^{18b}$, $(CH_2)_r C(O)OC_{1-5}$ alkyl, $(CH_2)_r C(O)C_{1-5}$ alkyl, and $(CH_2)_r N(R^{18a})R^{18b}$;

$R^{18a}$, $R^{18b}$, and $R^{18c}$ at each occurrence are independently selected from H, $C_{1-6}$ alkyl, and $C_{3-6}$ cycloalkyl;

$R^{19}$ at each occurrence is independently selected from $C_{1-6}$ alkyl, $C_{3-6}$ cycloalkyl, and phenyl substituted with 0-3 $R^{18}$;

alternatively, $R^{18a}$ and $R^{18b}$ along with the nitrogen to which both are attached form a pyrrolidine, piperidine, piperazine or morpholine ring;

$R^{24a}$ and $R^{24b}$, at each occurrence, are independently selected from H, $C_{1-6}$ alkyl, $C_{2-8}$ alkenyl, $C_{2-8}$ alkynyl, $(CH_2)_r C_{3-6}$ cycloalkyl, $(CF_2)_r CF_3$, $(CH_2)_r N(R^{18a})R^{18b}$, $(CH_2)_t OH$, $(CH_2)_t OR^{19}$, $(CH_2)_t SH$, $(CH_2)_t SR^{19}$, $(CH_2)_r C(O)OH$, $(CH_2)_r C(O)R^{19}$, $(CH_2)_r C(O)N(R^{18a})R^{18b}$, $(CH_2)_r N(R^{18c})C(O)R^{19}$, $(CH_2)_r C(O)OR^{19}$, $(CH_2)_t OC(O)R^{19}$, $(CH_2)_r S(O)R^{19}$, $(CH_2)_r S(O)_2 R^{19}$, $(CH_2)_r S(O)_2 N(R^{18a})R^{18b}$, $(CH_2)_r N(R^{18c})S(O)_2 R^{19}$, and $(CH_2)_r$phenyl substituted with 0-3 $R^{18}$;

g is selected from 0, 1, 2, 3, 4, and 5;
t is selected from 0, 1, 2, 3, 4, and 5, with the proviso that when s is 1, then t can not be 0;
r is selected from 0, 1, 2, 3, 4, and 5;
q is selected from 1, 2, 3, 4, and 5; and
p is selected from 0, 1, and 2.

9. The compound of claim 8, wherein:
$R^{4'}$ is absent, taken with the nitrogen to which it is attached to form an N-oxide, or selected from $C_{1-8}$ alkyl, $(CH_2)_r C_{3-6}$ cycloalkyl, and $(CH_2)_r$-phenyl substituted with 0-3 $R^{4c}$;

$R^1$ and $R^2$ are independently selected from H and $C_{1-4}$ alkyl;

$R^{24a}$ and $R^{24b}$, at each occurrence, are independently selected from H, $C_{1-6}$ alkyl, $C_{2-8}$ alkenyl, $C_{2-8}$ alkynyl, $(CH_2)_r C_{3-6}$ cycloalkyl, $(CF_2)_r CF_3$, $(CH_2)_r N(R^{18a})R^{18b}$, $(CH_2)_t OH$, $(CH_2)_t OR^{19}$, $(CH_2)_t SH$, $(CH_2)_t SR^{19}$, $(CH_2)_r C(O)OH$, $(CH_2)_r C(O)R^{19}$, $(CH_2)_r C(O)N(R^{18a})R^{18b}$, $(CH_2)_r N(R^{18c})C(O)R^{19}$, $(CH_2)_r C(O)OR^{19}$, $(CH_2)_t OC(O)R^{19}$, and $(CH_2)_r$phenyl substituted with 0-3 $R^{18}$;

q is selected from 1, 2, and 3; and
r is selected from 0, 1, 2, and 3.

10. The compound of claim 9, wherein:
$R^3$ is selected from a $(CR^{3'}H)_r$-carbocyclic residue substituted with 0-5 $R^{15}$, wherein the carbocyclic residue is selected from phenyl, $C_{3-6}$ cycloalkyl, naphthyl, and adamantyl; and a $(CR^{3'}H)_r$-heterocyclic system substituted with 0-3 $R^{15}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{5a}$ is selected from $(CR^{5'}H)_r$-phenyl substituted with 0-5 $R^{16}$; and a $(CR^{5'}H)_r$-heterocyclic system substituted with 0-3 $R^{16}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

11. The compound of claim 10, wherein
$R^{18}$ at each occurrence is independently selected from $C_{1-6}$ alkyl, $C_{3-6}$ cycloalkyl, Cl, F, Br, I, CN, $NO_2$, $(CF_2)_r CF_3$, $OC_{1-5}$ alkyl, $(CH_2)_r OH$, $SC_{1-5}$ alkyl, $N(R^{18c})C(O)C_{1-5}$ alkyl, $C(O)N(R^{18a})R^{18b}$, $C(O)OC_{1-5}$ alkyl, $C(O)C_{1-5}$ alkyl, and $N(R^{18a})R^{18b}$;

$R^{18a}$, $R^{18b}$, and $R^{18c}$ at each occurrence are independently selected from H, methyl, ethyl, propyl, i-propyl, butyl, i-butyl, t-butyl, cyclopropyl, cyclopentyl, and cyclohexyl;

$R^{19}$ at each occurrence is independently selected from methyl, ethyl, propyl, i-propyl, butyl, i-butyl, t-butyl, cyclopropyl, cyclopentyl, and cyclohexyl, and phenyl substituted with 0-3 $R^{18}$;

alternatively, $R^{18a}$ and $R^{18b}$ along with the nitrogen to which both are attached form a pyrrolidine, piperidine, piperazine or morpholine ring.

12. The compound of claim 11, wherein:
$R^5$ is selected from

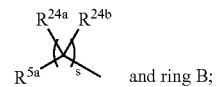

and ring B;

ring B is 1,2,3,4-tetrahydronaphthylenyl substituted with 0-3 $R^{16}$;

alternatively, ring B is selected from a $C_{3-10}$ carbocyclic residue substituted with 1-5 $R^{5a}$, wherein the carbocyclic residue is selected from phenyl and cyclohexyl;

r is selected from 0, 1, and 2.

13. The compound of claims 12, wherein:
$R^3$ is a $C_{3-10}$ carbocyclic residue substituted with 0-3 $R^{15}$, wherein the carbocyclic residue is selected from cyclopropyl, cyclopentyl, cyclohexyl, phenyl, naphthyl and adamantyl, and a $(CR^{3'}H)_r$-heterocyclic system substituted with 0-3 $R^{15}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is selected from $C_{1-8}$ alkyl, $(CH_2)_r C_{3-6}$ cycloalkyl, $CF_3$, Cl, Br, I, F, $(CH_2)_r$ $NR^{15a}R^{15a}$, $NO_2$, CN, OH, $(CH_2)_r OR^{15d}$, $(CH_2)_r C(O)R^{15b}$, $(CH_2)_r C(O)NR^{15a}R^{15a}$, $(CH_2)_r NR^{15f}C(O)R^{15b}$, $(CH_2)_r OC(O)NR^{15a}R^{15a}$, $(CH_2)_r NR^{15f}C(O)OR^{15b}$, $(CH_2)_r S(O)_p R^{15b}$, $(CH_2)_r S(O)_2 NR^{15a}R^{15a}$, $(CH_2)_r NR^{15f}S(O)_2 R^{15b}$, $C_{1-6}$ haloalkyl, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$;

$R^{15a}$, at each occurrence, are selected from H, $C_{1-6}$ alkyl, $C_{3-6}$ cycloalkyl, and $(CH_2)_r$phenyl substituted with 0-3 $R^{15e}$;

alternatively, $R^{15a}$, along with the N to which they are attached, join to form a 5-6 membered heterocyclic system containing 1-2 heteroatoms selected from $NR^{15g}$, O, and S and optionally fused with a benzene ring or a 6-membered aromatic heterocycle;

$R^{15b}$, at each occurrence, is selected from H, $C_{1-6}$ alkyl, $C_{3-6}$ cycloalkyl, and $(CH_2)_r$phenyl substituted with 0-3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_r CF_3$, OH, and $(CH_2)_r OC_{1-5}$ alkyl; and $R^{15f}$, at each occurrence, is selected from H, and $C_{1-5}$ alkyl.

14. The compound of claim 13, wherein:
Z is selected from O and S;
$R^1$ is H;
$R^2$ is H;
$R^3$ is a $C_{3-10}$ carbocyclic residue substituted with 0-3 $R^{15}$, wherein the carbocyclic residue is phenyl, and a $(CR^{3'}H)_r$-heterocyclic system substituted with 0-3 $R^{15}$, wherein the heterocyclic system is selected from pyridinyl, thiophenyl, furanyl, indazolyl, benzo[1,3]dioxolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{5a}$ is selected from a $(CH_2)_r$—$C_{3-10}$ carbocyclic residue substituted with 1-5 $R^{16}$ and a heterocyclic system substituted with 0-3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

15. A pharmaceutical composition, comprising a pharmaceutically acceptable carrier and a therapeutically effective amount of a compound of claim 1.

16. A method for treating asthma, comprising administering to a patient in need thereof a therapeutically effective amount of a compound of claim 1.

17. A pharmaceutical composition, comprising a pharmaceutically acceptable carrier and a therapeutically effective amount of a compound claim 14.

18. A method for treating asthma, comprising administering to a patient in need thereof a therapeutically effective amount of a compound of claim 14.

19. A method for treating disorders, comprising administering to a patient in need thereof a therapeutically effective amount of a compound of claim 14, said disorders being selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

20. A method for treating disorders, comprising administering to a patient in need thereof a therapeutically effective amount of a compound of claim 1, said disorders being selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

21. A method of treating disorders comprising administering to a patient in need thereof a therapeutically effective amount of a compound according to claim 1, or a pharmaceutically acceptable salt thereof, wherein the disorder is selected from rheumatoid arthritis, transplantation, and multiple sclerosis.

22. A method of treating disorders comprising administering to a patient in need thereof a therapeutically effective amount of a compound according to claim 14, or a pharmaceutically acceptable salt thereof, wherein the disorder is selected from rheumatoid arthritis, transplantation, and multiple sclerosis.

* * * * *